United States Patent [19]
Takatani et al.

[11] Patent Number: 5,840,732
[45] Date of Patent: Nov. 24, 1998

[54] IMIDAZOPYRIDINE OR IMIDAZOPYRIMIDINE COMPOUNDS, THEIR PRODUCTION AND USE

[75] Inventors: Muneo Takatani, Kyoto; Hitoshi Ikeda, Higashiosaka; Kyoko Iida, Osaka; Hidenori Abe, Ikeda, all of Japan

[73] Assignee: Takeda Chemical Industries Ltd., Osaka, Japan

[21] Appl. No.: 481,391

[22] PCT Filed: Jun. 15, 1995

[86] PCT No.: PCT/JP95/01192

§ 371 Date: Dec. 6, 1996

§ 102(e) Date: Dec. 6, 1996

[87] PCT Pub. No.: WO95/35296

PCT Pub. Date: Dec. 28, 1995

[30] Foreign Application Priority Data

Jun. 20, 1994 [JP] Japan ................................ 6-137600
Mar. 23, 1995 [JP] Japan ................................ 7-064128

[51] Int. Cl.[6] ........................ A61K 31/44; A61K 31/505; C07D 405/00; C07D 409/00; C07D 239/72
[52] U.S. Cl. ...................... 514/300; 514/266; 514/269; 544/54; 544/55; 544/281; 544/299; 544/300; 546/121
[58] Field of Search .................... 546/121; 514/300, 514/269, 266; 544/54, 55, 281, 299, 300

[56] References Cited

U.S. PATENT DOCUMENTS

| | | | |
|---|---|---|---|
| 2,514,649 | 7/1950 | Knott | 546/121 |
| 4,105,767 | 8/1978 | Bochis et al. | 546/121 X |
| 4,414,390 | 11/1983 | Tominaga et al. | 546/121 |
| 4,470,986 | 9/1984 | Browne | 546/121 X |
| 4,507,481 | 3/1985 | Davidson et al. | 546/121 |
| 4,590,196 | 5/1986 | Smith et al. | 514/253 |
| 4,782,055 | 11/1988 | Ueda et al. | 514/241 |
| 5,112,834 | 5/1992 | Senn-Bilfinger | 514/300 |
| 5,244,908 | 9/1993 | Takatani et al. | 514/300 |
| 5,260,303 | 11/1993 | Becker et al. | 514/300 |
| 5,491,161 | 2/1996 | Jannsen et al. | 514/394 |

FOREIGN PATENT DOCUMENTS

| | | |
|---|---|---|
| 0 404 525 | 12/1990 | European Pat. Off. . |
| 0 471 236 | 2/1992 | European Pat. Off. . |
| 0 522 606 | 1/1993 | European Pat. Off. . |
| 3530089 | 3/1986 | Germany . |
| 63-83067 | 4/1988 | Japan . |
| 63-83085 | 4/1988 | Japan . |
| 94/18199 | 8/1994 | WIPO ...................... 548/121 |

OTHER PUBLICATIONS

Ricci et al., Ann. Chim. (Rome), 53(5), 577–587 (1963).
Meth–Cohn et al., Synthesis (1), 58–60 (1978).
Mylari et al., "Potent, Orally Active Reductase Inhibitors Related to Zopolrestat: Surrogates for Benzothiazole Side Chain," J. Med. Chem. 1992, 35, pp. 457–465.

*Primary Examiner*—Floyd D. Higel
*Attorney, Agent, or Firm*—Foley & Lardner

[57] ABSTRACT

This invention provides a new condensed imidazole compound possessing inhibitory activity of adhesion molecule expression.

This invention also provides a therapeutic and prophylactic agent for diabetic nephritis and/or autoimmune disease and an immunosuppressor for organ transplantation.

51 Claims, No Drawings

IMIDAZOPYRIDINE OR IMIDAZOPYRIMIDINE COMPOUNDS, THEIR PRODUCTION AND USE

This application is a 371 of PCT/JP95/01192 filed Jun. 18, 1995.

TECHNICAL FIELD

The present invention relates to a new condensed imidazole compound that inhibits adhesion molecule expression and is useful as a therapeutic and prophylactic agent for diabetic nephritis and/or autoimmune diseases and as an immunosuppressor for organ transplantation, a method of its production and its composition.

BACKGROUND ART

In recent years, inhibitors of adhesion molecules expression designed to suppress inflammatory cell infiltration or prevent binding of immune cells involved in antigen recognition have drawn attention [Jikken Igaku, Vol. 9, p. 289 (1991); Immunology Today, Vol. 10, p. 375 (1989)].

In insulin-dependent diabetes mellitus, severe complications, namely retinopathy, nephropathy and neuropathy, occur, despite insulin therapy, 10 to 20 years after onset, which can threaten the patient's life, as well as quality of life. Diabetic nephropathy, in particular, is a severe complication seen in about 20–30% of diabetics, with no well-established effective therapy.

In organ transplantation, several kinds of immunosuppressors must be used for immunosuppression therapy to control graft rejection. Moreover, the functional survival of grafts depends on a delicate equilibrium between the kinds of immunosuppressors and the patient's capability of immune response. It is therefore desirable to be able to select drugs out of as many kinds of immunosuppressors as possible.

On the other hand, Japanese Patent Unexamined Publication No. 125048/1993 discloses that a pyridine derivative represented by the following formula (or salt or solvate thereof) is useful as an immunotherapeutic drug, therapeutic drug for transplantation immune response, etc.:

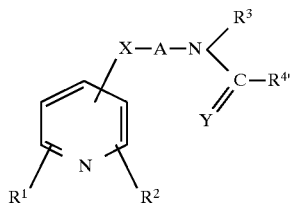

wherein $R^1$ and $R^2$, whether identical or not, represent a hydrogen atom, a halogen, a lower alkyl group, a lower alkenyl group, a lower alkoxy group, a hydroxyl group, a nitro group, a cyano group, an amino group, a carbamoyl group, an acylamino group, a lower alkylamino group, a lower alkenylamino group or an aralkylamino group; X represents an oxygen atom or $—S(O)_n—$ (n represents 0, 1 or 2); A represents a divalent $C_{1-5}$ hydrocarbon residue that may be substituted at a branch thereof; Y represents an atom of oxygen or sulfur; $R^3$ represents a hydrogen atom or a hydrocarbon residue that may be substituted; $R^4$ represents (1) a $C_{2-30}$ alkyl group, (2) a $C_{2-30}$ alkenyl group, (3) a lower alkyl group substituted by a halogen, an aryl or a heterocyclic group, (4) a lower alkenyl group substituted by a halogen or a heterocyclic group, (5) an aralkyl group that may be substituted, (6) an aryl group that may be substituted, or (7) a monocyclic or bicyclic heterocyclic group that may be substituted.

Japanese Patent Unexamined Publication No. 51383/1993 discloses that a calmodulin-inhibiting compound represented by the following formula (or salt thereof) is useful as an anti-inflammatory drug etc.:

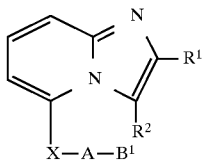

wherein X represents S, S(O), $S(O)_2$, O or $NR^3$ ($R^3$ represents a hydrogen or a hydrocarbon group that may be substituted); A represents a divalent linear or branched $C_{1-15}$ hydrocarbon group that may contain ethereal oxygen at any possible position thereof and that may be substituted at a branch thereof; $B^1$ represents an amino group acylated by an acyl group derived from a carboxylic acid, sulfonic acid, carbamic acid or thiocarbamic acid having 2 or more carbon atoms; $R^1$ and $R^2$, whether identical or not, represent a hydrogen, a hydrocarbon group that may be substituted, a halogen, a nitro group, a nitroso group, an amino group that may be protected, a lower alkoxycarbonyl group or a lower alkylcarbamoyl group. In examples of that patent publication, the following compounds were synthesized.

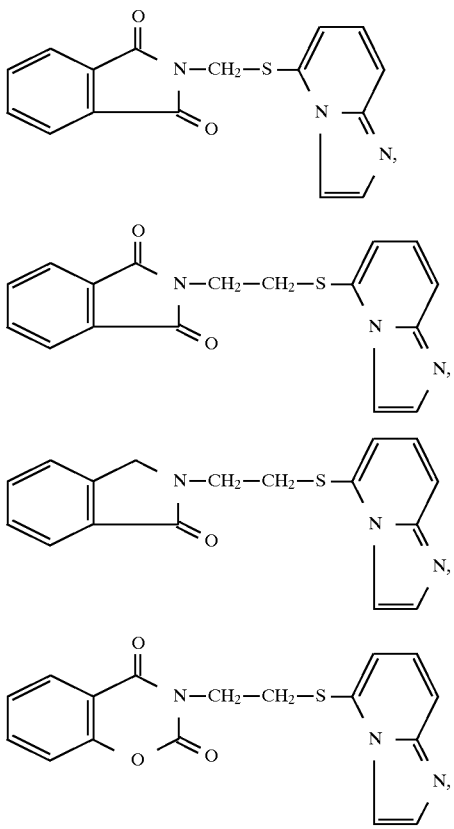

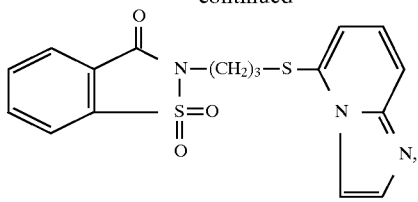

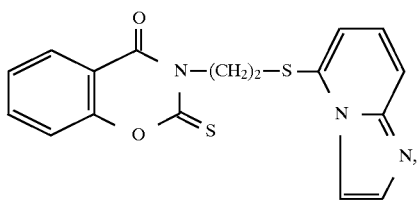

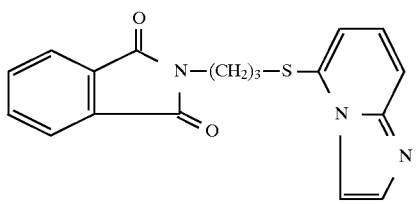

and

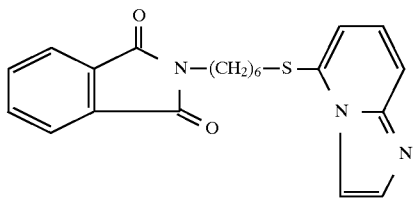

Japanese Patent Unexamined Publication No. 39221/1993 discloses an angiogenesis inhibitor containing a compound represented by the formula (or pharmaceutically acceptable salt thereof):

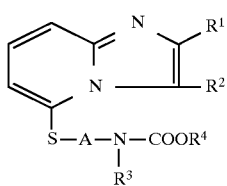

wherein A represents a divalent linear or branched $C_{1-15}$ hydrocarbon group that may contain ethereal oxygen at any possible position thereof, and that may be substituted at a branch thereof; $R^1$ and $R^2$ independently represent a hydrogen, a hydrocarbon group that may be substituted, a halogen, a nitro group, a nitroso group, an amino group that may be protected, a lower alkoxycarbonyl group or a lower alkylcarbamoyl group; $R^3$ represents a hydrogen or a hydrocarbon group that may be substituted, and may form a ring in combination with the carbon atom for A; $R^4$ represents a hydrocarbon group that may be substituted.

Japanese Patent Unexamined Publication No. 86887/1991 discloses that a compound represented by the following formula(or salt thereof), which possesses endothelin-antagonistic activity, interleukin-1-suppressing activity and nerve growth factor-stimulating activity, is useful as a therapeutic drug for inflammatory or immune diseases:

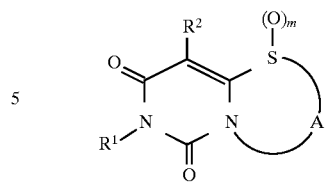

wherein $R^1$ represents an aliphatic hydrocarbon group that may be substituted for, an aralkyl group that may be substituted for or an aryl group that may be substituted for; $R^2$ represents a hydrogen, an aliphatic hydrocarbon group having 1 or more than 1 substituent, an aryl group that may be substituted for, an amino group that may be substituted for, an alkanoyl group that may be substituted for, a formyl group, a nitro group or a halogeno group; A represents a divalent hydrocarbon chain having 2 to 4 carbon atoms that may be substituted for; m represents an integer from 0 to 2.

In these circumstances, there is strong need for development of therapeutic drugs for diabetic nephritis (yet to be well established) and immunosuppressors for organ transplantation with a mode of action distinct from currently available drugs, as well as inhibitors of adhesion molecule expression.

DISCLOSURE OF INVENTION

Through extensive investigation, the present inventors synthesized a new imidazole compound (or a salt thereof) (hereinafter referred to as compound (I)) represented by formula (I) (or salt thereof):

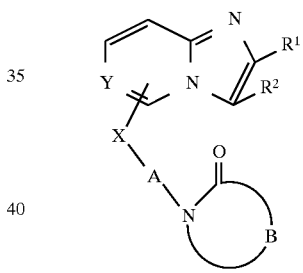

wherein X represents a bond, $-S(O)_m-$, $-O-$, $-NR^{3a}-$, $-Alk-$, $-Alk-W-$ or $-S-Alk-W-$ (Alk represents a divalent hydrocarbon group that may be substituted; W represents $-O-$, $-NR^{3a}-$, $-CO-O-$ or $-O-CO-NR^{3a}-$; $R^{3a}$ represents a hydrogen or a hydrocarbon group that may be substituted; m represents an integer from 0 to 2); Y represents CH or N; $R^1$ and $R^2$ independently represent a hydrogen, a hydrocarbon group that may be substituted, a halogen, a nitro group, a nitroso group, an amino group that may be protected, a carboxyl group that may be esterified or an acyl group; A represents a divalent hydrocarbon group that may be substituted; B represents the following:

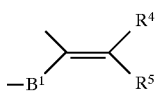

wherein $B^1$ represents $-(CH_2)_f-$ or $-CZ^1-Z^2-$ (f represents an integer from 1 to 6; $Z^1$ represents O or S; $Z^2$ represents O, S, $-Alk^1-$, $-Alk^1-S-$ or $NR^{3b}$; Alk1 represents a divalent hydrocarbon group that may be substituted; $R^{3b}$ represents a hydrogen or a hydrocarbon group that may be substituted); $R^4$ and $R^5$ independently represent a hydrogen, a carboxyl group that may be esterified, an amino group that may be substituted, a heterocyclic group that may be substituted, $-W^1$, $-S-W^1$ or $-O-W^1$ ($W^1$ represents a hydrocarbon group that may be substituted); $R^4$ and $R^5$ may bind together to form a ring; or B represents the formula:

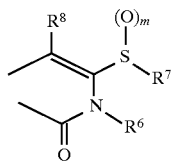

wherein $R^6$ and $R^7$ independently represent a hydrocarbon group that may be substituted or a heterocyclic group that may be substituted; $R^6$ and $R^7$ may bind together to form a ring; $R^8$ represents a hydrogen, a hydrocarbon group that may be substituted, a heterocyclic group that may be substituted, a nitro group, a cyano group, an amino group that may be protected, a halogen or an acyl group; m represents an integer from 0 to 2, and found that this compound (I) unexpectedly possesses excellent inhibitory activity of adhesion molecule expression and can be safely used as a therapeutic composition for diabetic nephritis and an immunosuppressor for organ transplantation. The inventors made further investigation based on this finding, and completed the present invention.

Accordingly, the present invention relates to:
(1) compound (I),
(2) the compound of term (1) above, wherein X is S, S(O), $S(O)_2$, O, $-N(R^3)-$, $-(CH_2)_i-O-$, $-(CH_2)_i-N(R^3)-$, $-CH_2-$, $-CH=CH-$, $-(CH_2)_j-CO-N(R^3)-$, $-S-(CH_2)_k-CO-N(R^3)-$, $-(CH_2)_j-COO-$, $-S-(CH_2)_k-COO-$ or $-(CH_2)_i-O-CO-N(R^3)-$ ($R^3$ represents a hydrogen, a lower alkyl group that may be substituted, a lower alkenyl group that may be substituted, an aralkyl group that may be substituted or an aryl group that may be substituted; i represents an integer of 1 or 2, j represents an integer of 0 or 1, and k represents an integer from 1 to 5),
(3) the compound of term (1) above, wherein X is S, O or $-CH_2-$,
(4) the compound of term (1) above, wherein Y is CH,
(5) the compound of term (1) above, wherein each of $R^1$ and $R^2$ is a hydrogen, a lower alkyl group that may be substituted, an aryl group that may be substituted, a lower alkoxycarbonyl group or a lower alkanoyl group that may be substituted by halogen,
(6) the compound of term (1) above, wherein each of $R^1$ and $R^2$ independently represent a hydrogen, a lower alkyl group, a phenyl group, a lower alkoxycarbonyl group or a halogeno-lower alkylcarbonyl group,
(7) the compound of term (1) above, wherein A is a divalent $C_{1-15}$ chain hydrocarbon group that may be substituted,
(8) the compound of term (1) above, wherein A is a $C_{1-6}$ alkylene group,
(9) the compound of term (1) above, wherein X is bound to the 5-position of an imidazo[1,2-a]pyridine ring or an imidazo[1,2-c]pyrimidine ring,
(10) the compound of term (1) above, wherein X is bound to the 8-position of an imidazo[1,2-a]pyridine ring or an imidazo[1,2-c]pyrimidine ring,
(11) the compound of term (1) above represented by the formula (or salt thereof):

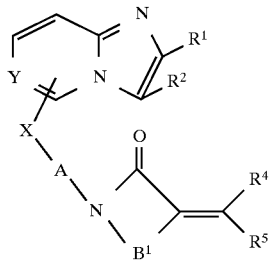

wherein the symbols have the same definitions as those given above,
(12) the compound of term (11) above, wherein $B^1$ is $-(CH_2)_f-$, $-CO-O-$, $-CO-S-$, $-CS-S-$, $-CO-CH_2-$, $-CO-CH_2-S-$ or $-CO-N(R^3)-$ ($R^3$ and f have the same definitions as those given above),
(13) the compound of term (11) above, wherein $B^1$ is $-CO-S-$, $-CO-O-$, $-CO-CH_2-$ or $-CO-N(R^3)-$ ($R^3$ has the same definition as that given above),
(14) the compound of term (11) above, wherein $B^1$ is $-CO-S-$ or $-CO-O-$,
(15) the compound of term (11) above, wherein $R^4$ and $R^5$ independently represent a hydrogen atom, a lower alkyl group that may be substituted, an aryl group that may be substituted, an amino group that may be substituted or a heterocyclic group that may be substituted,
(16) the compound of term (11) above, wherein $R^4$ and $R^5$ independently represent a hydrogen or a lower alkyl group that may be substituted,
(17) the compound of term (11) above, wherein X is S, O or $-CH_2-$,
(18) the compound of term (11) above, wherein Y is CH,
(19) the compound of term (11) above, wherein A is a $C_{1-6}$ alkylene group,
(20) the compound of term (11) above, wherein $R^1$ and $R^2$ independently represent a hydrogen, a lower alkyl group, a phenyl group, a lower alkoxycarbonyl group or a halogeno-lower alkylcarbonyl group,
(21) the compound of term (11) above, wherein X is bound to the 5-position of an imidazo[1,2-a]pyridine ring or an imidazo[1,2-c]pyrimidine ring,
(22) the compound of term (1) above represented by the formula (or salt thereof):

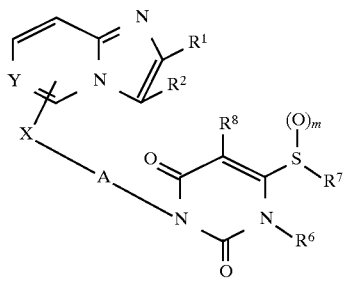

wherein the symbols have the same definitions as those given above,
(23) the compound of term (22) above, wherein $R^6$ and $R^7$ independently represent a lower alkyl group that may be substituted, or $R^6$ and $R^7$ has bound together to form $-C(R^{15})-C(R16)-(CH_2)_s-$ ($R^{15}$ and $R^{16}$ independently represent a hydrogen or a lower alkyl group; s represents an integer of 0 or 1),
(24) the compound of term (22) above, wherein $R^8$ is a hydrogen, a lower alkyl group that may be substituted or an aryl group that may be substituted,

(25) the compound of term (22) above, wherein $R^8$ is a hydrogen, a lower alkyl group, an aralkyl group or a phenyl group,

(26) the compound of term (22) above, wherein m is 1 or 2,

(27) the compound of term (22) above, wherein X is S, O or —$CH_2$—,

(28) the compound of term (22) above, wherein Y is CH,

(29) the compound of term (22) above, wherein A is a $C_{1-6}$ alkylene group,

(30) the compound of term (22) above, wherein $R^1$ and $R^2$ independently represent a hydrogen, a lower alkyl group, a phenyl group, a lower alkoxycarbonyl group or a halogeno-lower alkylcarbonyl group,

(31) the compound of term (22) above, wherein X is bound to the 5-position of an imidazo[1,2-a]pyridine ring or an imidazo[1,2-c]pyrimidine ring,

(32) a process for producing the compound of term (1) above which comprises reacting a compound represented by the formula (or salt thereof):

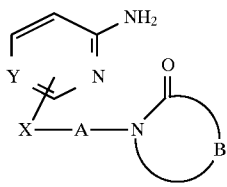

wherein the symbols have the same definitions as those given in term (1) above, with a compound represented by the formula (or salt thereof):

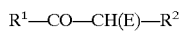

$R^1$—CO—CH(E)—$R^2$ wherein E represents a halogen; the other symbols have the same definitions as those given in term (1) above,

(33) a process for producing the compound of term (1) above having S, O or $N(R^3)$ for X which comprises reacting a compound represented by the formula (or salt thereof):

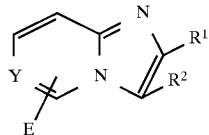

wherein the symbols have the same definitions as those given in term (1) above, with a compound represented by the formula (or salt thereof):

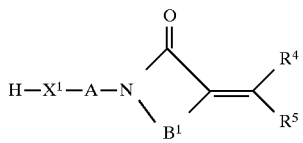

wherein $X^1$ represents S, O or —$N(R^3)$— ($R^3$ represents a hydrogen, a lower alkyl group that may be substituted, a lower alkenyl group that may be substituted, an aralkyl group that may be substituted or an aryl group that may be substituted); the other symbols have the same definitions as those given in term (1) above,

(34) A process for producing the compound of term (1) above having S, O, —$(CH_2)_i$—O— or —$(CH_2)_i$—N($R^3$)— for X which comprises reacting a compound represented by the formula (or salt thereof):

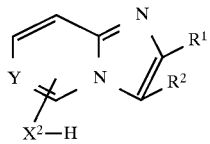

wherein $X^2$ represents S, O, —$(CH_2)_i$—O— or —$(CH_2)_i$—$N(R^3)$— ($R^3$ represents a hydrogen, a lower alkyl group that may be substituted, a lower alkenyl group that may be substituted, an aralkyl group that may be substituted or an aryl group that may be substituted; i represents 1 or 2); the other symbols have the same definitions as those given in term (1) above, with a compound represented by the formula (or salt thereof):

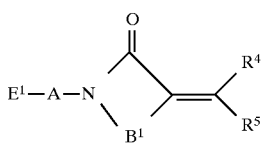

wherein $E^1$ represents a leaving group; the other symbols have the same definitions as those given in term (1) above,

(35) a process for producing the compound of term (1) above having —$(CH_2)_j$—$CON(R^3)$—, —$(CH_2)_j$—COO—, —S—$(CH_2)_k$—$CON(R^3)$— or —S—$(CH_2)_k$—COO— for X which comprises reacting a compound represented by the formula (or salt thereof):

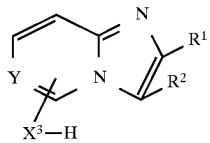

wherein $X^3$ represents —$(CH_2)_j$—COO— (j represents 0 or 1) or —S—$(CH_2)_k$—COO— (k represents an integer from 1 to 5); the other symbols have the same definitions as those given in term (1) above, with a compound represented by the formula(or salt thereof):

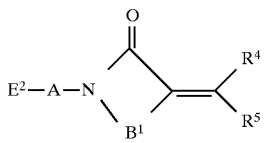

wherein $E^2$ represents $HN(R^3)$— ($R^3$ represents a hydrogen, a lower alkyl group that may be substituted, a lower alkenyl group that may be substituted, an aralkyl group that may be substituted or an aryl group that may be substituted) or HO—; the other symbols have the same definitions as those given in term (1) above,

(36) a process for producing the compound of term (1) above having —$(CH_2)_i$—$OCON(R^3)$— for X which comprises reacting a compound represented by the formula (or salt thereof):

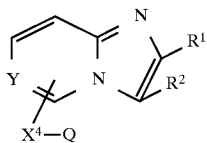

wherein X⁴ represents —(CH₂)ᵢ—OCO— (i represents 1 or 2); Q represents a leaving group; the other symbols have the same definitions as those given in term (1) above, with a compound (or salt thereof) represented by the formula:

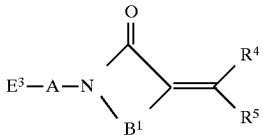

wherein E³ represents HN(R³)— (R³ represents a hydrogen, a lower alkyl group that may be substituted, a lower alkenyl group that may be substituted, an aralkyl group that may be substituted or an aryl group that may be substituted); the other symbols have the same definitions as those given in term (1) above,

(37) a process for producing the compound of term (1) above which comprises reacting a compound represented by the formula (or salt thereof):

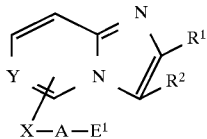

wherein E¹ represents a leaving group; the other symbols have the same definitions as those given in term (1) above, with a compound represented by the formula (or salt thereof):

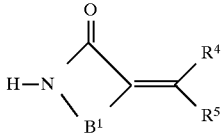

wherein the symbols have the same definitions as those given in term (1) above,

(38) a process for producing the compound of claim 1 having S, O or N(R³) for X which comprises reacting a compound represented by the formula:

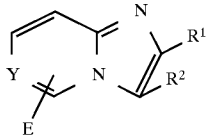

wherein the symbols have the same definitions as those given in claims 1 and 47 above, or a salt thereof with a compound represented by the formula:

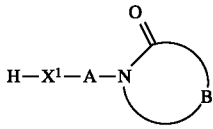

wherein X¹ represents S, O or —N(R³)— (R³ represents a hydrogen, a lower alkyl group that may be substituted, a lower alkenyl group that may be substituted, an aralkyl group that may be substituted or an aryl group that may be substituted); the other symbols have the same definitions as those given in claim 1, or a salt thereof.

(39) a process for producing the compound of claim 1 having S, O, —(CH₂)ᵢ—O— or —(CH₂)ᵢ—N(R³)— for X which comprises reacting a compound represented by the formula:

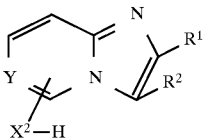

wherein X² represents S, O, —(CH₂)ᵢ—O— or —(CH₂)ᵢ—N(R³)— (R³ represents a hydrogen, a lower alkyl group that may be substituted, a lower alkenyl group that may be substituted, an aralkyl group that may be substituted or an aryl group that may be substituted; i represents 1 or 2); the other symbols have the same definitions as those given in claim 1, or a salt thereof with a compound represented by the formula:

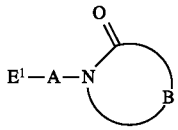

wherein E¹ represents a leaving group; the other symbols have the same definitions as those given in claim 1, or a salt thereof.

(40) a process for producing the compound of claim 1 having —(CH₂)ⱼ—CON(R³)—, —(CH₂)ⱼ—COO—, —S—(CH₂)ₖ—CON(R³)— or —S—(CH₂)ₖ—COO— for X which comprises reacting a compound represented by the formula:

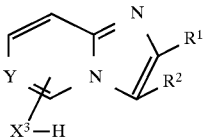

wherein X³ represents —(CH₂)ⱼ—COO— (j represents 0 or 1) or —S—(CH₂)ₖ—COO— (k represents an integer from 1 to 5); the other symbols have the same definitions as those given in claim 1, or a salt thereof with a compound represented by the formula:

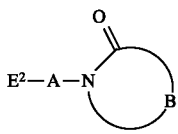

wherein $E^2$ represents $HN(R^3)-$ ($R^3$ represents a hydrogen, a lower alkyl group that may be substituted, a lower alkenyl group that may be substituted, an aralkyl group that may be substituted or an aryl group that may be substituted) or HO—; the other symbols have the same definitions as those given in claim 1, or a salt thereof.

(41) a process for producing the compound of claim 1 having $-(CH_2)_i-OCON(R^3)-$ for X which comprises reacting a compound represented by the formula:

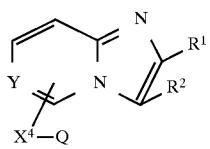

wherein $X^4$ represents $-(CH_2)_i-OCO-$ (i represents 1 or 2); Q represents a leaving group; the other symbols have the same definitions as those given in claim 1, or a salt thereof with a compound represented by the formula:

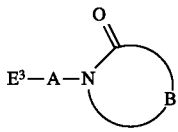

wherein $E^3$ represents $HN(R^3)-$ ($R^3$ represents a hydrogen, a lower alkyl group that may be substituted, a lower alkenyl group that may be substituted, an aralkyl group that may be substituted or an aryl group that may be substituted); the other symbols have the same definitions as those given in claim 1, or a salt thereof.

(42) a process for producing the compound of claim 1 which comprises reacting a compound represented by the formula:

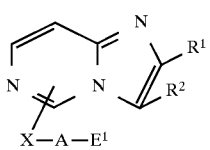

wherein $E^1$ represents a leaving group; the other symbols have the same definitions as those given in claim 1, or a salt thereof with a compound represented by the formula:

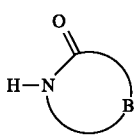

wherein the symbols have the same definitions as those given in claim 1, or a salt thereof.

(43) a process for producing the compound of term (11) above which comprises reacting a compound represented by the formula (or salt thereof):

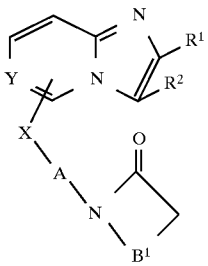

wherein the symbols have the same definitions as those given in term (1) above, with a compound represented by the formula (or salt thereof):

wherein the symbols have the same definitions as those given in term (1) above,

(44) a pharmaceutical composition, which contains the compound of term (1)

(45) an inhibitor of adhesion molecule expression, which contains the compound of term (1) above,

(46) a therapeutic agent for diabetic nephritis, which contains the compound of term (1) above, and

(47) an immunosuppressor for organ transplantation, which contains the compound of term (1) above.

In the above formulas, A represents a divalent hydrocarbon group that may be substituted.

The divalent hydrocarbon group represented by A is exemplified by divalent $C_{1-15}$ chain hydrocarbon groups, divalent $C_{5-8}$ cyclic hydrocarbon groups and combinations thereof. Useful divalent $C_{1-15}$ chain hydrocarbon groups include $C_{-16}$ alkylene groups (e.g., methylene, ethylene, propylene, butyrene, pentamethylene, hexamethylene), $C_{2-6}$ alkenylene groups (e.g., vinylene) and $C_{2-6}$ alkynylene groups (e.g., ethynylene). Useful divalent $C_{5-8}$ cyclic hydrocarbon groups include phenylene.

These divalent hydrocarbon groups represented by A may have at any possible position 1 or 2 substituents selected from the group comprising halogens (e.g., fluorine, chlorine, bromine, iodine), lower alkoxy groups (e.g., $C_{1-6}$ alkoxy groups such as methoxy, ethoxy, propoxy, isopropoxy, butoxy and pentoxy), acyl groups, carboxyl groups that may be esterified, hydroxyl group, pyridylthio group, nitro group, cyano group and oxo group.

Acyl groups useful as substituents for the divalent hydrocarbon group for A include lower alkanoyl groups (e.g., $C_{1-8}$ alkanoyl groups such as formyl, acetyl, propionyl, butyryl, isobutyryl, valeryl, isovaleryl, pivaloyl and hexanoyl), lower alkylsulfonyl groups (e.g., $C_{1-6}$ alkylsulfonyl groups such as methylsulfonyl and ethylsulfonyl), lower alkylsulfinyl groups (e.g., $C_{1-6}$ alkylsulfinyl groups such as methylsulfinyl and ethyl sulfinyl), $C_{6-10}$ arylcarbonyl groups (e.g., benzoyl group), carbamoyl groups, lower alkylcarbamoyl groups (e.g., N-$C_{1-6}$ alkylcarbamoyl groups such as N-methylcarbamoyl, N-ethylcarbamoyl, N-propylcarbamoyl and N-butylcarbamoyl, N,N-di-$C_{1-6}$ alkylcarbamoyl groups such as N,N-dimethylcarbamoyl, N,N-diethylcarbamoyl, N,N-dipropylcarbamoyl, N,N-dibutylcarbamoyl and N-ethyl-N-methylcarbamoyl), lower alkenylcarbamoyl groups (e.g., N-$C_{2-6}$ alkylcarbamoyl groups such as N-vinylcarbamoyl and N-allylcarbamoyl, N,N-di-$C_{2-6}$ alkylcarbamoyl groups such as N,N-divinylcarbamoyl and N,N-diallylcarbamoyl) and cyclic aminocarbonyl groups wherein the dialkyl moiety has formed a 5- or 6-membered ring structure in combine with the nitrogen of a carbamoyl group (e.g., 1-azetizinylcarbonyl, morpholinocarbonyl, 1-pyrrolidinylcarbonyl, 1-piperidinocarbonyl, 1-piperazinylcarbonyl, 1-piperazinylcarbonyl groups having at 4-position a lower alkyl group, a cycloalkyl group, an aralkyl group, an aryl group, an acyl group, or the like). Here, the lower alkanoyl group may be substituted by 1 to 3 substituents, such as halogens (e.g., fluorine, chlorine, bromine, iodine).

The carboxyl group that may be esterified as a substituent for the divalent hydrocarbon group for A is exemplified by carboxyl groups, lower alkoxycarbonyl groups (e.g., $C_{1-6}$ alkoxycarbonyl groups such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl, neopentyloxycarbonyl and tert-pentyloxycarbonyl).

The group for A is preferably represented by the formula:

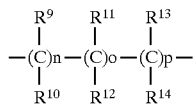

wherein n, o and p independently represent an integer from 0 to 5; $R^9$, $R^{10}$, $R^{11}$, $R^{12}$, $R^{13}$ and $R^{14}$ independently represent hydrogen, a lower alkyl group that may have a substituent, an aralkyl group that may be substituted or an aryl group that may be substituted; $R^9$ and $R^{10}$ or $R^{11}$ and $R^{12}$ or $R^{13}$ and $R^{14}$ may be combined together to form a ring; $R^9$ or $R^{11}$ may bind with $R^{13}$ or $R^{14}$, respectively, to form a ring, or the formula:

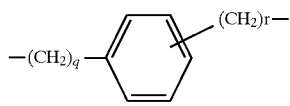

wherein q and r independently represent an integer from 0 to 5.

The lower alkyl group, aralkyl group or aryl group that may be substituted for $R^9$, $R^{10}$, $R^{11}$, $R^{12}$, $R^{13}$ or $R^{14}$ is exemplified by the same groups as the lower alkyl group, aralkyl group and aryl group that may be substituted for $R^3$ below.

The ring formed by combining $R^9$ and $R^{10}$ or $R^{11}$ and $R^{12}$ or $R^{13}$ and $R^{14}$ is exemplified by $C_{3-8}$ cycloalkyl groups such as cyclopropyl, cyclobutyl, cyclopentyl and cyclohexyl. The ring formed by $R^9$ or $R^{11}$ in combine with $R^{13}$ or $R^{14}$, respectively, is exemplified by $C_{3-8}$ cycloalkyl groups such as cyclopropyl, cyclobutyl, cyclopentyl and cyclohexyl.

The group for A is more preferably a $C_{1-6}$ alkylene group, or the like.

With respect to the above formulas, $R^1$ and $R^2$, independently, represent a hydrogen, a hydrocarbon group that may be substituted, a halogen, a nitroso group, an amino group that may be protected, a carboxyl group that may be esterified or an acyl group.

The hydrocarbon group for $R^1$ or $R^2$ is exemplified by $C_{1-30}$ chain hydrocarbon groups, $C_{3-14}$ cyclic hydrocarbon groups and combinations thereof. Useful $C_{1-30}$ chain hydrocarbon groups for $R^1$ or $R^2$ include $C_{1-30}$ alkyl groups (e.g., methyl, ethyl, propyl, butyl, pentyl, hexyl, heptyl, octyl, nonyl, decyl, undecyl, tridecyl, tetradecyl, pentadecyl, hexadecyl, heptadecyl, octadecyl, nonadecyl, eicosadecyl, heneicosanyl, docosanyl, tricosanyl, tetracosanyl, pentacosanyl, hexacosanyl, heptacosanyl, octacosanyl, nonacosanyl, triacontanyl, farnesyl and dihydrophytyl, preferably $C_{1-10}$ alkyl groups such as methyl, ethyl, propyl, butyl, pentyl, hexyl, heptyl, octyl, nonyl and decyl) and $C_{2-30}$ alkenyl groups (e.g., vinyl, allyl, 2-butenyl, 3-butenyl, 9-octadecenyl). Useful $C_{3-14}$ cyclic hydrocarbon groups include $C_{3-8}$ cycloalkyl groups (e.g., cyclopropyl, cyclobutyl, cyclopentyl, cyclohexyl, cycloheptyl, cyclooctyl), $C_{5-8}$ cycloalkenyl groups (e.g., cyclopentenyl, cyclohexenyl) and aryl groups (e.g., $C_{6-14}$ aryl groups such as phenyl, 1-naphthyl, 2-naphthyl, phenanthryl and anthryl). Useful hydrocarbon groups consisting of a combination of a $C_{1-30}$ chain hydrocarbon group and a $C_{3-14}$ cyclic hydrocarbon group include aralkyl groups (e.g., phenyl-$C_{1-6}$ alkyl groups such as benzyl, phenethyl, 3-phenylpropyl and 4-phenylbutyl, and naphthyl-$C_{1-6}$ alkyl groups such as (1-naphthyl)methyl, 2-(1-naphthyl)ethyl and 2-(2-naphthyl) ethyl).

These hydrocarbon groups represented by $R^1$ or $R^2$ may have at any possible position 1 to 5 substituents selected from the group comprising nitro group, hydroxyl group, oxo group, thioxo group, cyano group, sulfone group, halogens (e.g., fluorine, chlorine, bromine, iodine), lower alkoxy groups (e.g., $C_{1-6}$ alkoxy groups such as methoxy, ethoxy, propoxy, isopropoxy, butoxy and pentoxy), phenoxy group, halogenophenoxy groups (e.g., o-, m- or p-chlorophenoxy, o-, m- or p-bromophenoxy), lower alkylthio groups (e.g., $C_{1-6}$ alkylthio groups such as methylthio, ethylthio, n-propylthio, isopropylthio and n-butylthio), phenylthio group, amino groups that may be substituted, carboxyl groups that may be esterified, acyl groups and heterocyclic groups.

Useful substituents of the amino group as a substituent of the hydrocarbon group for $R^1$ or $R^2$ include lower alkyl groups (e.g., methyl, ethyl, propyl, isopropyl, butyl, isobutyl, sec-butyl, tert-butyl, pentyl, hexyl) and acyl groups. Optionally substituted amino groups include lower alkanoylamino groups (e.g., $C_{1-6}$ alkanoylamino groups such as acetylamino and propionylamino) and mono- or di-substituted amino groups (e.g., methylamino, ethylamino, n-propylamino, isopropylamino, n-butylamino, dimethylamino, diethylamino).

The acyl group as a substituent of the hydrocarbon group for $R^1$ or $R^2$ or as a substituent of the amino group as a substituent of that hydrocarbon group is exemplified by the same groups as the above-mentioned acyl groups as substituents of the divalent hydrocarbon group for A above.

The carboxyl group that may be esterified as a substituent of the hydrocarbon group for $R^1$ or $R^2$ is exemplified by the same groups as the above-mentioned carboxyl groups as substituents of the divalent hydrocarbon group for A above.

The heterocyclic group as a substituent of the hydrocarbon group for $R^1$ or $R^2$ is exemplified by the same groups as the optionally substituted heterocyclic groups for $R^4$ or $R^5$ described later.

The halogen for $R^1$ or $R^2$ is exemplified by fluorine, chlorine, bromine and iodine.

Protecting groups for the amino group for $R^1$ or $R^2$ include amide-forming protective groups, such as formyl, acetyl, chloroacetyl, dichloroacetyl, trichloroacetyl, trifluoroacetyl, acetoacetyl and o-nitrophenylacetyl; carbamate-forming protecting groups, such as tert-butoxycarbonyl, benzyloxycarbonyl, p-methoxybenzyloxycarbonyl, p-nitrobenzyloxycarbonyl, 2,4-dichlorobenzyloxycarbonyl, benzhydryloxycarbonyl, 2,2,2-trichloroethoxycarbonyl, 2-trimethylsilylethoxycarbonyl, 1-methyl-1-(4-biphenyl) ethoxycarbonyl, 9-fluorenylmethoxycarbonyl, 9-anthrylmethoxycarbonyl, isonicotinyloxycarbonyl and 1-adamantyloxycarbonyl; and trityl and phthaloyl.

The carboxyl group that may be esterified represented by $R^1$ or $R^2$ is exemplified by the same groups as the above-mentioned carboxyl groups that may be esterified as substituents of the divalent hydrocarbon group for A.

The acyl group for $R^1$ or $R^2$ is exemplified by the same groups as the above-mentioned acyl groups as substituents of the divalent hydrocarbon group for A.

Preferable groups for $R^1$ or $R^2$ include a hydrogen, lower alkyl groups that may be substituted, aryl groups that may be substituted, lower alkoxycarbonyl groups and lower alkanoyl groups that may be substituted for by 1 to 3 halogens, with greater preference given to a hydrogen, lower alkyl groups, phenyl groups, lower alkoxycarbonyl groups, halogeno-lower alkylcarbonyl groups (e.g., halogeno-$C_{1-6}$ alkylcarbonyl groups such as trifluoromethyl) etc.

The preferable lower alkyl group or aryl group that may be substituted for $R^1$ or $R^2$ is exemplified by the same groups as the optionally substituted lower alkyl groups and aryl groups for $R^3$ described later.

With respect to the above formulas, X represents a bond, —S(O)$_m$—, —O—, —NR$^{3a}$—, —Alk—, —Alk—W— or —S—Alk—W— (Alk represents a divalent hydrocarbon group that may be substituted; W represents —O—, —NR$^{3a}$—, —CO—O— or —O—CO—NR$^{3a}$—; $R^{3a}$ represents a hydrogen or a hydrocarbon group that may be substituted; m represents an integer from 0 to 2).

The divalent hydrocarbon group that may be substituted for Alk is exemplified by the same groups as the above-mentioned divalent hydrocarbon groups for A that may be substituted.

The hydrocarbon group that may be substituted for $R^{3a}$ is exemplified by the same groups as the above-mentioned hydrocarbon groups for $R^1$ or $R^2$ that may be substituted.

X is preferably S, S(O), S(O)$_2$, O, —N(R$^3$)—, —(CH$_2$)$_i$—O—, —(CH$_2$)$_i$—N(R$^3$)—, —CH$_2$—, —CH=CH—, —(CH$_2$)$_j$—CO—N(R$^3$)—, —S—(CH$_2$)$_k$—CO—N(R$^3$)—, —(CH$_2$)$_j$—COO—, —S—(CH$_2$)$_k$—COO—, —(CH$_2$)$_i$—O—CO—N(R$^3$)—, or the like (R$^3$ represents a hydrogen, a lower alkyl group that may be substituted, a lower alkenyl group that may be substituted, an aralkyl group that may be substituted or an aryl group that may be substituted; i represents an integer of 1 or 2, j represents an integer of 0 or 1, and k represents an integer from 1 to 5), with greater preference given to S, O, —CH$_2$— etc.

Useful lower alkyl groups for $R^3$ include $C_{1-6}$ alkyl groups such as methyl, ethyl, propyl, isopropyl, butyl, isobutyl, sec-butyl, tert-butyl, pentyl and hexyl. These lower alkyl groups may have 1 or 2 substituents selected from the group comprising halogens (e.g., fluorine, chlorine, bromine, iodine), lower alkoxy groups (e.g., $C_{1-6}$ alkoxy groups such as methoxy, ethoxy, propoxy, isopropoxy, butoxy and pentoxy), hydroxy group, lower alkoxycarbonyl groups (e.g., $C_{1-6}$ alkoxycarbonyl groups such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl, neopentyloxycarbonyl and tert-pentyloxycarbonyl), carboxyl group, carbamoyl groups, lower alkylcarbamoyl groups (e.g., N-$C_{1-6}$ alkylcarbamoyl groups such as N-methylcarbamoyl, N-ethylcarbamoyl, N-propylcarbamoyl and N-butylcarbamoyl, N,N-di-$C_{1-6}$ alkylcarbamoyl groups such as N,N-dimethylcarbamoyl, N,N-diethylcarbamoyl, N,N-dipropylcarbamoyl, N,N-dibutylcarbamoyl and N-ethyl-N-methylcarbamoyl) and pyridylthio groups.

The lower alkenyl group for $R^3$ is exemplified by $C_{2-6}$ alkenyl groups such as vinyl, allyl, 2-butenyl and 3-butenyl. These lower alkenyl groups may be substituted by the same substituents as the above-mentioned substituents of the lower alkyl group for $R^3$.

Useful aralkyl groups for $R^3$ include phenyl-lower alkyl groups (e.g., phenyl-$C_{1-6}$ alkyl groups such as benzyl, phenethyl, 3-phenylpropyl and 4-phenylbutyl) and naphthyl-lower alkyl groups (e.g., naphthyl-$C_{1-6}$ alkyl groups such as (1-naphthyl)methyl, 2-(1-naphthyl)ethyl and 2-(2-naphthyl)ethyl). The phenyl moiety of the phenyl-lower alkyl group or the naphthyl moiety of the naphthyl-lower alkyl group may have 1 to 4 substituents selected from the group comprising halogens (e.g., fluorine, chlorine, bromine, iodine), lower alkyl groups (e.g., $C_{1-6}$ alkyl groups such as methyl, ethyl, propyl, isopropyl, butyl, isobutyl, sec-butyl, tert-butyl, pentyl and hexyl), lower alkenyl groups (e.g., $C_{2-6}$ alkenyl groups such as vinyl, allyl, 2-butenyl and 3-butenyl), lower alkoxy groups (e.g., $C_{1-6}$ alkoxy groups such as methoxy, ethoxy, propoxy, isopropoxy, butoxy and pentoxy), nitro group, cyano group, hydroxy group, lower alkoxycarbonyl groups (e.g., $C_{1-6}$ alkoxycarbonyl groups such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl, neopentyloxycarbonyl and tert-pentyloxycarbonyl), carbamoyl groups, lower alkylcarbamoyl groups (e.g., N-$C_{1-6}$ alkylcarbamoyl groups such as N-methylcarbamoyl, N-ethylcarbamoyl, N-propylcarbamoyl and N-butylcarbamoyl, N,N-di-$C_{1-6}$ alkylcarbamoyl groups such as N,N-dimethylcarbamoyl, N,N-diethylcarbamoyl, N,N-dipropylcarbamoyl, N,N-dibutylcarbamoyl and N-ethyl-N-methylcarbamoyl) and lower alkenylcarbamoyl groups (e.g., N-$C_{2-6}$ alkenylcarbamoyl groups such as N-vinylcarbamoyl and N-allylcarbamoyl, N,N-di-$C_{2-6}$ alkenylcarbamoyl groups such as N,N-divinylcarbamoyl and N,N-diallylcarbamoyl).

The aryl group that may be substituted for $R^3$ is exemplified by $C_{6-14}$ aryl groups such as phenyl, 1-naphthyl, 2-naphthyl, phenanthryl and anthryl. These aryl groups may have 1 to 4, preferably 1 or 2 substituents selected from the group comprising halogens (e.g., fluorine, chlorine, bromine, iodine), lower alkyl groups (e.g., $C_{1-6}$ alkyl groups such as methyl, ethyl, propyl, isopropyl, butyl, isobutyl, sec-butyl, tert-butyl, pentyl and hexyl), lower alkenyl groups (e.g., $C_{2-6}$ alkenyl groups such as vinyl, allyl, 2-butenyl and 3-butenyl), lower alkoxy groups (e.g., $C_{1-6}$ alkoxy groups such as methoxy, ethoxy, propoxy, isopropoxy, butoxy and pentoxy), nitro group, cyano group, oxo group, hydroxy group, amino groups, lower acylamino groups (e.g., $C_{1-6}$ acylamino groups such as acetylamino and propionylamino), lower alkoxycarbonyl groups (e.g., $C_{1-6}$ alkoxycarbonyl groups such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl, neopentyloxycarbonyl and tert-pentyloxycarbonyl), carbamoyl groups, lower alkylcarbamoyl groups (e.g., N-$C_{1-6}$ alkylcarbamoyl groups such as N-methylcarbamoyl, N-ethylcarbamoyl, N-propylcarbamoyl and N-butylcarbamoyl, N,N-di-$C_{1-6}$ alkylcarbamoyl groups such as N,N-dimethylcarbamoyl, N,N-diethylcarbamoyl, N,N-dipropyl-carbamoyl, N,N-dibutylcarbamoyl and N-ethyl-N-methylcarbamoyl) and lower alkenylcarbamoyl groups (e.g., N-C$_{2-6}$ alkenylcarbamoyl groups such as N-vinylcarbamoyl and N-allylcarbamoyl, N,N-di-C$_{2-6}$ alkenylcarbamoyl groups such as N,N-divinylcarbamoyl and N,N-diallylcarbamoyl). The aryl group having an oxo group is exemplified by benzoquinolyl, naphthoquinolyl and anthraquinolyl.

With respect to the above formulas, Y represents CH or N, preferably CH.

With respect to the above formulas, B represents the following:

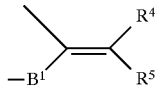

wherein B$^1$ represents —(CH$_2$)$_f$— or —CZ$^1$—Z$^2$— (f represents an integer from 1 to 6; Z$^1$ represents O or S; Z$^2$ represents O, S, —Alk$^1$—, —Alk$^1$S— or NR$^{3b}$; Alk$^1$ represents a divalent chain hydrocarbon group that may be substituted; R$^{3b}$ represents a hydrogen or a hydrocarbon group that may be substituted); R$^4$ and R$^5$ independently represent a hydrogen or a carboxyl group that may be esterified, an amino group that may be substituted, a heterocyclic group that may be substituted, —W$^1$, —S—W$^1$ or —O—W$^1$ (W$^1$ represents a hydrocarbon group that may be substituted); R$^4$ and R$^5$ may bind together to form a ring.

The divalent hydrocarbon group that may be substituted for Alk$^1$ is exemplified by the same groups as the above-mentioned divalent hydrocarbon groups that may be substituted for A or Alk.

The hydrocarbon group that may be substituted for R$^{3b}$ is exemplified by the same groups as the above-mentioned hydrocarbon groups that may be substituted for R$^1$ or R$^2$.

Preferable groups for B$^1$ include —CO—S—, —CO—O—, —CO—CH$_2$— and —CO—N(R$^3$)— (R$^3$ represents a hydrogen, a lower alkyl group that may be substituted, a lower alkenyl group that may be substituted, an aralkyl group that may be substituted or an aryl group that may be substituted), with greater preference given to —CO—S—, —CO—O— etc. Here, R$^3$ in B$^1$ has the same definition as R$^3$ in X.

The hydrocarbon group that may be substituted for W$^1$ is exemplified by the same groups as the above-mentioned hydrocarbon groups that may be substituted for R$^1$ or R$^2$.

The carboxyl group that may be esterified for R$^4$ or R$^5$ is exemplified by the same groups as the above-mentioned carboxyl groups that may be esterified as substituents of the divalent hydrocarbon group for A above.

Useful substituents of the amino group for R$^4$ and R$^5$ include lower alkyl groups (e.g., methyl, ethyl, propyl, isopropyl, butyl, isobutyl, sec-butyl, tert-butyl, pentyl, hexyl) and acyl groups. The acyl group as a substituent of the amino group for R$^4$ and R$^5$ is exemplified by the same groups as the above-mentioned acyl groups as substituents of the divalent hydrocarbon group for A. Useful optionally substituted amino groups for R$^4$ and R$^5$ include lower alkanoylamino groups (e.g., C$_{1-6}$ alkanoylamino groups such as acetylamino and propionylamino), mono- or di-substituted amino groups (e.g., methylamino, ethylamino, n-propylamino, isopropylamino, n-butylamino, dimethylamino, diethylamino).

The heterocyclic group for R$^4$ and R$^5$ is exemplified by 5- or 6-membered heterocyclic groups containing 1 to 4 heteroatoms selected from atoms of oxygen, sulfur, nitrogen etc., or bicyclic heterocyclic groups containing 1 to 6 heteroatoms selected from atoms of oxygen, sulfur, nitrogen etc.

Of the heterocyclic groups represented by R$^4$ or R$^5$, monocyclic ones are 5- or 6-membered aromatic heterocyclic groups containing 1 to 4 heteroatoms selected from atoms of oxygen, sulfur and nitrogen as ring-constituting atoms (ring atoms), or saturated or unsaturated monocyclic non-aromatic heterocyclic groups. Useful such heterocyclic groups include thienyl (e.g., 2-thienyl, 3-thienyl), furyl (e.g., 2-furyl, 3-furyl), pyranyl, 2H-pyrrolyl, pyrrolyl (e.g., 2-pyrrolyl, 3-pyrrolyl), imidazolyl (e.g., 2-imidazolyl, 4-imidazolyl), pyrazolyl (e.g., 3-pyrazolyl, 4-pyrazolyl), isothiazolyl (e.g., 3-isothiazolyl, 4-isothiazolyl), isoxazolyl (e.g., 3-isoxazolyl, 4-isoxazolyl), pyridyl (e.g., 2-pyridyl, 3-pyridyl, 4-pyridyl), pyrazinyl, pyrimidinyl (e.g., 2-pyrimidinyl, 4-pyrimidinyl) and pyridazinyl (e.g., 3-pyridazinyl, 4-pyridazinyl). These monocyclic heterocyclic groups may be partially saturated. Such partially saturated monocyclic heterocyclic groups include pyrrolidinyl (e.g., 2-pyrrolidinyl, 3-pyrrolidinyl), pyrrolinyl (e.g., 2-pyrrolin-3-yl), imidazolyl (e.g., 2-imidazolin-4-yl), piperidyl (e.g., 2-piperidyl, 3-piperidyl), piperazinyl (e.g., 2-piperazinyl) and morpholinyl (e.g., 3-morpholinyl).

Of the heterocyclic groups represented by R$^4$ or R$^5$, bicyclic ones are bicyclic aromatic heterocyclic groups containing 1 to 6 heteroatoms selected from atoms of oxygen, sulfur and nitrogen as ring-constituting atoms (ring atoms), or condensed saturated or unsaturated bicyclic non-aromatic heterocyclic groups. Useful heterocyclic groups include isobenzofuranyl (e.g., 1-isobenzofuranyl), chromenyl (e.g., 2H-chromen-3-yl), benzothienyl (e.g., 2-benzothienyl), indolidinyl (e.g., 2-indolidinyl, 3-indolidinyl), isoindolyl (e.g., 1-isoindolyl), 3H-indolyl (e.g., 3H-indol-2-yl), indolyl (e.g., 2-indolyl), 1H-indazolyl (e.g., 1H-indazol-3-yl), purinyl (e.g., 8-purinyl), isoquinolyl (e.g., 1-isoquinolyl, 3-isoquinolyl), quinolyl (e.g., 2-quinolyl, 3-quinolyl), phthalazyl (e.g., 1-phthalazyl), naphthyridinyl (e.g., 1,8-naphthyridin-2-yl), quinoxalinyl (e.g., 2-quinoxalinyl), quinazolinyl (e.g., 2-quinazolinyl) and cinnolinyl (e.g., 3-cinnolinyl). These dicyclic heterocyclic groups may be partially saturated. Such partially saturated bicyclic heterocyclic groups include isochromanyl (e.g., 3-isochromanyl), indolinyl (e.g., 2-indolinyl), isoindolinyl (e.g., 1-isoindolinyl), 1,2,3,4-tetrahydro-2-quinolyl and 1,2,3,4-tetrahydro-3-isoquinolyl.

The heterocyclic group for R$^4$ or R$^5$ may have 1 to 4 substituents selected from the group comprising halogens (e.g., fluorine, chlorine, bromine, iodine), lower alkyl groups (e.g., methyl, ethyl, propyl, isopropyl, butyl, isobutyl, sec-butyl, tert-butyl, pentyl, hexyl), lower alkenyl groups (e.g., C$_{2-6}$ alkenyl groups such as vinyl, allyl, 2-butenyl and 3-butenyl), lower alkoxy groups (e.g., C$_{1-6}$ alkoxy groups such as methoxy, ethoxy, propoxy, isopropoxy, butoxy and pentoxy), nitro group, cyano group, hydroxy group, lower alkoxycarbonyl groups (e.g., C$_{1-6}$ alkoxycarbonyl groups such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl, neopentyloxycarbonyl and tert-pentyloxycarbonyl), carboxy groups, carbamoyl groups, lower alkylcarbamoyl groups (e.g., N-C$_{1-6}$ alkylcarbamoyl groups such as N-methylcarbamoyl, N-ethylcarbamoyl, N-propylcarbamoyl and N-butylcarbamoyl, N,N-di-C$_{1-6}$ alkylcarbamoyl groups such as N,N-dimethylcarbamoyl, N,N-diethylcarbamoyl, N,N-dipropylcarbamoyl, N,N-dibutylcarbamoyl and N-ethyl-N-methylcarbamoyl) and lower alkenylcarbamoyl groups (e.g., N-$C_{2-6}$ alkenylcarbamoyl groups such as N-vinylcarbamoyl and N-allylcarbamoyl, N,N-di-$C_{2-6}$ alkenylcarbamoyl groups such as N,N-divinylcarbamoyl and N,N-diallylcarbamoyl).

The ring formed by combining $R^4$ and $R^5$ is exemplified by cyclopropyl, cyclobutyl, cyclopentyl and cyclohexyl.

Preferable groups for $R^4$ or $R^5$ include a hydrogen, lower alkyl groups that may be substituted, aryl groups that may be substituted, amino groups that may be substituted and heterocyclic groups that may be substituted, with greater preference given to hydrogen or lower alkyl groups that may be substituted etc. These lower alkyl groups that may be substituted and aryl groups that may be substituted, which exemplify preferable groups for $R^4$ or $R^5$ are the same groups as the above-mentioned lower alkyl groups and aryl groups that may be substituted for $R^3$.

With respect to the above formulas, B represents the following:

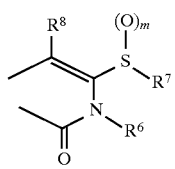

wherein $R^6$ and $R^7$ independently represent a hydrocarbon group that may be substituted or a heterocyclic group that may be substituted; $R^6$ and $R^7$ may bind together to form a ring; $R^8$ represents a hydrogen, a hydrocarbon group that may be substituted, a heterocyclic group that may be substituted, a nitro group, a cyano group, an amino group that may be protected, a halogen or an acyl group; m represents an integer from 0 to 2.

The hydrocarbon group that may be substituted for $R^6$ or $R^7$ is exemplified by the same groups as the hydrocarbon groups that may be substituted mentioned above for $R^1$ or $R^2$.

The heterocyclic group that may be substituted for $R^6$ or $R^7$ is exemplified by the same groups as the above-mentioned heterocyclic groups that may be substituted for $R^4$ or $R^5$.

The ring formed by combining $R^6$ and $R^7$ is exemplified by rings represented by the formula:

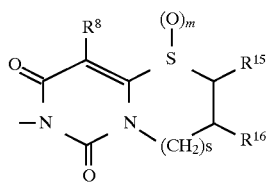

wherein $R^{15}$ represents a hydrogen, a lower alkyl group that may be substituted, an aralkyl group that may be substituted, an aryl group that may be substituted, a lower alkoxy group, a lower alkylthio group, an aryloxy group, an arylthio group, —COOR$^{15a}$ or —CH$_2$COOR$^{15a}$ ($R^{15a}$ represents a lower alkyl group); $R^{16}$ represents a hydrogen or a lower alkyl group; s represents an integer from 0 to 4, or the formula:

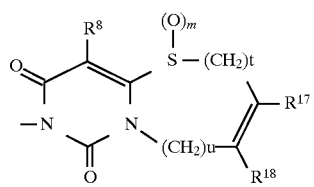

wherein $R^{17}$ and $R^{18}$ independently represent a hydrogen or a lower alkyl group; t and u independently represent an integer from 0 to 2.

The lower alkyl group, aralkyl group or aryl group that may be substituted for $R^{15}$ is exemplified by the same groups as the above-mentioned lower alkyl groups and aryl groups that may be substituted for $R^3$.

The lower alkoxy group for $R^{15}$ is exemplified by $C_{1-6}$ alkoxy groups such as methoxy, ethoxy, propoxy, isopropoxy, butoxy and pentoxy.

The lower alkylthio group for $R^{15}$ is exemplified by $C_{1-6}$ alkylthio groups such as methylthio, ethylthio, n-propylthio, isopropylthio and n-butylthio.

The aryloxy group for $R^{15}$ is exemplified by phenoxy and naphthyloxy.

The arylthio group for $R^{15}$ is exemplified by phenylthio.

The lower alkyl group for $R^{15a}$, $R^{17}$ or $R^{18}$ is exemplified by $C_{1-6}$ alkyl groups such as methyl, ethyl, propyl, isopropyl, butyl, isobutyl, sec-butyl, tert-butyl, pentyl and hexyl.

$R^6$ and $R^7$ are preferably lower alkyl groups that may be substituted, —C($R^{15}$)—C($R^{16}$)—(CH$_2$)$_s$— formed by combining $R^6$ and $R^7$ ($R^{15}$ and $R^{16}$ independently represent a hydrogen or a lower alkyl group; s represents 0 or 1), or the like.

The hydrocarbon group that may be substituted, amino group that may be protected or acyl group for $R^8$ is exemplified by the same groups as the above-mentioned hydrocarbon groups that may be substituted, amino groups that may be protected and acyl groups for $R^1$ and $R^2$.

The heterocyclic group that may be substituted for $R^8$ is exemplified by the same groups as the above-mentioned heterocyclic groups that may be substituted for $R^4$ and $R^5$.

Preferable groups for $R^8$ include a hydrogen, lower alkyl groups that may be substituted and aryl groups that may be substituted, with greater preference given to a hydrogen, lower alkyl groups (e.g., methyl, ethyl, propyl, isopropyl, butyl, isobutyl, sec-butyl, tert-butyl, pentyl, hexyl), aralkyl groups (e.g., phenyl-$C_{1-6}$ alkyl groups such as benzyl, phenethyl, 3-phenylpropyl and 4-phenylbutyl, naphthyl-$C_{1-6}$ alkyl groups such as (1-naphthyl)methyl, 2-(1-naphthyl)ethyl and 2-(2-naphthyl)ethyl) and phenyl groups. These lower alkyl groups and aryl groups that may be substituted, which exemplify preferable groups for $R^8$ are the same groups as the lower alkyl groups and aryl groups that may be substituted mentioned above for $R^3$.

m is preferably 1 or 2.

The position of X binding is preferably the 5- or 8-position, more preferably the 5-position, on the imidazo[1,2-a]pyridine ring (Y=CH) or imidazo[1,2-c]pyridine ring (Y=N).

Compound (I) may be a salt of the compound represented by formula (I). Salts of compound (I) include acid-adduct salts. Acids used to form acid-adduct salts include inorganic acids such as hydrochloric acid, hydrobromic acid, sulfuric acid and phosphoric acid, and organic acids such as acetic acid, oxalic acid, methanesulfonic acid, maleic acid, fumaric acid, citric acid, tartaric acid and lactic acid.

Compound (I) may be a solvate of the compound represented by formula (I). Useful solvents for such solvate include methanol, ethanol, propanol, isopropanol, acetone, tetrahydrofuran and dioxane.

Compound (I) may have an asymmetric carbon atom in the molecular structure thereof; when there are two stereoisomers, of the R- and S-configurations, respectively, both isomers and mixtures thereof are also included in the present invention.

Compound (I) is preferably a compound represented by formula (II) (or salt thereof):

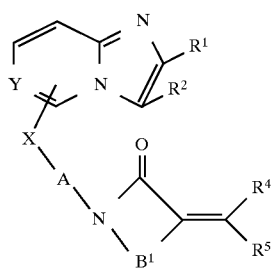

wherein the symbols have the same definitions as those given above, or a compound (or salt thereof) represented by formula (III):

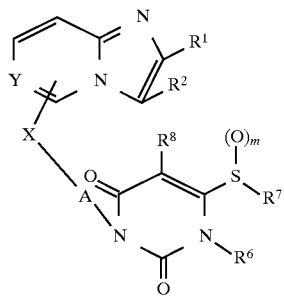

wherein the symbols have the same definitions as those given above, with preference given to a compound represented by formula (IV) (or salt thereof):

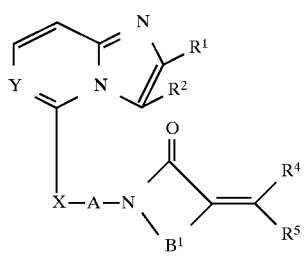

wherein the symbols have the same definitions as those given above, or with greater preference given to a compound represented by formula (V) (or salt thereof):

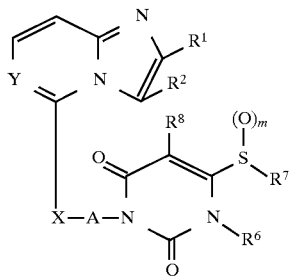

wherein the symbols have the same definitions as those given above.

Preference is given to compound (I) wherein X is S, O or $CH_2$; A is $(CH_2)_4$; Y is CH; both $R^1$ and $R^2$ are hydrogen; and the ring represented by

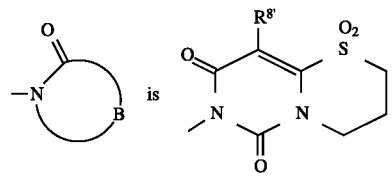

wherein $R^{8'}$ is phenyl, benzyl or isopropyl) or

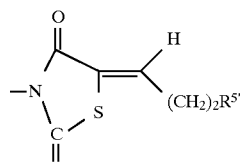

(wherein $R^{5'}$ is methyl, phenyl or pyridyl).

Preferable examples of compound (I) of the present invention include 5-butylidene-3-[4-(imidazo[1,2-a]pyridin-5-ylthio)butyl]thiazolidine-2,4-dione, 5-butylidene-3-[5-(imidazo[1,2-a]pyridin-5-yl)pentyl]thiazolidine-2,4-dione, 5-butylidene-3-[4-(imidazo[1,2-a]pyridin-5-yloxy)butyl]thiazolidine-2,4-dione, 5-butylidene-3-[4-(imidazo[1,2-a]pyridin-5-ylthio)butyl]oxazolidine-2,4-dione, 5-(3-phenylpropylidene)-3-[4-(imidazo[1,2-a]pyridin-5-ylthio)butyl]thiazolidine-2,4-dione, 5-butylidene-3-[4-(imidazo[1,2-a]pyridin-5-yl)butyl]thiazolidine-2,4-dione, 5-propylidene-3-[4-(imidazo[1,2-a]pyridin-5-ylthio)butyl]thiazolidine-2,4-dione, 5-butylidene-3-[4-(2-methyl-imidazo[1,2-a]pyridin-5-ylthio)butyl]thiazolidine-2,4-dione, 5-butylidene-3-[4-(3-trifluoroacetylimidazo[1,2-a]pyridin-5-ylthio)butyl]thiazolidine-2,4-dione, 5-[3-(3-pyridyl)propylidene]-3-[4-(imidazo[1,2-a]pyridin-5-ylthio)butyl]thiazolidine-2,4-dione, 5-(3-phenylpropylidene)-3-[4-(imidazo[1,2-a]pyridine-5-ylthio)butyl]oxazolidine-2,4-dione, 5-butylidene-3-[4-(imidazo[1,2-c]pyrimidin-5-ylthio)butyl]thiazolidine-2,4-dione, 5-butylidene-3-[4-(imidazo[1,2-a]pyridin-8-yloxy)butyl]thiazolidine-2,4-dione, 5-butylidene-3-[4-(2-phenyl-imidazo[1,2-a]pyridin-8-yloxy)butyl]thiazolidine-2,4-dione, 5-[3-(3-pyridyl)propylidene]-3-[4-(imidazo[1,2-a]pyridin-8-yloxy)butyl]thiazolidine-2,4-dione, 5-(3-phenylpropylidene)-3-[4-(imidazo[1,2-a]pyridin-8-yloxy)butyl]oxazolidine-2,4-dione, 5-butylidene-3-[4-(2-ethoxycarbonyl-imidazo[1,2-a]pyridin-8-yloxy)butyl]thiazolidine-2,4-dione or salts thereof, particularly hydrochlorides (all these compounds are included in compound (II)), and 7-[4-(imidazo[1,2-a]

pyridin-5-ylthio)butyl]-1,1-dioxo-3,4-dihydro-2H,6H-pyrimido[6,1-b][1,3]thiazine-6,8(7H)-dione, 7-[4-(imidazo[1,2-a]pyridin-5-ylthio)butyl]-1,1-dioxo-9-phenyl-3,4-dihydro-2H,6H-pyrimido[6,1-b][1,3]thiazine-6,8(7H)-dione, 7-[4-(imidazo[1,2-a]pyridin- 5-ylthio)butyl]-1-oxo-9-phenyl-3,4-dihydro-2H,6H-pyrimido[6,1-b][1,3]thiazine-6,8(7H)-dione, 6-[4-(imidazo[1,2-a]pyridin-5-ylthio)butyl]-1,1-dioxo-8-phenyl-2,3-dihydro-5H-thiazolo[3,2-c]pyrimidin-5,7(6H)-dione, 7-[4-(imidazo[1,2-a]pyridin-5-ylthio)butyl]-9-methyl-1,1-dioxo-3,4-dihydro-2H,6H-pyrimido[6,1-b][1,3]thiazine-6,8(7H)-dione, 7-[4-(imidazo[1,2-a]pyridin-5-ylthio)butyl]-9-benzyl-1,1-dioxo-3,4-dihydro-2H,6H-pyrimido[6,1-b][1,3]thiazine-6,8(7H)-dione, 7-[4-(imidazo[1,2-a]pyridin-5-ylthio)butyl]-9-isopropyl-1,1-dioxo-3,4-dihydro-2H,6H-pyrimido[6,1-b][1,3]thiazine-6,8(7H)-dione, 3-[4-(imidazo[1,2-a]pyridin-5-ylthio)butyl]-1-methyl-5-phenyl-6-ethylsulfonylpyrimidine-2,4(1H,3H)-dione, or 3-[4-(imidazo[1,2-a]pyridin-5-ylthio)butyl]-1-methyl-5-phenyl-6-benzylsulfonylpyrimidine-2,4(1H,3H)-dione and salts thereof, particularly hydrochlorides (all these compounds are included in compound (III)).

In the present specification, compounds from (I) to (LVI) or salts thereof, or starting material compounds or synthetic intermediates thereof or salts thereof are sometimes referred to as briefly "compounds from (I) to (LVI) or starting material compounds or synthetic intermediates thereof," wherein "or salts thereof" is omitted.

Compound (I) of the present invention can, for example, be synthesized by the following methods:

Method A

Used to synthesize compound (I) having O, S or $N(R^3)$ for X.

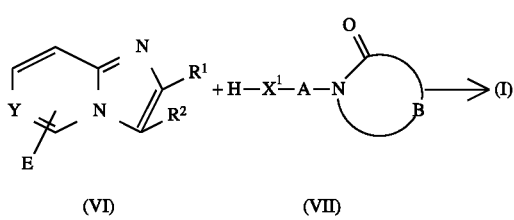

(VI)                (VII)

wherein the symbols have the same definitions as those given above.

Method B

Used to synthesize compound (I) having O, S, $-(CH_2)_i-O-$ or $-(CH_2)_i-N(R^3)-$ for X.

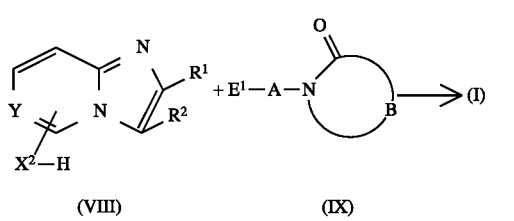

(VIII)              (IX)

wherein the symbols have the same definitions as those given above.

Method C

Used to synthesize compound (I) having $-(CH_2)_j CO-N(R^3)-$, $-(CH_2)_j COO-$, $-S-(CH_2)_k CO-N(R^3)-$ or $-S-(CH_2)_k COO-$ for X.

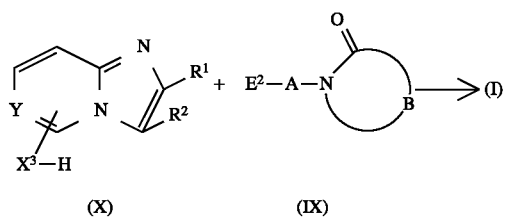

(X)                 (IX)

wherein the symbols have the same definitions as those given above.

Method D

Used to synthesize compound (I) having $-(CH_2)_i O-CO-N(R^3)-$ for X.

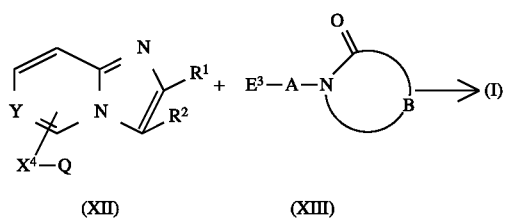

(XII)               (XIII)

wherein the symbols have the same definitions as those given above.

Method E

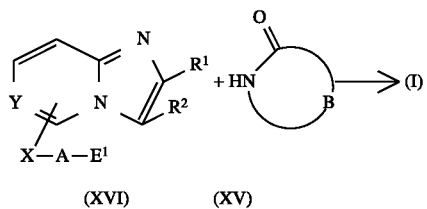

(XVI)               (XV)

wherein the symbols have the same definitions as those given above.

Method F

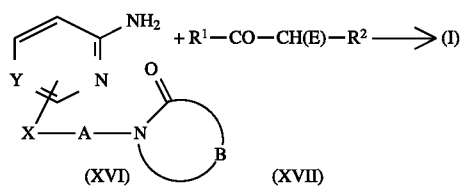

(XVI)               (XVII)

wherein the symbols have the same definitions as those given above.

Method G

Used to synthesize compound (I) having $S(O)$ or $S(O)_2$ for X by reacting compound (I) having $S(O)$ or $S(O)_2$ for X with an oxidizing agent.

Method H

Used to synthesize compound (II) having O, S or $N(R^3)$ for X.

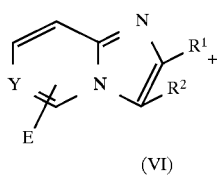

(VI)

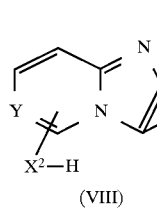

(XVIII)

wherein the symbols have the same definitions as those given above.

Method I

Used to synthesize compound (II) having O, S, —(CH$_2$)$_i$—O— or —(CH$_2$)$_i$—N(R$^3$)— for X.

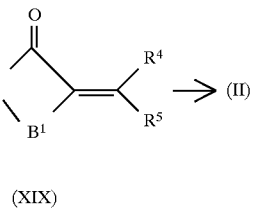

wherein the symbols have the same definitions as those given above.

Method J

Used to synthesize compound (II) having —(CH$_2$)$_j$CO—N(R$^3$)—, —(CH$_2$)$_j$COO—, —S—(CH$_2$)$_k$CO—N(R$^3$)— or —S—(CH$_2$)$_k$COO— for X.

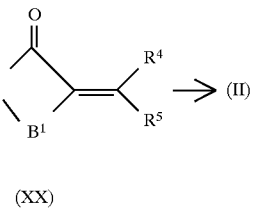

wherein the symbols have the same definitions as those given above.

Method K

Used to synthesize compound (II) having —(CH$_2$)$_i$O—CO—N (R$^3$)— for X.

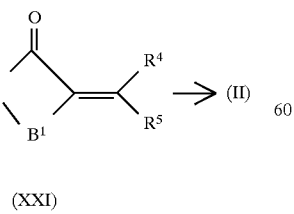

wherein the symbols have the same definitions as those given above.

Method L

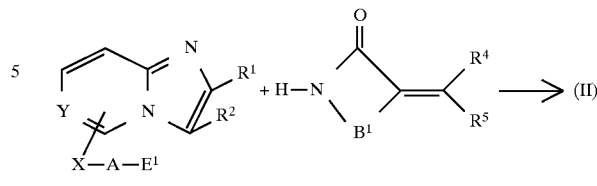

wherein the symbols have the same definitions as those given above.

Method M

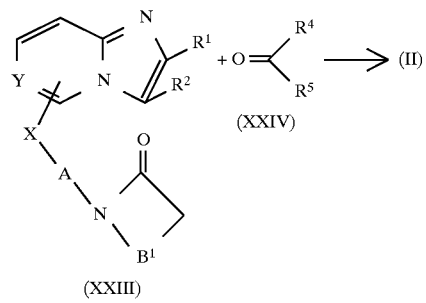

wherein the symbols have the same definitions as those given above.

Method N

Used to synthesize compound (II) having —(CH$_2$)$_l$— for B$^1$.

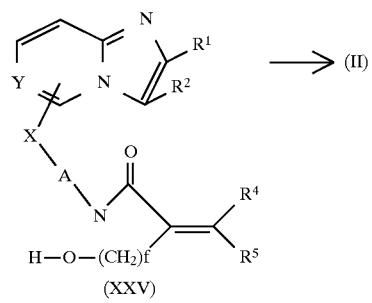

Method O

Used to synthesize compound (II) having —COO—, —CO—S—, —CS—S— or —CO—N(R$^3$)— for B$^1$.

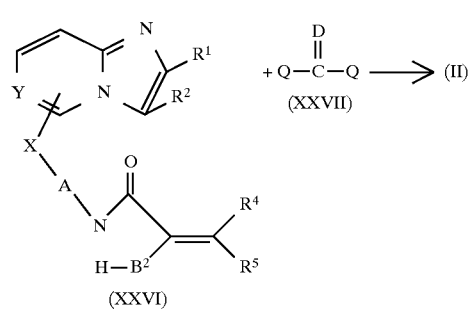

wherein B$^2$ represents O, S or —N(R$^3$)—; Q represents imidazoyl, chloro or phenoxy; D represents O or S; the other symbols have the same definitions as those given above.

Method P

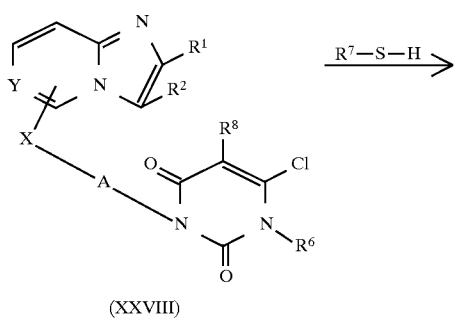

(XXVIII)

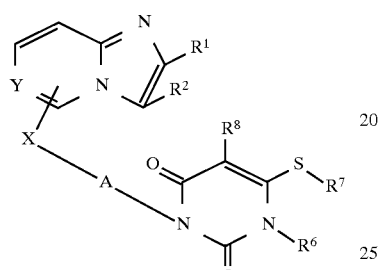

(XXIX)

wherein the symbols have the same definitions as those given above.

Method Q

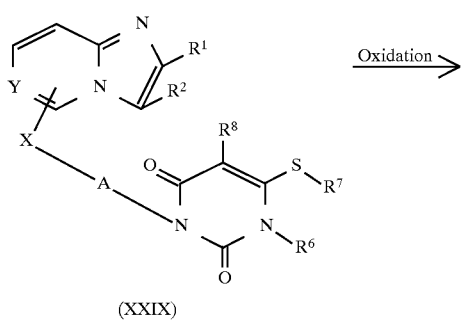

(XXIX)

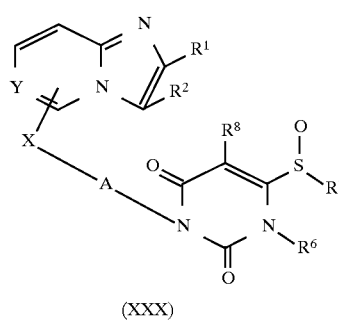

(XXX)

wherein the symbols have the same definitions as those given above.

Method R

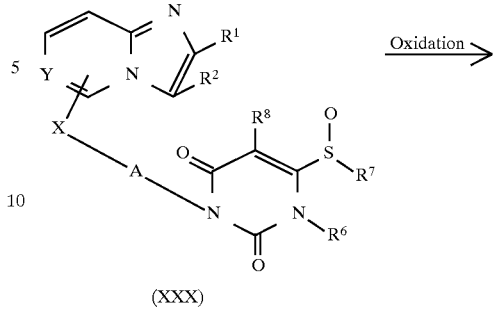

(XXX)

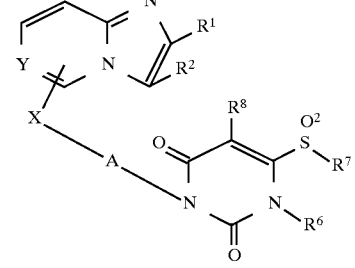

(XXXI)

wherein the symbols have the same definitions as those given above.

Method S

Used to synthesize compound (III) having O, S or N(R³) for X.

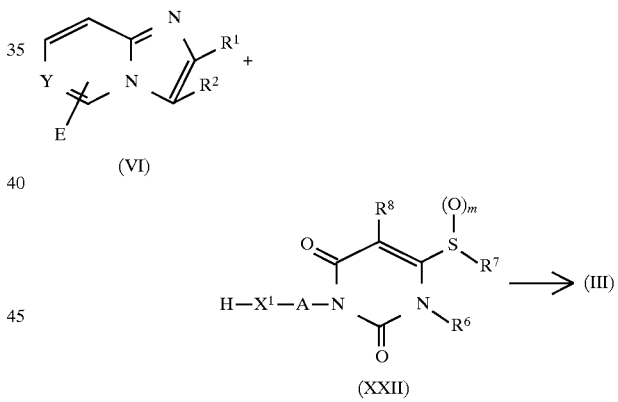

wherein the symbols have the same definitions as those given above.

Method T

Used to synthesize compound (III) having O, S, —(CH₂)ᵢ—O— or —(CH₂)ᵢ—N(R³)— for X.

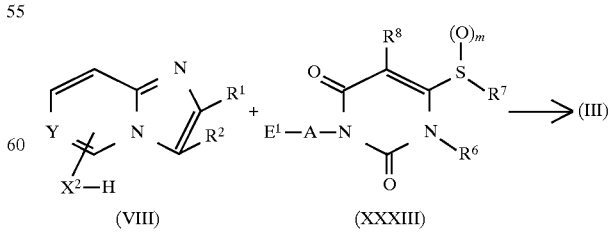

wherein the symbols have the same definitions as those given above.

Method U

Used to synthesize compound (III) having —(CH$_2$)$_j$CO—N (R$^3$)—, —(CH$_2$)$_j$COO—, —S—(CH$_2$)$_k$CO—N(R$^3$)— or —S—(CH$_2$)$_k$COO— for X.

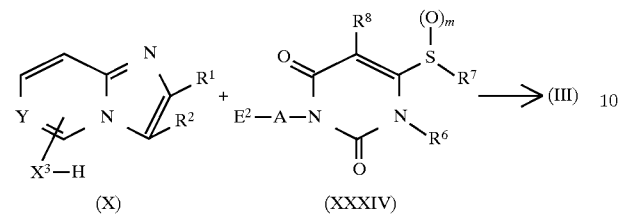

(X)  (XXXIV)

wherein the symbols have the same definitions as those given above.

Method V

Used to synthesize compound (III) having —(CH$_2$)$_i$—O—CO—N (R$^3$)— for X.

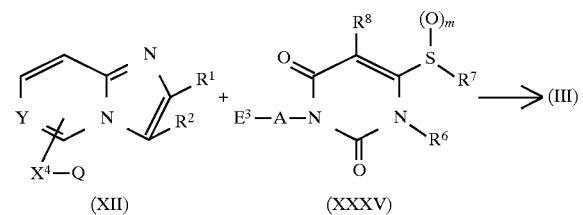

(XII)  (XXXV)

wherein the symbols have the same definitions as those given above.

Method W

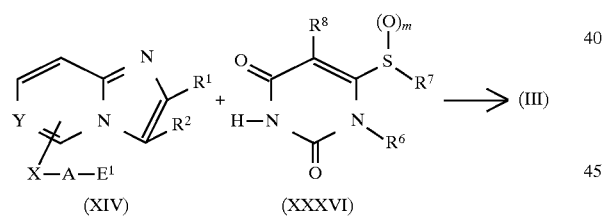

(XIV)  (XXXVI)

wherein the symbols have the same definitions as those given above.

Method X

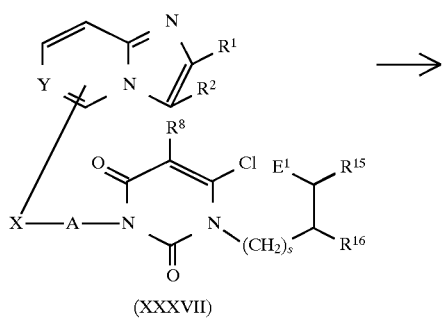

(XXXVII)

-continued

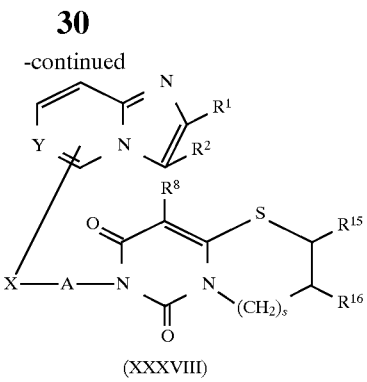

(XXXVIII)

wherein the symbols have the same definitions as those given above.

Method Y

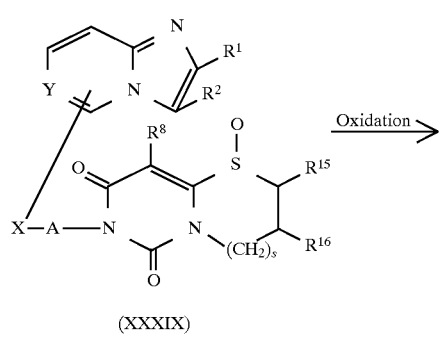

(XXXVIII)

(XXXIX)

wherein the symbols have the same definitions as those given above.

Method Z (XXXIX)

-continued

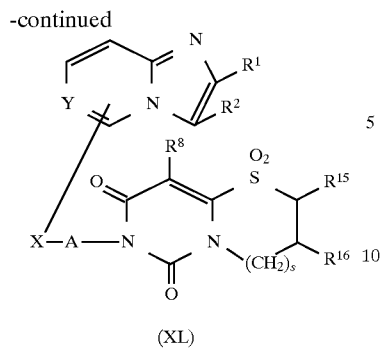

(XL)

wherein the symbols have the same definitions as those given above.

Method AA

Used to synthesize compound (XLII) having O, S or N(R³) for X.

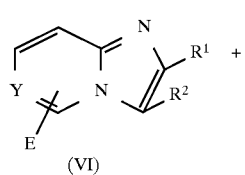

(VI)

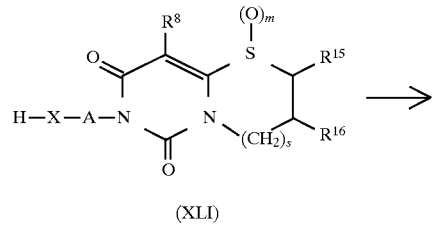

(XLI)

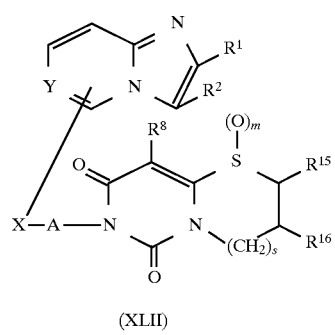

(XLII)

wherein the symbols have the same definitions as those given above.

Method BB

Used to synthesize compound (XLII) having O, S, —(CH₂)ᵢ—O— or —(CH₂)ᵢ—N(R³)— for X.

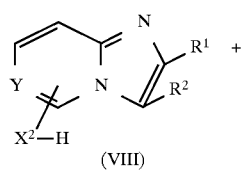

(VIII)

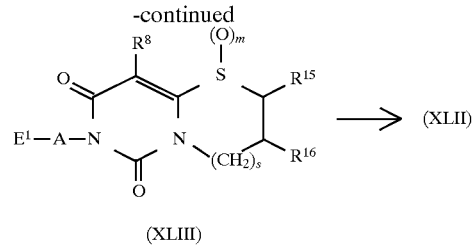

(XLIII)

wherein the symbols have the same definitions as those given above.

Method CC

Used to synthesize compound (XLII) having —(CH₂)ⱼCO—N (R³)—, —(CH₂)ⱼCOO—, —S—(CH₂)ₖCO—N(R³)— or —S—(CH₂)ₖCOO— for X.

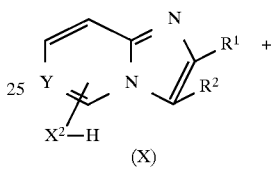

(X)

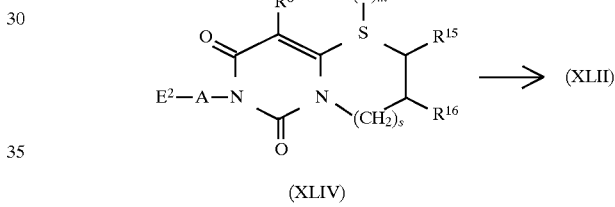

(XLIV)

wherein the symbols have the same definitions as those given above.

Method DD

Used to synthesize compound (XLII) having —(CH₂)ᵢO—CO—N(R³)— for X.

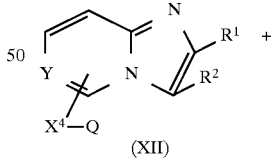

(XII)

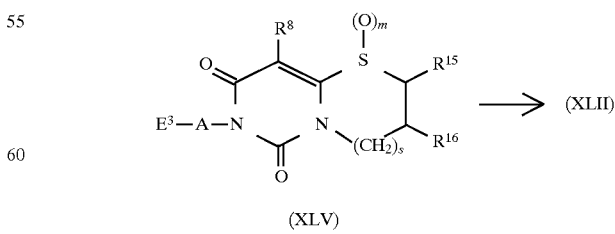

(XLV)

wherein the symbols have the same definitions as those given above.

Method EE

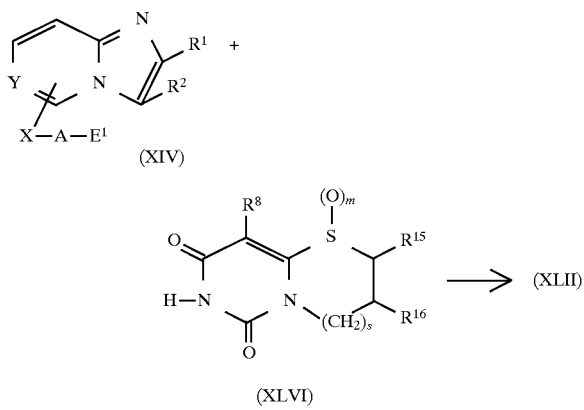

wherein the symbols have the same definitions as those given above.

Method FF

Used to synthesize compound (XLVIII) having O, S or N(R³) for X.

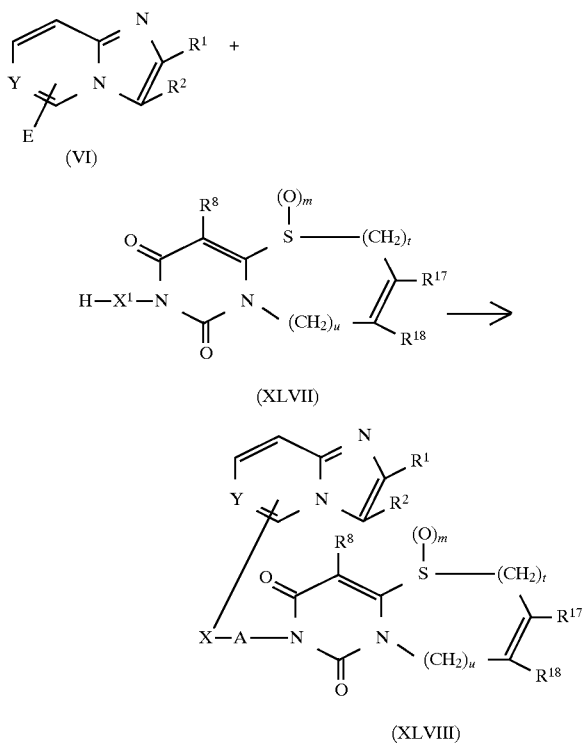

wherein the symbols have the same definitions as those given above.

Method GG

Used to synthesize compound (XLVIII) having O, S, —(CH₂)ᵢ—O— or —(CH₂)ᵢ—N(R³)— for X.

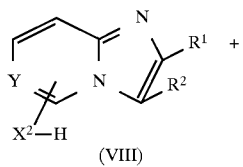

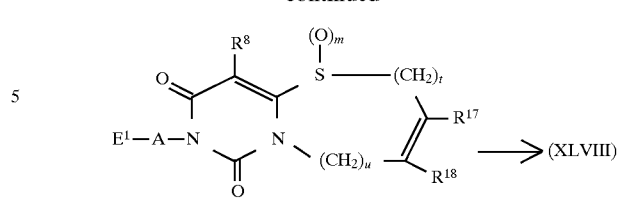

wherein the symbols have the same definitions as those given above.

Method HH

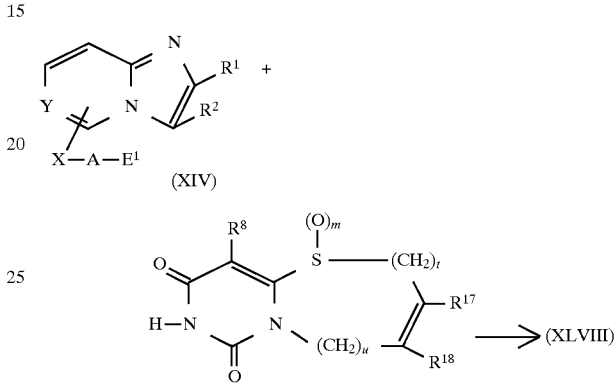

wherein the symbols have the same definitions as those given above.

It is advantageous that the reaction of compounds (VI) with (VII) in method A is carried out in a solvent. The solvent used is not subjected to limitation, as long as the reaction is not interfered with. Normally useful solvents include water, alcohols such as methanol, ethanol and propanol, ketones such as acetone and methyl ethyl ketone, ethers such as tetrahydrofuran, amides such as N,N-dimethylformamide and sulfoxides such as dimethyl sulfoxide. The reaction can be facilitated by addition of a basic compound to the reaction system. Such basic compounds include alkali metal hydroxides such as sodium hydroxide and potassium hydroxide, alkali metal hydrides such as sodium hydride, alkali metal carbonates such as potassium carbonate, amines such as triethylamine and diisopropylethylamine, and 1,8-diazabicyclo[5.4.0]-7-undecene. The amount of basic compound used is normally 1 equivalent to excess (normally 1 to 10 equivalents) per equivalent of compound (VI). It is preferable that the amount of compound (VII) be 1 equivalent to excess (preferably 1 to 10 equivalents) per equivalent of compound (VI). The reaction is normally carried out within the temperature range from −20° to 200° C., preferably 20° to 100° C. Reaction time is normally 10 minutes to 24 hours, preferably 0.5 to 6 hours. This reaction may be carried out in the presence of a reaction promoter added as necessary. Such reaction promoters include sodium iodide. The amount of reaction promoter used is 1 equivalent to excess (preferably 1 to 10 equivalents) per equivalent of compound (VI).

The reaction of compound (VIII) with compound (IX) in method B can, for example, be carried out under the same conditions as those of the reaction of compound (VI) with compound (VII) in method A.

It is advantageous that the dehydrating condensation reaction of compound (X) with compound (XI) in method C is carried out using an ordinary amide- or ester-linkage-forming reaction. This amide- or ester-forming reaction can be facilitated by the use of an amide- or ester-forming reagent alone. Useful amide- or ester-forming reagents include 1-ethoxycarbonyl-2-ethoxy-1,2-dihydroquinone, dicyclohexylcarbodiimide, 1-cyclohexyl-3-(2-morpholinoethyl)carbodiimide, meso-p-toluenesulfonate, N,N'-carbonyldiimidazole, diphenylphosphoric amide, diethyl cyanophosphate and 1-ethyl-3-(3-diethylaminopropyl)carbodiimide hydrochloride (hereinafter abbreviated as WSC). The amount of amide- or ester-forming reagent used is normally 1 to 3 equivalents per equivalent of compound (X). This amide- or ester-forming reaction can also be facilitated by converting compound (X) into an active ester by condensation with phenol, such as 2,4,5-trichlorophenol, pentachlorophenol, pentafluorophenol, 2-nitrophenol or 4-nitrophenol, an N-hydroxy compound, such as N-hydroxysuccinimide, 1-hydroxybenzotriazole (hereinafter abbreviated as HOBT), N-hydroxypiperidine or N-hydroxy-5-norbornane-2,3-dicarbodiimide, using dicyclohexylcarbodiimide, or the like, and reacting the ester with compound (XI). The amount of phenol or N-hydroxy compound used is normally 1 to 3 equivalents per equivalent of compound (X). The amount of dicyclohexylcarbodiimide used is normally 1 to 3 equivalents per equivalent of compound (X). This amide- or ester-linkage-forming reaction can also be facilitated by converting compound (X) into a mixed acid anhydride by reaction with an acid chloride, such as ethyl chlorocarbonate, isobutyl chlorocarbonate or benzyl chlorocarbonate, and reacting the mixed acid anhydride with compound (XI). The amount of acid chloride used is normally 1 to 3 equivalents per equivalent of compound (X). It is preferable that this amide- or ester-forming reaction is carried out by reacting compound (XI) in a ratio of normally 1 to 3 equivalents per equivalent of compound (X). This reaction can-be facilitated by adding an organic base, such as a tertiary amine (e.g., triethylamine, pyridine, dimethylpyridine, N-methylpiperidine) as necessary. The amount of such a reaction promoter used is normally 1 equivalent to excess (preferably 1 to 10 equivalents) per equivalent of compound (X). This reaction is normally carried out within the temperature range from −30° to 50° C., preferably 0° to 25° C. This reaction can be carried out in the presence or absence of solvent. The solvent used is not subjected to limitation, as long as the reaction is not interfered with. Useful solvents include ether, toluene, benzene, chloroform, methylene chloride, dioxane and tetrahydrofuran. Reaction time is normally 10 minutes to 48 hours, preferably 1 to 24 hours.

The reaction of compound (XII) with compound (XIII) in method D can be carried out in the presence or absence of solvent. The solvent used is not subjected to limitation, as long as the reaction is not interfered with. Useful solvents include halogenated hydrocarbons such as methylene chloride, chloroform and dichloroethane, ethers such as diethyl ether and tetrahydrofuran, and amides such as N,N-dimethylformamide. The amount of compound (XIII) is normally 1 equivalent to excess (preferably 1 to 10 equivalents) per equivalent of compound (XII). This reaction is normally carried out within the temperature range from −10° to 150° C., preferably 0° to 80° C. This reaction can be carried out in the presence of a reaction promoter added as necessary. Useful reaction promoters include tertiary amines (e.g., triethylamine, pyridine, dimethylpyridine, N-methylpiperidine). The amount of reaction promoter used is normally 1 equivalent to excess (preferably 1 to 10 equivalents) per equivalent of compound (XII). Reaction time is normally 10 minutes to 48 hours, preferably 5 to 24 hours.

The reaction of compound (XIV) with compound (XV) in method E can, for example, be carried out under the same conditions as those of the reaction of compound (VI) with compound (VII) in method A.

The reaction of compound (XVI) with compound (XVII) in method F can be carried out in the presence or absence of solvent. The solvent used is not subjected to limitation, as long as the reaction is not interfered with. Useful solvents include water, alcohols such as methanol, ethanol and propanol, ethers such as tetrahydrofuran, dimethoxyethane and dioxane, nitriles such as acetonitrile and propionitrile, amides such as N,N-dimethylformamide, and sulfoxides such as dimethyl sulfoxide. The amount of compound (XVI) is normally 1 equivalent to excess (preferably 1 to 10 equivalents) per equivalent of compound (XVI). This reaction is normally carried out within the temperature range from 0° to 200° C., preferably 25° to 100° C. Reaction time is normally 10 minutes to 7 days, preferably 1 hour to 2 days. This reaction may be carried out in the presence of a base added as necessary. Useful bases include inorganic bases such as potassium carbonate and sodium hydrogen carbonate, and organic bases such as triethylamine, pyridine and dimethylaniline. The amount of base used is normally 1 equivalent to excess (preferably 1 to 10 equivalents) per equivalent of compound (XVI).

It is normally advantageous that the oxidation reaction of compound (I) in method G (X represents S) is carried out in a solvent. The solvent used is not subjected to limitation, as long as the reaction is not interfered with. Useful solvents include water, acetic acid, methanol, ethanol, methylene chloride and chloroform. The amount of oxidizing agent used is normally 1 equivalent to excess (preferably 1 to 10 equivalents) per equivalent of compound (I) (X represents S). Useful oxidizing agents include m-chloroperbenzoic acid, sodium meta-periodate and hydrogen peroxide. The reaction is normally carried out within the temperature range from −30° to 100° C., preferably 0° to 100° C. Reaction time is normally 10 minutes to 48 hours, preferably 1 to 24 hours.

The reaction of compound (VI) with compound (XVIII) in method H can, for example, be carried out under the same conditions as those of the reaction of compound (VI) with compound (VII) in method A.

The reaction of compound (VIII) with compound (XIX) in method I can, for example, be carried out under the same conditions as those of the reaction of compound (VI) with compound (VII) in method A.

The reaction of compound (X) with compound (XX) in method J can, for example, be carried out under the same conditions as those of the reaction of compound (X) with compound (XI) in method C.

The reaction of compound (XII) with compound (XXI) in method K can, for example, be carried out under the same conditions as those of the reaction of compound (XII) with compound (XIII) in method D.

The reaction of compound (XIV) with compound (XXII) in method L can, for example, be carried out under the same conditions as those of the reaction of compound (VI) with compound (VII) in method A.

It is generally advantageous that the reaction of compound (XXIII) with compound (XXIV) in method M is carried out in a solvent. The solvent used is not subjected to limitation, as long as the reaction is not interfered with. Useful solvents include water, alcohols such as methanol, ethanol and propanol, ketones such as acetone and methyl ethyl ketone, amides such as N,N-dimethylformamide and sulfoxides such as dimethyl sulfoxide, and acetic acid and propionic acid. This reaction can be facilitated by adding an inorganic base such as potassium carbonate or sodium hydrogen carbonate, or an organic base such as piperidine or pyrrolidine, or sodium acetate, or the like, to the reaction system. The amount of such an additive used is normally 0.1 to 10 equivalents per equivalent of compound (XXIII). The amount of compound (XXIV) is normally 1 equivalent to excess (preferably 1 to 10 equivalents) per equivalent of compound (XXIII). This reaction is normally carried out within the temperature range from −30° to 200° C., preferably 25° to 100° C. Reaction time is normally 10 minutes to 48 hours, preferably 1 to 24 hours.

It is generally advantageous that the dehydrating cyclization of compound (XXV) in method N is carried out in a solvent. The solvent used is not subjected to limitation, as long as the reaction is not interfered with. Useful solvents include aprotic polar solvents, e.g., ketones such as acetone and methyl ethyl ketone, ethers such as tetrahydrofuran, halogenated hydrocarbons such as methylene chloride, chloroform and dichloroethane, amides such as N,N-dimethylformamide and sulfoxides such as dimethyl sulfoxide. This reaction can be facilitated by adding a dehydrating agent, such as a combination of methanesulfonyl chloride or p-toluenesulfonyl chloride and a base, to the reaction system. Useful bases include triethylamine, pyridine and diisopropylethylamine. The amount of such a dehydrating agent used is normally 0.1 to 10 equivalents per equivalent of compound (XXV). This reaction is normally carried out within the temperature range from −80° to 100° C., preferably 0° to 80° C. Reaction time is normally 10 minutes to 48 hours, preferably 1 to 24 hours.

It is generally advantageous that the reaction of compound (XXVI) with compound (XXVII) in method O be carried out in a solvent. The solvent used is not subject to limitation, as long as the reaction is not interfered with. Useful solvents include halogenated hydrocarbons such as methylene chloride, chloroform and dichloroethane, ethers such as diethyl ether and tetrahydrofuran and amides such as N,N-dimethylformamide. The amount of compound (XXVII) is normally 1 to 3 equivalents per equivalent of compound (XXVI). This reaction is normally carried out at the temperatures of −30° to 100° C., preferably 0° to 80° C. Reaction time is normally 10 minutes to 48 hours, preferably 1 to 24 hours.

The reaction of compound (XXVIII) with $R^7$-SH in method P can, for example, be carried out under the same conditions as those of the reaction of compound (VI) with compound (VII) in method A.

The oxidizing reaction with compound (XXIX) in method Q can, for example, be carried out under the same conditions as those of the oxidation of compound (I) in method G.

The oxidizing reaction with compound (XXX) in method R can, for example, be carried out under the same conditions as those of the oxidation of compound (I) in method G.

The reaction of compound (VI) with compound (XXXII) in method S can, for example, be carried out under the same conditions as those of the reaction of compound (VI) and (VII) in method A.

The reaction of compound (VIII) with compound (XXXIII) in method T can, for example, be carried out under the same conditions as those of the reaction of compound (VI) with compound (VII) in method A.

The reaction of compound (X) with compound (XXXIV) in method U can, for example, be carried out under the same conditions as those of the reaction of compound (X) with compound (XI) in method C.

The reaction of compound (XII) with compound (XXXV) in method V can, for example, be carried out under the same conditions as those of the reaction of compound (XII) with compound (XIII) in method D.

The reaction of compound (XIV) with compound (XXXVI) in method W can, for example, be carried out under the same conditions as those of the reaction of compound (VI) with compound (VII) in method A.

It is generally advantageous that the cyclization of compound (XXXVII) in method X be carried out in a solvent. The solvent used is not subjected to limitation, as long as the reaction is not interfered with. Useful solvents include carboxylic acid amides such as N,N-dimethylformamide, N,N-dimethylacetamide and N-methylpyrrolidone, sulfoxides such as dimethyl sulfoxide, ketones such as acetone, methyl ethyl ketone and methyl isobutyl ketone, and commonly used aprotic solvents such as acetonitrile, ethyleneglycol dimethyl ether, tetrahydrofuran and dioxane. This reaction can be carried out by adding a sulfur reagent to the reaction system. Useful sulfur reagents include sodium hydrosulfide (NaSH), sodium sulfide ($Na_2S$) and ammonium sulfide (($NH_4)_2S$), with preference given to sodium hydrosulfide etc. The amount of sulfur reagent used is normally 1 to 5 equivalents per equivalent of compound (XXXVII). This reaction is normally carried out within the temperatures range from −30° to 100° C., preferably 0° to 25° C. Reaction time is normally 10 minutes to 24 hours, preferably 1 to 8 hours.

The oxidation of compound (XXXVIII) in method Y can, for example, be carried out under the same conditions as those of the oxidation of compound (I) in method G.

The oxidation of compound (XXXIX) in method Z can, for example, be carried out under the same conditions as those of the oxidation of compound (I) in method G.

The reaction of compound (VI) with compound (XLI) in method AA can, for example, be carried out under the same conditions as those of the reaction of compound (VI) with compound (VII) in method A.

The reaction of compound (VIII) with compound (XLIII) in method BB can, for example, be carried out under the same conditions as those of the reaction of compound (VI) with compound (VII) in method A.

The reaction of compound (X) with compound (XLIV) in method CC can, for example, be carried out under the same conditions as those of the reaction of compound (X) with compound (XI) in method C.

The reaction of compound (XII) with compound (XLV) in method DD can, for example, be carried out under the same conditions as those of the reaction of compound (XII) with compound (XIII) in method D.

The reaction of compound (XIV) with compound (XLVI) in method EE can, for example, be carried out under the same conditions as those of the reaction of compound (VI) with compound (VII) in method A.

The reaction of compound (VI) with compound (XLVII) in method FF can, for example, be carried out under the same conditions as those of the reaction of compound (VI) with compound (VII) in method A.

The reaction of compound (VIII) with compound (XLIX) in method GG can, for example, be carried out under the same conditions as those of the reaction of compound (VI) with compound (VII) in method A.

The reaction of compound (XIV) with compound (L) in method HH can, for example, be carried out under the same conditions as those of the reaction of compound (VI) with compound (VII) in method A.

Compound (VI) can, for example, be prepared by the following method:

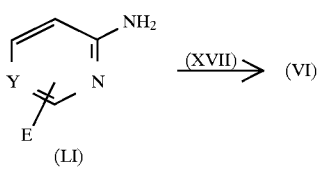

(LI)

The reaction of compound (LI) with compound (XVII) can, for example, be carried out under the same conditions as those of the reaction of compound (XVI) with compound (XVII) in method F.

Compound (VIII) can, for example, be prepared by the following methods:

(i) $X^2 = O$

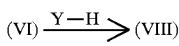

wherein Y represents NaS—, KS—, NaO— or KO—.

It is generally advantageous that the reaction of compound (VI) and Y-H is carried out in a solvent. The solvent used is not subjected to limitation, as long as the reaction is not interfered with. Useful solvents include water, alcohols such as methanol, ethanol and propanol, ethers such as tetrahydrofuran, dimethoxyethane and dioxane, amides such as N,N-dimethylformamide and sulfoxides such as dimethyl sulfoxide. The amount of compound Y-H used is normally 1 equivalent to excess (preferably 1 to 10 equivalents) per equivalent of compound (VI). This reaction is normally carried out within the temperature range from 0° to 250° C., preferably 80° to 200° C. Reaction time is normally 1 hour to 7 days, preferably 8 hours to 2 days.

(ii) $X^2 = -(CH_2)_i - O$

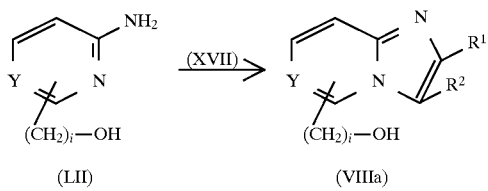

(LII)                        (VIIIa)

The reaction of compound (LII) with compound (XVII) can, for example, be carried out under the same conditions as those of the reaction of compound (XVI) with compound (XVII) in method F.

Compound (VIIIa) can be advantageously prepared by reacting compound (X) [$X^3 = -(CH_2)_j - COO-$] with a reducing agent. Useful reducing agents include metal-hydrogen complex compounds such as sodium borohydride and lithium aluminum hydride, and borane complexes. The amount of reducing agent used is normally 1 equivalent to excess (preferably 1 to 10 equivalents) per equivalent of compound (X). It is generally advantageous that this reaction be carried out in a solvent. The solvent used is not subjected to limitation, as long as the reaction is not interfered with. Useful solvents include alcohols such as methanol and ethanol and ethers such as ethyl ether, tetrahydrofuran and dioxane. This reaction is normally carried out within the temperature range from −20° to 100° C., preferably 0° to 25° C. Reaction time is normally 10 minutes to 24 hours, preferably 0.5 to 6 hours.

(iii) $X^2 = -(CH_2)_i - N(R^3) -$

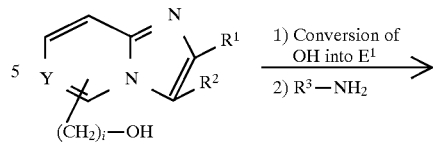

(VIIIa)

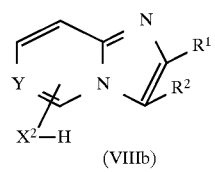

(VIIIb)

When $E^1$ is a halogen, conversion of the hydroxyl group of compound (VIIIa) into $E^1$ is facilitated by reacting compound (VIIIa) with a phosphorus halide such as phosphorus trichloride, phosphorus oxychloride, phosphorus pentachloride or phosphorus tribromide, or red phosphorus, and a halogenating agent such as a halogen or thionyl chloride. The amount of phosphorus halide used is normally 1 equivalent to excess (preferably 1 to 10 equivalents) per equivalent of compound (VIIIa). The amount of halogenating agent used is normally 1 equivalent to excess (preferably 1 to 10 equivalents) per equivalent of compound (VIIIa). When $E^1$ is a toluenesulfonyloxy group or a methanesulfonyloxy group, it is advantageous that compound (VIIIa) is reacted with toluenesulfonyl chloride or methanesulfonyl chloride. The amount of toluenesulfonyl chloride or methanesulfonyl chloride used is normally 1 to 3 equivalents per equivalent of compound (VIIIa). The subsequent reaction with $R^3 - NH_2$ can be carried out in the presence or absence of solvent. The amount of $R^3 - NH_2$ used is normally 1 to 5 equivalents per equivalent of compound (VIIIa). This reaction is normally carried out within the temperature range from 0° to 200° C., preferably 25° to 100° C. Reaction time is normally 10 minutes to 24 hours, preferably 0.5 to 12 hours. All these reactions per se are known reactions, and can be carried out under usual conditions.

Compound (X) can, for example, be prepared by the following methods:

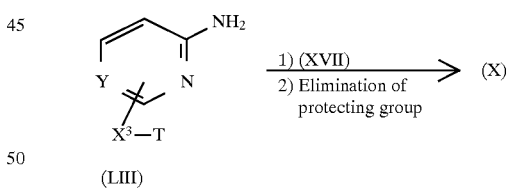

(LIII)

wherein T represents a carboxyl group protecting group. The reaction of compound (LIII) with compound (XVII) can, for example, be carried out under the same conditions as those of the reaction of compound (XVI) with compound (XVII) in method F. Preferable carboxyl group protecting groups include ester-forming protecting groups such as methyl, ethyl, methoxyethyl, methoxyethoxymethyl, benzyloxymethyl, tert-butyl, benzyl, p-methoxybenzyl, p-nitrobenzyl, o-nitrobenzyl, benzhydryl, trityl, 2,2,2-trichloroethyl, 2-trimethylsilylethyl and allyl; and silyl ester-forming protecting groups such as trimethylsilyl, triethylsilyl, tert-butyldimethylsilyl, isopropyldimethylsilyl and dimethylphenylsilyl. Useful methods of eliminating carboxyl group protecting groups include acid methods, base methods, reduction methods, ultraviolet methods, tetrabutylammonium fluoride methods and palladium acetate methods. These conventional methods and other known methods can be used as appropriate. Preferable acids for acid methods include organic acids such as formic acid, trifluoroacetic acid, benzenesulfonic acid and p-toluenesulfonic acid, and inorganic acids such as hydrochloric acid, hydrobromic acid and sulfuric acid. Preferable bases for base methods include inorganic bases, e.g., alkali metal hydroxides such as lithium hydroxide, sodium hydroxide and potassium hydroxide, alkaline earth metal hydroxides such as magnesium hydroxide and calcium hydroxide, alkali metal carbonates such as sodium carbonate and potassium carbonate, alkaline earth metal carbonates such as magnesium carbonate and calcium carbonate, alkali metal hydrogen carbonates such as sodium hydrogen carbonate and potassium hydrogen carbonate, alkali metal acetates such as sodium acetate and potassium acetate, alkaline earth metal phosphates such as calcium phosphate and magnesium phosphate, alkali metal hydrogen phosphates such as disodium hydrogen phosphate and dipotassium hydrogen phosphate, and inorganic bases such as aqueous ammonia; and organic bases, e.g., trimethylamine, triethylamine, diisopropylethylamine, pyridine, picoline, N-methylpyrrolidine, N-methylpiperidine, N-methylmorpholine, 1,5-diazabicyclo[4.3.0]non-5-ene, 1,4-diazabicyclo[2.2.2]octane and 1,8-diazabicyclo[5.4.0]-7-undecene. Reduction methods are applied to deprotection of those carboxyl groups protected by, for example, benzyloxymethyl, benzyl, p-nitrobenzyl and benzhydryl. Preferable reduction methods include reduction with sodium borohydride, reduction with zinc/acetic acid and catalytic hydrogenation. Ultraviolet methods are used to deprotect those carboxyl groups protected by, for example, o-nitrobenzyl. Tetrabutylammonium fluoride methods are used to eliminate protecting groups from, for example, 2-trimethylsilylethyl carbamate, silyl ethers and silyl esters, to yield free carboxyl groups. Palladium acetate methods are used to eliminate protecting groups from, for example, allyl esters, to yield free carboxyl groups.

It is generally advantageous that this reaction is carried out in a solvent. Useful solvents include water, alcohols such as methanol, ethanol and propanol, ethers such as tetrahydrofuran, dimethoxyethane and dioxane, amides such as N,N-dimethylformamide and sulfoxides such as dimethyl sulfoxide, mixtures thereof, and other solvents that do not interfere with the reaction. Liquid acids or bases can be used as solvents. This reaction is normally carried out within the temperature range from −20° to 100° C., preferably 0° to 80° C. Reaction time is normally 10 minutes to 24 hours, preferably 0.5 to 6 hours.

(ii) $X^3$=—$CH_2COO$—

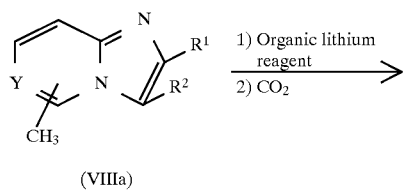

(VIIIa)

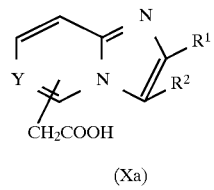

(Xa)

It is generally advantageous that the reaction of compound (LIV) with organic lithium reagent is carried out in a solvent. Useful solvents include ethers such as tetrahydrofuran, dimethoxyethane and dioxane, hydrocarbons such as hexane, pentane, benzene and toluene, aprotic polar solvents, e.g., hexamethylphosphoramide, 1,3-dimethyl-2-imidazolidinone and N,N,N',N'-tetramethylethylenediamine, mixtures thereof and other solvents that do not interfere with the reaction. Useful organic lithium reagents include butyl lithium, phenyl lithium and lithium diisopropylamide. The amount of organic lithium reagent used is normally 1 to 3 equivalents per equivalent of compound (LIV). This reaction is normally carried out within the temperature range from −100° to 50° C., preferably −80° to 0° C. Reaction time is normally 10 minutes to 24 hours, preferably 0.5 to 6 hours. The subsequent reaction with carbon dioxide may be carried out by adding dry ice to the above reaction system, or by bubbling sufficient gaseous carbon dioxide through the above reaction system. The amount of dry ice used is normally 1 equivalent to excess (preferably 1 to 10 equivalents) per equivalent of compound (LIV). All these reactions are known reactions, and can be carried out under usual conditions.

(iii) $X^3$=—$S$-$(CH_2)_kCOO$—

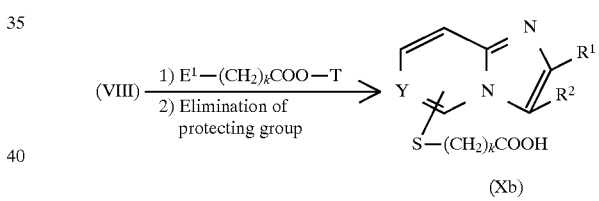

(Xb)

wherein T represents a carboxyl group protecting group. The reaction of compound (VIII) ($X^2$=S) with $E^1$—$(CH_2)_kCOO$—T can, for example, be carried out under the same conditions as those of the reaction of compound (VI) with compound (VII) in method A. The subsequent elimination of the carboxyl group protecting group can be carried out in the same manner as in term (i) above.

Compound (XII) can, for example, be prepared by the following method:

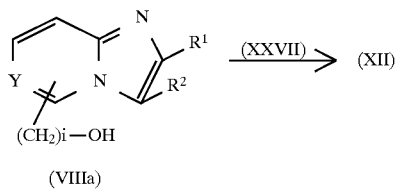

(VIIIa)

The reaction of compound (VIIIa) with compound (XXVII) (D=O) can, for example, be carried out under the same conditions as those of the reaction of compound (XXVI) with compound (XXVII) in method O.

Compound (XIV) can, for example, be prepared by the following methods:

(i) X=O, S, -(CH$_2$)$_i$—O— or —(CH$_2$)$_i$—N(R$^3$)—

(VIII) $\xrightarrow{E^1-A-E^1}$ (XIV)

The reaction of compound (VIII) with E$^1$-A-E$^1$ can, for example, be carried out under the same conditions as those of the reaction of compound (VIII) with compound (IX) in method B.

(ii) X =—CH$_2$—

(LIV) $\xrightarrow[2) E^1-A-E^1]{1) \text{Organic lithium reagent}}$ (XIV)

The reaction of compound (LIV) with organic lithium reagent can be carried out under the same conditions as those of the reaction of compound (LIV) with organic lithium reagent in method (ii) above for synthesizing compound (X). The subsequent reaction with compound E$^1$-A-E$^1$ is carried out by adding E$^1$-A-E$^1$ to the above reaction system. The amount of E$^1$-A-E$^1$ used is normally 1 equivalent to excess (preferably 1 to 10 equivalents) per equivalent of compound (LIV). All these reactions are well-known reactions, and can be carried out under usual conditions.

(iii) X=—(CH$_2$)$_j$—CON(R$^3$)—, —(CH$_2$)$_j$—COO—, —S—(CH$_2$)$_k$—CON(R$^3$)— or —S—(CH$_2$)$_k$—COO—.

(X) $\xrightarrow{E^2-A-E^1}$ (XIV)

The reaction of compound (X) with E$^2$-A-E$^1$ can, for example, be carried out under the same conditions as those of the dehydrating condensation of compounds (X) with compound (XI) in method C.

(iv) X —CH=CH—

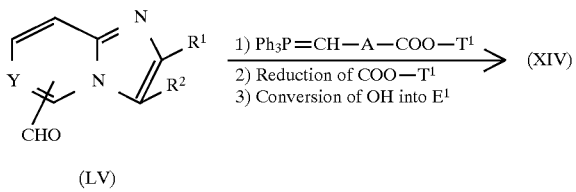

(LV)

wherein T$^1$ represents a hydrogen or a carboxyl group protecting group.

It is generally advantageous that the reaction of compound (LV) with Wittig reagent Ph$_3$P=CH—A—COO—T$^1$ is carried out in a solvent. Useful solvents include halogenated hydrocarbons such as methylene chloride and chloroform, ethers such as tetrahydrofuran, dimethoxyethane and dioxane, aromatic hydrocarbons such as benzene and toluene, alcohols such as methanol, ethanol and propanol, amides such as N,N-dimethylformamide and sulfoxides such as dimethyl sulfoxide, mixtures thereof and other solvents that do not interfere with the reaction. The amount of Wittig reagent used is normally 1 to 3 equivalents per equivalent of compound (LV). This reaction is normally carried out within the temperature range from 0° C. to the solvent's boiling point, preferably from 20° to 80° C. Reaction time is normally about 1 to 24 hours, preferably 5 to 20 hours. The subsequent reduction of the COO—T$^1$ group into CH$_2$OH group and conversion of the hydroxyl group into E$^1$ are carried out under the same conditions as those of the reduction of compound (X) and converting reaction of compound (VIIIa) into a hydroxyl group, respectively. All these reactions are known reactions, and can be carried out under usual conditions.

(v) R$^2$=a halogen such as chlorine, bromine or iodine

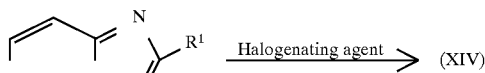

(LVI)

The reaction of compound (LVI) with a halogenating agent can be carried out in the presence or absence of solvent. The solvent used is not subjected to limitation, as long as the reaction is not interfered with. Useful solvents include halogenated hydrocarbons such as methylene chloride, chloroform, dichloroethane and carbon tetrachloride, acetic acid and propionic acid. Useful halogenating agents include molecular halogens such as chlorine and bromine, and N-halogeno-succinimides such as N-chlorosuccinimide, N-bromosuccinimide and N-iodosuccinimide. The amount of halogenating agent used is normally 1 equivalent to excess (preferably 1 to 10 equivalents) per equivalent of compound (LVI). This reaction is normally carried out within the temperature range from –20° to 150° C., preferably 0° to 80° C. Reaction time is normally 0.5 hours to 2 days, preferably 1 to 12 hours. This reaction may be carried out in the presence of a radical reaction initiator such as benzoyl peroxide.

(vi) When R$^2$ is a nitro group, compound (LVI) is nitrated to compound (XIV). The nitrating reaction of compound (LVI) can be carried out in the presence or absence of solvent. The solvent used is not subjected to limitation, as long as the reaction is not interfered with. Useful solvents include acetic acid, acetic anhydride and sulfuric acid. Useful nitrating agents include fuming nitric acid, concentrate nitric acid and mixed acids (e.g., sulfuric acid, fuming nitric acid, phosphoric acid or acetic anhydride with nitric acid). The amount of nitrating agent used is normally 1 equivalent to excess (preferably 1 to 10 equivalents) per equivalent of compound (LVI). This reaction is normally carried out within the temperature range from –20° to 100° C., preferably 0° to 25° C. Reaction time is normally 0.5 to 24 hours, preferably 0.5 to 6 hours.

(vii) When R$^2$ is a nitroso group, compound (LVI) is converted to compound (XIV) by nitrosation in the presence or absence of solvent. The solvent used is not subjected to limitation, as long as the reaction is not interfered with. Useful solvents include water, lower fatty acids such as acetic acid and propionic acid, ethers such as tetrahydrofuran and dioxane, amides such as N,N-dimethylformamide, and sulfoxides such as dimethyl sulfoxide. The amount of nitrosation agent used is normally 1 equivalent to excess (preferably 1 to 10 equivalents) per equivalent of compound (LVI). This reaction is normally carried out within the temperature range from –20° to 100° C., preferably 0° to 25° C. Reaction time is normally 0.5 to 24 hours, preferably 0.5 to 6 hours. It is advantageous that this reaction is carried out in the presence of an acid such as hydrochloric acid, sulfuric acid, phosphoric acid or acetic acid.

(viii) R$^2$=—CH$_2$R$^{2a}$ (R$^{2a}$ represents a lower dialkylamino group or a cyclic amino group)

(LVI) $\xrightarrow[R^{2a}-H]{HCHO}$ (XIV)

It is generally advantageous that the Mannich reaction of compound (LVI) with lower dialkylamine and formalin or with cyclic amine and formalin is carried out in a solvent. The solvent used is not subjected to limitation, as long as the reaction is not interfered with. Useful solvents include water, alcohols such as methanol, ethanol, propanol and isopropanol, and lower fatty acids such as acetic acid and propionic acid. The amount of Mannich reagent used is normally I equivalent to excess (preferably 1 to 10 equivalents) per equivalent of compound (LVI). This reaction is normally carried out within the temperature range from −20° to 100° C., preferably 60° to 100° C. Reaction time is normally 30 minutes to 1 day, preferably 1 to 12 hours.

Separation and/or purification from the reaction mixture for compound (I) is carried out by a conventional method (e.g., extraction, concentration, filtration, recrystallization, column chromatography, thin-layer chromatography).

Compound (I) of the present invention and pharmaceutically acceptable salts thereof exhibit inhibitory activity of adhesion molecule expression, diabetic nephritis improving action and immunosuppression of organ transplantation in animals, especially mammals (e.g., humans, monkeys, dogs, cats, horses, bovines, sheep, rabbits, guinea pigs, rats, mice), and is useful as an inhibitor of adhesion molecule expression, a therapeutic agent for diabetic nephritis or an immunosuppressor for organ transplantation. These compounds are also useful as immunotherapeutic drugs (immunosuppressors and immunomodulators) for autoimmune diseases (e.g., rheumatic arthritis, systemic lupus erythematosus, multiple sclerosis, ulcerative colitis, systemic scleroderma, mixed connective tissue disease, necrotizing angitis polymyositis/dermatomyositis, Sjogren's syndrome, Behcet's syndrome, Hashimoto's disease, myasthenia gravis, chronic active cholecystitis, autoimmune hemolytic anemia, idiopathic thrombocytopenic purpura) and cancer; suppressors for tumor metastasis; anti-allergic drugs; anti-asthmatics; insulin-dependent diabetes mellitus remedies; They are also useful as therapeutic drugs for thrombotic diseases, such as myocardial infarction, arterial/venous embolism and cerebral infarction, myocarditis, inflammatory ophthalmic diseases, adult respiratory distress syndrome (ARDS), acute renal failure, nephritis, fulminant hepatitis, psoriasis, sepsis and shock. Adhesion molecules in question include those associated with inflammatory cell infiltration-or immune cell antigen recognition, such as ICAM-1 (intercellular adhesion molecule-1), ICAM-2 (intercellular adhesion molecule-2), ICAM-3 (intercellular adhesion molecule-3), ELAM-1 (endothelial leukocyte adhesion molecule-1) and VCAM-1 (vascular cell adhesion molecule-1), and LFA-1 (lymphocyte function-associated antigen-1) and Mac-1 (macrophage antigen 1).

Since compound (I) (or salt thereof) of the present invention is of low toxicity, is highly absorbable in oral administration, and is stable, it can be used as a pharmaceutical for humans and so on. When it is used as such a pharmaceutical, it can be safely administered orally or parenterally as a pharmaceutical as described above, as it is or in a mix with an appropriate pharmacologically acceptable carrier, excipient or diluent (e.g., starch, physiological saline), in a well-known dosage form of powder, granules, tablets, capsules or injectable preparations. Although dosage may vary, depending on route of administration, symptoms, patient age and weight etc., it is desirable that compound (I) (or salt thereof) of the present invention be administered at 0.2 to 50 mg/kg/day, preferably 0.5 to 30 mg/kg/day, more preferably 1 to 20 mg/kg/day, in 1 to several portions a day, when given orally to an adult patient to use as an inhibitor of adhesion molecule expression or an agent for treating diabetic nephritis or to suppress hyper immune reaction of transplantation.

BEST MODES FOR CARRYING OUT THE INVENTION

The present invention is hereinafter described in more detail by means of, but not limited to, the following reference examples, preparation examples and working examples.

Reference Example 1
Synthesis of 5-(4-chlorobutylthio)imidazo[1,2-a]pyridine In a nitrogen atmosphere, 8.87 ml (77 mmol) of 1-bromo-4-chlorobutane was added to a solution of 10.51 g (70 mmol) of 5-mercaptoimidazo[1,2-a]pyridine and 10.73 ml (77 mmol) of triethylamine in 150 ml of ethanol was added, followed by stirring at room temperature for 16 hours. After the solvent was distilled off, the residue was dissolved in dichloromethane. This solution was washed with saturated aqueous sodium hydrogen carbonate and dried, after which the solvent was distilled off. The residue was purified by column chromatography (eluent: ethyl acetate) to yield 12.93 g (76.7%, light brown oily substance) of the desired product.

$^1$H-NMR (CDCl$_{13}$, 200 MHz) δ 1.78–2.02 (4H, m), 3.03 (2H, t, J=6.6 Hz), 3.55 (2H, t, J=6.2 Hz), 6.93 (1H, dd, J=0.8, 7.0 Hz), 7.17 (1H, dd, J=6.8, 9.0 Hz), 7.60 (1H, d, J=9.0 Hz), 7.71 (1H, d, J=1.0 Hz), 7.85 (1H, s)

Reference Example 2
Synthesis of 3-[4-(imidazo[1,2-a]pyridin-5-ylthio)butyl]-thiazolidine-2,4-dione To a solution of 8.35 g (35.4 mmol) of 5-(4-chlorobutylthio)imidazo[1,2-a]pyridine and 4.15 g (35.4 mmol) of thiazolidine-2,4-dione in 200 ml of N,N-dimethylformamide, 5.30 ml (35.4 mmol) of 1,8-diazabicyclo[5.4.0]-7-undecene was added, followed by heating at 80° C. for 16 hours. After cooling, the reaction mixture was poured into water, extracted with ethyl acetate, washed with water and dried, after which the solvent was distilled off. The residue was purified by column chromatography (eluent: ethyl acetate). The resulting crude crystal was purified by recrystallization (solvent: chloroform/diethyl ether) to yield 10.01 g (88.0%, light orange crystal) of the desired product.

$^1$H-NMR (CDCl$_3$, 200 MHz) δ 1.58–1.84 (4H, m), 3.02 (2H, t, J=7.0 Hz), 3.63 (2H, t, J=7.0 Hz), 3.92 (2H, s), 6.93 (1H, d, J=6.8 Hz), 7.18 (1H, dd, J=7.0, 9.2 Hz), 7.62 (1H, d, J=9.2 Hz), 7.71 (1H, s), 7.85 (1H, s)

Reference Example 3
Synthesis of 5-(5-chloropentyl)imidazo[1,2-a]pyridine

In an argon atmosphere, 51.5 ml (103 mmol) of a 2M lithium diisopropylamide solution (produced by Aldrich Company) was added to a solution of 13.6 g (103 mmol) of 5-metylimidazo[1,2-a]pyridine in 100 ml of tetrahydrofuran at −78° C. After stirring at constant temperature for 15 minutes, 17.64 g (103 mmol) of 1-bromo-4-chlorobutane was added, followed by stirring for 1 more hour. After stirring at 0° C. for 1 hour, the reaction mixture was poured into water, extracted with ethyl acetate, washed with water and dried, after which the solvent was distilled off. The residue was purified by column chromatography (eluent; ethyl acetate) to yield 18.74 g (81.7%, light yellow oily substance) of the desired product.

$^1$H-NMR (CDCl$_3$, 200 MHz) δ 1.54–1.68 (2H, m), 1.80–1.92 (4H, m), 2.91 (2H, t, J=7.8 Hz), 3.57 (2H, t, J=6.6

Hz), 6.62 (1H, d, J=6.2 Hz), 7.16 (1H, dd, J=7.0, 9.2 Hz), 7.53–7.57 (2H, m), 7.69 (1H, s)

Reference Example 4
Synthesis of 3-[5-(imidazo[1,2-a]pyridin-5-yl)pentyl]thiazolidine-2,4-dione A suspension of 2.22 g (10 mmol) of 5-(5-chloropentylthio)imidazo[1,2-a]pyridine and 1.40 g (10 mmol) of thiazolidine-2,4-dione sodium salt in 30 ml of N,N-dimethylformamide was heated at 80° C. for 16 hours. After cooling, the reaction mixture was poured into water, extracted with ethyl acetate, washed with water and dried, after which the solvent was distilled off. The residue was purified by column chromatography (eluent: ethyl acetate→ethyl acetate/ethanol=10/1) to yield 1.56 g (51.4%, light brown oily substance) of the desired product.

$^1$H-NMR (CDCl$_3$, 200 MHz) δ 1.42–1.56 (2H, m), 1.62–1.92 (4H, m), 2.90 (2H, t, J=8.0 Hz), 3.66 (2H, t, J=7.4 Hz), 3.95 (2H, s), 6.62 (1H, d, J=7.2 Hz), 7.18 (1H, dd, J=6.8, 9.0 Hz), 7.55–7.59 (2H, m), 7.70 (1H, s); IR (neat) 2945, 1749, 1682, 1633, 1514, 1387, 1350, 1294, 1147, 787, 746 cm$^{-1}$

Reference Example 5
Synthesis of 3-[3-(imidazo[1,2-a]pyridin-5-ylthio)propyl]thiazolidine-2,4-dione In a nitrogen atmosphere, 3.87 g (20 mmol) of 3-(3-bromopropyl)thiazolidine-2,4-dione was added to a suspension of 3.0 g (20 mmol) of 5-mercaptoimidazo[1,2-a]pyridine, 2.76 g (20 mmol) of potassium carbonate and 3.00 g (20 mmol) of sodium iodide in 100 ml of N,N-dimethylformamide was added, followed by stirring at room temperature for 64 hours. The reaction mixture was poured into water, extracted with ethyl acetate, washed with water and dried, after which the solvent was distilled off. The residue was purified by column chromatography (eluent: ethyl acetate) to yield 2.44 g (39.7%, light red-purple solid) of the desired product.

$^1$H-NMR (CDCl$_3$, 200 MHz) δ 1.93 (2H, quint., J=7.0 Hz), 2.97 (2H, t, J=7.0 Hz), 3.79 (2H, t, J=7.2 Hz), 3.95 (2H, s), 7.00 (1H, d, J=7.0 Hz), 7.17 (1H, dd, J=7.2, 8.8 Hz), 7.62 (1H, d, J=8.8 Hz), 7.71 (1H, d, J=1.2 Hz), 7.88 (1H, s); IR (neat) 2943, 1749, 1682, 1616, 1487, 1362, 1290, 1140, 785, 739 cm$^{-1}$

Reference Example 6
Synthesis of 5-(2-chloroethylthio)imidazo[1,2-a]pyridine Using 3.0 g (20 mmol) of 5-mercaptoimidazo[1,2-a]pyridine, 2.79 ml (20 mmol) of triethylamine and 1.66 ml (20 mmol) of 1-bromo-2-chloroethane, the same procedure as in Reference Example 1 was followed, to yield 2.29 g (54.0%, light brown oily substance) of the desired product.

$^1$H-NMR (CDCl$_3$, 200 MHz) δ 3.28 (2H, t, J=6.8 Hz), 3.64 (2H, t, J=7.4 Hz), 7.05 (1H, dd, J=1.0, 7.0 Hz), 7.17 (1H, dd, J=7.0, 8.8 Hz), 7.66 (1H, d, J=8.8 Hz), 7.73 (1H, s), 7.93 (1H, s); IR (neat) 3105, 1618, 1487, 1286, 1142, 783, 737, 692 cm$^{-1}$

Reference Example 7
Synthesis of 3-[2-(imidazo[1,2-a]pyridin-5-ylthio)ethyl]thiazolidine-2,4-dione Using 2.29 g (10.8 mmol) of 5-(2-chloroethylthio)-imidazo[1,2-a]pyridine, 1.27 g (10.8 mmol) of thiazolidine-2,4-dione and 1.62 ml (10.8 mmol) of 1,8-diazabicyclo-[5.4.0]-7-undecene, the same procedure as in Reference Example 2 was followed, to yield 1.49 g (38.7%, light orange crystal) of the desired product.

$^1$H-NMR (CDCl$_3$, 200 MHz) δ 3.24 (2H, t, J=6.6 Hz), 3.89 (2H, t, J=6.6 Hz), 3.89 (2H, s), 7.11 (1H, dd, J=1.0, 7.0 Hz), 7.21 (1H, dd, J=7.2, 8.8 Hz), 7.64 (1H, d, J=8.7 Hz), 7.73 (1H, s), 7.85 (1H, s)

Reference Example 8
Synthesis of 3-[4-(imidazo[1,2-a]pyridin-5-yl)butyl]thiazolidine-2,4-dione To a solution of 1.59 g (7.0 mmol) of 5-(4-hydroxybutyl)imidazo[1,2-a]pyridine hydrochloride and 2.25 ml (16 mmol) of triethylamine in 30 ml of dichloromethane, 0.62 ml (8.0 mmol) of methanesulfonyl chloride was added at 0° C. After stirring at room temperature for 1 hour, saturated aqueous sodium hydrogen carbonate was added. The reaction mixture was extracted with dichloromethane and dried, after which the solvent was distilled off to yield 5-(4-methanesulfonyloxybutyl)imidazo[1,2-a]pyridine.

$^1$H-NMR (CDCl$_3$, 200 MHz) δ 1.91–2.00 (4H, m), 2.96 (2H, t, J=7.0 Hz), 3.01 (3H, s), 4.30 (2H, t, J=5.8 Hz), 6.64 (1H, d, J=6.6 Hz), 7.17 (1H, dd, J=7.0, 8.6 Hz), 7.54–7.59 (2H, m), 7.70 (1H, d, J=1.2 Hz)

To a solution of the above product and 0.82 g (7.0 mmol) of thiazolidine-2,4-dione in 30 ml of N,N-dimethylformamide, 1.05 ml (7.0 mmol) of 1,8-diazabicyclo-[5.4.0]-7-undecene was added, followed by stirring at 80° C. for 16 hours. After cooling, the reaction mixture was poured into water and extracted with ethyl acetate. The organic layer was washed with water and dried, after which the solvent was distilled off. The residue was purified by column chromatography (eluent: ethyl acetate→ethyl acetate/ethanol=10/1) to yield 1.18 g (58.3%, white powder) of the desired product.

$^1$H-NMR (CDCl$_3$, 200 MHz) δ 1.78–1.88 (4H, m), 2.94 (2H, t, J=7.0 Hz), 3.71 (2H, t, J=6.6 Hz), 3.96 (2H, s), 6.62 (1H, d, J=7.0 Hz), 7.17 (1H, t, J=6.6 Hz), 7.54–7.58 (2H, m), 7.69 (1H, s)

Reference Example 9
Synthesis of 5-(4-hydroxybutyloxy)imidazo[1,2-a]pyridine In a nitrogen stream, 8.0 g (200 mmol) of 60% oily sodium hydride was added to a solution of 18.90 g (100 mmol) of 5-chloroimidazo[1,2-a]pyridine hydrochloride in 200 ml of dimethyl sulfoxide at 0° C., followed by stirring for 15 minutes. To this mixture, 20.44 g (100 mmol) of 4-hydroxy-1-t-butyldimethylsiloxybutane was added, followed by stirring room temperature for 5 hours. The reaction mixture was poured into water and extracted with ethyl acetate. The organic layer was washed with water and dried, after which the solvent was distilled off. The residue was purified by column chromatography (eluent: ethyl acetate) to yield 3.73 g (11.6%, orange oily substance) of the desired product.

$^1$H-NMR (CDCl$_3$, 200 MHz) δ 0.07 (6H, s), 0.90 (9H, s), 1.70–2.05 (4H, m), 3.72 (2H, t, J=6.0 Hz), 4.28 (1H, t, J=6.4 Hz), 6.03 (1H, dd, J=1.0, 7.2 Hz), 7.12–7.28 (2H, m), 7.58 (1H, d, J=1.2 Hz), 7.65 (1H, s); IR (neat) 2953, 1637, 1539, 1514, 1470, 1282, 1109, 835, 775, 731, 702 cm$^{-1}$ To a solution of the this silyl ether in 10 ml of tetrahydrofuran, 12.5 ml (12.5 mmol) of a 1M tetrabutylammonium fluoride solution was added at room temperature, followed by stirring for 30 minutes. After addition of saturated aqueous sodium hydrogen carbonate, the reaction mixture was extracted with dichloromethane and dried, after which the solvent was distilled off. The residue was purified by column chromatography (eluent: ethyl acetate→ethyl acetate/ethanol=10/1) to yield 1.85 g (77.3%, light orange solid) of the desired product.

$^1$H-NMR (CDCl$_3$, 200 MHz) δ 1.76–1.90 (2H, m), 2.00–2.12 (2H, m), 2.46 (1H, s), 3.78 (2H, t, J=6.2 Hz), 4.28 (2H, t, J=6.3 Hz), 6.01 (1H, d, J=7.2 Hz), 7.10–7.27 (2H, m), 7.56 (1H, d, J=1.3 Hz), 7.62 (1H, s)

Reference Example 10
Synthesis of 3-[4-(imidazo[1,2-a]pyridin-5-yloxy)butyl]-thiazolidine-2,4-dione Using 1.65 g (8.0 mmol) of 5-(4-hydroxybutyloxy)-imidazo[1,2-a]pyridine, 1.23 ml (8.8 mmol) of triethylamine and 0.68 ml (8.8 mmol) of methanesulfonyl chloride, the same procedure as in Reference Example 8 was followed, to yield 5-(4-methanesulfonyloxybutyloxy)imidazo[1,2-a]pyridine.

$^1$H-NMR (CDCl$_3$, 200 MHz) δ 2.03–2.10 (4H, m), 3.03 (3H, s), 4.28–4.39 (4H, m), 6.05 (1H, dd J=1.0, 7.4 Hz), 7.18 (1H, dd, J=7.2, 9.0 Hz), 7.30 (1H, d, J=9.0 Hz), 7.60 (1H, d, J=1.2 Hz), 7.65 (1H, s); IR (neat) 2941, 1637, 1543, 1514, 1350, 1286, 1173, 1113, 941, 770, 735, 528 cm$^{-1}$ Using the above product, 1.05 g (9.0 mmol) of thiazolidine-2,4-dione and 1.34 ml (9.0 mmol) of 1,8-diazabicyclo[5.4.0]-7-undecene, the same procedure as in Reference Example 8 was followed, to yield 1.85 g (75.7%, light orange oily substance) of the desired product.

$^1$H-NMR (CDCl$_3$, 200 MHz) δ 1.86–1.96 (4H, m), 3.76 (2H, t, J=6.4 Hz), 3.96 (2H, s), 4.27 (2H, t, J=5.8 Hz), 6.04 (1H, d, J=7.2 Hz), 7.17 (1H, dd, J=7.4, 9.2 Hz), 7.29 (1H, d, J=9.0 Hz), 7.60 (1H, d, J=1.2 Hz), 7.65 (1H, d, J=0.6 Hz); IR (neat) 2958, 1743, 1689, 1541, 1354, 1111, 1061, 770, 733 cm$^{-1}$

Reference Example 11
Synthesis of 3-[4-(imidazo[1,2-a]pyridin-5-ylthio)butyl]-oxazolidine-2,4-dione To a solution of 6.30 g (26.2 mmol) of 5-(4-chlorobutylthio)imidazo[1,2-a]pyridine and 3.64 g (26.2 mmol) of oxazolidine-2,4-dione potassium salt in 100 ml of N,N-dimethylformamide, 3.92 g (26.2 mmol) of sodium iodide was added, followed by stirring at 80° C. for 16 hours. After cooling, the reaction mixture was poured into water and extracted with ethyl acetate. The organic layer was washed with water and dried, after which the solvent was distilled off. The residue was purified by column chromatography (eluent: ethyl acetate) to yield 5.70 g (71.4%, light orange crystal) of the desired product.

$^1$H-NMR (CDCl$_3$, 200 MHz) δ 1.58–1.92 (4H, m), 3.02 (2H, t, J=7.0 Hz), 3.57 (2H, t, J=7.0 Hz), 4.68 (2H, s), 6.92 (1H, dd, J=1.2, 7.0 Hz), 7.16 (1H, dd, J=7.0, 9.0 Hz), 7.59 (2H, d, J=9.0 Hz), 7.70 (1H, d, J=1.4 Hz), 7.84 (1H, d, J=0.8 Hz); IR (neat) 2958, 1818, 1734, 1697, 1408, 1288, 766, 737 cm$^{-1}$

Reference Example 12
Synthesis of 5-(3-hydroxypropyl)imidazo[1,2-a]pyridine hydrochloride Using 13.22 g (100 mmol) of 5-methylimidazo[1,2-a]pyridine, 50 ml (100 mmol) of a 2M lithium diisopropylamide solution (produced by Aldrich Company) and 23.92 g (100 mmol) of 1-bromo-2-t-butyldimethylsiloxyethane, the same procedure as in Reference Example 3 was followed, to yield 18.81 g (64.8%, yellow oily substance) of 5-(3-t-butyldimethylsiloxypropyl)imidazo[1,2-a]pyridine.

$^1$H-NMR (CDCl$_3$, 200 MHz) δ 0.09 (6H, s), 0.94 (9H, s), 1.92–2.06 (2H, m), 3.01 (2H, t, J=7.4 Hz), 3.75 (2H, t, J=5.8 Hz), 6.64 (1H, d, J=7.2 Hz), 7.17 (1H, dd, J=7.0, 9.0 Hz), 7.55 (1H, d, J=9.2 Hz), 7.62 (1H, s), 7.69 (1H, d, J=1.2 Hz)

To a solution of the above product in 100 ml of methanol, 15 ml of concentrated hydrochloric acid was added, followed by stirring at 60° C. for 1 hour. After the reaction mixture was cooled, the solvent was distilled off. The residue was purified by recrystallization (solvent: methanol-diethyl ether) to yield 12.29 g (89.2%, white crystal) of the desired product.

$^1$H-NMR (D$_2$O, 200 MHz) δ 2.03 (2H, quint., J=8.2 Hz), 3.16 (2H, t, J=8.0 Hz), 3.71 (2H, t, J=6.2 Hz), 7.28 (1H, d, J=7.4 Hz), 7.73 (1H, d, J=8.8 Hz), 7.85 (1H, dd, J=7.4, 9.0 Hz), 7.91 (1H, d, J=2.2 Hz), 8.07 (1H, d, J=2.2 Hz)

Reference Example 13
Synthesis of 3-[3-(imidazo[1,2-a]pyridin-5-yl)propyl]-thiazolidine-2,4-dione Using 2.55 g (12 mmol) of 5-(3-hydroxypropyl)imidazo-[1,2-a]pyridine hydrochloride, 3.90 ml (28 mmol) of triethylamine and 1.08 ml (14 mmol) of methanesulfonyl chloride, the same procedure as in Reference Example 8 was followed, to yield 5-(3-methanesulfonyloxypropyl)imidazo-[1,2-a]pyridine.

$^1$H-NMR (CDCl$_3$, 200 MHz) δ 2.20–2.36 (2H, m), 3.04 (3H, s), 3.08 (2H, t, J=7.4 Hz), 4.36 (2H, t, J=6.4 Hz), 6.67 (1H, d, J=7.0 Hz), 7.18 (1H, dd, J=7.0, 9.2 Hz), 7.56–7.60 (2H, m), 7.70 (1H, d, J=1.0 Hz); IR (neat) 1639, 1543, 1514, 1350, 1171, 978, 930, 883, 789, 746 cm$^{-1}$ Using the above product, 1.41 g (12 mmol) of thiazolidine-2,4-dione and 1.79 ml (12 mmol) of 1,8-diazabicyclo[5.4.0]-7-undecene, the same procedure as in Reference Example 8 was followed, to yield 1.88 g (56.9%, light yellow powder) of the desired product.

$^1$H-NMR (CDCl$_3$, 200 MHz) δ 2.16 (2H, quint., J=7.4 Hz), 2.92 (2H, t, J=7.6 Hz), 3.81 (2H, t, J=7.4 Hz), 3.96 (3H, s), 6.69 (1H, d, J=6.6 Hz), 7.17 (1H, dd, J=6.8, 9.0 Hz), 7.51 (1H, s), 7.56 (1H, d, J=9.0 Hz), 7.70 (1H, s)

Reference Example 14
Synthesis of 3-[2-(imidazo[1,2-a]pyridin-5-yl)ethyl]thiazolidine-2,4-dione To a suspension of 4.0 g (24.7 mmol) of 5-(2-hydroxyethyl)imidazo[1,2-a]pyridine in 30 ml of chloroform, 5 ml (68 mmol) of thionyl chloride was added. After refluxing for 2 hours, the solvent was distilled off. To a suspension of the residue and 8.36 g (60 mmol) of 2,4-thiazolidinedione sodium salt in 50 ml of N,N-dimethylformamide, 3.75 g (25 mmol) of sodium iodide was added, followed by stirring at 80° C. for 16 hours. After the reaction mixture was cooled, water was added. The reaction mixture was then extracted with ethyl acetate and dried, after which the solvent was distilled off. The residue was purified by column chromatography (eluent: n-hexane/ethyl acetate=2/1→1/1→1/4) to yield 1.00 g (15.5%, light orange powder) of the desired product.

$^1$H-NMR (CDCl$_3$, 200 MHz) δ 3.22 (2H, t, J=7.6 Hz), 3.98 (2H, s), 3.99–4.07 (2H, m), 6.69 (1H, d, J=6.6 Hz), 7.16 (1H, dd, J=6.8, 9.0 Hz), 7.60 (1H, d, J=9.2 Hz), 7.73 (1H, d, J=0.8 Hz), 7.85 (1H, d, J=1.2 Hz)

Reference Example 15
Synthesis of 3-[5-(imidazo[1,2-a]pyridin-5-yl)pentyl]-oxazolidine-2,4-dione To a solution of 15.59 g (70 mmol) of 5-(5-chloropentyl)imidazo[1,2-a]pyridine and 9.74 g (70 mmol) of oxazolidine-2,4-dione potassium salt in 300 ml of N,N-dimethylformamide, 10.49 g (70 mmol) of sodium iodide was added, followed by stirring at 80° C. for 16 hours. After cooling, the reaction mixture was poured into water and extracted with ethyl acetate. The organic layer was washed with water and dried, after which the solvent was distilled off. The residue was purified by column chromatography (eluent: ethyl acetate→ethyl acetate/ethanol=10/1) to yield 11.90 g (59.2%, light orange crystal) of the desired product.

$^1$H-NMR (CDCl$_3$, 200 MHz) δ 1.44–1.56 (2H, m), 1.68–1.92 (4H, m), 2.89 (2H, t, J=8.0 Hz), 3.59 (2H, t, J=7.2 Hz), 4.70 (2H, s), 6.61 (1H, d, J=6.1 Hz), 7.16 (1H, dd, J=6.9, 9.1 Hz), 7.52–7.57 (2H, m), 7.69 (1H, d, J=1.3 Hz)

Reference Example 16
Synthesis of 2-amino-3-(4-chlorobutyloxy)pyridine

To a suspension of 20 g (500 mmol) of 60% oily sodium hydride in 500 ml of dimethyl sulfoxide, 55.06 g (500 mmol) of 2-amino-3-hydroxypyridine was added at room temperature, followed by stirring for 15 minutes. To this mixture, 57.62 ml (500 mmol) of 1-bromo-4-chlorobutane was added, followed by stirring at 80° C. for 3 hours. After cooling, the reaction mixture was poured into water, extracted with ethyl acetate, washed with water and dried, after which the solvent was distilled off. The residue was purified by column chromatography (eluent: n-hexane/ethyl acetate=1/1→1/4→1/9). The resulting crude crystal was purified by recrystallization (solvent: chloroform-diethyl ether) to yield 10.35 g (10.3%, white crystal) of the desired product.

$^1$H-NMR (CDCl$_3$, 200 MHz) δ 1.96–2.02 (4H, m), 3.63 (2H, t, J=6.2 Hz), 4.02 (2H, t, J=5.8 Hz), 4.67 (2H, s), 6.60 (1H, dd, J=5.0, 8.0 Hz), 6.89 (1H, dd, J=1.4, 7.6 Hz), 7.66 (1H, dd, J=1.4, 5.0 Hz)

Reference Example 17
Synthesis of 3-[4-(2-aminopyridin-3-yloxy)butyl]-thiazolidine-2,4-dione Using 10.06 g (50 mmol) of 2-amino-3-(4-chlorobutyloxy)pyridine, 6.97 g (50 mmol) of thiazolidine-2,4-dione sodium salt and 7.49 g (50 mmol) of sodium iodide, the same procedure as in Reference Example 11 was followed, to yield 9.53 g (67.8%, light yellow oily substance) of the desired product.

$^1$H-NMR (CDCl$_3$, 200 MHz) δ 1.80–1.86 (4H, m), 3.73 (2H, t, J=7.0 Hz), 3.96 (2H, s), 3.97–4.03 (2H, m), 4.67 (2H, s), 6.59 (1H, dd, J=5.2, 8.0 Hz), 6.89 (1H, dd, J=1.2, 7.8 Hz), 7.66 (1H, dd, J=1.4, 5.2 Hz)

Reference Example 18
Synthesis of 3-[4-(imidazo[1,2-a]pyridin-8-yloxy)butyl]-thiazolidine-2,4-dione To a solution of 14.08 g (50 mmol) of 3-[4-(2-aminopyridin-3-yloxy)butyl]thiazolidine-2,4-dione in 150 ml of ethanol, 50 ml of a 40% chloroacetaldehyde solution was added at 60° C., followed by refluxing for 2 hours. After the reaction mixture was cooled, the solvent was distilled off. The residue was dissolved in dichloromethane, washed with saturated aqueous sodium hydrogen carbonate and dried, after which the solvent was distilled off. The residue was purified by column chromatography (eluent: n-hexane/residue=1/4) to yield 10.04 g (65.8%, light yellow crystal) of the desired product.

$^1$H-NMR (CDCl$_3$, 200 MHz) δ 1.88–1.96 (4H, m), 3.74 (2H, t, J=7.0 Hz), 3.95 (2H, s), 4.18 (2H, t, J=6.0 Hz), 6.43 (1H, dd, J=0.6, 7.2 Hz), 6.67 (1H, t, J=6.6 Hz), 7.54 (1H, d, J=1.0 Hz), 7.57 (1H, d, J=1.2 Hz), 7.77 (1H, dd, J=0.8, 6.6 Hz)

Reference Example 19
Synthesis of 5-chloro-2-methylimidazo[1,2-a]pyridine hydrobromide To a solution of 19.28 g (150 mmol) of 2-amino-6-chloropyridine in 150 ml of ethanol, 25 g (180 mmol) of bromoacetone was added at room temperature, followed by refluxing for 64 hours. After the reaction mixture was cooled, the solvent was distilled off. The residue was purified by recrystallization (solvent: ethanol-ethyl acetate) to yield 20.22 g (54.5%, light brown crystal) of the desired product.

$^1$H-NMR (D$_2$O, 200 MHz) δ 2.52 (3H, d, J=0.8 Hz), 7.50 (1H, dd, J=1.8, 6.8 Hz), 7.73–7.85 (2H, m), 7.96 (1H, s)

Reference Example 20
Synthesis of 5-mercapto-2-methylimidazo[1,2-a]pyridine

In a nitrogen atmosphere, 17.33 g (70 mmol) of 5-chloro-2-methylimidazo[1,2-a]pyridine hydrobromide was added to 70 ml of a sodium hydrosulfide solution at room temperature, followed by stirring at 90° C. for 24 hours. After the reaction mixture was cooled, concentrated hydrochloric acid was added until the reaction mixture's pH became 3–4. The resulting precipitate was collected by filtration, washed with water and dried to yield 12.32 g (quant, yellow powder) of the desired product.

$^1$H-NMR (DMSO-d$_6$, 200 MHz) δ 2.42 (3H, s), 6.85 (1H, d, J=8.4 Hz), 6.95 (1H, d, J=8.0 Hz), 7.28 (1H, t, J=8.0 Hz), 8.13 (1H, s)

Reference Example 21
Synthesis of 5-(4-chlorobutylthio)-2-methylimidazo[1,2-a]pyridine Using 657 mg (4.0 mmol) of 5-mercapto-2-methylimidazo-[1,2-a]pyridine, 0.70 ml (5.0 mmol) of triethylamine and 0.58 ml (5.0 mmol) of 1-bromo-4-chlorobutane, the same procedure as in Reference Example 1 was followed, to yield 838 mg (82.3%, light orange solid) of the desired product.

$^1$H-NMR (CDCl$_3$, 200 MHz) δ 1.62–1.96 (4H, m), 2.49 (3H, d, J=1.2 Hz), 3.01 (2H, t, J=7.0 Hz), 3.55 (2H, t, J=6.2 Hz), 6.86 (1H, dd, J=1.0, 7.2 Hz), 7.11 (1H, dd, J=7.2, 9.0 Hz), 7.47 (1H, d, J=9.2 Hz), 7.59 (1H, d, J=0.6 Hz); IR (neat) 3059, 2943, 1487, 1319, 1215, 1157, 771, 735, 690 cm$^{-1}$

Reference Example 22
Synthesis of 3-[4-(2-methylimidazo[1,2-a]pyridin-5-ylthio)butyl]thiazolidine-2,4-dione Using 0.76 g (3.0 mmol) of 5-(4-chlorobutylthio)-2-methylimidazo[1,2-a]pyridine, 0.35 g (3.0 mmol) of thiazolidine-2,4-dione and 0.45 ml (3.0 mmol) of 1,8-diazabicyclo[5.4.0]-7-undecene, the same procedure as in Reference Example 2 was followed, to yield 0.78 g (77.7%, light yellow oily substance) of the desired product.

$^1$H-NMR (CDCl$_3$, 200 MHz) δ 1.58–1.84 (2H, m), 2.49 (3H, s), 2.99 (2H, t, J=5.8 Hz), 3.63 (2H, t, J=7.0 Hz), 3.93 (3H, s), 6.86 (1H, dd, J=0.8, 7.8 Hz), 7.11 (1H, dd, J=7.2, 9.0 Hz), 7.48 (2H, d, J=9.2 Hz), 7.60 (1H, s); IR (neat) 2939, 1749, 1674, 1485, 1348, 1321, 1132, 771, 735 cm$^{-1}$

Reference Example 23
Synthesis of 4-amino-2-(3-ethoxycarbonylpropylthio) pyrimidine In a nitrogen atmosphere, 28.6 ml (200 mmol) of ethyl 4-bromobutyrate was added to a solution of 25.44 g (200 mmol) of 2-thiocytosine and 30.7 ml (220 mmol) of triethylamine in 400 ml of ethanol at room temperature, followed by refluxing for 16 hours. After the reaction mixture was cooled, the solvent was distilled off. The residue was dissolved in chloroform, washed with saturated aqueous sodium hydrogen carbonate and dried, after which the solvent was distilled off. The residue was purified by column chromatography (eluent, n-hexane/ethyl acetate=1/4→1/9) to yield 46.31 g (96.0%, white crystal) of the desired product.

$^1$H-NMR (CDCl$_3$, 200 MHz) δ 1.26 (3H, t, J=7.2 Hz), 2.06 (2H, quint., J=7.0 Hz), 2.47 (2H, t, J=7.4 Hz), 3.14 (1H, t, J=7.2 Hz), 4.14 (2H, q, J=7.0 Hz), 5.03 (2H, s), 6.12 (1H, d, J=5.6 Hz), 8.02 (1H, d, J=5.8 Hz)

Reference Example 24
Synthesis of 4-amino-2-(4-hydroxybutylthio)pyrimidine

To a solution of 6.03 g (25 mmol) of 4-amino-2-(3-ethoxycarbonylpropylthio)pyrimidine in 150 ml of tetrahydrofuran, 0.949 g (150 mmol) of lithium aluminum hydride was added at room temperature, followed by stirring at 60° C. for 2 hours. After the reaction mixture was cooled, water was added little by little to decompose the excess aluminum reagent. After anhydrous magnesium sulfate was added to the mixture, the precipitate was filtered off, after which the solvent was distilled off to yield 8.85 g (88.8%, white crystal) of the desired product.

$^1$H-NMR (DMSO-$d_6$, 200 MHz) δ 1.49–1.69 (4H, m), 3.01 (2H, t, J=6.6 Hz), 3.40–3.46 (2H, m), 4.41 (1H, t, J=5.0 Hz), 6.12 (1H, d, J=5.8 Hz), 6.86 (1H, s), 7.88 (1H, d, J=5.4 Hz)

Reference Example 25

Synthesis of 5-(4-hydroxybutylthio)imidazo[1,2-c]pyrimidine

To a solution of 4.98 g (25 mmol) of 4-amino-2-(4-hydroxybutylthio)pyrimidine in 70 ml of ethanol, 30 ml of a 40% chloroacetaldehyde solution was added, followed by refluxing for 4 hours. After the reaction mixture was cooled, the solvent was distilled off. The residue was dissolved in chloroform, washed with saturated aqueous sodium hydrogen carbonate and dried, after which the solvent was distilled off. The residue was purified by column chromatography (eluent, n-hexane/ethyl acetate=1/1→1/4→ethyl acetate) to yield 3.15 g (56.4%, white crystal) of the desired product.

$^1$H-NMR (CDCl$_3$, 200 MHz) δ 1.69–1.83 (2H, m), 1.92–1.97 (2H, m), 2.42 (1H, s), 3.43 (2H, t, J=7.2 Hz), 3.75 (2H, t, J=5.8 Hz), 7.30 (1H, dd, J=0.6, 6.6 Hz), 7.52 (1H, dd, J=0.6, 1.4 Hz), 7.65 (1H, d, J=1.8 Hz), 7.83 (1H, d, J=6.6 Hz)

Reference Example 26

Synthesis of 3-[4-(imidazo[1,2-c]pyrimidin-5-ylthio)butyl]thiazolidine-2,4-dione Using 2.23 g (10 mmol) of 5-(4-hydroxybutylthio)imidazo[1,2-c]pyrimidine, 1.53 ml (11 mmol) of triethylamine and 0.85 ml (11 mmol) of methanesulfonyl chloride, the same procedure as in Reference Example 8 was followed, to yield 5-(4-methanesulfonyloxybutylthio)-imidazo[1,2-c]pyrimidine.

$^1$H-NMR (CDCl$_3$, 200 MHz) δ 1.94–2.10 (4H, m), 3.02 (3H, s), 3.42–3.49 (2H, m), 4.27–4.33 (2H, m), 7.33 (1H, d, J=6.4 Hz), 7.52 (1H, d, J=1.4 Hz), 7.67 (1H, d, J=1.4 Hz), 7.85 (1H, d, J=6.4 Hz); IR (neat) 2927, 1624, 1466, 1344, 1196, 1171, 1039, 970, 933, 771, 528 cm$^{-1}$ Using the above product, 1.17 g (10 mmol) of thiazolidine-2,4-dione and 1.50 ml (10 mmol) of 1,8-diazabicyclo[5.4.0]-7-undecene, the same procedure as in Reference Example 8 was followed, to yield 1.95 g (60.5%, yellow crystal) of the desired product.

$^1$H-NMR (CDCl$_3$, 200 MHz) δ 1.81–1.90 (4H, m), 3.42 (2H, t, J=7.0 Hz), 3.70 (2H, t, J=7.0 Hz), 3.96 (2H, s), 7.31 (1H, d, J=6.2 Hz), 7.51 (1H, s), 7.66 (1H, d, J=1.4 Hz), 7.84 (1H, d, J=6.4 Hz)

Reference Example 27

Synthesis of 3-[4-(2-phenylimidazo[1,2-a]pyridin-8-yloxy)butyl]thiazolidine-2,4-dione To a solution of 5.69 g (20 mmol) of 3-[4-(2-aminopyridin-3-yloxy)butyl]thiazolidine-2,4-dione in 40 ml of ethanol, 3.98 g (20 mmol) of bromoacetophenone was added at room temperature, followed by refluxing for 1.5 hours. After the reaction mixture was cooled, the solvent was distilled off. The residue was dissolved in chloroform, washed with saturated aqueous sodium hydrogen carbonate and dried, after which the solvent was distilled off. The residue was purified by column chromatography (eluent, n-hexane/ethyl acetate=1/4) to yield 5.24 g (68.7%, light orange crystal) of the desired product.

$^1$H-NMR (CDCl$_3$, 200 MHz) δ 1.86–2.04 (4H, m), 3.74 (2H, t, J=6.8 Hz), 3.96 (2H, s), 4.23 (2H, t, J=6.4 Hz), 6.45 (1H, dd, J=0.6, 7.8 Hz), 6.66 (1H, dd, J=6.8, 7.6 Hz), 7.30–7.46 (3H, m), 7.76 (1H, dd, J=1.2, 6.8 Hz), 7.83 (1H, s), 7.97–8.02 (2H, m)

Reference Example 28

Synthesis of 3-[4-(2-ethoxycarbonylimidazo[1,2-a]pyridin-8-yloxy)butyl]thiazolidine-2,4-dione Using 5.69 g (20 mmol) of 3-[4-(2-aminopyridin-3-yloxy)butyl]thiazolidine-2,4-dione and 2.51 ml (20 mmol) of ethyl bromopyruvate, the same procedure as in Reference Example 27 was followed, to yield 3.28 g (43.5%, light orange oily substance) of the desired product.

$^1$H-NMR (CDCl$_3$, 200 MHz) δ 1.43 (3H, t, J=7.2 Hz), 1.86–2.04 (4H, m), 3.73 (2H, t, J=6.6 Hz), 4.00 (2H, s), 4.18 (2H, t, J=6.0 Hz), 4.44 (2H, q, J=7.2 Hz), 6.49 (1H, d, J=7.6 Hz), 6.76 (1H, t, J=6.8 Hz), 7.76 (1H, dd, J=0.8, 6.8 Hz), 8.16 (1H, s)

Reference Example 29

Synthesis of 3-[4-(2-aminopyridin-3-yloxy)butyl]oxazolidine-2,4-dione

Using 15.05 g (75 mmol) of 2-amino-3-(4-chlorobutyloxy)pyridine, 10.44 g (75 mmol) of oxazolidine-2,4-dione potassium salt and 11.24 g (75 mmol) of sodium iodide, the same procedure as in Reference Example 11 was followed, to yield 12.34 g (62.0%, yellow powder) of the desired product.

$^1$H-NMR (CDCl$_3$, 200 MHz) δ 1.84–1.92 (4H, m), 3.67 (2H, t, J=6.8 Hz), 4.02 (2H, t, J=5.8 Hz), 4.71 (2H, s), 6.60 (1H, dd, J=5.0, 7.8 Hz), 6.89 (1H, dd, J=1.4, 8.0 Hz), 7.66 (1H, dd, J=1.2, 5.0 Hz); IR (KBr) 3132, 1749, 1626, 794 cm$^{-1}$

Reference Example 30

Synthesis of 3-[4-(imidazo[1,2-a]pyridin-8-yloxy)butyl]oxazolidine-2,4-dione

Using 6.63 g (25 mnmol) of 3-[4-(2-aminopyridin-3-yloxy)butyl]oxazolidine-2,4-dione and 25 ml of a 40% chloroacetaldehyde solution, the same procedure as in Reference Example 18 was followed, to yield 6.48 g (89.5%, yellow oily substance) of the desired product.

$^1$H-NMR (CDCl$_3$, 200 MHz) δ 1.90–2.05 (4H, m), 3.60–3.75 (2H, m), 4.15–4.25 (2H, m), 4.71 (2H, s), 6.46 (1H, d, J=7.4 Hz), 6.69 (1H, t, J=7.0 Hz), 7.55–7.65 (2H, m), 7.78 (1H, d, J=5.8 Hz); IR (neat) 2949, 1817, 1732, 1549, 740 cm$^{-1}$ Preparation Example 1

Synthesis of 5-(2-thienylmethylene)-3-[4-(imidazo[1,2-a]pyridin-5-ylthio) butyl]thiazolidine-2,4-dione To a solution of 1.81 g (7.5 mmol) of 5-(4-chlorobutylthio)imidazo[1,2-a]pyridine and 1.59 g (7.5 mmol) of 5-(2-thienylmethylene)thiazolidine-2,4-dione in 70 ml of N,N-dimethylformamide, 1.12 ml (7.5 mmol) of 1,8-diazabicyclo[5.4.0-7-undecene was added, followed by heating at 80° C. for 16 hours. After cooling, the reaction mixture was poured into water, extracted with ethyl acetate, washed with water and dried, after which the solvent was distilled off. The residue was purified by column chromatography (eluent, hexane/ethyl acetate=2/1→1/1→ethyl acetate). The resulting crude crystal was purified by recrystallization (solvent, chloroform/diethyl ether) to yield 1.54 g (49.5%, light yellow crystal) of the desired product.m.p.

116.0°–117.0° C.; $^1$H-NMR (CDCl$_3$, 200 MHz) δ 1.64–1.92 (4H, m), 3.03 (2H, t, J=7.0 Hz), 3.76 (2H, t, J=7.0 Hz), 6.92 (1H, dd, J=1.0, 7.0 Hz), 7.15 (1H, dd, J=7.2, 9.2 Hz), 7.21 (1H, dd, J=3.8, 5.2 Hz), 7.42 (1H, d, J=3.6 Hz), 7.58 (1H, d, J=9.0 Hz), 7.68 (1H, d, J=5.0 Hz), 7.70 (1H, d, J=1.4 Hz), 7.85 (1H, s), 8.05 (1H, s); IR (KBr) 1728, 1678, 1599, 1369, 1128, 773, 727 cm$^{-1}$; Anal. Calcd for C$_{19}$H$_{17}$N$_3$O$_2$S$_3$: C, 54.92; H, 4.12; N, 10.11. Found: C, 54.67, H, 4.18; N, 10.03

Preparation Example 2
Synthesis of 5-butylidene-3-[4-(imidazo[1,2-a]pyridin-5-ylthio)butyl]thiazolidine-2,4-dione hydrochloride
i) Synthesis of 5-butylidene-3-[4-(imidazo[1,2-a]pyridin-5-ylthio)butyl]thiazolidine-2,4-dione To a solution of 1.61 g (5.0 mmol) of 3-[4-(imidazo[1,2-a]pyridin-5-ylthio)butyl]thiazolidine-2,4-dione and 0.45 ml (5.0 mmol) of n-butyraldehyde in 50 ml of ethanol, 0.05 ml (0.5 mmol) of piperidine was added, followed by refluxing for 2 hours. After the reaction mixture was cooled, the solvent was distilled off. The residue was dissolved in chloroform, washed with saturated aqueous sodium hydrogen carbonate and dried, after which the solvent was distilled off. The residue was purified by column chromatography (eluent, ethyl acetate) to yield 1.89 g (quant, light yellow oily substance) of the desired product.

$^1$H-NMR (CDCl$_3$, 200 MHz) δ 0.98 (3H, t, J=7.4 Hz), 1.48–1.98 (6H, m), 2.21 (2H, q, J=7.4 Hz), 3.02 (2H, t, J=6.8 Hz), 3.70 (2H, t, J=7.0 Hz), 6.92 (1H, dd, J=1.0, 7.0 Hz), 7.07 (2H, t, J=7.6 Hz), 7.17 (1H, dd, J=7.2, 9.0 Hz), 7.60 (1H, d, J=8.8 Hz), 7.71 (1H, s), 7.84 (1H, s); IR (neat) 2958, 1741, 1682, 1633, 1350, 1143, 957, 781, 734 cm$^{-1}$
ii) Synthesis of 5-butylidene-3-[4-(imidazo[1,2-a]pyridin-5-ylthio)butyl]thiazolidine-2,4-dione hydrochloride To a solution of 1.89 g (5.0 mmol) of 5-butylidene-3-[4-(imidazo[1,2-a]pyridin-5-ylthio)butyl]thiazolidine-2,4-dione in 50 ml of methanol, 0.5 ml of concentrated hydrochloric acid was added. After the solvent was distilled off, the residue was washed with diethyl ether to yield 2.01 g (98%, light yellow solid) of the desired product.

m.p. 119.0°–120.0° C.; $^1$H-NMR (CD$_3$OD, 200 MHz) δ 0.98 (3H, t, J=7.4 Hz), 1.50–1.88 (6H, m), 2.23 (2H, q, J=7.4 Hz), 3.34 (2H, t, J=6.8 Hz), 3.72 (2H, t, J=6.6 Hz), 7.04 (1H, t, J=7.6 Hz), 7.58 (1H, dd, J=1.2, 7.4 Hz), 7.82–7.99 (2H, m), 8.14 (1H, d, J=2.2 Hz), 8.32 (1H, d, J=2.2 Hz); Anal. Calcd for C$_{18}$H$_{22}$ClN$_3$O$_2$S$_2$: C, 52.48; H, 5.38; N, 10.20. Found: C, 52.41, H, 5.29; N, 9.97

Preparation Example 3
Synthesis of 5-butylidene-3-[5-(imidazo[1,2-a]pyridin-5-yl)pentyl]thiazolidine-2,4-dione hydrochloride
i) Synthesis of 5-butylidene-3-[5-(imidazo[1,2-a]pyridin-5-yl)pentyl]thiazolidine-2,4-dione To a solution of 1.56 g (5.14 mmol) of 3-[5-(imidazo[1,2-a]pyridin-5-yl)pentyl]thiazolidine-2,4-dione and 0.46 ml (5.14 mmol) of n-butyraldehyde in 50 ml of ethanol, 0.05 ml (0.5 mmol) of piperidine was added, followed by refluxing for 2 hours. After the reaction mixture was cooled, the solvent was distilled off. The residue was dissolved in chloroform, washed with saturated aqueous sodium hydrogen carbonate and dried, after which the solvent was distilled off. The residue was purified by column chromatography (eluent, ethyl acetate→ethyl acetate/ethanol=10/1) to yield 1.37 g (74.6%, light yellow oily substance) of the desired product.

$^1$H-NMR (CDCl$_3$, 200 MHz) δ 0.98 (3H, t, J=7.4 Hz), 1.43–1.94 (6H, m), 2.22 (2H, q, J=7.4 Hz), 2.89 (2H, t, J=8.2 Hz), 3.72 (2H, t, J=7.2 Hz), 6.62 (1H, d, J=7.0 Hz), 7.09 (1H, t, J=7.6 Hz), 7.18 (1H, dd, J=6.8, 9.0 Hz), 7.55 (1H, s), 7.56 (1H, d, J=8.4 Hz), 7.70 (1H, s); IR (neat) 2924, 1738, 1674, 1633, 1512, 1342, 1147, 781, 737, 696 cm$^{-1}$
ii) Synthesis of 5-butylidene-3-[5-(imidazo[1,2-a]pyridin-5-yl)pentyl]thiazolidine-2,4-dione hydrochloride To a solution of 1.11 g (3.11 mmol) of 5-butylidene-3-[5-(imidazo[1,2-a]pyridin-5-yl)pentyl]thiazolidine-2,4-dione in 50 ml of methanol, 0.4 ml of concentrated hydrochloric acid was added. After the solvent was distilled off, the residue was washed with diethyl ether to yield 1.18 g (96%, light yellow oily substance) of the desired product.

$^1$H-NMR (CD$_3$OD, 200 MHz) δ 0.98 (3H, t, J=7.4 Hz), 1.44–1.95 (8H, m), 2.24 (2H, q, J=7.6 Hz), 3.18 (2H, t, J=7.2 Hz), 3.71 (2H, t, J=7.0 Hz), 7.05 (1H, t, J=7.6 Hz), 7.37 (1H, d, J=6.6 Hz), 7.82–7.99 (2H, m), 8.10 (1H, d, J=2.2 Hz), 8.32 (1H, d, J=2.2 Hz); Anal. Calcd for C$_{19}$H$_{24}$ClN$_3$O$_2$S.0.5H$_2$O: C, 56.64; H, 6.25; N, 10.43. Found; C, 56.67, H, 6.37; N, 10.17

Preparation Example 4
Synthesis of 5-butylidene-3-[3-(imidazo[1,2-a]pyridin-5-ylthio)propyl]thiazolidine-2,4-dione hydrochloride
i) Synthesis of 5-butylidene-3-[3-(imidazo[1,2-a]pyridin-5-ylthio)propyl]thiazolidine-2,4-dione To a solution of 2.0 g (6.51 mmol) of 3-[3-(imidazo-[1,2-a]pyridin-5-ylthio)propyl]thiazolidine-2,4-dione and 0.59 ml (6.51 mmol) of n-butyraldehyde in 30 ml of ethanol, 0.06 ml (0.65 mmol) of piperidine was added, followed by refluxing for 2 hours. After the reaction mixture was cooled, the solvent was distilled off. The residue was dissolved in chloroform, washed with saturated aqueous sodium hydrogen carbonate and dried, after which the solvent was distilled off. The residue was purified by column chromatography (eluent, hexane/ethyl acetate=1/1→1/4) to yield 1.57 g (66.7%, light orange oily substance) of the desired product.

$^1$H-NMR (CDCl$_3$, 200 MHz) δ 0.98 (3H, t, J=7.4 Hz), 1.51–1.66 (2H, m), 1.94 (2H, quint., J=7.0 Hz), 2.22 (2H, q, J=7.2 Hz), 2.98 (2H, t, J=7.2 Hz), 3.85 (2H, t, J=7.2 Hz), 6.98 (1H, d, J=6.6 Hz), 7.09 (1H, t, J=7.6 Hz), 7.16 (1H, dd, J=7.0, 9.2 Hz), 7.61 (1H, d, J=8.4 Hz), 7.71 (1H, s), 7.88 (1H, s); IR (neat) 2960, 2872, 1743, 1684, 1635, 1487, 1360, 1344, 1288, 1142, 783, 735 cm$^{-1}$
ii) Synthesis of 5-butylidene-3-[3-(imidazo[1,2-a]pyridin-5-ylthio)propyl]thiazolidine-2,4-dione hydrochloride To a solution of 1.27 g (3.51 mmol) of 5-butylidene-3-[3-(imidazo[1,2-a]pyridin-5-ylthio)propyl]thiazolidine-2,4-dione in 30 ml of methanol, 0.35 ml of concentrated hydrochloric acid was added. After the solvent was distilled off, the residue was washed with diethyl ether to yield 1.33 g (95.4%, light orange solid) of the desired product.

m.p. 147.0°–149.0° C.; Anal. Calcd for C$_{17}$H$_{20}$ClN$_3$O$_2$S$_2$.0.4H$_2$O: C, 50.40; H, 5.17; N, 10.37. Found: C, 50.60; H, 5.30; N, 10.04

Preparation Example 5
Synthesis of 5-butylidene-3-[2-(imidazo[1,2-a]pyridin-5-ylthio)ethyl]thiazolidine-2,4-dione hydrochloride
i) Synthesis of 5-butylidene-3-[2-(imidazo[1,2-a]pyridin-5-ylthio)ethyl]thiazolidine-2,4-dione To a solution of 1.49 g (3.9 mmol) of 3-[2-(imidazo-[1,2-a]pyridin-5-ylthio)ethyl]thiazolidine-2,4-dione and 0.36 ml (4.0 mmol) of n-butyraldehyde in 30 ml of ethanol, 0.04 ml (0.4 mmol) of piperidine was added, followed by refluxing for 2 hours. After the reaction mixture was cooled, the solvent was distilled off. The residue was dissolved in chloroform, washed with saturated aqueous sodium hydrogen carbonate and dried, after which the solvent was distilled off. The residue was purified by column chromatography (eluent, hexane/ethyl acetate=2/1→1/4), followed by recrystallization (solvent, chloroform-diethyl ether-n-hexane) to yield 0.872 g (56.1%, white crystal) of the desired product.

$^1$H-NMR (CDCl$_3$, 200 MHz) δ 0.99 (3H, t, J=7.4 Hz), 1.61 (2H, quint., J=7.6 Hz), 2.21 (2H, q, J=7.6 Hz), 3.26 (2H, t, J=6.6 Hz), 3.96 (2H, t, J=7.0 Hz), 7.07 (1H, t, J=7.6 Hz), 7.11–7.24 (2H, m), 7.61 (1H, dd, J=1.6, 9.6 Hz), 7.71 (1H, d, J=1.2 Hz), 7.85 (1H, s)

ii) Synthesis of 5-butylidene-3-[2-(imidazo[1,2-a]pyridin-5-ylthio)ethyl]thiazolidine-2,4-dione hydrochloride To a solution of 0.723 g (2.1 mmol) of 5-butylidene-3-[2-(imidazo[1,2-a]pyridin-5-ylthio)ethyl]thiazolidine-2,4-dione in 20 ml of methanol, 0.25 ml of concentrated hydrochloric acid was added. After the solvent was distilled off, the residue was washed with diethyl ether to yield 0.755 g (94.2%, light yellow solid) of the desired product.

m.p. 164.0°–166.0° C.; Anal. Calcd for C$_{16}$H$_{18}$ClN$_3$O$_2$S$_2$: C, 50.06; H, 4.73; N, 10.94. Found: C, 49.82; H, 4.65; N, 10.93

Preparation Example 6

Synthesis of 5-decylidene-3-[4-(imidazo[1,2-a]pyridin-5-ylthio)butyl]thiazolidine-2,4-dione hydrochloride i) Synthesis of 5-decylidene-3-[4-(imidazo[1,2-a]pyridin-5-ylthio)butyl]thiazolidine-2,4-dione To a solution of 2.41 g (7.5 mmol) of 3-[4-(imidazo-[1,2-a]pyridin-5-ylthio)butyl]thiazolidine-2,4-dione and 1.41 ml (7.5 mmol) of decylaldehyde in 50 ml of ethanol, 0.08 ml (0.8 mmol) of piperidine was added, followed by refluxing for 2 hours. After the reaction mixture was cooled, the solvent was distilled off. The residue was dissolved in chloroform, washed with saturated aqueous sodium hydrogen carbonate and dried, after which the solvent was distilled off. The residue was purified by column chromatography (eluent, hexane/ethyl acetate=1/1→1/2) to yield 2.59 g (75.1%, light yellow oily substance) of the desired product.

$^1$H-NMR (CDCl$_3$, 200 MHz) δ 0.88 (3H, t, J=6.8 Hz), 1.20–1.35 (12H, m), 1.48–1.90 (6H, m), 2.23 (2H, q, J=7.4 Hz), 3.02 (2H, t, J=7.0 Hz), 3.70 (2H, t, J=6.8 Hz), 6.91 (1H, d, J=6.6 Hz), 7.07 (1H, t, J=7.6 Hz), 7.15 (1H, dd, J=7.0, 9.0 Hz), 7.59 (1H, d, J=9.2 Hz), 7.70 (1H, s), 7.85 (1H, s); IR (neat) 2924, 1741, 1684, 1635, 1350, 1142, 781, 735 cm$^{-1}$ ii) Synthesis of 5-decylidene-3-[4-(imidazo[1,2-a]pyridin-5-ylthio)butyl]thiazolidine-2,4-dione hydrochloride To a solution of 2.24 g (4.87 mmol) of 5-decylidene-3-[4-(imidazo[1,2-a]pyridin-5-ylthio)butyl]thiazolidine-2,4-dione in 50 ml of methanol, 0.55 ml of concentrated hydrochloric acid was added. After the solvent was distilled off, the residue was washed with diethyl ether to yield 2.38 g (98%, light yellow solid) of the desired product.

Anal. Calcd for C$_{24}$H$_{34}$ClN$_3$O$_2$S$_2$.1.0H$_2$O: C, 56.07; H, 7.06; N, 8.17. Found: C, 56.06; H, 7.04; N, 8.22

Preparation Example 7

Synthesis of 5-butylidene-3-[4-(imidazo[1,2-a]pyridin-5-yl)butyl]thiazolidine-2,4-dione hydrochloride i) Synthesis of 5-butylidene-3-[4-(imidazo[1,2-a]pyridin-5-yl)butyl]thiazolidine-2,4-dione To a solution of 1.00 g (3.46 mmol) of 3-[4-(imidazo-[1,2-a]pyridin-5-yl)butyl]thiazolidine-2,4-dione and 0.31 ml (3.46 mmol) of n-butyraldehyde in 25 ml of ethanol, 0.03 ml (0.35 mmol) of piperidine was added, followed by refluxing for 2 hours. After the reaction mixture was cooled, the solvent was distilled off. The residue was dissolved in chloroform, washed with saturated aqueous sodium hydrogen carbonate and dried, after which the solvent was distilled off. The residue was purified by column chromatography (eluent, ethyl acetate→ethyl acetate/ethanol=10/1) to yield 1.08 g (90.8%, light yellow oily substance) of the desired product.

$^1$H-NMR (CDCl$_3$, 200 MHz) δ 0.98 (3H, t, J=7.4 Hz), 1.50–1.70 (2H, m), 1.74–1.87 (4H, m), 2.21 (2H, q, J=7.4 Hz), 2.90–2.95 (2H, m), 3.78 (2H, t, J=6.8 Hz), 6.62 (1H, d, J=6.6 Hz), 7.09 (1H, t, J=7.6 Hz), 7.16 (1H, dd, J=6.8, 9.2 Hz), 7.54 (1H, d, J=0.8 Hz), 7.55 (1H, d, J=8.8 Hz), 7.69 (1H, d, J=1.4 Hz); IR (neat) 2956, 2870, 1741, 1686, 1635, 1342, 1147, 781, 739 cm$^{-1}$ ii) Synthesis of 5-butylidene-3-[4-(imidazo[1,2-a]pyridin-5-yl)butyl]thiazolidine-2,4-dione hydrochloride To a solution of 1.08 g (3.14 mmol) of 5-butylidene-3-[4-(imidazo[1,2-a]pyridin-5-yl)butyl]thiazolidine-2,4-dione in 50 ml of methanol, 0.4 ml of concentrated hydrochloric acid was added. After the solvent was distilled off, the residue was washed with diethyl ether to yield 1.10 g (92.3%, yellow oily substance) of the desired product.

Anal. Calcd for C$_{18}$H$_{22}$ClN$_3$O$_2$S.1.0H$_2$O: C, 54.33; H, 6.08; N, 10.56. Found: C, 54.63; H, 6.01; N, 10.67

Preparation Example 8

Synthesis of 5-butylidene-3-[4-(imidazo[1,2-a]pyridin-5-yloxy)butyl]thiazolidine-2,4-dione hydrochloride i) Synthesis of 5-butylidene-3-[4-(imidazo[1,2-a]pyridin-5-yloxy)butyl]thiazolidine-2,4-dione To a solution of 1.71 g (5.6 mmol) of 3-[4-(imidazo-[1,2-a]pyridin-5-yloxy)butyl]thiazolidine-2,4-dione and 0.51 ml (5.6 mmol) of n-butyraldehyde in 50 ml of ethanol, 0.05 ml (0.5 mmol) of piperidine was added, followed by refluxing for 2 hours. After the reaction mixture was cooled, the solvent was distilled off. The residue was dissolved in chloroform, washed with saturated aqueous sodium hydrogen carbonate and dried, after which the solvent was distilled off. The residue was purified by column chromatography (eluent, ethyl acetate) to yield 1.79 g (88.9%, yellow oily substance) of the desired product.

$^1$H-NMR (CDCl$_3$, 200 MHz) δ 0.98 (3H, tr J=7.4 Hz), 1.49–1.68 (2H, m), 1.90–1.98 (4H, m), 2.22 (2H, q, J=7.6 Hz), 3.82 (2H, t, J=7.0 Hz), 4.27 (2H, t, J=5.6 Hz), 6.03 (1H, d, J=6.6 Hz), 7.16 (2H, dd, J=7.2, 9.0 Hz), 7.28 (2H, d, J=9.0 Hz), 7.59 (1H, d, J=1.0 Hz), 7.65 (1H, d, J=1.0 Hz); IR (neat) 2947, 1751, 1681, 1540, 1111, 897, 770, 734, 521 cm$^{-1}$ ii) Synthesis of 5-butylidene-3-[4-(imidazo[1,2-a]pyridin-5-yloxy)butyl]thiazolidine-2,4-dione hydrochloride To a solution of 1.79 g (4.98 mmol) of 5-butylidene-3-[4-(imidazo[1,2-a]pyridin-5-yloxy)butyl]thiazolidine-2,4-dione in 50 ml of methanol, 0.5 ml of concentrated hydrochloric acid was added. After the solvent was distilled off, the residue was washed with diethyl ether to yield 2.16 g (100%, yellow oily substance) of the desired product.

$^1$H-NMR (CD$_3$OD, 200 MHz), δ 0.99 (3H, t, J=7.2 Hz), 1.51–1.69 (2H, m), 1.92–2.05 (4H, m), 2.25 (2H, q, J=7.4 Hz), 3.83 (2H, t, J=6.8 Hz), 4.57 (2H, t, J=5.8 Hz), 6.96 (1H, d, J=8.0 Hz), 7.08 (1H, t, J=7.6 Hz), 7.54 (1H, d, J=8.8 Hz), 7.96–8.04 (2H, m), 8.15 (1H, d, J=2.2 Hz); Anal. Calcd for C$_{18}$H$_{22}$ClN$_3$O$_3$S.0.9H$_2$O: C, 52.46; H, 5.82; N, 10.20. Found: C, 52.63; H, 6.00; N, 10.01

Preparation Example 9

Synthesis of 5-butylidene-3-[4-(imidazo[1,2-a]pyridin-5-ylthio)butyl]oxazolidine-2,4-dione hydrochloride i) Synthesis of 5-butylidene-3-[4-(imidazo[1,2-a]pyridin-5-ylthio)butyl]oxazolidine-2,4-dione To a solution of 3.66 g (12 mmol) of 3-[4-(imidazo[1,2-a]pyridin-5-ylthio)butyl]oxazolidine-2,4-dione and 1.08 ml (12 mmol) of n-butyraldehyde in 50 ml of ethanol, 0.12 ml (1.2 mmol) of piperidine was added, followed by refluxing for 16 hours. After the reaction mixture was cooled, the solvent was distilled off. The residue was dissolved in chloroform, washed with saturated aqueous sodium hydrogen carbonate and dried, after which the solvent was distilled off. The residue was purified by column chromatography (eluent, hexane/ethyl acetate=2/1→1/2) to yield 1.05 g (24.3%, light yellow oily substance) of the desired product.

$^1$H-NMR (CDCl$_3$, 200 MHz) δ 0.97 (3H, t, J=7.4 Hz), 1.42–1.90 (6H, m), 2.33 (2H, q, J=7.6 Hz), 3.03 (2H, t, J=6.8 Hz), 3.61 (2H, t, J=7.0 Hz), 6.06 (1H, t, J=7.8 Hz), 6.92 (1H, d, J=6.0 Hz), 7.15 (1H, dd, J=7.0, 9.0 Hz), 7.60 (2H, d, J=9.0 Hz), 7.70 (1H, s), 7.85 (1H, s); IR (neat) 2958, 1818, 1734, 1697, 1408, 1288, 766, 737 cm$^{-1}$ ii) Synthesis of 5-butylidene-3-[4-(imidazo[1,2-a]pyridin-5-ylthio)butyl]oxazolidine-2,4-dione hydrochloride To a solution of 1.29 g (2.92 mmol) of 5-butylidene-3-[4-(imidazo[1,2-a]pyridin-5-ylthio)butyl]oxazolidine-2,4-dione in 50 ml of methanol, 0.4 ml of concentrated hydrochloric acid was added. After the solvent was distilled off, the residue was washed with diethyl ether to yield 1.29 g (100%, yellow oily substance) of the desired product.

$^1$H-NMR (CD$_3$OD, 200 MHz), δ 0.98 (3H, t, J=7.2 Hz), 1.55 (2H, quint., J=7.2 Hz), 1.75–1.91 (4H, m), 2.31 (2H, q, J=7.8 Hz), 3.35 (2H, t, J=7.0 Hz), 3.61 (2H, t, J=6.2 Hz), 6.01 (1H, t, J=7.8 Hz), 7.59 (1H, d, J=7.4 Hz), 7.81–7.99 (2H, m), 8.13 (1H, d, J=2.2 Hz), 8.32 (1H, d, J=1.8 Hz); Anal. Calcd for C$_{18}$H$_{22}$ClN$_3$O$_3$S.1.0H$_2$O: C, 52.23; H, 5.84; N, 10.15. Found: C, 54.62; H, 6.27; N, 9.64

Preparation Example 10

Synthesis of 5-propylidene-3-[4-(imidazo[1,2-a]pyridin-5-ylthio)butyl]thiazolidine-2,4-dione hydrochloride i) Synthesis of 5-propylidene-3-[4-(imidazo[1,2-a]pyridin-5-ylthio)butyl]thiazolidine-2,4-dione To a solution of 1.61 g (5 mmol) of 3-[4-(imidazo[1,2-a]pyridin-5-ylthio)butyl]thiazolidine-2,4-dione and 0.36 ml (5 mmol) of propionaldehyde in 20 ml of ethanol, 0.05 ml (0.5 mmol) of piperidine was added, followed by refluxing for 2 hours. After the reaction mixture was cooled, the solvent was distilled off. The residue was dissolved in chloroform, washed with saturated aqueous sodium hydrogen carbonate and dried, after which the solvent was distilled off. The residue was purified by column chromatography (eluent, n-hexane/ethyl acetate=1:1→1:2→1:4) to yield 1.37 g (75.8%, light orange oily substance) of the desired product.

$^1$H-NMR (CDCl$_3$, 200 MHz) δ 1.16 (3H, t, J=7.8 Hz), 1.62–1.86 (4H, m), 2.25 (2H, quint., J=7.6 Hz), 3.01 (2H, t, J=7.0 Hz), 3.70 (2H, t, J=7.0 Hz), 6.91 (1H, dd, J=1.2, 7.0 Hz), 7.05 (1H, t, J=7.2 Hz), 7.15 (1H, dd, J=7.0, 8.8 Hz), 7.58 (1H, d, J=9.2 Hz), 7.69 (1H, d, J=1.4 Hz), 7.85 (1H, s); IR (neat) 2940, 1744, 1696, 1488, 1146, 785, 738 cm$^{-1}$ ii) Synthesis of 5-propylidene-3-[4-(imidazo[1,2-a]pyridin-5-ylthio)butyl]thiazolidine-2,4-dione hydrochloride To a solution of 1.37 g (3.79 mmol) of 5-propylidene-3-(4-(imidazo[1,2-a]pyridin-5-ylthio)butyl]thiazolidine-2,4-dione in 50 ml of methanol, 0.35 ml of concentrated hydrochloric acid was added. After the solvent was distilled off, the residue was washed with diethyl ether to yield 1.66 g (100%, yellow oily substance) of the desired product.

m.p. 107.0°–109.0° C.; Anal. Calcd for C$_{17}$H$_{20}$ClN$_3$O$_2$S$_2$.0.5H$_2$O: C, 50.17; H, 5.20; N, 10.33. Found: C, 50.26; H, 5.24; N, 10.37

Preparation Example 11

Synthesis of 5-ethylidene-3-[4-(imidazo[1,2-a]pyridin-5-ylthio)butyl]thiazolidine-2,4-dione hydrochloride i) Synthesis of 5-ethylidene-3-[4-(imidazo[1,2-a]pyridin-5-ylthio)butyl]thiazolidine-2,4-dione To a solution of 2.25 g (7.0 mmol) of 3-[4-(imidazo[1,2-a]pyridin-5-ylthio)butyl]thiazolidine-2,4-dione and 0.35 g (7.0 mmol) of acetaldehyde in 30 ml of ethanol, 0.07 ml (0.7 mmol) of piperidine was added, followed by refluxing for 5 hours. After the reaction mixture was cooled, the solvent was distilled off. The residue was dissolved in chloroform, washed with saturated aqueous sodium hydrogen carbonate and dried, after which the solvent was distilled off. The residue was purified by column chromatography (eluent, hexane/ethyl acetate=1/1→1/2) to yield 0.48 g (19.7%, yellow oily substance) of the desired product.

$^1$H-NMR (CDCl$_3$, 200 MHz) δ 1.58–1.88 (4H, m), 1.95 (3H, d, J=7.2 Hz), 3.01 (2H, t, J=7.0 Hz), 3.70 (2H, t, J=7.0 Hz), 6.90 (1H, dd, J=1.2, 7.2 Hz), 7.10 (1H, q, J=7.2 Hz), 7.14 (1H, dd, J=7.0, 9.0 Hz), 7.58 (1H, d, J=9.0 Hz), 7.69 (1H, d, J=1.2 Hz), 7.83 (1H, d, J=1.0 Hz); IR (neat) 2945, 1740, 1684, 1637, 1350, 1147, 957, 771, 729 cm$^{-1}$ ii) Synthesis of 5-ethylidene-3-[4-(imidazo[1,2-a]pyridin-5-ylthio)butyl]thiazolidine-2,4-dione hydrochloride To a solution of 0.48 g (1.38 mmol) of 5-ethylidene-3-[4-(imidazo[1,2-a]pyridin-5-ylthio)butyl]thiazolidine-2,4-dione in 50 ml of methanol, 0.25 ml of concentrated hydrochloric acid was added. After the solvent was distilled off, the residue was washed with diethyl ether to yield 0.54 g (100%, yellow oily substance) of the desired product.

Anal. Calcd for C$_{16}$H$_{18}$ClN$_3$O$_2$S$_2$.1.2H$_2$O: C, 47.39; H, 5.07; N, 10.36. Found: C, 47.25; H, 4.97; N, 10.29

Preparation Example 12

Synthesis of 5-butylidene-3-[3-(imidazo[1,2-a]pyridin-5-yl)propyl]thiazolidine-2,4-dione hydrochloride i) Synthesis of 5-butylidene-3-[3-(imidazo[1,2-a]pyridin-5-yl)propyl]thiazolidine-2,4-dione To a solution of 1.51 g (5.5 mmol) of 3-[3-(imidazo[1,2-a]pyridin-5-yl)propyl]thiazolidine-2,4-dione and 0.50 ml (5.5 mmol) of n-butyraldehyde in 30 ml of ethanol, 0.05 ml (0.5 mmol) of piperidine was added, followed by refluxing for 2 hours. After the reaction mixture was cooled, the solvent was distilled off. The residue was dissolved in chloroform, washed with water and dried, after which the solvent was distilled off. The residue was purified by column chromatography (eluent, ethyl acetate→ethyl acetate/ethanol=10/1) to yield 1.22 g (67.3%, light yellow oily substance) of the desired product.

$^1$H-NMR (CDCl$_3$, 200 MHz) δ 0.99 (3H, t, J=7.4 Hz), 1.50–1.68 (2H, m), 2.93 (2H, t, J=7.8 Hz), 3.88 (2H, t, J=7.2 Hz), 6.70 (1H, d, J=7.8 Hz), 7.11 (1H, t, J=7.8 Hz), 7.18 (1H, dd, J=7.0, 9.0 Hz), 7.52 (1H, s), 7.56 (1H, d, J=9.2 Hz), 7.70 (1H, s); IR (neat) 2962, 1745, 1693, 1637, 1362, 1153, 785, 739 cm$^{-1}$ ii) Synthesis of 5-butylidene-3-[3-(imidazo[1,2-a]pyridin-5-yl)propyl]thiazolidine-2,4-dione hydrochloride To a solution of 1.22 g (3.70 mmol) of 5-butylidene-3-[3-(imidazo[1,2-a]pyridin-5-yl)propyl]thiazolidine-2,4-dione in 50 ml of methanol, 0.4 ml of concentrated hydrochloric acid was added. After the solvent was distilled off, the residue was washed with diethyl ether to yield 1.36 g (100%, light yellow solid) of the desired product.

$^1$H-NMR (CD$_3$OD, 200 MHz) δ 0.99 (3H, t, J=7.6 Hz), 1.51–1.69 (2H, m), 2.16–2.30 (2H, m), 3.23 (2H, t, J=7.2 Hz), 3.88 (2H, t, J=7.4 Hz), 7.08 (1H, t, J=7.8 Hz), 7.45 (1H, d, J=7.0 Hz), 7.84–8.02 (2H, m), 8.12 (1H, d, J=2.6 Hz), 8.28 (1H, d, J=2.2 Hz); Anal. Calcd for C$_{17}$H$_{20}$ClN$_3$O$_2$S.0.7H$_2$O: C, 53.95; H, 5.70; N, 11.10. Found: C, 54.28; H, 6.11; N, 10.55

Preparation Example 13

Synthesis of 5-butylidene-3-(imidazo[1,2-a]pyridin-5-ylthio)methylthiazolidine-2,4-dione hydrochloride i) Synthesis of 3-(imidazo[1,2-a]pyridin-5-ylthio)methyl-thiazolidine-2,4-dione In a nitrogen atmosphere, 2.10 g (10 mmol) of 3-bromomethylthiazolidine-2,4-dione was added to a solution of 1.50 g (10 mmol) of 5-mercaptoimidazo[1,2-a]pyridine and 1.67 ml (10 mmol) of triethylamine in 50 ml of ethanol, followed by stirring at room temperature for 16 hours. After the solvent was distilled off, the residue was dissolved in dichloromethane, washed with saturated aqueous sodium hydrogen carbonate and dried, after which the solvent was distilled off. The residue was purified by column chromatography (eluent, ethyl acetate) to yield 1.41 g (50.5%, light brown solid) of the desired product.

$^1$H-NMR (CDCl$_3$, 200 MHz) δ 3.81 (2H, s), 4.97 (2H, s), 7.10–7.19 (2H, m), 7.66–7.72 (1H, m), 7.33 (1H, d, J=1.0 Hz), 7.98 (1H, d, J=0.8 Hz)

ii) Synthesis of 5-butylidene-3-(imidazo[1,2-a]pyridin-5-ylthio)methylthiazolidine-2,4-dione To a solution of 1.41 g (5.1 mmol) of 3-(imidazo[1,2-a]pyridin-5-ylthio)methylthiazolidine-2,4-dione and 0.46 ml (5.1 mmol) of n-butyraldehyde in 30 ml of ethanol, 0.06 ml (0.6 mmol) of piperidine was added, followed by refluxing for 2 hours. After the reaction mixture was cooled, the solvent was distilled off. The residue was dissolved in chloroform, washed with water and dried, after which the solvent was distilled off. The residue was purified by column chromatography (eluent, hexane/ethyl acetate=1/2) to yield 1.26 g (74.8%, yellow oily substance) of the desired product.

$^1$H-NMR (CDCl$_3$, 200 MHz) δ 0.97 (3H, t, J=7.4 Hz), 1.50–1.63 (2H, m), 2.19 (2H, q, J=7.4 Hz), 5.03 (2H, s), 7.01 (1H, t, J=7.6 Hz), 7.06–7.13 (2H, m), 7.64–7.68 (1H, m), 7.71 (1H, d, J=1.2 Hz), 7.98 (1H, d, J=1.4 Hz); IR (neat) 2960, 2872, 1747, 1697, 1633, 1362, 1282, 1146, 899, 785, 737, 540 cm$^{-1}$ iii) Synthesis of 5-butylidene-3-(imidazo[1,2-a]pyridin-5-ylthio)methylthiazolidine-2,4-dione hydrochloride To a solution of 1.26 g (3.78 mmol) of 5-butylidene-3-(imidazo[1,2-a]pyridin-5-ylthio)methylthiazolidine-2,4-dione in 30 ml of methanol, 0.5 ml of concentrated hydrochloric acid was added. After the solvent was distilled off, the residue was washed with diethyl ether to yield 1.33 g (100%, light yellow solid) of the desired product.

Anal. Calcd for C$_{15}$H$_{16}$ClN$_3$O$_2$S$_2$.0.5H$_2$O: C, 47.55; H, 4.52; N, 11.09. Found: C, 47.81; H, 4.53; N, 11.25

Preparation Example 14

Synthesis of 5-butylidene-3-[2-(imidazo[1,2-a]pyridin-5-yl)ethyl]thiazolidine-2,4-dione hydrochloride i) Synthesis of 5-butylidene-3-[2-(imidazo[1,2-a]pyridin-5-yl)ethyl]thiazolidine-2,4-dione To a solution of 1.18 g (4.5 mmol) of 3-[2-(imidazo[1,2-a]pyridin-5-yl)ethyl]thiazolidine-2,4-dione and 0.41 ml (4.5 mmol) of n-butyraldehyde in 20 ml of ethanol, 0.05 ml (0.5 mmol) of piperidine was added, followed by refluxing for 2 hours. After the reaction mixture was cooled, the solvent was distilled off. The residue was dissolved in chloroform, washed with water and dried, after which the solvent was distilled off. The residue was purified by column chromatography (eluent, hexane/ethyl acetate=1/2) to yield 1.15 g (81.0%, light yellow oily substance) of the desired product.

$^1$H-NMR (CDCl$_3$, 200 MHz) δ 1.00 (3H, t, J=7.8 Hz), 1.55–1.70 (2H, m), 2.24 (2H, q, J=7.8 Hz), 3.25 (2H, t, J=7.8 Hz), 4.05–4.14 (2H, m), 7.70 (1H, dd, J=0.6, 6.8 Hz), 7.15 (1H, t, J=7.6 Hz), 7.15 (1H, dd, J=6.8, 9.0 Hz), 7.59 (1H, d, J=8.8 Hz), 7.73 (1H, s), 7.89 (1H, s); IR (neat) 3030, 2950, 1745, 1680, 1575, 1350, 1130, 805, 710, 650, 540 cm$^{-1}$ ii) Synthesis of 5-butylidene-3-[2-(imidazo[1,2-a]pyridin-5-yl)ethyl]thiazolidine-2,4-dione hydrochloride To a solution of 1.15 g (3.65 mmol) of 5-butylidene-3-[2-(imidazo[1,2-a]pyridin-5-yl)ethyl]thiazolidine-2,4-dione in 50 ml of methanol, 0.33 ml of concentrated hydrochloric acid was added. After the solvent was distilled off, the residue was washed with diethyl ether to yield 1.00 g (77.9%, light yellow solid) of the desired product.

m.p. 185.0°–188.0° C.; Anal. Calcd for C$_{16}$H$_{18}$ClN$_3$O$_2$S.0.2H$_2$O: C, 54.06; H, 5.22; N, 11.82. Found: C, 53.80; H, 5.21; N, 11.76

Preparation Example 15

Synthesis of 5-butylidene-3-(imidazo[1,2-a]pyridin-5-yl)methylthiazolidine-2,4-dione hydrochloride i) Synthesis of 3-(imidazo[1,2-a]pyridin-5-yl)methylthiazolidine-2,4-dione To a suspension of 1.19 g (8.0 mmol) of 5-hydroxymethylimidazo[1,2-a]pyridine in 10 ml of dichloromethane, 4.05 ml (56 mmol) of thionyl chloride was added, followed by stirring at room temperature for 1 hour, after which the solvent was distilled off. To a solution of this residue and 0.94 g (8.0 mmol) of thiazolidine-2,4-dione in 15 ml of N,N-dimethylformamide, 2.40 ml (16.0 mmol) of 1,8-diazabicyclo[5.4.0]-7-undecene was added, followed by stirring at 80° C. for 16 hours. After the reaction mixture was cooled, water was added; the mixture was extracted with ethyl acetate and dried, after which the solvent was distilled off. The residue was purified by recrystallization (solvent, chloroform/ethyl acetate/diethyl ether) to yield 247 mg (12.5%, light brown powder) of the desired product.

$^1$H-NMR (CDCl$_3$, 200 MHz) δ 4.02 (2H, s), 5.06 (2H, s), 6.98 (1H, d, J=6.6 Hz), 7.18 (1H, dd, J=7.0, 9.0 Hz), 7.66 (1H, d, J=9.0 Hz), 7.70 (1H, d, J=1.0 Hz), 7.89 (1H, s)

ii) Synthesis of 5-butylidene-3-(imidazo[1,2-a]pyridin-5-yl)methylthiazolidine-2,4-dione To a solution of 223 mg (0.9 mmol) of 3-(imidazo[1,2-a]pyridin-5-yl)methylthiazolidine-2,4-dione and 0.09 ml (1.0 mmol) of n-butyraldehyde in 5 ml of ethanol, 0.001 ml (0.1 mmol) of piperidine was added, followed by refluxing for 2 hours. After the reaction mixture was cooled, the solvent was distilled off. The residue was dissolved in chloroform, washed with water and dried, after which the solvent was distilled off. The residue was purified by column chromatography (eluent, hexane/ethyl acetate=1/4) to yield 222 mg (82.2%, light yellow oily substance) of the desired product.

$^1$H-NMR (CDCl$_3$, 200 MHz) δ 0.98 (3H, t, J=7.4 Hz), 1.59 (2H, quint., J=7.6 Hz), 2.23 (2H, q, J=7.6 Hz), 5.12 (2H, s), 6.97 (1H, d, J=7.0 Hz), 7.16 (1H, t, J=7.6 Hz), 7.19 (1H, dd, J=7.0, 9.2 Hz), 7.65 (1H, d, J=9.0 Hz), 7,70 (1H, d, J=1.4 Hz), 7.92 (1H, s); IR (neat) 2960, 2872, 1743, 1685, 1635, 748, 663, 527 cm$^{-1}$ iii) Synthesis of 5-butylidene-3-(imidazo[1,2-a]pyridin-5-yl)methylthiazolidine-2,4-dione hydrochloride To a solution of 220 mg (0.74 mmol) of 5-butylidene-3-(imidazo[1,2-a]pyridin-5-yl)methyl]thiazolidine-2,4-dione in 10 ml of methanol, 0.08 ml (1.0 mmol) of concentrated hydrochloric acid was added. After the solvent was distilled off, the residue was washed with diethyl ether to yield 250 mg (100%, light yellow oily substance) of the desired product.

Anal. Calcd for C$_{15}$H$_{15}$ClN$_3$O$_2$S.1.0H$_2$O: C, 50.77; H, 4.83; N, 11.84. Found: C, 50.81; H, 5.00; N, 11.54

Preparation Example 16

Synthesis of 5-butylidene-3-[5-(imidazo[1,2-a]pyridin-5-yl)pentyl]oxazolidine-2,4-dione hydrochloride i) Synthesis of 5-butylidene-3-[5-(imidazo[1,2-a]pyridin-5-yl)pentyl]oxazolidine-2,4-dione To a solution of 3.45 g (12 mmol) of 3-[5-(imidazo[1,2-a]pyridin-5-yl)pentyl]oxazolidine-2,4-dione and 1.08 ml (12 mmol) of n-butyraldehyde in 50 ml of ethanol, 0.12 ml (1.2 mmol) of piperidine was added, followed by refluxing for 16 hours. After the reaction mixture was cooled, the solvent was distilled off. The residue was dissolved in chloroform, washed with saturated aqueous sodium hydrogen carbonate and dried, after which the solvent was distilled off. The residue was purified by column chromatography (eluent, hexane/ethyl acetate=1/2→ethyl acetate/ethanol=10/1) to yield 1.36 g (33.2%, light yellow oily substance) of the desired product.

$^1$H-NMR (CDCl$_3$, 200 MHz) δ 0.97 (3H, t, J=7.3 Hz), 1.45–1.60 (2H, m), 1.72–1.94 (4H, m), 2.33 (2H, q, J=7.5 Hz), 2.90 (2H, t, J=8.1 Hz), 3.63 (2H, t, J=7.1 Hz), 6.06 (1H, t, J=8.1 Hz), 6.61 (1H, d, J=6.3 Hz), 7.16 (1H, dd, J=6.9, 9.1 Hz), 7.52–7.57 (2H, m), 7.69 (1H, d, J=1.3 Hz); IR (neat) 2933, 1815, 1734, 1409, 765 cm$^{-1}$ ii) Synthesis of 5-butylidene-3-[5-(imidazo[1,2-a]pyridin-5-yl)pentyl]oxazolidine-2,4-dione hydrochloride To a solution of 1.36 g (3.98 mmol) of 5-butylidene-3-[5-(imidazo[1,2-a]pyridin-5-yl)pentyl]oxazolidine-2,4-dione in 50 ml of methanol, 0.45 ml of concentrated hydrochloric acid was added. After the solvent was distilled off, the residue was washed with diethyl ether to yield 1.52 g (100%, yellow oily substance) of the desired product.

Anal. Calcd for C$_{19}$H$_{24}$ClN$_3$O$_3$.0.8H$_2$O: C, 58.17; H, 6.58; N, 10.71. Found: C, 58.26; H, 6.84; N, 10.49

Preparation Example 17

Synthesis of 3-[4-(imidazo[1,2-a]pyridin-5-ylthio)butyl]-5-butylidenehydantoin hydrochloride i) Synthesis of 3-[4-(imidazo[1,2-a]pyridin-5-ylthio)-butyl]hydantoin To a solution of 2.41 g (10.0 mmol) of 5-(4-chlorobutylthio)imidazo[1,2-a]pyridine and 1.00 g (10.0 mmol) of hydantoin in 30 ml of N,N-dimethylformamide, 1.50 ml (10.0 mmol) of 1,8-diazabicyclo[5.4.0]-7-undecene was added, followed by stirring at 80° C. for 16 hours. After the reaction mixture was cooled, water was added; the mixture was extracted with ethyl acetate and dried, after which the solvent was distilled off. The residue was purified by column chromatography (eluent, chloroform/methanol=20/1→10/1) to yield 1.27 g (41.7%, yellow solid) of the desired product.

$^1$H-NMR (CDCl$_3$, 200 MHz) δ 1.59–1.89 (4H, m), 3.03 (2H, t, J=7.2 Hz), 3.53 (2H, t, J=6.8 Hz), 3.94 (2H, d, J=1.2 Hz), 5.68 (1H, s), 6.92 (1H, dd, J=1.0, 7.0 Hz), 7.16 (1H, dd, J=7.0, 8.8 Hz), 7.59 (1H, dd, J=1.0, 9.0 Hz), 7.70 (1H, d, J=1.2 Hz), 7.84 (1H, d, J=1.2 Hz); IR (neat) 2937, 2860, 1770, 1724, 1695, 1454, 752 cm$^{-1}$ ii) Synthesis of 3-[4-(imidazo[1,2-a]pyridin-5-ylthio)-butyl]-5-butylidenehydantoin To a solution of 1.00 g (3.29 mmol) of 3-[4-(imidazo-[1,2-a]pyridin-5-ylthio)butyl]hydantoin and 0.30 ml (3.29 mmol) of n-butyraldehyde in 10 ml of ethanol, 0.05 ml (0.6 mmol) of pyrrolidine was added, followed by refluxing for 16 hours. After the reaction mixture was cooled, the solvent was distilled off. The residue was dissolved in chloroform, washed with water and dried, after which the solvent was distilled off. The residue was purified by column chromatography (eluent, ethyl acetate/ethanol=10/1→chloroform/methanol=10/1) to yield 0.43 g (36.5%, orange-yellow oily substance) of the desired product.

$^1$H-NMR (CDCl$_3$, 200 MHz) δ 0.96 (3H, t, J=7.4 Hz), 1.44–1.59 (2H, m), 1.63–1.88 (4H, m), 2.16 (2H, q, J=7.7 Hz), 3.03 (2H, t, J=7.0 Hz), 3.58 (2H, t, J=6.9 Hz), 5.89 (1H, t, J=8.0 Hz), 6.91 (1H, dd, J=0.9, 7.0 Hz), 7.15 (1H, dd, J=7.1, 8.9 Hz), 7.58 (1H, dd, J=0.9, 8.1 Hz), 7.69 (1H, d, J=1.3 Hz), 7.84 (1H, d, J=0.9 Hz), 8.13 (1H, s); IR (neat) 2964, 2873, 1770, 1714, 1684, 764 cm$^{-1}$ iii) Synthesis of 3-[4-(imidazo[1,2-a]pyridin-5-ylthio)-butyl]-5-butylidenehydantoin hydrochloride To a solution of 0.43 g (1.20 mmol) of 3-[4-(imidazo-[1,2-a]pyridin-5-ylthio)butyl]-5-butylidenehydantoin in 10 ml of methanol, 0.17 ml of concentrated hydrochloric acid was added. After the solvent was distilled off, the residue was washed with diethyl ether to yield 0.53 g (100%, brown solid) of the desired product.

Anal. Calcd for C$_{18}$H$_{23}$ClN$_4$O$_2$S.0.6H$_2$O: C, 53.29; H, 6.01; N, 13.81. Found: C, 53.60; H, 6.11; N, 13.31

Preparation Example 18

Synthesis of 3-butylidene-1-[4-(imidazo[1,2-a]pyridin-5-ylthio)butyl]succinimide hydrochloride i) Synthesis of 3-butylidenesuccinimide A solution of 1.00 g (10.0 mmol) of maleimide and 2.00 g (10.0 mmol) of tri-n-butylphosphine in 15 ml of acetic acid was stirred at 100° C. for 40 minutes. After the reaction mixture was cooled, the solvent was distilled off at 50° C. (1 mmHg). To the residue (red oily substance), 40.6 ml (450 mmol) of n-butyraldehyde was added, followed by stirring at 100° C. for 3 hours. After the reaction mixture was cooled, the excess aldehyde was distilled off. The resulting oily substance was subjected to column chromatography (eluent, diethyl ether). The obtained residue was purified by flush chromatography (eluent, hexane/ethyl acetate=4/1→2/1) to yield 0.89 g (58.1%, light yellow solid) of the desired product.

$^1$H-NMR (CDCl$_3$, 200 MHz) δ 0.97 (3H, t, J=7.6 Hz), 1.45–1.64 (2H, m), 2.08–2.24 (2H, m), 3.27 (2H, dt, J=1.6, 2.4 Hz), 6.83 (1H, tt, J=2.2, 7.8 Hz), 8.24 (1H, s)

ii) Synthesis of 3-butylidene-1-[4-(imidazo[1,2-a]pyridin-5-ylthio)butyl]succinimide To a solution of 613 mg (4.0 mmol) of 5-(4-chlorobutylthio)imidazo[1,2-a]pyridine and 963 mg (4.0 mmol) of 3-butylidenesuccinimide in 10 ml of N,N-dimethylformamide, 0.60 ml (4.0 mmol) of 1,8-diazabicyclo-[5.4.0]-7-undecene was added, followed by stirring at 80° C. for 16 hours. After the reaction mixture was cooled, water was added; the mixture was extracted with ethyl acetate and dried, after which the solvent was distilled off. The residue was subjected to column chromatography (eluent, hexane/ethyl acetate=1/4). The obtained residue was purified using a Rober column (eluent, hexane/ethyl acetate=1/2→1/4; flow rate, 6.0 ml/min) to yield 280 mg (19.6%, light yellow oily substance) of the desired product.

$^1$H-NMR (CDCl$_3$, 200 MHz) δ 0.97 (3H, t, J=7.4 Hz), 1.45–1.82 (6H, m), 3.02 (2H, t, J=7.2 Hz), 3.17–3.20 (2H, m), 3.58 (2H, t, J=7.0 Hz), 6.82 (1H, tt, J=2.4, 7.6 Hz), 6.91 (1H, dd, J=1.0, 7.0 Hz), 7.16 (1H, dd, J=7.2, 9.0 Hz), 7.58 (1H, d, J=9.0 Hz), 7.70 (1H, d, J=1.2 Hz), 7.84 (1H, d, J=1.2 Hz); IR (neat) 2930, 2865, 1765, 1703, 1676, 775, 735 cm$^{-1}$ iii) Synthesis of 3-butylidene-1-[4-(imidazo[1,2-a]pyridin-5-ylthio)butyl]succinimide hydrochloride To a solution of 280 mg (0.78 mmol) of 3-butylidene-1-[4-(imidazo[1,2-a]pyridin-5-ylthio)butyl]succinimide in 10 ml of methanol, 0.1 ml of concentrated hydrochloric acid was added. After the solvent was distilled off, the residue was washed with diethyl ether to yield 310 mg (100%, yellow oily substance) of the desired product.

Anal. Calcd for C$_{19}$H$_{24}$ClN$_3$O$_2$S.1.2H$_2$O: C, 54.92; H, 6.40; N, 10.11. Found: C, 54.93; H, 6.29; N, 10.03

Preparation Example 19

Synthesis of 5-(3-phenylpropylidene)-3-[4-(imidazo[1,2-a]pyridin-5-ylthio)butyl]thiazolidine-2,4-dione hydrochloride i) Synthesis of 5-(3-phenylpropylidene)-3-[4-(imidazo[1,2-a]pyridin-5-ylthio)butyl]thiazolidine-2,4-dione To a solution of 1.61 g (5.0 mmol) of 3-[4-(imidazo-[1,2-a]pyridin-5-ylthio)butyl]thiazolidine-2,4-dione and 1.34 g (10 mmol) of 3-phenylpropionaldehyde in 20 ml of ethanol, 0.05 ml (0.5 mmol) of piperidine was added, followed by refluxing for 2 hours. After the reaction mixture was cooled, the solvent was distilled off. The residue was dissolved in chloroform, washed with water and dried, after which the solvent was distilled off. The residue was purified by column chromatography (eluent, hexane/ethyl acetate=1/4) to yield 2.27 g (quant, brown oily substance) of the desired product.

$^1$H-NMR (CDCl$_3$, 200 MHz) δ 1.60–1.88 (4H, m), 2.55 (2H, q, J=7.6 Hz), 2.86 (2H, t, J=7.4 Hz), 3.01 (2H, t, J=7.0 Hz), 3.68 (2H, t, J=7.0 Hz), 6.90 (1H, dd, J=1.0, 7.0 Hz), 7.08 (1H, t, J=7.6 Hz), 7.15–7.36 (6H, m), 7.58 (1H, d, J=9.0 Hz), 7.70 (1H, d, J=1.2 Hz), 7.84 (1H, s)

ii) Synthesis of 5-(3-phenylpropylidene)-3-[4-(imidazo[1,2-a]pyridin-5-ylthio)butyl]thiazolidine-2,4-dione hydrochloride To a solution of 2.27 g (5.0 mmol) of 5-(3-phenylpropylidene)-3-[4-(imidazo[1,2-a]pyridin-5-ylthio)butyl]thiazolidine-2,4-dione in 50 ml of methanol, 0.5 ml of concentrated hydrochloric acid was added. After the solvent was distilled off, the residue was washed with diethyl ether to yield 2.29 g (100%, brown oily substance) of the desired product.

Anal. Calcd for $C_{23}H_{24}ClN_3O_2S_2.0.6H_2O$: C, 56.98; H, 5.24; N, 8.67. Found: C, 56.88; H, 5.40; N, 8.55

Preparation Example 20

Synthesis of 5-phenylmethylene-3-[5-(imidazo[1,2-a]pyridin-5-ylthio)butyl]thiazolidine-2,4-dione hydrochloride i) Synthesis of 5-phenylmethylene-3-[5-(imidazo[1,2-a]pyridin-5-ylthio)butyl]thiazolidine-2,4-dione To a solution of 1.61 g (5.0 mmol) of 3-[5-(imidazo-[1,2-a]pyridin-5-ylthio)butyl]thiazolidine-2,4-dione and 0.51 ml (5.0 mmol) of benzaldehyde in 20 ml of ethanol, 0.05 ml (0.5 mmol) of piperidine was added, followed by refluxing for 3 hours. After the reaction mixture was cooled, the solvent was distilled off. The residue was dissolved in chloroform, washed with saturated aqueous sodium hydrogen carbonate and dried, after which the solvent was distilled off. The residue was purified by column chromatography (eluent, hexane/ethyl acetate=1/1→1/4) to yield 1.60 g (78.2%, light yellow solid) of the desired product.

$^1$H-NMR (CDCl$_3$, 200 MHz) δ 1.60–1.92 (4H, m), 3.03 (2H, t, J=7.2 Hz), 3.78 (2H, t, J=7.0 Hz), 6.92 (1H, dd, J=1.0, 7.0 Hz), 7.15 (1H, dd, J=7.0, 9.0 Hz), 7.44–7.60 (6H, m), 7.70 (1H, d, J=1.4 Hz), 7.86 (1H, s), 7.89 (1H, s); IR (neat) 3025, 2943, 1738, 1674, 1608, 766, 734, 689, 598, 536 cm$^{-1}$ ii) Synthesis of 5-phenylmethylene-3-[5-(imidazo[1,2-a]pyridin-5-ylthio)butyl]thiazolidine-2,4-dione hydrochloride To a solution of 1.60 g (3.91 mmol) of 5-phenylmethylene-3-[5-(imidazo[1,2-a]pyridin-5-ylthio)butyl]thiazolidine-2,4-dione in 50 ml of methanol, 0.4 ml of concentrated hydrochloric acid was added. After the solvent was distilled off, the residue was washed with diethyl ether to yield 1.68 g (96%, white solid) of the desired product.

m.p. 163.0°–164.0° C.; Anal. Calcd for $C_{21}H_{20}ClN_3O_2S_2.1.5H_2O$: C, 53.32; H, 4.90; N, 8.88. Found: C, 53.51; H, 5.03; N, 9.00

Preparation Example 21

Synthesis of 5-(4-phenylbutylidene)-3-[4-(imidazo[1,2-a]pyridin-5-ylthio)butyl]thiazolidine-2,4-dione hydrochloride i) Synthesis of 5-(4-phenylbutylidene)-3-[4-(imidazo[1,2-a]pyridin-5-ylthio)butyl]thiazolidine-2,4-dione To a solution of 1.61 g (5.0 mmol) of 5-[4-(thiazolidine-2,4-dione)butylthio]imidazo[1,2-a]pyridine and 3.86 g (10 mmol) of 4-phenylbutyraldehyde in 30 ml of ethanol, 0.05 ml (0.5 mmol) of piperidine was added, followed by refluxing for 1.5 hours. After the reaction mixture was cooled, the solvent was distilled off. The residue was dissolved in chloroform, washed with saturated aqueous sodium hydrogen carbonate and dried, after which the solvent was distilled off. The residue was purified by column chromatography (eluent, hexane/ethyl acetate=1/2) to yield 1.56 g (69.0%, light yellow oily substance) of the desired product.

$^1$H-NMR (CDCl$_3$, 200 MHz) δ 1.60–1.96 (6H, m), 2.25 (2H, q, J=7.5 Hz), 2.68 (2H, t, J=7.7 Hz), 3.01 (2H, t, J=7.0 Hz), 3.70 (2H, t, J=7.0 Hz), 6.91 (1H, dd, J=1.0, 7.0 Hz), 7.07 (1H, t, J=7.6 Hz), 7.15–7.35 (6H, m), 7.58 (1H, d, J=9.0 Hz), 7.70 (1H, d, J=1.3 Hz), 7.84 (1H, d, J=1.0 Hz); IR (neat) 3026, 2937, 1741, 1682, 1633, 1350, 1140, 957, 771, 734, 700 cm$^{-1}$ ii) Synthesis of 5-(4-phenylbutylidene)-3-[4-(imidazo[1,2-a]pyridin-5-ylthio)butyl]thiazolidine-2,4-dione hydrochloride To a solution of 1.56 g (3.45 mmol) of 5-(4-phenylbutylidene)-3-[4-(imidazo[1,2-a]pyridin-5-ylthio)butyl]thiazolidine-2,4-dione in 50 ml of methanol, 0.4 ml of concentrated hydrochloric acid was added. After the solvent was distilled off, the residue was washed with diethyl ether to yield 1.47 g (87%, light yellow foamy substance) of the desired product.

Anal. Calcd for $C_{24}H_{26}ClN_3O_2S_2.0.4H_2O$: C, 58.20; H, 5.45; N, 8.48. Found: C, 58.34; H, 5.68; N, 8.14

Preparation Example 22

Synthesis of 5-butylidene-3-[4-(imidazo[1,2-a]pyridin-8-yloxy)butyl]thiazolidine-2,4-dione hydrochloride i) Synthesis of 5-butylidene-3-[4-(imidazo[1,2-a]pyridin-8-yloxy)butyl]thiazolidine-2,4-dione To a solution of 1.22 g (4.0 mmol) of 3-[4-(imidazo-[1,2-a]pyridin-8-yloxy)butyl]thiazolidine-2,4-dione and 0.36 ml (4.0 mmol) of n-butyraldehyde in 20 ml of ethanol, 0.04 ml (0.4 mmol) of piperidine was added, followed by refluxing for 2 hours. After the reaction mixture was cooled, the solvent was distilled off. The residue was dissolved in chloroform, washed with saturated aqueous sodium hydrogen carbonate and dried, after which the solvent was distilled off. The residue was purified by column chromatography (eluent, n-hexane/ethyl acetate=1/4) to yield 1.44 g (quant, yellow oily substance) of the desired product.

$^1$H-NMR (CDCl$_3$, 200 MHz) δ 0.98 (3H, t, J=7.4 Hz), 1.49–1.67 (2H, m), 1.82–2.00 (4H, m), 2.21 (2H, q, J=7.4 Hz), 3.76–3.83 (2H, m), 4.15–4.21 (2H, m), 6.43 (1H, d, J=7.6 Hz), 6.67 (1H, t, J=7.0 Hz), 7.08 (1H, t, J=7.8 Hz), 7.54 (1H, d, J=1.2 Hz), 7.57 (1H, s), 7.76 (1H, d, J=7.8 Hz); IR (neat) 3105, 2956, 1738, 1687, 1543, 1279, 1111, 735 cm$^{-1}$ ii) Synthesis of 5-butylidene-3-[4-(imidazo[1,2-a]pyridin-8-yloxy)butyl]thiazolidine-2,4-dione hydrochloride To a solution of 1.44 g (4.0 mmol) of 5-butylidene-3-[4-(imidazo[1,2-a]pyridin-8-yloxy)butyl]thiazolidine-2,4-dione in 20 ml of methanol, 0.4 ml of concentrated hydrochloric acid was added. After the solvent was distilled off, the residue was washed with diethyl ether to yield 1.58 g (quant, yellow oily substance) of the desired product.

Anal. Calcd for $C_{18}H_{22}ClN_3O_3S.0.9H_2O$: C, 52.46; H, 5.82; N, 10.20. Found: C, 52.73; H, 5.86; N, 9.92

Preparation Example 23

Synthesis of 5-butylidene-3-[4-(2-methyl-imidazo[1,2-a]pyridin-5-ylthio)butyl]thiazolidine-2,4-dione hydrochloride i) Synthesis of 5-butylidene-3-[4-(2-methyl-imidazo[1,2-a]pyridin-5-ylthio)butyl]thiazolidine-2,4-dione To a solution of 0.67 g (2.0 mmol) of 3-[4-(2-methylimidazo[1,2-a]pyridin-5-ylthio)butyl]thiazolidine-2,4-dione and 0.18 ml (2.0 mmol) of n-butyraldehyde in 10 ml of ethanol, 0.02 ml (0.2 mmol) of piperidine was added, followed by refluxing for 2 hours. After the reaction mixture was cooled, the solvent was distilled off. The residue was dissolved in chloroform, washed with saturated aqueous sodium hydrogen carbonate and dried, after which the solvent was distilled off. The residue was purified by column chromatography (eluent, n-hexane/ethyl acetate=1/4) to yield 0.794 g (quant, light yellow oily substance) of the desired product.

$^1$H-NMR (CDCl$_3$, 200 MHz) δ 0.98 (3H, t, J=7.4 Hz), 1.48–1.86 (6H, m), 2.22 (2H, q, J=7.4 Hz), 2.49 (3H, s), 3.00 (2H, t, J=7.0 Hz), 3.70 (2H, t, J=7.0 Hz), 6.85 (1H, dd, J=1.0, 7.0 Hz), 7.08 (1H, t, J=7.6 Hz), 7.10 (1H, dd, J=7.0, 8.8 Hz), 7.47 (2H, d, J=8.8 Hz), 7.59 (1H, s); IR (neat) 2960, 2872, 1743, 1686, 1350, 771, 733 cm$^{-1}$ ii) Synthesis of 5-butylidene-3-[4-(2-methyl-imidazo[1,2-a]pyridin-5-ylthio)butyl]thiazolidine-2,4-dione hydrochloride To a solution of 0.794 g (2.0 mmol) of 5-butylidene-3-[4-(2-methyl-imidazo[1,2-a]pyridin-5-ylthio)butyl]thiazolidine-2,4-dione in 10 ml of methanol, 0.25 ml of concentrated hydrochloric acid was added. After the solvent was distilled off, the residue was washed with diethyl ether to yield 0.801 g (94.0%, light yellow solid) of the desired product.

m.p. 68.0°–69.0° C.; Anal. Calcd for C$_{19}$H$_{24}$ClN$_3$O$_2$S$_2$.1.0H$_2$O: C, 51.40; H, 5.90; N, 9.46. Found; C, 51.32; H, 5.96; N, 8.87

Preparation Example 24
Synthesis of 7-[4-(imidazo[1,2-a]pyridin-5-ylthio)butyl]-1,1-dioxo-9-phenyl-3,4-dihydro-2H,6H-pyrimido[6,1-b][1,3]thiazine-6,8(7H)-dione hydrochloride i) Synthesis of 3-benzyl-5-phenylpyrimidine-2,4,6(1H,3H)-trione To a suspension of 100 g (666 mmol) of benzylurea and 156.8 g (666 mmol) of diethyl phenylmalonate in 340 ml of methanol, 164 ml (666 mmol) of a 4.1M sodium methylate solution was added at room temperature, followed by refluxing for 16 hours. After the reaction mixture was cooled, the solvent was distilled off. After the residue was dissolved in water and insoluble substances were filtered out, the filtrate was adjusted to pH 3–4 by adding concentrated hydrochloric acid. The resulting precipitate was collected by filtration, washed with water and n-hexane-diethyl ether and dried to yield 163.23 g (83.3%, white crystal) of the desired product.

$^1$H-NMR (CDCl$_3$, 200 MHz) δ 4.61 (1H, s), 5.06 (2H, d, J=6.6 Hz), 7.14–7.43 (10H, m), 8.49 (1H, s)

ii) Synthesis of 3-benzyl-6-chloro-5-phenylpyrimidine-2,4(1H,3H)-dione

To 64 ml of 50% ethanol, 300 ml (844 mmol) of phosphorus oxychloride was added drop by drop, with stirring under ice cooling conditions. To this solution, 120 g (380 mmol) of 3-benzyl-5-phenylpyrimidine-2,4,6(1H,3H)-trione was added little by little. This mixture was stirred at 50° C. for 30 minutes and then at 100° C. for 90 minutes. After cooling, the reaction mixture was poured into ice water and stirred for 1 hour. The resulting precipitate was collected by filtration, washed with water and n-hexane and dried to yield 112.89 g (94.7%, light white crystal) of the desired product.

$^1$H-NMR (DMSO-d$_6$, 200 MHz) δ 4.98 (2H, s), 7.27–7.40 (10H, m)

iii) Synthesis of 3-benzyl-6-chloro-1-(3-chloropropyl)-5-phenylpyrimidine-2,4(1H,3H)-dione To a suspension of 78.19 g (250 mmol) of 3-benzyl-6-chloro-5-phenylpyrimidine-2,4(1H,3H)-dione and 55.3 g (400 mmol) of potassium carbonate in 450 ml of N,N-dimethylformamide, 49.4 ml (500 mmol) of 1-bromo-3-chloropropane was added at room temperature. This mixture was stirred at 80° C. for 5 hours. After cooling, the reaction mixture was concentrated to dryness; the resulting residue was dissolved in chloroform-water. After the organic layer was washed with water and dried, the solvent was distilled off to yield an oily substance, which was then purified by column chromatography (eluent, n-hexane/ethyl acetate=5/1→2/1) to yield 71.89 g (73.9%, yellow oily substance) of the desired product.

$^1$H-NMR (CDCl$_3$, 200 MHz) δ 2.18–2.30 (2H, m), 3.44–3.67 (2H, m), 4.29–4.36 (2H, m), 5.16 (2H, s), 7.28–7.56 (10H, m); IR (neat) 3032, 2968, 1711, 1649, 1612, 1431, 1360, 1281, 752, 700, 513 cm$^{-1}$ iv) Synthesis of 7-benzyl-9-phenyl-3,4-dihydro-2H,6H-pyrimido[6,1-b][1,3]thiazine-6,8(7H)-dione To a solution of 71.89 g (184.7 mmol) of 3-benzyl-6-chloro-1-(3-chloropropyl)-5-phenylpyrimidine-2,4(1H,3H)-dione in 350 ml of N,N-dimethylformamide, 29.8 g of sodium hydrosulfide n-hydrate was added under ice cooling conditions, followed by stirring for 1 hour. The reaction mixture was concentrated to dryness; the resulting residue was dissolved in methylene chloride-water. After the organic layer was washed with water and dried, the solvent was distilled off to yield a crude crystal, which was then recrystallized from dichloromethane-diethyl ether to yield 17.52 g (27.1%, white crystal) of the desired product.

$^1$H-NMR (CDCl$_3$, 200 MHz) δ 2.21 (2H, quint., J=5.8 Hz), 2.94 (2H, t, J=6.6 Hz), 4.05–4.11 (2H, m), 5.17 (2H, s), 7.23–7.42 (8H, m), 7.53–7.58 (2H, m)

v) Synthesis of 9-phenyl-3,4-dihydro-2H,6H-pyrimido[6,1-b][1,3]thiazine-6,8(7H)-dione To a solution of 17.52 g (50 mmol) of 7-benzyl-9-phenyl-3,4-dihydro-2H,6H-pyrimido-[6,1-b][1,3]thiazine-6,8(7H)-dione in 500 ml of toluene, 25 g (100 mmol) of boron tribromide was added under ice cooling conditions, followed by refluxing for 16 hours. After the reaction mixture was cooled, 100 ml of methanol was added, followed by stirring for 30 minutes. After this mixture was concentrated to dryness, methanol-diethyl ether was added to the residue. The resulting precipitate was collected by filtration, washed with diethyl ether and dried to yield 4.21 g (32.4%, light white crystal) of the desired product.

$^1$H-NMR (DMSO-d$_6$, 200 MHz) δ 2.11 (2H, quint., J=6.0 Hz), 2.99 (2H, t, J=6.6 Hz), 3.88–3.93 (2H, m), 7.16–7.21 (2H, m), 7.31–7.39 (3H, m), 11.37 (1H, s)

vi) Synthesis of 7-(4-chlorobutyl)-9-phenyl-3,4-dihydro-2H,6H-pyrimido[6,1-b][1,3]thiazine-6,8(7H)-dione To a suspension of 5.28 g (20.3 mmol) of 9-phenyl-3,4-dihydro-2H,6H-pyrimido-[6,1-b][1,3]thiazine-6,8(7H)-dione and 2.80 g (20.3 mmol) of potassium carbonate in 80 ml of N,N-dimethylformamide, 3.46 ml (30 mmol) of 1-bromo-4-chlorobutane was added at room temperature, followed by stirring at 60° C. for 2 hours and then at 100° C. for 3 hours. After cooling, the reaction mixture was concentrated to dryness. The residue was dissolved in methylene chloride-water; the organic layer was washed with water and dried. The oily substance obtained by distilling off the solvent was purified by column chromatography (eluent, n-hexane/ethyl acetate=5/1→2/1) to yield 4.58 g (64.5%, light white powder) of the desired product.

$^1$H-NMR (CDCl$_3$, 200 MHz) δ 1.73–1.79 (4H, m), 2.25 (2H, quint., J=6.0 Hz), 2.97 (2H, t, J=6.6 Hz), 3.99–4.23 (6H, m), 7.23–7.29 (2H, m), 7.36–7.43 (3H, m); IR (neat) 2954, 1720, 1687, 1628, 1439, 1180, 777, 717, 698, 532 cm$^{-1}$ vii) Synthesis of 7-(4-chlorobutyl)-1,1-dioxo-9-phenyl-3,4-dihydro-2H,6H-pyrimido[6,1-b][1,3]thiazine-6,8(7H)-dione To a solution of 4.58 g (13.1 mmol) of 7-(4-chlorobutyl)-9-phenyl-3,4-dihydro-2H$_{1,6}$H-pyrimido[6,1-b][1,3]thiazine-6,8(7H)-dione in 50 ml of methylene chloride, 3.45 g (20 mmol) of 50% m-chloroperbenzoic acid was added under ice cooling conditions, followed by stirring for 1 hour. After the resulting crystal was filtered off, the filtrate was washed with aqueous sodium hydroxide and dried. The oily substance (1-oxo compound) obtained by distilling off the solvent was used for the next reaction without purification. To a solution of the crude product in 10 ml of acetic acid, 1.25 ml (40 mmol) of 30% aqueous hydrogen peroxide was added at room temperature, followed by stirring at 100° C. for 1 hour. After cooling, the reaction mixture was poured into ice water; the aqueous layer was neutralized with aqueous sodium hydroxide (pH ~8). The resulting crystal was collected by filtration, washed with water-n-hexane and dried to yield 4.376 g (87.2%, white powder) of the desired product.

$^1$H-NMR (CDCl$_3$, 200 MHz) δ 1.80–1.87 (4H, m), 2.50 (2H, quint., J=6.6 Hz), 3.36 (2H, t, J=7.0 Hz), 3.40–3.60 (2H, m), 3.99–4.06 (2H, m), 4.25–4.32 (2H, m), 7.29–7.34 (2H, m), 7.39–7.44 (3H, m)

viii) Synthesis of 7-[4-(imidazo[1,2-a]pyridin-5-ylthio)butyl]-1,1-dioxo-9-phenyl-3,4-dihydro-2H,6H-pyrimido[6,1-b][1,3]thiazine-6,8(7H)-dione To a suspension of 0.24 g (6.0 mmol) of 60% oily sodium hydride in 40 ml of N,N-dimethylformamide, 0.98 g (6.0 mmol) of 5-mercaptoimidazo[1,2-a]pyridine was added at room temperature, followed by stirring for 10 minutes. To this mixture, 2.87 g (5.97 mmol) of 7-(4-chlorobutyl)-1,1-dioxo-9-phenyl-3,4-dihydro-2H,6H-pyrimido[6,1-b][1,3]-thiazine-6,8(7H)-dione and 0.90 g (6.0 mmol) of sodium iodide were added, followed by stirring at 80° C. for 3 hours. After cooling, the reaction mixture was poured into water and extracted with ethyl acetate 3 times. The organic layer was washed with water and dried, after which the solvent was distilled off. The residue was purified by column chromatography (eluent, ethyl acetate/ethanol=10/1) to yield 1.26 g (43.7%, white foamy substance) of the desired product.

$^1$H-NMR (CDCl$_3$, 200 MHz) δ 1.62–1.88 (4H, m), 2.50 (2H, quint., J=6.4 Hz), 3.02 (2H, t, J=7.2 Hz), 3.99 (2H, t, J=7.2 Hz), 4.25 (2H, t, J=6.4 Hz), 6.90 (1H, d, J=6.2 Hz), 7.14 (1H, dd, J=7.0, 9.0 Hz), 7.25–7.33 (2H, m), 7.40–7.45 (3H, m), 7.57 (1H, d, J=8.6 Hz), 7.68 (1H, d, J=1.2 Hz), 7.83 (1H, s)

ix) Synthesis of 7-[4-(imidazo[1,2-a]pyridin-5-ylthio)butyl]-1,1-dioxo-9-phenyl-3,4-dihydro-2H,6H-pyrimido[6,1-b][1,3]thiazine-6,8(7H)-dione hydrochloride To a solution of 1.26 g (2.61 mmol) of 7-[4-(imidazo-[1,2-a]pyridin-5-ylthio)butyl]-1,1-dioxo-9-phenyl-3,4-dihydro-2H,6H-pyrimido[6,1-b][1,3]thiazine-6,8(7H)-dione in 20 ml of methanol, 0.25 ml (3 mmol) of concentrated hydrochloric acid was added. After the reaction mixture was concentrated to dryness, diethyl ether was added to the residue. The resulting crystal was collected by filtration and dried to yield 1.35 g (quant, light white crystal) of the desired product.

m.p. 124.0°–125.0° C.; $^1$H-NMR (CD$_3$OD, 200 MHz) δ 1.80–1.90 (4H, m), 2.49 (2H, quint., J=6.4 Hz), 3.30–3.35 (2H, m), 3.50 (2H, t, J=6.6 Hz), 4.01 (2H, t, J=6.6 Hz), 4.17 (2H, t, J=5.8 Hz), 7.22–7.29 (2H, m), 7.34–7.38 (3H, m), 7.56 (1H, dd, J=1.2, 7.0 Hz), 7.77–7.90 (2H, m), 8.10 (1H, d, J=2.6 Hz), 8.28 (1H, d, J=2.0 Hz); Anal. Calcd for C$_{24}$H$_{25}$ClN$_4$O$_4$S$_2$.1.0H$_2$O: C, 52.31; H, 4.94; N, 10.17. Found: C, 52.55; H, 5.14; N, 10.16

Preparation Example 25

Synthesis of 5-butylidene-3-[4-(imidazo[1,2-c]pyrimidin-5-ylthio)butyl]thiazolidine-2,4-dione hydrochloride i) Synthesis of 5-butylidene-3-[4-(imidazo[1,2-c]pyrimidin-5-ylthio)butyl]thiazolidine-2,4-dione 1.612 g (5 mmol) of 3-[4-(imidazo[1,2-c]pyrimidin-5-ylthio)butyl]thiazolidine-2,4-dione and 20 ml of ethanol were placed in a reaction flask, followed by stirring at 60° C. for 20 minutes, to dissolve the starting materials. After this mixture was kept standing to 50° C., an ethanol solution of 0.05 ml (0.5 mmol) of piperidine was added. Next, an ethanol solution of 0.45 ml (5 mmol) of n-butyraldehyde was added, followed by refluxing for 100 minutes. After the reaction mixture was cooled, the solvent was distilled off, followed by extraction with dichloromethane and water. After the organic layer was dried with sodium sulfate, the solvent was distilled off. The residue was eluted by column chromatography (eluent, hexane/ethyl acetate=1/4) to yield 1.052 g (55.9%, white crystal) of the desired product.

$^1$H-NMR (CDCl$_3$, 200 MHz) δ 0.98 (3H, t, J=7.4 Hz), 1.50–1.66 (2H, m), 1.83–1.90 (4H, m), 2.21 (2H, q, J=7.4 Hz), 3.39–3.46 (2H, m), 3.72–3.78 (2H, m), 7.08 (1H, t, J=7.8 Hz), 7.31 (1H, d, J=6.6 Hz), 7.50–7.52 (1H, m), 7.66 (1H, d, J=1.4 Hz), 7.84 (1H, d, J=6.4 Hz)

ii) Synthesis of 5-butylidene-3-[4-(imidazo[1,2-c]pyrimidin-5-ylthio)butyl]thiazolidine-2,4-dione hydrochloride To a methanol solution of 1.052 g (2.79 mmol) of 5-butylidene-3-[4-(imidazo[1,2-c]pyrimidin-5-ylthio)butyl]thiazolidine-2,4-dione, 3 ml of 4N hydrochloric acid-ethyl acetate was added, followed by stirring, after which the solvent was distilled off, to yield 0.914 g (79.3%, white powder) of the desired product.

m.p. 115.0°–116.0° C.; Anal. Calcd for C$_{17}$H$_{21}$ClN$_4$O$_2$S$_2$.1.0H$_2$O: C, 47.38; H, 5.38; N, 13.00. Found: C, 47.21; H, 4.82; N, 14.17

Preparation Example 26

Synthesis of 5-butylidene-3-[4-(2-phenylimidazo[1,2-a]pyridin-8-yloxy)butyl]thiazolidine-2,4-dione hydrochloride i) Synthesis of 5-butylidene-3-[4-(2-phenyl-imidazo[1,2-a]pyridin-8-yloxy)butyl]thiazolidine-2,4-dione To a solution of 1.91 g (5.0 mmol) of 3-[4-(2-phenylimidazo[1,2-a]pyridin-8-yloxy)butyl]thiazolidine-2,4-dione and 0.45 ml (5.0 mmol) of n-butyraldehyde in 20 ml of ethanol, 0.05 ml (0.5 mmol) of piperidine was added, followed by refluxing for 2 hours. After the reaction mixture was cooled, the solvent was distilled off. The residue was dissolved in chloroform, washed with saturated aqueous sodium hydrogen carbonate and dried, after which the solvent was distilled off. The residue was purified by column chromatography (eluent, n-hexane/ethyl acetate=2/1) to yield 1.70 g (78.0%, yellow foamy substance) of the desired product.

$^1$H-NMR (CDCl$_3$, 200 MHz) δ 0.98 (3H, t, J=7.4 Hz), 1.49–1.62 (2H, m), 1.92–2.01 (4H, m), 2.22 (2H, q, J=7.4 Hz), 3.82 (2H, t, J=6.6 Hz), 4.24 (2H, t, J=6.2 Hz), 6.46 (1H, d, J=7.0 Hz), 6.67 (1H, t, J=6.6 Hz), 7.09 (1H, t, J=7.6 Hz), 7.31–7.46 (3H, m), 7.77 (1H, dd, J=1.0, 6.6 Hz), 7.84 (1H, s), 7.97 (1H, d, J=1.2 Hz), 8.01 (1H, d, J=1.4 Hz); IR (neat) 2958, 1741, 1684, 1547, 1350, 1111, 768, 733, 696 cm$^{-1}$ ii) Synthesis of 5-butylidene-3-[4-(2-phenylimidazo[1,2-a]pyridin-8-yloxy)butyl]thiazolidine-2,4-dione hydrochloride To a solution of 1.70 g (3.90 mmol) of 5-butylidene-3-[4-(2-phenylimidazo[1,2-a]pyridin-8-yloxy)butyl]thiazolidine-2,4-dione in 20 ml of methanol, 0.4 ml of concentrated hydrochloric acid was added. After the solvent was distilled off, the residue was washed with diethyl ether to yield 1.80 g (97.7%, yellow solid) of the desired product.

m.p. 90.0°–92.0° C.; Anal. Calcd for $C_{24}H_{26}ClN_3O_3S.1.0H_2O$: C, 58.83; H, 5.76; N, 8.58. Found: C, 58.88; H, 5.91; N, 8.58

Preparation Example 27

Synthesis of 5-butylidene-3-[4-(2-ethoxycarbonylimidazo-[1,2-a]pyridin-8-yloxy)butyl]thiazolidine-2,4-dione hydrochloride i) Synthesis of 5-butylidene-3-[4-(2-ethoxycarbonylimidazo[1,2-a]pyridin-8-yloxy)butyl]thiazolidine-2,4-dione To a solution of 1.88 g (5.0 mmol) of 3-[4-(2-ethoxycarbonylimidazo[1,2-a]pyridin-8-yloxy)butyl]-thiazolidine-2,4-dione and 0.45 ml (5.0 mmol) of n-butyraldehyde in 20 ml of ethanol, 0.05 ml (0.5 mmol) of piperidine was added, followed by refluxing for 2 hours. After the reaction mixture was cooled, the solvent was distilled off. The residue was dissolved in chloroform, washed with saturated aqueous sodium hydrogen carbonate and dried, after which the solvent was distilled off. The residue was purified by column chromatography (eluent, n-hexane/ethyl acetate=1/2) to yield 2.14 g (99.2%, yellow oily substance) of the desired product.

$^1$H-NMR (CDCl$_3$, 200 MHz) δ 0.99 (3H, t, J=7.4 Hz), 1.42 (3H, t, J=7.0 Hz), 1.50–1.68 (2H, m), 1.90–2.05 (4H, m), 2.19 (2H, q, J=7.4 Hz), 3.80 (2H, t, J=6.4 Hz), 4.19 (2H, t, J=6.2 Hz), 4.44 (2H, q, J=7.2 Hz), 6.49 (1H, d, J=7.6 Hz), 6.76 (1H, t, J=7.0 Hz), 7.09 (1H, t, J=7.6 Hz), 7.76 (1H, d, J=6.8 Hz), 8.16 (1H, s); IR (neat) 2960, 1720, 1692, 1362, 777, 741 cm$^{-1}$ ii) Synthesis of 5-butylidene-3-[4-(2-ethoxycarbonylimidazo[1,2-a]pyridin-8-yloxy)butyl]thiazolidine-2,4-dione hydrochloride To a solution of 2.14 g (4.96 mmol) of 5-butylidene-3-[4-(2-ethoxycarbonylimidazo[1,2-a]pyridin-8-yloxy)butyl]-thiazolidine-2,4-dione in 20 ml of methanol, 0.45 ml of concentrated hydrochloric acid was added. After the solvent was distilled off, the residue was washed with diethyl ether to yield 2.07 g (89.2%, yellow oily substance) of the desired product.

Anal. Calcd for $C_{21}H_{26}ClN_3O_5S.2.0H_2O$: Cf 50.05; H, 6.00; N, 8.34. Found: C, 49.82; H, 5.40; N, 8.92

Preparation Example 28

Synthesis of 5-(1-methylpiperazin-4-yl)methylene-3-[4-(imidazo[1,2-a]pyridin-5-ylthio)butyl]thiazolidine-2,4-dione trihydrochloride i) Synthesis of 5-(1-methylpiperazin-4-yl)methylene-3-[4-(imidazo[1,2-a]pyridin-5-ylthio)butyl]thiazolidine-2,4-dione To a solution of 241 mg (1.0 mmol) of 5-(4-chlorobutylthio)imidazo[1,2-a]pyridine and 227 mg (1.0 mmol) of 5-(1-methylpiperazin-4-yl)methylene-thiazolidine-2,4-dione in 10 ml of N,N-dimethylformamide, 0.15 ml (1.0 mmol) of 1,8-diazabicyclo[5.4.0]-7-undecene was added, followed by stirring at 80° C. for 3 hours. After the reaction mixture was cooled, water was added; the mixture was extracted with ethyl acetate and dried, after which the solvent was distilled off. The residue was purified by column chromatography (eluent, chloroform/ethanol=50/1) to yield 330 mg (76.0%, light yellow oily substance) of the desired product.

$^1$H-NMR (CDCl$_3$, 200 MHz) δ 1.58–1.88 (4H, m), 2.33 (3H, s), 2.48 (4H, t, J=5.0 Hz), 3.02 (2H, t, J=7.0 Hz), 3.49 (4H, t, J=5.2 Hz), 3.69 (2H, t, J=6.8 Hz), 6.90 (1H, dd, J=1.0, 7.0 Hz), 7.15 (1H, dd, J=7.2, 9.0 Hz), 7.56 (1H, d, J=9.0 Hz), 7.58 (1H, s), 7.69 (1H, d, J=1.2 Hz), 7.84 (1H, s); IR (neat) 2941, 2797, 1711, 1662, 1649, 1603, 1356, 1120, 741 cm$^{-1}$ ii) Synthesis of 5-(1-methylpiperazin-4-yl)methylene-3-[4-(imidazo[1,2-a]pyridin-5-ylthio)butyl]thiazolidine-2,4-dione trihydrochloride To a solution of 330 mg (0.76 mmol) of 5-(1-methylpiperazin-4-yl)methylene-3-[4-(imidazo[1,2-a]pyridin-5-ylthio)butyl]thiazolidine-2,4-dione in 10 ml of methanol, concentrated hydrochloric acid was added. After the solvent was distilled off, the residue was washed with diethyl ether to yield 360 mg (82.0%, white crystal) of the desired product.

m.p. 152.0°–153.0° C.; Anal. Calcd for $C_{20}H_{28}Cl_3N_5O_2S_2.2.0H_2O$: C, 41.63; H, 5.59; N, 12.14. Found: C, 41.78; H, 5.75; N, 12.44

Preparation Example 29

Synthesis of 5-(morpholin-1-yl)methylene-3-[4-(imidazo[1,2-a]pyridin-5-ylthio)butyl]thiazolidine-2,4-dione dihydrochloride i) Synthesis of 5-(morpholin-1-yl)methylene-3-[4-(imidazo[1,2-a]pyridin-5-ylthio)butyl]thiazolidine-2,4-dione To a solution of 241 mg (1.0 mmol) of 5-(4-chlorobutylthio)imidazo[1,2-a]pyridine and 214 mg (1.0 mmol) of 5-(morpholin-1-yl)methylene-thiazolidine-2,4-dione in 10 ml of N,N-dimethylformamide, 0.15 ml (1.0 mmol) of 1,8-diazabicyclo[5.4.0]-7-undecene was added, followed by stirring at 80° C. for 3 hours. After the reaction mixture was cooled, water was added; the mixture was extracted with ethyl acetate and dried, after which the solvent was distilled off. The residue was purified by column chromatography (eluent, n-hexane/ethyl acetate=1/4→ethyl acetate→ethyl acetate/ethanol=10/1) to yield 220 mg (52.6%, white powder) of the desired product.

$^1$H-NMR (CDCl$_3$, 200 MHz) δ 1.62–1.96 (4H, m), 3.02 (2H, t, J=7.0 Hz), 3.46–3.51 (4H, m), 3.69 (2H, t, J=6.8 Hz), 3.74–3.79 (4H, m), 6.91 (1H, dd, J=1.2, 7.0 Hz), 7.15 (1H, dd, J=7.0, 9.2 Hz), 7.57 (1H, d, J=9.2 Hz), 7.56 (1H, s), 7.69 (1H, d, J=1.6 Hz), 7.84 (1H, d, J=0.6 Hz)

ii) Synthesis of 5-(morpholin-1-yl)methylene-3-[4-(imidazo[1,2-a]pyridin-5-ylthio)butyl]thiazolidine-2,4-dione dihydrochloride To a solution of 220 mg (0.526 mmol) of 5-(morpholin-1-yl)methylene-3-[4-(imidazo[1,2-a]pyridin-5-ylthio)butyl]-thiazolidine-2,4-dione in 10 ml of methanol, concentrated hydrochloric acid was added. After the solvent was distilled off, the residue was washed with diethyl ether to yield 272 mg (quant, white crystal) of the desired product.

m.p. 137.0°–138.0° C.; Anal. Calcd for $C_{19}H_{24}Cl_2N_4O_3S_2.1.0H_2O$: C, 44.79; H, 5.14; N, 11.00. Found; C, 44.49; H, 5.01; N, 11.00

Preparation Example 30

Synthesis of 5-(piperidin-1-yl)methylene-3-[4-(imidazo[1,2-a]pyridin-5-ylthio)butyl]thiazolidine-2,4-dione dihydrochloride i) Synthesis of 5-(piperidin-1-yl)methylene-3-[4-(imidazo[1,2-a]pyridin-5-ylthio)butyl]thiazolidine-2,4-dione To a solution of 241 mg (1.0 mmol) of 5-(4-chlorobutylthio)imidazo[1,2-a]pyridine and 212 mg (1.0 mmol) of 5-(piperidin-1-yl)methylene-thiazolidine-2,4-dione in 10 ml of N,N-dimethylformamide, 0.15 ml (1.0 mmol) of 1,8-diazabicyclo[5.4.0]-7-undecene was added, followed by stirring at 80° C. for 3 hours. After the reaction mixture was cooled, water was added; the mixture was extracted with ethyl acetate and dried, after which the solvent was distilled off. The residue was purified by column chromatography (eluent, n-hexane/ethyl acetate=1/4→ethyl acetate) to yield 330 mg (79.2%, white powder) of the desired product.

$^1$H-NMR (CDCl$_3$, 200 MHz) δ 1.58–1.96 (10H, m), 3.02 (2H, t, J=7.0 Hz), 3.43 (4H, s), 3.69 (2H, t, J=7.0 Hz), 6.90 (1H, d, J=6.2 Hz), 7.15 (1H, dd, J=7.0, 9.0 Hz), 7.56 (1H, d, J=9.0 Hz), 7.61 (1H, s), 7.69 (1H, d, J=1.2 Hz), 7.84 (1H, s)

ii) Synthesis of 5-(piperidin-1-yl)methylene-3-[4-(imidazo[1,2-a]pyridin-5-ylthio)butyl]thiazolidine-2,4-dione dihydrochloride To a solution of 220 mg (0.526 mmol) of 5-(piperidin-1-yl)methylene-3-[4-(imidazo[1,2-a]pyridin-5-ylthio)butyl]-thiazolidine-2,4-dione in 10 ml of methanol, concentrated hydrochloric acid was added. After the solvent was distilled off, the residue was washed with diethyl ether to yield 218 mg (56.2%, white powder) of the desired product.

m.p. 138.0°–139.0° C.; Anal. Calcd for $C_{20}H_{26}Cl_2N_4O_2S_2 \cdot 1.0H_2O$: C, 47.33; H, 5.56; N, 11.04. Found: C, 47.06; H, 5.21; N, 11.01

Preparation Example 31

Synthesis of 5-(dimethylamino)methylene-3-[4-(imidazo[1,2-a]pyridin-5-ylthio)butyl]thiazolidine-2,4-dione dihydrochloride i) Synthesis of 5-(dimethylamino)methylene-3-[4-(imidazo-[1,2-a]pyridin-5-ylthio)butyl]thiazolidine-2,4-dione To a solution of 241 mg (1.0 mmol) of 5-(4-chlorobutylthio)imidazo[1,2-a]pyridine and 173 mg (1.0 mmol) of 5-(dimethylamino)methylene-thiazolidine-2,4-dione in 10 ml of N,N-dimethylformamide, 0.15 ml (1.0 mmol) of 1,8-diazabicyclo[5.4.0]-7-undecene was added, followed by stirring at 80°C. for 3 hours. After the reaction mixture was cooled, water was added; the mixture was extracted with ethyl acetate and dried, after which the solvent was distilled off. The residue was purified by column chromatography (eluent, n-hexane/ethyl acetate=1/4→ethyl acetate→chloroform/ethanol=10/1) to yield 310 mg (82.3%, yellow oily substance) of the desired product.

$^1$H-NMR (CDCl$_3$, 200 MHz) δ 1.58–1.88 (4H, m), 3.02 (2H, t, J=7.0 Hz), 3.13 (6H, s), 3.69 (2H, t, J=6.6 Hz), 6.90 (1H, dd, J=0.8, 7.2 Hz), 7.15 (1H, dd, J=7.0, 9.0 Hz), 7.56 (1H, d, J=9.2 Hz), 7.60 (1H, s), 7.68 (1H, d, J=1.0 Hz), 7.84 (1H, d, J=1.0 Hz); IR (KBr) 1643, 1597, 1363, 1103 cm$^{-1}$ ii) Synthesis of 5-(dimethylamino)methylene-3-[4-(imidazo[1,2-a]pyridin-5-ylthio)butyl]thiazolidine-2,4-dione dihydrochloride To a solution of 310 mg (0.823 mmol) of 5-(dimethylamino)methylene-3-[4-(imidazo[1,2-a]pyridin-5-ylthio)butyl]thiazolidine-2,4-dione in 10 ml of methanol, concentrated hydrochloric acid was added. After the solvent was distilled off, the residue was washed with diethyl ether to yield 311 mg (84.1%, white powder) of the desired product.

m.p. 115.0°–117.0° C.; Anal. Calcd for $C_{17}H_{22}Cl_2N_4O_2S_2 \cdot 0.8H_2O$: C, 44.02; H, 5.13; N, 12.08. Found: C, 43.95; H, 5.23; N, 12.32

Preparation Example 32

Synthesis of 5-(3-phenylpropylidene)-3-[4-(imidazo[1,2-a]pyridin-8-yloxy)butyl]oxazolidine-2,4-dione hydrochloride i) Synthesis of 5-(3-phenylpropylidene)-3-[4-(imidazo[1,2-a]pyridin-8-yloxy)butyl]oxazolidine-2,4-dione 1.45 g (5 mmol) of 3-[4-(imidazo[1,2-a]pyridin-8-yloxy)butyl]oxazolidine-2,4-dione and 20 ml of ethanol were placed in a reaction flask, followed by stirring at 60° C. for 20 minutes, to dissolve the starting materials. After this mixture was kept standing to 50° C., an ethanol solution of 0.05 ml (0.5 mmol) of pyrrolidine was added. Next, an ethanol solution of 0.66 ml (5 mmol) of 3-phenylpropionaldehyde was added, followed by refluxing for 19 hours. 3.5 hours later, 0.66 ml (5 mmol) of 3-phenylpropionaldehyde and 0.05 ml (0.5 mmol) of pyrrolidine were added. After the reaction mixture was cooled, the solvent was distilled off, followed by extraction with dichloromethane and water. After the organic layer was dried with sodium sulfate, the solvent was distilled off. The residue was eluted by column chromatography (eluent, hexane/ethyl acetate=1/2) to yield 15 mg (0.74%, yellow oily substance) of the desired product.

$^1$H-NMR (CDCl$_3$, 200 MHz) δ 1.80–2.10 (4H, m), 2.40–2.90 (4H, m), 3.65–3.80 (2H, m), 4.15–4.25 (2H, m), 6.05 (1H, t, J=7.7 Hz), 6.45 (1H, d, J=7.6 Hz), 6.68 (1H, t, J=7.0 Hz), 7.15–7.40 (5H, m), 7.57 (2H, d, J=4.8 Hz), 7.77 (1H, d, J=6.8 Hz)

ii) Synthesis of 5-(3-phenylpropylidene)-3-[4-(imidazo[1,2-a]pyridin-8-yloxy)butyl]oxazolidine-2,4-dione hydrochloride To a methanol solution of 15 mg (0.037 mmol) of 5-(3-phenylpropylidene)-3-[4-(imidazo[1,2-a]pyridin-8-yloxy)-butyl]oxazolidine-2,4-dione, 10 ml of 4N hydrochloric acid-ethyl acetate was added, followed by stirring, after which the solvent was distilled off, to yield 16 mg (97.8%, yellow oily substance) of the desired product.

$^1$H-NMR (D$_2$O, 200 MHz) δ 1.80–2.10 (4H, m), 2.55–2.75 (2H, m), 2.75–2.90 (2H, m), 3.60–3.75 (2H, m), 4.30–4.45 (2H, m), 6.03 (1H, t, J=7.7 Hz), 7.15–7.35 (5H, m), 7.35–7.45 (2H, m), 8.00 (1H, d, J=1.8 Hz), 8.23 (1H, d, J=1.8 Hz), 8.35–8.45 (1H, m)

Preparation Example 33

Synthesis of 5-(3-phenylpropylidene)-3-[4-(imidazo[1,2-a]pyridin-5-ylthio)butyl]oxazolidine-2,4-dione hydrochloride i) Synthesis of 5-(3-phenylpropylidene)-3-[4-(imidazo[1,2-a]pyridin-5-ylthio)butyl]oxazolidine-2,4-dione 1.53 g (5 mmol) of 3-[4-(imidazo[1,2-a]pyridin-5-ylthio)butyl]oxazolidine-2,4-dione and 20 ml of ethanol were placed in a reaction flask, followed by stirring at 60° C. for 20 minutes, to dissolve the starting materials. After this mixture was kept standing to 50° C., an ethanol solution of 0.05 ml (0.5 mmol) of pyrrolidine was added. Next, an ethanol solution of 0.66 ml (5 mmol) of 3-phenylpropionaldehyde was added, followed by refluxing for 19 hours. Six hours later, 0.66 ml (5 mmol) of 3-phenylpropionaldehyde and 0.05 ml (0.5 mmol) of pyrrolidine were added. After the reaction mixture was cooled, the solvent was distilled off, followed by extraction with dichloromethane and water. After the organic layer was dried with sodium sulfate, the solvent was distilled off. The residue was eluted by column chromatography (eluent, hexane/ethyl acetate=1/1) to yield 26 mg (1.2%, yellow oily substance) of the desired product.

$^1$H-NMR (CDCl$_3$, 200 MHz) δ 1.60–1.99 (4H, m), 2.60–2.90 (4H, m), 3.02 (2H, t, J=7.0 Hz), 3.59 (2H, t, J=7.0 Hz), 6.05 (1H, t, J=7.7 Hz), 6.92 (1H, d, J=7.0 Hz), 7.10–7.35 (6H, m), 7.60 (1H, d, J=9.2 Hz), 7.71 (1H, s), 7.85 (1H, s)

ii) Synthesis of 5-(3-phenylpropylidene)-3-[4-(imidazo[1,2-a]pyridin-5-ylthio)butyl]oxazolidine-2,4-dione hydrochloride To a methanol solution of 26 mg (0.062 mmol) of 5-(3-phenylpropylidene)-3-[4-(imidazo[1,2-a]pyridin-5-ylthio)butyl]oxazolidine-2,4-dione, 0.02 ml of 4N hydrochloric acid-ethyl acetate was added, followed by stirring, after which the solvent was distilled off, to yield 29 mg (quant, yellow oily substance) of the desired product.

$^1$H-NMR (D$_2$O, 200 MHz) δ 1.70–1.95 (4H, m), 2.55–2.90 (4H, m), 3.25–3.40 (2H, m), 3.55–3.70 (2H, m), 6.00 (1H, t, J=7.7 Hz), 7.15–7.35 (5H, m), 7.55–7.65 (1H, m), 7.80–8.00 (2H, m), 8.14 (1H, d, J=2.4 Hz), 8.30 (1H, d, J=2.4 Hz)

Preparation Example 34

Synthesis of 5-butylidene-3-[4-(3-trifluoroacetylimidazo-[1,2-a]pyridin-8-yloxy)butyl]thiazolidine-2,4-dione hydrochloride i) Synthesis of 3-[4-(3-trifluoroacetylimidazo[1,2-a]-pyridin-8-yloxy)butyl]thiazolidine-2,4-dione To a solution of 1.53 g (5.0 mmol) of 3-[4-(imidazo[1,2-a]pyridin-8-yloxy)butyl]thiazolidine-2,4-dione in 50 ml of dichloromethane, 7.06 ml (50 mmol) of trifluoroacetic anhydride was added under ice cooling conditions, followed by addition of 8.36 ml (60 mmol) of triethylamine and stirring for 1 hour. After the reaction was stopped by adding 2N aqueous sodium hydroxide, the reaction mixture was extracted with dichloromethane and dried. The residue obtained by distilling off the solvent was purified by column chromatography (eluent, n-hexane/ethyl acetate=5/1→2/1→1/1) to yield 415 mg (20.7%, white powder) of the desired product.

$^1$H-NMR (CDCl$_3$, 200 MHz) δ 1.68–1.98 (4H, m), 3.03 (2H, t, J=7.0 Hz), 3.82 (2H, t, J=6.7 Hz), 7.11 (2H, d, J=5.3 Hz), 7.35 (2H, d, J=6.0 Hz), 7.79 (1H, s), 8.39 (2H, s), 8.75 (2H, d, J=4.5 Hz); IR (neat) 3030, 2950, 1745, 1680, 1575, 1350, 1130, 805, 710, 650, 540 cm$^{-1}$ ii) Synthesis of 5-butylidene-3-[4-(3-trifluoroacetylimidazo[1,2-a]pyridin-8-yloxy)butyl]thiazolidine-2,4-dione To a solution of 271 mg (0.69 mmol) of 3-[4-(3-trifluoroacetylimidazo[1,2-a]pyridin-8-yloxy)butyl]thiazolidine-2,4-dione and 69 μl (0.69 mmol) of n-butyraldehyde in 5 ml of ethanol, 7 μl (0.07 mmol) of piperidine was added, followed by refluxing for 1 hour. After the reaction mixture was cooled, the solvent was distilled off. The residue was dissolved in chloroform, washed with water and dried, after which the solvent was distilled off. The residue was purified by column chromatography (eluent, n-hexane/ethyl acetate=2/1) to yield 250 mg (79.7%, light yellow oily substance) of the desired product.

$^1$H-NMR (CDCl$_3$, 200 MHz) δ 1.52–1.64 (2H, m), 1.90–1.97 (4H, m), 2.22 (2H, quint., J=7.4 Hz), 3.81 (2H, t, J=6.8 Hz), 4.28 (2H, t, J=6.0 Hz), 7.00 (1H, d, J=7.2 Hz), 7.09 (1H, t, J=7.6 Hz), 7.15 (1H, t, J=8.0 Hz), 8.49 (1H, d, J=2.0 Hz), 9.21 (1H, d, J=6.6 Hz); IR (neat) 2960, 2875, 1745, 1687, 1662, 1556, 1350, 1257, 1205, 1161, 903, 783, 748, 737, 669, 609 cm$^{-1}$ iii) Synthesis of 5-butylidene-3-[4-(3-trifluoroacetylimidazo[1,2-a]pyridin-8-yloxy)butyl]thiazolidine-2,4-dione hydrochloride To a solution of 250 mg (0.55 mmol) of 5-butylidene-3-[4-(3-trifluoroacetylimidazo[1,2-a]pyridin-8-yloxy)butyl]-thiazolidine-2,4-dione in 5 ml of methanol, 0.05 ml of concentrated hydrochloric acid was added. After the solvent was distilled off, the residue was washed with diethyl ether to yield 290 mg (100%, white solid) of the desired product.

m.p. 66.0°–67.0° C.; Anal. Calcd for C$_{20}$H$_{21}$ClF$_3$N$_3$O$_4$S.1.5H$_2$O: C, 46.29; H, 4.66; N, 8.10. Found: C, 46.21; H, 4.68; N, 8.20

Preparation Example 35
Synthesis of 5-butylidene-3-[4-(3-trifluoroacetylimidazo[1,2-a]pyridin-5-ylthio)butyl]thiazolidine-2,4-dione hydrochloride i) Synthesis of 3-[4-(3-trifluoroacetylimidazo[1,2-a]-pyridin-5-ylthio)butyl]thiazolidine-2,4-dione To a solution of 1.53 g (5.0 mmol) of 3-[4-(imidazo[1,2-a]pyridin-5-ylthio)butyl]thiazolidine-2,4-dione in 50 ml of dichloromethane, 7.06 ml (50 mmol) of trifluoroacetic anhydride was added under ice cooling conditions. To this reaction mixture, 8.36 ml (60 mmol) of triethylamine was added, followed by stirring for 1 hour. The reaction mixture was poured into 1N aqueous sodium hydroxide, extracted with dichloromethane and dried, after which the solvent was distilled off. The obtained residue was purified by column chromatography (eluent, n-hexane/ethyl acetate=5/1→2/1→1/1) to yield 415 mg (20.7%, white powder) of the desired product.

$^1$H-NMR (CDCl$_3$, 200 MHz) δ 1.86–2.02 (4H, m), 3.75 (2H, t, J=6.6 Hz), 3.97 (2H, t, J=7.0 Hz), 4.28 (2H, t, J=6.0 Hz), 7.00 (1H, d, J=7.6 Hz), 7.15 (1H, dd, J=6.8, 7.6 Hz), 8.50 (1H, d, J=1.6 Hz), 9.22 (1H, d, J=6.6 Hz)

ii) Synthesis of 5-butylidene-3-[4-(3-trifluoroacetylimidazo[1,2-a]pyridin-5-ylthio)butyl]thiazolidine-2,4-dione To a solution of 250 mg (0.6 mmol) of 3-[4-(3-trifluoroacetylimidazo[1,2-a]pyridin-5-ylthio)butyl]thiazolidine-2,4-dione and 54 μl (0.6 mmol) of n-butyraldehyde in 5 ml of ethanol, 6 μl (0.06 mmol) of piperidine was added, followed by refluxing for 1 hour. After the reaction mixture was cooled, the solvent was distilled off. The residue was dissolved in chloroform, washed with saturated aqueous sodium hydrogen carbonate and dried, after which the solvent was distilled off. The residue was purified by column chromatography (eluent, n-hexane/ethyl acetate=2/1) to yield 200 mg (70.0%, light yellow oily substance) of the desired product.

$^1$H-NMR (CDCl$_3$, 200 MHz) δ 0.99 (3H, t, J=7.4 Hz), 1.50–1.80 (6H, m), 2.02 (2H, q, J=7.4 Hz), 3.11 (2H, t, J=7.2 Hz), 3.69 (2H, t, J=6.8 Hz), 7.08 (1H, t, J=7.6 Hz), 7.20 (1H, dd, J=2.4, 6.4 Hz), 7.10 (1H, dd, J=7.0, 8.8 Hz), 7.68–7.72 (2H, m), 7.47 (2H, d, J=1.8 Hz); IR (neat) 2960, 2872, 1743, 1682, 1350, 1253, 1182, 1146, 891, 787, 737 cm$^{-1}$ iii) Synthesis of 5-butylidene-3-[4-(3-trifluoroacetylimidazo[1,2-a]pyridin-5-ylthio)butyl]thiazolidine-2,4-dione hydrochloride To a solution of 200 mg (0.42 mmol) of 5-butylidene-3-[4-(3-trifluoroacetylimidazo[1,2-a]pyridin-5-ylthio)butyl]-thiazolidine-2,4-dione in 5 ml of methanol, 0.1 ml of concentrated hydrochloric acid was added. After the solvent was distilled off, the residue was washed with diethyl ether to yield 220 mg (100%, yellow oily substance) of the desired product.

Anal. Calcd for C$_{20}$H$_{21}$ClF$_3$N$_3$O$_3$S$_2$.0.5H$_2$O: C, 46.46; H, 4.29; N, 8.13. Found: C, 46.21; H, 4.45; N, 8.24

Preparation Example 36
Synthesis of 6-[4-(imidazo[1,2-a]pyridin-5-ylthio)butyl]-1,1-dioxo-8-phenyl-2,3-dihydro-5H-thiazolo[3,2-c]pyrimidine-5,7(6H)-dione hydrochloride i) Synthesis of 6-chloro-3-[4-chlorobutyl)-1-(2-chloroethyl)-5-phenylpyrimidine-2,4(1H,3H)-dione To a suspension of 2.43 g (7.7 mmol) of 6-chloro-3-(4-chlorobutyl)-5-phenylpyrimidine-2,4(1H,3H)-dione and 1.70 g (12.3 mmol) of potassium carbonate in 40 ml of N,N-dimethylformamide, 1.25 ml (15 mmol) of 1-bromo-2-chloroethane was added at room temperature, followed by stirring at 60° C. for 2 hours and then at 100° C. for 3 hours. After cooling, the reaction mixture was concentrated to dryness. The residue was dissolved in dichloromethane-water; the organic layer was washed with water and dried. The oily substance obtained by distilling off the solvent was purified by column chromatography (eluent, n-hexane/ethyl acetate=5/1→2/1) to yield 1.56 g (54.5%, white powder) of the desired product.

$^1$H-NMR (CDCl$_3$, 200 MHz) δ 1.80–1.88 (4H, m), 3.42–3.60 (2H, m), 3.54 (2H, t, J=7.0 Hz), 3.99–4.07 (2H, m), 4.51 (2H, t, J=6.6 Hz), 7.30–7.44 (5H, m)

ii) Synthesis of 6-(4-chlorobutyl)-8-phenyl-2,3-dihydro-5H-thiazolo[3,2-c]pyrimidine-5,7(6H)-dione To a solution of 1.56 g (4.2 mmol) of 3-(4-chlorobutyl)-6-chloro-1-(2-chloroethyl)-5-phenylpyrimidine-2,4(1H,3H)-dione in 15 ml of N,N-dimethylformamide, 0.94 g of sodium hydrosulfide n-hydrate was added under ice cooling conditions, followed by stirring for 1 hour. The reaction mixture was concentrated to dryness; the resulting residue was dissolved in dichloromethane-water. After the organic layer was washed with water and dried, the solvent was distilled off to yield a crude crystal, which was then recrystallized from dichloromethane-diethyl ether to yield 1.41 g (quant., colorless crystal) of the desired product.

$^1$H-NMR (CDCl$_3$, 200 MHz) δ 1.79–1.88 (4H, m), 2.51–2.63 (0.8H, m), 3.30 (2H, t, J=7.0 Hz), 3.54–3.61 (1.8H, m), 3.94–4.04 (2H, m), 4.44 (2H, t, J=7.0 Hz), 7.30–7.41 (5H, s)

iii) Synthesis of 6-(4-chlorobutyl)-1,1-dioxo-8-phenyl-2,3-dihydro-5H-thiazolo[3,2-c]pyrimidine-5,7(6H)-dione To a solution of 1.41 g (4.2 mmol) of 6-(4-chlorobutyl)-8-phenyl-2,3-dihydro-5H-thiazolo(3,2-c]pyrimidine-5,7(6H)-dione in 50 ml of dichloromethane, 1.83 g (5.3 mmol) of 50% m-chloroperbenzoic acid was added under ice cooling conditions, followed by stirring for 1 hour. After the resulting crystal was filtered off, the filtrate was washed with aqueous sodium hydroxide and dried. The oily substance (1-oxo compound) obtained by distilling off the solvent was used for the next reaction without purification. To a solution of the crude product in 20 ml of acetic acid, 0.4 ml (12.8 mmol) of 30% aqueous hydrogen peroxide was added at room temperature, followed by stirring at 100° C. for 1 hour. After cooling, the reaction mixture was poured into ice water; the aqueous layer was neutralized with aqueous sodium hydroxide (pH≦8). The resulting crystal was collected by filtration, washed with water-n-hexane and dried to yield 580 mg (29.6%, white powder) of the desired product.

$^1$H-NMR (CDCl$_3$, 200 MHz) δ 1.82–1.89 (4H, m), 3.51 (2H, t, J=6.6 Hz), 3.55–3.61 (2H, m), 4.02–4.09 (2H, m), 4.35 (2H, t, J=6.6 Hz), 7.46 (5H, s)

iv) Synthesis of 6-[4-(imidazo[1,2-a]pyridin-5-ylthio)-butyl]-1,1-dioxo-8-phenyl-2,3-dihydro-5H-thiazolo[3,2-c]pyrimidine-5,7(6H)-dione To a suspension of 60 mg (1.5 mmol) of 60% oily sodium hydride in 10 ml of N,N-dimethylformamide, 225 mg (1.5 mmol) of 5-mercaptoimidazo[1,2-a]pyridine was added at room temperature, followed by stirring for 10 minutes. To this mixture, 480 mg (1.3 mmol) of 6-(4-chlorobutyl)-1,1-dioxo-8-phenyl-2,3-dihydro-5H-thiazolo[3,2-c]pyrimidine-5,7(6H)-dione and 225 mg (1.5 mmol) of sodium iodide were added, followed by stirring at 80° C. for 3 hours. After cooling, the reaction mixture was poured into water and extracted with ethyl acetate 3 times. The organic layer was washed with water and dried, after which the solvent was distilled off. The residue was purified by column chromatography (eluent, ethyl acetate/ethanol=10/1) to yield 400 mg (65.7%, white foamy substance) of the desired product.

$^1$H-NMR (CDCl$_3$, 200 MHz) δ 1.62–1.92 (4H, m), 3.04 (2H, t, J=7.0 Hz), 3.54 (2H, t, J=6.6 Hz), 4.01 (2H, t, J=7.0 Hz), 4.33 (2H, t, J=7.0 Hz), 6.92 (1H, dd, J=1.0, 7.0 Hz), 7.14 (1H, dd, J=7.0, 9.2 Hz), 7.47 (5H, s), 7.57 (1H, dd, J=9.2 Hz), 7.69 (1H, d, J=1.4 Hz), 7.85–7.86 (1H, m)

v) Synthesis of 6-[4-(imidazo[1,2-a]pyridin-5-ylthio)-butyl]-1,1-dioxo-8-phenyl-2,3-dihydro-5H-thiazolo[3,2-c]pyrimidine-5,7(6H)-dione hydrochloride To a solution of 400 mg (0.85 mmol) of 6-[4-(imidazo[1,2-a]pyridin-5-ylthio)butyl]-1,1-dioxo-8-phenyl-2,3-dihydro-5H-thiazolo-[3,2-c]pyrimidine-5,7(6H)-dione in 20 ml of methanol, 0.10 ml of concentrated hydrochloric acid was added. After the reaction mixture was concentrated to dryness, diethyl ether was added to the residue. The resulting crystal was collected by filtration and dried to yield 430 mg (97.4%, light white powder) of the desired product.

m.p. 119.0°–120.0° C.; Anal. Calcd for C$_{23}$H$_{23}$ClN$_4$O$_4$S$_2$.1.0H$_2$O: C, 51.44; H, 4.69; N, 10.43. Found: C, 51.76; H, 4.92; N, 10.79

Preparation Example 37

Synthesis of imidazo[1,2-a]pyridin-5-ylthioacetic acid [3-(1,1,6,8-tetraoxo-9-phenyl-2,3,4,8-tetrahydro-pyrimido[6,1-b][1,3]thiazin-7-yl)propyl]amide hydrochloride i) Synthesis of imidazo[1,2-a]pyridin-5-ylthioacetic acid [3-(1,1,6,8-tetraoxo-9-phenyl-2,3,4,8-tetrahydro-pyrimido[6,1-b][1,3]thiazin-7-yl)propyl]amide To a suspension of 208 mg (1.0 mmol) of imidazo[1,2-a]pyridin-5-ylthioacetic acid, 153 mg (1.0 mmol) of N-hydroxybenzotriazole (HOBt) and 192 mg (1.0 mmol) of WSC in 20 ml of dichloromethane, 0.14 ml (1.0 mmol) of triethylamine was added under ice cooling conditions, followed by stirring for 30 minutes. To this mixture, 208 mg (1.0 mmol) of 3-(1,1,6,8-tetraoxo-9-phenyl-2,3,4,8-tetrahydro-pyrimido[6,1-b][1,3]thiazin-7-yl)propyl]amine was added, followed by addition of 0.28 ml (2.0 mmol) of triethylamine and stirring for 64 hours. The reaction mixture was poured into water, extracted with dichloromethane and dried, after which the solvent was distilled off. The residue was purified by column chromatography (eluent, chloroform/methanol=25/1) to yield 190 mg (35.2%, white foamy substance) of the desired product.

$^1$H-NMR (CDCl$_3$, 200 MHz) δ 1.70–1.84 (2H, m), 2.48 (2H, quint., J=6.4 Hz), 3.18 (2H, q, J=6.0 Hz), 3.36 (2H, t, J=6.8 Hz), 3.69 (2H, s), 3.83 (2H, t, J=6.2 Hz), 4.17 (2H, t, J=6.2 Hz), 6.95 (1H, dd, J=1.2, 7.2 Hz), 7.09 (1H, dd, J=7.0, 8.8 Hz), 7.14–7.18 (1H, m), 7.28–7.31 (2H, m), 7.41–7.46 (3H, m), 7.56 (1H, d, J=8.8 Hz), 7.67 (1H, d, J=0.8 Hz), 7.83 (1H, s)

ii) Synthesis of imidazo[1,2-a]pyridin-5-ylthioacetic acid [3-(1,1,6,8-tetraoxo-9-phenyl-2,3,4,8-tetrahydro-pyrimido [6,1-b][1,3]thiazin-7-yl)propyl]amide hydrochloride To a solution of 390 mg (0.72 mmol) of imidazo[1,2-a]pyridin-5-ylthioacetic acid [3-(1,1,6,8-tetraoxo-9-phenyl-2,3,4,8-tetrahydro-pyrimido[6,1-b][1,3]thiazin-7-yl)propyl]amide in 10 ml of methanol, 0.07 ml (0.85 mmol) of concentrated hydrochloric acid was added. After the reaction mixture was concentrated to dryness, the residue was washed with diethyl ether to yield 370 mg (89.2%, white solid) of the desired product.

m.p. 165.0°–166.0° C.; Anal. Calcd for C$_{25}$H$_{26}$ClN$_5$O$_5$S$_2$.0.5H$_2$O: C, 51.32; H, 4.65; N, 11.97. Found: C, 51.08; H, 4.81; N, 12.10

Preparation Example 38

Synthesis of 5-[3-(3-pyridyl)propylidene]-3-[4-(imidazo[1,2-a]pyridin-5-ylthio)butyl]thiazolidine-2,4-dione dihydrochloride i) Synthesis of 5-[3-(3-pyridyl)propylidene]-3-[4-(imidazo[1,2-a]pyridin-5-ylthio)butyl]thiazolidine-2,4-dione To a solution of 1.61 g (5.0 mmol) of 3-[4-(imidazo[1,2-a]pyridin-5-ylthio)butyl]thiazolidine-2,4-dione and 676 mg (5.0 mmol) of 3-(2-pyridyl)-1-propanol in 20 ml of ethanol, 43 mg (0.5 mmol) of piperidine-was added, followed by refluxing for 4 hours. After the reaction mixture was cooled, the solvent was distilled off. The residue was dissolved in dichloromethane, washed with purified water and dried, after which the solvent was distilled off. The residue was purified by column chromatography (eluent, chloroform/methanol=50/1) to yield 1.56 g (71.1%, yellow oily substance) of the desired product.

$^1$H-NMR (CDCl$_3$, 200 MHz) δ 1.60–1.90 (4H, m), 2.56 (2H, q, J=7.6 Hz), 2.88 (2H, t, J=7.4 Hz), 3.01 (2H, t, J=6.8 Hz), 3.69 (2H, t, J=6.7 Hz), 6.91 (1H, d, J=7.0 Hz), 7.03 (1H, t, J=7.8 Hz), 7.16 (1H, dd, J=7.2 Hz, 9.0 Hz), 7.20–7.30 (1H, m), 7.45–7.55 (1H, m), 7.59 (1H, d, J=9.2 Hz), 7.70 (1H, d, J=1.0 Hz), 7.84 (1H, d, J=0.8 Hz), 8.40 –8.55 (2H, m); IR (neat) 2950, 1680, 1490, 1140, 750 cm$^{-1}$ ii) Synthesis of 5-[3-(3-pyridyl)propylidene]-3-[4-(imidazo [1,2-a]pyridin-5-ylthio)butyl]thiazolidine-2,4-dione dihydrochloride To a methanol solution of 1.56 g (3.6 mmol) of 5-[3-(3-pyridyl)propylidene]-3-[4-(imidazo[1,2-a]pyridin-5-ylthio) butyl]thiazolidine-2,4-dione, 1.5 ml of 4N hydrochloric acid-ethyl acetate was added, followed by stirring. After the solvent was distilled off, the residue was dissolved in methanol and recrystallized from ether to yield 1.38 g (75.0%, white crystal) of the desired product.

m.p. 115.0°–117.0° C.; $^1$H-NMR (D$_2$O, 200 MHz) δ 1.60–1.90 (4H, m), 2.70 (2H, q, J=7.4 Hz), 3.17 (2H, t, J=7.2 Hz), 3.27 (2H, t, J=6.6 Hz), 3.67 (2H, t, J=6.4 Hz), 7.09 (1H, t, J=7.7 Hz), 7.49 (1H, d, J=7.4 Hz), 7.75–7.90 (2H, m), 7.99 (1H, d, J=2.4 Hz), 8.04 (1H, d, J=5.8 Hz), 8.20 (1H, d, J=2.2 Hz), 8.53 (1H, d, J=8.0 Hz), 8.68 (1H, d, J=5.6 Hz), 8.72 (1H, s); Anal. Calcd for C$_{22}$H$_{24}$Cl$_2$N$_4$O$_2$S$_2$·1.0H$_2$O: C, 49.90; H, 4.95; N, 10.58. Found: C, 50.22; H, 5.01; N, 10.48

Preparation Example 39
Synthesis of 5-[3-(3-pyridyl)propylidene]-3-[4-(imidazo[1,2-a]pyridin-8-yloxy)butyl]thiazolidine-2,4-dione dihydrochloride
i) Synthesis of 5-[3-(3-pyridyl)propylidene]-3-[4-(imidazo [1,2-a]pyridin-8-yloxy)butyl]thiazolidine-2,4-dione To a solution of 1.53 g (5.0 mmol) of 3-[4-(imidazo[1,2-a]pyridin-8-yloxy)butyl]thiazolidine-2,4-dione and 676 mg (5.0 mmol) of 3-(3-pyridyl)-1-propanol in 20 ml of ethanol, 43 mg (0.5 mmol) of piperidine was added, followed by refluxing for 3.5 hours. After the reaction mixture was cooled, the solvent was distilled off. The residue was dissolved in dichloromethane, washed with purified water and dried, after which the solvent was distilled off. The residue was purified by column chromatography (eluent, chloroform/methanol=50/1→25/1) to yield 0.49 g (23.0%, yellow oily substance) of the desired product.

$^1$H-NMR (CDCl$_3$, 200 MHz) δ 1.80–2.05 (4H, m), 2.55 (2H, q, J=7.5 Hz), 2.87 (2H, t, J=7.4 Hz), 3.70–3.85 (2H, m), 4.10–4.25 (2H, m), 6.43 (1H, d, J=7.6 Hz), 6.67 (1H, t, J=7.1 Hz), 7.04 (1H, t, J=7.4 Hz), 7.20–7.35 (1H, m), 7.51–7.60 (3H, m), 7.76 (1H, dd, J=1.0, 6.8 Hz), 8.40–8.55 (2H, m); IR (neat) 2950, 1740, 1680, 1550, 1280, 1110, 740 cm$^{-1}$
ii) Synthesis of 5-[3-(3-pyridyl)propylidene]-3-[4-(imidazo [1,2-a]pyridin-8-yloxy)butyl]thiazolidine-2,4-dione dihydrochloride To a methanol solution of 0.49 g (1.2 mmol) of 5-[3-(3-pyridyl)propylidene]-3-[4-(imidazo[1,2-a]pyridin-8-yloxy) butyl]thiazolidine-2,4-dione, 0.5 ml of 4N hydrochloric acid-ethyl acetate was added, followed by stirring, after which the solvent was distilled off, to yield 0.44 g (74.2%, white oily substance) of the desired product.

$^1$H-NMR (D$_2$O, 200 MHz) δ 1.80–2.00 (4H, m), 2.67 (2H, q, J=7.4 Hz), 3.11 (2H, t, J=7.2 Hz), 3.75 (2H, t, J=6.1 Hz), 4.35 (2H, t, J=5.4 Hz), 7.09 (1H, t, J=7.8 Hz), 7.25–7.35 (2H, m), 7.85–7.90 (2H, m), 8.05 (1H, d, J=2.2 Hz), 8.24 (1H, dd, J=2.1, 5.5 Hz), 8.37 (1H, d, J=8.4 Hz), 8.60 (1H, d, J=5.2 Hz), 8.64 (1H, s); Anal. Calcd for C$_{22}$H$_{24}$Cl$_2$N$_4$O$_3$S·1.0H$_2$O: C, 51.46; H, 5.10; N, 10.91. Found: C, 51.66; H, 5.40; N, 10.83

Preparation Example 40
Synthesis of 7-[4-(imidazo[1,2-a]pyridin-5-ylthio)butyl]-9-methyl-1,1-dioxo-3,4-dihydro-2H,6H-pyrimido[6,1-b][1,3]-thiazine-6,8(7H)-dione hydrochloride
i) Synthesis of 3-benzyl-5-methylpyrimidine-2,4,6(1H,3H)-trione To a suspension of 21.83 g (145 mmol) of benzylurea and 25 ml (145 mmol) of diethyl methylmalonate in 74 ml of methanol, 35.4 ml (145 mmol) of a 4.1M sodium methylate solution was added at room temperature, followed by refluxing for 16 hours. After the reaction mixture was cooled, the solvent was distilled off. After the residue was dissolved in water and insoluble substances were filtered out, the filtrate was adjusted to pH 3–4 by adding concentrated hydrochloric acid. The resulting precipitate was collected by filtration, washed with water and n-hexane-diethyl ether and dried to yield 30.11 g (84.8%, white crystal) of the desired product.

m.p. 128.0°–129.0° C.; $^1$H-NMR (CDCl$_3$, 200 MHz) δ 1.58 (3H, d, J=7.8 Hz), 3.45 (1H, q, J=7.8 Hz), 4.99 (2H, s), 7.25–7.43 (5H, m), 8.97 (1H, s); IR (KBr) 3232, 1724, 1678, 696, 509 cm$^{-1}$; Anal. Calcd for C$_{12}$H$_{12}$N$_2$O$_3$: C, 62.06; H, 5.21; N, 12.06. Found: C, 62.10; H, 5.00; N, 12.06
ii) Synthesis of 3-benzyl-6-chloro-5-methylpyrimidine-2,4 (1H,3H)-dione To 16.8 ml of 50% ethanol, 78.7 ml (844 mmol) of phosphorus oxychloride was added dropwise, with stirring under ice cooling conditions. To this solution, 23.22 g (100 mmol) of 3-benzyl-5-methylpyrimidine-2,4,6(1H,3H)-trione was added little by little. This mixture was stirred at 50° C. for 30 minutes and then at 100° C. for 90 minutes. After cooling, the reaction mixture was poured into ice water and stirred for 1 hour. The resulting precipitate was collected by filtration, washed with water and n-hexane and dried to yield 27.50 g (quant, light white crystal) of the desired product.

m.p. 202.0°–205.0° C.; $^1$H-NMR (CDCl$_3$, 200 MHz) δ 2.03 (3H, s), 5.09 (2H, s), 7.27–7.33 (3H, m), 7.45–7.50 (2H, m), 10.51 (1H, s); IR (KBr) 3147, 1726, 1618, 1495, 1433, 754, 704, 500 cm$^{-1}$
iii) Synthesis of 3-benzyl-6-chloro-1-(3-chloropropyl)-5-methylpyrimidine-2,4(1H,3H)-dione To a suspension of 18.8 g (75 mmol) of 3-benzyl-6-chloro-5-methylpyrimidine-2,4(1H,3H)-dione and 16.58 g (120 mmol) of potassium carbonate in 120 ml of N,N-dimethyl-formamide, 14.8 ml (150 mmol) of 1-bromo-3-chloropropane was added at room temperature. This mixture was stirred at 80° C. for 5 hours. After cooling, the reaction mixture was concentrated to dryness; the resulting residue was dissolved in chloroform-water. After the organic layer was washed with water and dried, the solvent was distilled off to yield an oily substance, which was then purified by column chromatography (eluent, n-hexane/ethyl acetate=5/1→3/1) to yield 13.76 g (56.1%, yellow oily substance) of the desired product.

$^1$H-NMR (CDCl$_3$, 200 MHz) δ 2.02–2.28 (2H, m), 2.09 (3H, s), 3.41–3.63 (2H, m), 4.21–4.29 (2H, m), 5.12 (2H, s), 7.25–7.33 (3H, m), 7.45–7.50 (2H, m); IR (neat) 2964, 1703, 1647, 1437, 756, 702, 507, 474 cm$^{-1}$
iv) Synthesis of 7-benzyl-9-methyl-3,4-dihydro-2H,6H-pyrimido[6,1-b][1,3]thiazine-6,8(7H)-dione To a solution of 13.76 g (42.1 mmol) of 3-benzyl-6-chloro-1-(3-chloropropyl)-5-methylpyrimidine-2,4(1H,3H)-dione in 80 ml of N,N-dimethylformamide, 6.79 g of sodium hydrosulfide n-hydrate was added under ice cooling conditions, followed by stirring for 1 hour. The reaction mixture was concentrated to dryness; the resulting residue was dissolved in dichloromethane-water. After the organic layer was washed with water and dried, the solvent was distilled off to yield a crude crystal, which was then recrystallized from dichloromethane-diethyl ether to yield 7.81 g (64.4%, white crystal) of the desired product.

m.p. 141.0°–142.0° C.; $^1$H-NMR (CDCl$_3$, 200 MHz) δ 1.98 (3H, s), 2.14–2.24 (2H, m), 3.07 (2H, t, J=6.6 Hz), 3.99–4.05 (2H, m), 5.14 (2H, s), 7.21–7.35 (3H, m), 7.46–7.51 (2H, m); IR (KBr) 3036, 2974, 1684, 1630, 1570, 1450, 760, 700, 644 cm$^{-1}$; Anal. Calcd for C$_{15}$H$_{16}$N$_2$O$_2$S: C, 62.48; H, 5.59; N, 9.71. Found: C, 62.29; H, 5.39; N, 9.78 v) Synthesis of 9-methyl-3,4-dihydro-2H,6H-pyrimido[6,1-b][1,3]thiazine-6,8(7H)-dione To a solution of 7.21 g (25 mmol) of 7-benzyl-9-methyl-3,4-dihydro-2H,6H-pyrimido[6,1-b][1,3]thiazine-6,8(7H)-dione in 200 ml of toluene, 12.5 g (50 mmol) of boron tribromide was added under ice cooling conditions, followed by refluxing for 16 hours. After the reaction mixture was cooled, 50 ml of methanol was added, followed by stirring for 30 minutes. After this mixture was concentrated to dryness, methanol-diethyl ether was added to the residue. The resulting precipitate was collected by filtration, washed with diethyl ether and dried to yield 3.97 g (80.1%, light white crystal) of the desired product.

m.p. 196.0°–198.0° C.; $^1$H-NMR (DMSO-d$_6$, 200 MHz) δ 2.10 (2H, quint., J=6.2 Hz), 3.13 (2H, t, J=6.6 Hz), 3.38 (3H, s), 3.81–3.86 (2H, m), 11.20 (1H, s); IR (KBr) 3151, 3022, 2819, 1687, 1650, 750, 702 cm$^{-1}$ vi) Synthesis of 7-(4-chlorobutyl)-9-methyl-3,4-dihydro-2H,6H-pyrimido[6,1-b][1,3]thiazine-6,8(7H)-dione To a suspension of 3.28 g (16.5 mmol) of 9-methyl-3,4-dihydro-2H,6H-pyrimido[6,1-b][1,3]thiazine-6,8(7H)-dione and 3.81 g (28.8 mmol) of potassium carbonate in 70 ml of N,N-dimethylformamide, 2.07 ml (36 mmol) of 1-bromo-4-chlorobutane was added at room temperature, followed by stirring at 60° C. for 2 hours and then at 100° C. for 3 hours. After cooling, the reaction mixture was concentrated to dryness. The residue was dissolved in dichloromethane-water; the organic layer was washed with water and dried. The oily substance obtained by distilling off the solvent was purified by column chromatography (eluent, n-hexane/ethyl acetate=5/1–2/1) to yield 3.24 g (67.9%, light yellow oily substance) of the desired product.

$^1$H-NMR (CDCl$_3$, 200 MHz) δ 1.76–1.87 (4H, m), 1.97 (3H, s), 2.17–2.29 (2H, m), 3.10 (2H, t, J=6.4 Hz), 3.41–3.60 (2H, m), 3.96–4.06 (4H, m); IR (neat) 2954, 1693, 1633, 1579, 1454, 761, 457 cm$^{-1}$ vii) Synthesis of 7-(4-chlorobutyl)-1,1-dioxo-9-methyl-3,4-dihydro-2H,6H-pyrimido[6,1-b][1,3]thiazine-6,8(7H)-dione To a solution of 3.24 g (11.2 mmol) of 7-(4-chlorobutyl)-9-methyl-3,4-dihydro-2H,6H-pyrimido[6,1-b][1,3]thiazine-6,8(7H)-dione in 50 ml of dichloromethane, 3.87 g (11.2 mmol) of 50% m-chloroperbenzoic acid was added under ice cooling conditions, followed by stirring for 1 hour. After the resulting crystal was filtered off, the filtrate was washed with aqueous sodium hydroxide and dried. The oily substance (1-oxo compound) obtained by distilling off the solvent was used for the next reaction without purification.

To a solution of the crude product in 20 ml of acetic acid, 2.5 ml (80 mmol) of 30% aqueous hydrogen peroxide was added at room temperature, followed by stirring at 100° C. for 1 hour. After cooling, the reaction mixture was poured into ice water; the aqueous layer was neutralized with aqueous sodium hydroxide (pH~8). The resulting crystal was collected by filtration, washed with water-n-hexane and dried to yield 2.13 g (59.3%, colorless oily substance) of the desired product.

$^1$H-NMR (CDCl$_3$, 200 MHz) δ 1.78–1.85 (4H, m), 2.37 (3H, s), 2.51 (2H, quint., J=6.2 Hz) 3.44–3.52 (2H, m), 3.57 (2H, t, J=6.4 Hz), 4.00 (2H, t, J=6.6 Hz), 4.11 (2H, m); IR (neat) 2960, 1701, 1653, 1486, 1321, 1134, 762, 565, 480 cm$^{-1}$ viii) Synthesis of 7-[4-(imidazo[1,2-a]pyridin-5-ylthio)-butyl]-9-methyl-1,1-dioxo-3,4-dihydro-2H,6H-pyrimido[6,1-b][1,3]thiazine-6,8(7H)-dione To a suspension of 0.26 g (6.5 mmol) of 60% oily sodium hydride in 30 ml of N,N-dimethylformamide, 0.98 g (6.5 mmol) of 5-mercaptoimidazo[1,2-a]pyridine was added at room temperature, followed by stirring for 30 minutes. To this mixture, 1.92 g (6 mmol) of 7-(4-chlorobutyl)-1,1-dioxo-9-methyl-3,4-dihydro-2H,6H-pyrimido[6,1-b][1,3]thiazine-6,8(7H)-dione and 0.97 g (6.5 mmol) of sodium iodide were added, followed by stirring at 100° C. for 3 hours. After cooling, the reaction mixture was poured into water and extracted with ethyl acetate 3 times. The organic layer was washed with water and dried, after which the solvent was distilled off. The residue was purified by column chromatography (eluent, chloroform/methanol=25/1) to yield 1.61 g (61.8%, white powder) of the desired product.

$^1$H-NMR (CDCl$_3$, 200 MHz) δ 1.73–1.83 (4H, m), 2.36 (3H, s), 2.42–2.58 (2H, m) 3.03 (2H, t, J=7.0 Hz), 3.50 (2H, t, J=6.2 Hz), 3.97 (2H, t, J=6.6 Hz), 4.07 (2H, t, J=6.0 Hz), 6.92 (1H, d, J=7.0 Hz), 7.15 (1H, dd, J=7.0, 8.8 Hz), 7.58 (1H, d, J=8.8 Hz), 7.69 (1H, s), 7.85 (1H, s); IR (KBr) 1701, 1649, 1486, 1446, 1321, 762, 567 cm$^{-1}$ ix) Synthesis of 7-[4-(imidazo[1,2-a]pyridin-5-ylthio)-butyl]-9-methyl-1,1-dioxo-3,4-dihydro-2H,6H-pyrimido[6,1-b][1,3]thiazine-6,8(7H)-dione hydrochloride To a solution of 1.61 g (3.71 mmol) of 7-[4-(imidazo[1,2-a]pyridin-5-ylthio)butyl]-1,1-dioxo-9-methyl-3,4-dihydro-2H,6H-pyrimido[6,1-b][1,3]thiazine-6,8(7H)-dione in 20 ml of methanol, 0.38 ml (4.6 mmol) of concentrated hydrochloric acid was added. After the reaction mixture was concentrated to dryness, diethyl ether was added to the residue. The resulting crystal was collected by filtration and dried to yield 1.64 g (93.8%, light white crystal) of the desired product.

m.p. 192.0°–193.0° C.; $^1$H-NMR (D$_2$O, 200 MHz) δ 1.66–1.86 (4H, m), 2.19 (3H, s), 2.45–2.58 (2H, m), 3.28 (2H, t, J=5.8 Hz), 3.71–3.77 (2H, m), 3.90–4.02 (4H, m), 7.46 (1H, d, J=7.4 Hz), 7.74–7.90 (2H, m), 7.99 (1H, d, J=2.2 Hz), 8.17 (1H, d, J=2.2 Hz); Anal. Calcd for C$_{19}$H$_{23}$ClN$_4$O$_4$S$_2$.0.3H$_2$O: C, 47.90; H, 4.99; N, 11.76. Found: C, 47.99; H, 4.99; N, 11.72

Preparation Example 41

Synthesis of 7-[4-(imidazo[1,2-a]pyridin-5-ylthio)butyl]-9-benzyl-1,1-dioxo-3,4-dihydro-2H,6H-pyrimido[6,1-b][1,3]thiazine-6,8(7H)-dione hydrochloride i) Synthesis of 3,5-dibenzylpyrimidine-2,4,6(1H,3H)-trione To a suspension of 22.53 g (150 mmol) of benzylurea and 37.5 g (150 mmol) of diethyl benzylmalonate in 77 ml of methanol, 36.6 ml (150 mmol) of a 4.1M sodium methylate solution was added at room temperature, followed by refluxing for 16 hours. After the reaction mixture was cooled, the solvent was distilled off. After the residue was dissolved in water and insoluble substances were filtered out, the filtrate was adjusted to pH 3–4 by adding concentrated hydrochloric acid. The resulting precipitate was collected by filtration, washed with water and n-hexane-diethyl ether and dried to yield 48.35 g (quant., white crystal) of the desired product.

m.p. 107.0°–109.0° C.; $^1$H-NMR (CDCl$_3$, 200 MHz) δ 3.47 (2H, d, J=4.6 Hz), 3.74 (1H, t, J=4.8 Hz), 4.89 (2H, s), 6.99–7.31 (10H, m), 8.62 (1H, s); IR (KBr) 3215, 1713, 1676, 1439, 1381, 741, 698, 504 cm$^{-1}$ ii) Synthesis of 6-chloro-3,5-dibenzylpyrimidine-2,4(1H,3H)-dione To 16.8 ml of 50% ethanol, 78.7 ml (844 mmol) of phosphorus oxychloride was added drop by drop, with stirring under ice cooling conditions. To this solution, 30.83 g (100 mmol) of 3,5-dibenzylpyrimidine-2,4,6(1H,3H)-trione was added little by little. This mixture was stirred at 50° C. for 30 minutes and then at 100° C. for 90 minutes. After cooling, the reaction mixture was poured into ice water and stirred for 1 hour. The resulting precipitate was collected by filtration, washed with water and n-hexane and dried to yield 32.62 g (99.8%, light white crystal) of the desired product.

m.p. 146.0°–148.0° C.; $^1$H-NMR (CDCl$_3$, 200 MHz) δ 3.82 (2H, s), 5.07 (2H, s), 7.20–7.47 (10H, m), 10.55 (1H, s); IR (KBr) 1707, 1651, 1638, 1495, 1441, 764, 698, 525 cm$^{-1}$ iii) Synthesis of 6-chloro-1-(3-chloropropyl)-3,5-dibenzylpyrimidine-2,4(1H,3H)-dione To a suspension of 24.51 g (75 mmol) of 6-chloro-3,5-dibenzylpyrimidine-2,4(1H,3H)-dione and 16.58 g (120 mmol) of potassium carbonate in 120 ml of N,N-dimethylformamide, 14.8 ml (150 mmol) of 1-bromo-3-chloropropane was added at room temperature. This mixture was stirred at 90° C. for 2 hours. After cooling, the reaction mixture was concentrated to dryness; the resulting residue was dissolved in chloroform-water. After the organic layer was washed with water and dried, the solvent was distilled off to yield an oily substance, which was then purified by column chromatography (eluent, n-hexane/ethyl acetate=5/1→3/1) to yield 22.68 g (74.9%, yellow oily substance) of the desired product.

$^1$H-NMR (CDCl$_3$, 200 MHz) δ 2.18–2.27 (2H, m), 3.40–3.63 (2H, m), 3.89 (2H, s), 4.18–4.27 (2H, m), 5.12 (2H, s), 7.23–7.48 (10H, m); IR (neat) 3030, 2964, 1705, 1655, 1614, 1438, 750, 700, 497 cm$^{-1}$ iv) Synthesis of 7,9-dibenzyl-3,4-dihydro-2H,6H-pyrimido[6,1-b][1,3]thiazine-6,8(7H)-dione To a solution of 22.68 g (56.2 mmol) of 6-chloro-1-(3-chloropropyl)-3,5-dibenzylpyrimidine-2,4(1H,3H)-dione in 100 ml of N,N-dimethylformamide, 9.06 g of sodium hydrosulfide n-hydrate was added under ice cooling conditions, followed by stirring for 1 hour. The reaction mixture was concentrated to dryness; the resulting residue was dissolved in dichloromethane-water. After the organic layer was washed with water and dried, the solvent was distilled off to yield a crude crystal, which was then recrystallized from dichloromethane-diethyl ether to yield 15.23 g (74.4%, white crystal) of the desired product.

m.p. 110.0°–112.0° C.; $^1$H-NMR (CDCl$_3$, 200 MHz) δ 2.17 (2H, quint., J=5.6 Hz), 3.03 (2H, t, J=6.6 Hz), 3.87 (2H, s), 3.99–4.04 (2H, m), 5.15 (2H, s), 7.20–7.51 (10H, m); IR (KBr) 3028, 2927, 1693, 1663, 1568, 1444, 751, 700, 501 cm$^{-1}$ v) Synthesis of 9-benzyl-3,4-dihydro-2H,6H-pyrimido[6,1-b][1,3]thiazine-6,8(7H)-dione To a solution of 9.11 g (25 mmol) of 7,9-dibenzyl-3,4-dihydro-2H,6H-pyrimido-[6,1-b][1,3]thiazine-6,8(7H)-dione in 200 ml of toluene, 12.5 g (50 mmol) of boron tribromide was added under ice cooling conditions, followed by refluxing for 16 hours. After the reaction mixture was cooled, 50 ml of methanol was added, followed by stirring for 30 minutes. After this mixture was concentrated to dryness, methanol-diethyl ether was added to the residue. The resulting precipitate was collected by filtration, washed with diethyl ether and dried to yield 4.88 g (71.1%, light white crystal) of the desired product.

m.p. 227.0°–229.0° C.; $^1$H-NMR (DMSO-d$_6$, 200 MHz) δ 2.02–2.14 (2H, m), 3.10 (2H, t, J=6.4 Hz), 3.69 (2H, s), 3.82–3.88 (2H, m), 7.02–7.23 (5H, m), 11.33 (1H, s); IR (KBr) 1711, 1633, 1551, 1456, 704 cm$^{-1}$ vi) Synthesis of 9-benzyl-7-(4-chlorobutyl)-3,4-dihydro-2H,6H-pyrimido[6,1-b][1,3]thiazine-6,8(7H)-dione To a suspension of 4.11 g (15 mmol) of 9-benzyl-3,4-dihydro-2H,6H-pyrimido[6,1-b][1,3]thiazine-6,8(7H)-dione and 3.32 g (24 mmol) of potassium carbonate in 70 ml of N,N-dimethylformamide, 3.46 ml (60 mmol) of 1-bromo-4-chlorobutane was added at room temperature, followed by stirring at 60° C. for 2 hours and then at 100° C. for 3 hours. After cooling, the reaction mixture was concentrated to dryness. The residue was dissolved in dichloromethane-water; the organic layer was washed with water and dried. The oily substance obtained by distilling off the solvent was purified by column chromatography (eluent, n-hexane/ethyl acetate=5/1→2/1) to yield 4.96 g (90.6%, light yellow oily substance) of the desired product.

$^1$H-NMR (CDCl$_3$, 200 MHz) δ 1.78–1.85 (4H, m), 2.16–2.26 (2H, m), 3.08 (2H, t, J=6.8 Hz), 3.40–3.59 (2H, m), 3.86 (2H, s), 3.97–4.07 (4H, m), 7.18–7.30 (5H, m); IR (neat) 2956, 1693, 1633, 1633, 1571, 1446, 750, 700, 519 cm$^{-1}$ vii) Synthesis of 9-benzyl-7-(4-chlorobutyl)-1,1-dioxo-3,4-dihydro-2H,6H-pyrimido[6,1-b][1,3]thiazine-6,8(7H)-dione To a solution of 4.96 g (13.6 mmol) of 9-benzyl-7-(4-chlorobutyl)-3,4-dihydro-2H,6H-pyrimido[6,1-b][1,3]thiazine-6,8(7H)-dione in 60 ml of dichloromethane, 4.69 g (13.6 mmol) of 50% m-chloroperbenzoic acid was added under ice cooling conditions, followed by stirring for 1 hour. After the resulting crystal was filtered off, the filtrate was washed with aqueous sodium hydroxide and dried. The oily substance (1-oxo compound) obtained by distilling off the solvent was used for the next reaction without purification. To a solution of the crude product in 20 ml of acetic acid, 3.0 ml (98 mmol) of 30% aqueous hydrogen peroxide was added at room temperature, followed by stirring at 100° C. for 1 hour. After cooling, the reaction mixture was poured into ice water; the aqueous layer was neutralized with aqueous sodium hydroxide (pH~8). The resulting crystal was collected by filtration, washed with water-n-hexane and dried to yield 4.06 g (75.2%, colorless powder) of the desired product.

m.p. 103.0°–105.0° C.; $^1$H-NMR (CDCl$_3$, 200 MHz) δ 1.72–1.80 (4H, m), 2.47 (2H, quint., J=6.6 Hz) 3.36–3.53 (4H, m), 3.94 (2H, t, J=7.0 Hz), 4.16 (2H, t, J=6.2 Hz), 4.27 (2H, s), 7.17–7.38 (5H, m); IR (KBr) 2962, 1705, 1645, 1446, 1319, 1136, 768, 698, 588, 567, 478 cm$^{-1}$ viii) Synthesis of 7-[4-(imidazo[1,2-a]pyridin-5-ylthio)-butyl]-9-benzyl-1,1-dioxo-3,4-dihydro-2H,6H-pyrimido[6,1-b][1,3]thiazine-6,8(7H)-dione To a suspension of 0.22 g (5.5 mmol) of 60% oily sodium hydride in 30 ml of N,N-dimethylformamide, 0.83 g (5.5 mmol) of 5-mercaptoimidazo[1,2-a]pyridine was added at room temperature, followed by stirring for 30 minutes. To this mixture, 1.98 g (5 mmol) of 9-benzyl-7-(4-chlorobutyl)-1,1-dioxo-3,4-dihydro-2H,6H-pyrimido[6,1-b][1,3]thiazine-6,8(7H)-dione and 0.82 g (5.5 mmol) of sodium iodide were added, followed by stirring at 100° C. for 2 hours. After cooling, the reaction mixture was poured into water and extracted with ethyl acetate 3 times. The organic layer was washed with water and dried, after which the solvent was distilled off. The residue was purified by column chromatography (eluent, ethyl acetate→ethyl acetate/ethanol=10/1) to yield 1.95 g (78.2%, white powder) of the desired product.

m.p. 53.0°–54.0° C.; $^1$H-NMR (CDCl$_3$, 200 MHz) δ 1.58–1.82 (4H, m), 2.50 (2H, quint., J=6.6 Hz), 2.99 (2H, t, J=6.6 Hz), 3.53 (2H, t, J=6.8 Hz), 3.92 (2H, t, J=7.2 Hz), 4.12–4.19 (2H, m), 4.28 (2H, s), 6.88 (1H, dd, J=1.0, 7.0 Hz), 7.14 (1H, dd, J=7.2, 9.0 Hz), 7.18–7.40 (5H, m), 7.58 (1H, dd, J=1.0, 9.0 Hz), 7.69 (1H, d, J=1.4 Hz), 7.83 (1H, d, J=1.0 Hz); IR (KBr) 1705, 1651, 1487, 1443, 1324, 1292, 1142, 752, 700, 476 cm$^{-1}$ ix) Synthesis of 7-[4-(imidazo[1,2-a]pyridin-5-ylthio)-butyl]-9-benzyl-1,1-dioxo-3,4-dihydro-2H,6H-pyrimido[6,1-b][1,3]thiazine-6,8(7H)-dione hydrochloride To a solution of 1.95 g (3.91 mmol) of 7-[4-(imidazo[1,2-a]pyridin-5-ylthio)butyl]-1,1-dioxo-9-benzyl-3,4-dihydro-2H,6H-pyrimido[6,1-b][1,3]thiazine-6,8(7H)-dione in 20 ml of methanol, 0.5 ml (6 mmol) of concentrated hydrochloric acid was added. After the reaction mixture was concentrated to dryness, diethyl ether was added to the residue. The resulting crystal was collected by filtration and dried to yield 1.90 g (90.8%, light white crystal) of the desired product.

m.p. 96.0°–97.0° C.; $^1$H-NMR (D$_2$O, 200 MHz) δ 1.66–1.80 (4H, m), 2.34–2.48 (2H, m), 2.98–3.14 (2H, m), 3.54–4.24 (8H, m), 7.04–7.32 (7H, m), 7.69–7.74 (2H, m), 7.83 (1H, s), 7.98 (1H, d, J=2.2 Hz); Anal. Calcd for C$_{25}$H$_{27}$ClN$_4$O$_4$S$_2$.0.5H$_2$O: C, 54.00; H, 5.07; N, 10.07. Found: C, 54.02; H, 5.25; N, 9.82

Preparation Example 42

Synthesis of 7-[4-(imidazo[1,2-a]pyridin-5-ylthio)butyl]-9-isopropyl-1,1-dioxo-3,4-dihydro-2H,6H-pyrimido[6,1-b][1,3]thiazine-6,8(7H)-dione hydrochloride i) Synthesis of 3-benzyl-5-isopropylpyrimidine-2,4,6(1H,3H)-trione To a suspension of 22.53 g (150 mmol) of benzylurea and 30.34 g (150 mmol) of diethyl isopropylmalonate in 77 ml of methanol, 36.6 ml (150 mmol) of a 4.1M sodium methylate solution was added at room temperature, followed by refluxing for 16 hours. After the reaction mixture was cooled, the solvent was distilled off. After the residue was dissolved in water and insoluble substances were filtered out, the filtrate was adjusted to pH 3–4 by adding concentrated hydrochloric acid. The resulting precipitate was collected by filtration, washed with water and n-hexane-diethyl ether and dried to yield 34.96 g (89.5%, white crystal) of the desired product.

$^1$H-NMR (CDCl$_3$, 200 MHz) δ 1.02 (6H, d, J=7.0 Hz), 2.58 (1H, d, quint., J=4.0, 7.0 Hz), 3.29 (1H, d, J=4.0 Hz), 5.02 (2H, s), 7.28–7.46 (5H, m), 8.95 (1H, s); IR (KBr) 1684, 1441, 1375, 1120, 700 cm$^{-1}$ ii) Synthesis of 3-benzyl-6-chloro-5-isopropylpyrimidine-2,4(1H,3H)-dione To 16.8 ml of 50% ethanol, 78.7 ml (844 mmol) of phosphorus oxychloride was added drop by drop, with stirring under ice cooling conditions. To this solution, 26.03 g (100 mmol) of 3-benzyl-5-isopropylpyrimidine-2,4,6(1H,3H)-trione was added little by little. This mixture was stirred at 50° C. for 30 minutes and then at 100° C. for 90 minutes. After cooling, the reaction mixture was poured into ice water and stirred for 1 hour. The resulting precipitate was collected by filtration, washed with water and n-hexane and dried to yield 27.05 g (97.0%, white crystal) of the desired product.

$^1$H-NMR (CDCl$_3$, 200 MHz) δ 1.27 (6H, d, J=6.8 Hz), 3.17 (1H, quint., J=7.0 Hz), 5.07 (2H, s), 7.26–7.33 (3H, m), 7.45–7.49 (2H, m), 10.49 (1H, s); IR (KBr) 1711, 1647, 1441, 704 cm$^{-1}$ iii) Synthesis of 3-benzyl-6-chloro-1-(3-chloropropyl)-5-isopropylpyrimidine-2,4(1H,3H)-dione To a suspension of 20.91 g (75 mmol) of 3-benzyl-6-chloro-5-isopropylpyrimidine-2,4(1H,3H)-dione and 16.58 g (120 mmol) of potassium carbonate in 120 ml of N,N-dimethylformamide, 14.8 ml (150 mmol) of 1-bromo-3-chloropropane was added at room temperature. This mixture was stirred at 90° C. for 2 hours. After cooling, the reaction mixture was concentrated to dryness; the resulting residue was dissolved in chloroform-water. After the organic layer was washed with water and dried, the solvent was distilled off to yield an oily substance, which was then purified by column chromatography (eluent, n-hexane/ethyl acetate=5/1→3/1) to yield 8.06 g (30.1%, yellow oily substance) of the desired product.

$^1$H-NMR (CDCl$_3$, 200 MHz) δ 1.29 (6H, d, J=7.0 Hz), 2.11–2.23 (2H, m), 3.26 (1H, quint., J=7.0 Hz), 3.41–3.63 (2H, m), 4.19–4.28 (2H, m), 5.10 (2H, s), 7.26–7.31 (3H, m), 7.44–7.49 (2H, m); IR (neat) 2962, 1704, 1651, 1599, 1435, 775, 752, 700 cm$^{-1}$ iv) Synthesis of 7-benzyl-9-isopropyl-3,4-dihydro-2H,6H-pyrimido[6,1-b][1,3]thiazine-6,8(7H)-dione To a solution of 8.06 g (22.6 mmol) of 3-benzyl-6-chloro-1-(3-chloropropyl)-5-isopropylpyrimidine-2,4(1H,3H)-dione in 40 ml of N,N-dimethylformamide, 3.64 g of sodium hydrosulfide n-hydrate was added under ice cooling conditions, followed by stirring for 1 hour. The reaction mixture was concentrated to dryness; the resulting residue was dissolved in dichloromethane-water. The organic layer was washed with water and dried. The oily substance obtained by distilling off the solvent was purified by column chromatography (eluent, n-hexane/ethyl acetate=2/1→1/4) to yield 5.86 g (81.9%, light yellow oily substance) of the desired product.

$^1$H-NMR (CDCl$_3$, 200 MHz) δ 1.29 (6H, d, J=7.0 Hz), 2.11–2.23 (2H, m), 3.05 (2H, t, J=6.6 Hz), 3.14 (2H, quint., J=7.0 Hz), 4.01–4.07 (2H, m), 7.26–7.30 (3H, m), 7.45–7.50 (2H, m); IR (KBr) 2960, 1693, 1637, 1554, 1441, 775, 750, 702, 640 cm$^{-1}$ v) Synthesis of 9-isopropyl-3,4-dihydro-2H,6H-pyrimido[6,1-b][1,3]thiazine-6,8(7H)-dione To a solution of 4.75 g (15 mmol) of 7-benzyl-9-isopropyl-3,4-dihydro-2H,6H-pyrimido[6,1-b][1,3]thiazine-6,8(7H)-dione in 120 ml of toluene, 7.52 g (30 mmol) of boron tribromide was added under ice cooling conditions, followed by refluxing for 16 hours. After the reaction mixture was cooled, 50 ml of methanol was added, followed by stirring for 30 minutes. After this mixture was concentrated to dryness, methanol-diethyl ether was added to the residue. The resulting precipitate was collected by filtration, washed with diethyl ether and dried to yield 1.95 g (57.4%, light white powder) of the desired product.

$^1$H-NMR (DMSO-d$_6$, 200 MHz) δ 1.20 (6H, d, J=6.8 Hz), 2.09 (2H, quint., J=6.0 Hz), 3.02 (1H, quint., J=7.0 Hz), 3.12 (2H, t, J=6.6 Hz), 3.84–3.90 (2H, m), 11.09 (1H, s); IR (KBr) 3016, 1678, 1545, 1452, 685 cm$^{-1}$ vi) Synthesis of 7-(4-chlorobutyl)-9-isopropyl-3,4-dihydro-2H,6H-pyrimido[6,1-b][1,3]thiazine-6,8(7H)-dione To a suspension of 1.81 g (8 mmol) of 9-isopropyl-3,4-dihydro-2H,6H-pyrimido[6,1-b][1,3]thiazine-6,8(7H)-dione and 1.77 g (12.8 mmol) of potassium carbonate in 30 ml of N,N-dimethylformamide, 1.84 ml (16 mmol) of 1-bromo-4-chlorobutane was added at room temperature, followed by stirring at 60° C. for 2 hours and then at 100° C. for 3 hours. After cooling, the reaction mixture was concentrated to dryness. The residue was dissolved in dichloromethane-water; the organic layer was washed with water and dried. The oily substance obtained by distilling off the solvent was purified by column chromatography (eluent, n-hexane/ethyl acetate=5/1→2/1) to yield 2.12 g (83.6%, colorless oily substance) of the desired product. $^1$H-NMR (CDCl$_3$, 200 MHz) δ 1.28 (6H, d, J=6.8 Hz), 1.77–1.86 (4H, m), 2.15–2.26 (2H, m), 3.08 (2H, t, J=6.8 Hz), 3.13 (1H, quint., J=7.0 Hz), 3.41–3.60 (2H, m), 3.95 (2H, t, J=7.2 Hz), 4.04–4.10 (2H, m); IR (neat) 2956, 1691, 1637, 1560, 1439, 777, 752 cm$^{-1}$ vii) Synthesis of 7-(4-chlorobutyl)-9-isopropyl-1,1-dioxo-3,4-dihydro-2H,6H-pyrimido[6,1-b][1,3]thiazine-6,8(7H)-dione To a solution of 2.12 g (6.69 mmol) of 7-(4-chlorobutyl)-9-isopropyl-3,4-dihydro-2H,6H-pyrimido-[6,1-b][1,3]thiazine-6,8(7H)-dione in 30 ml of dichloromethane, 2.31 g (6.69 mmol) of 50% m-chloroperbenzoic acid was added under ice cooling conditions, followed by stirring for 1 hour. After the resulting crystal was filtered off, the filtrate was washed with aqueous sodium hydroxide and dried. The oily substance (1-oxo compound) obtained by distilling off the solvent was used for the next reaction without purification. To a solution of the crude product in 10 ml of acetic acid, 1.2 ml (40 mmol) of 30% aqueous hydrogen peroxide was added at room temperature, followed by stirring at 100° C. for 1 hour. After cooling, the reaction mixture was poured into ice water; the aqueous layer was neutralized with aqueous sodium hydroxide (pH~8). The resulting crystal was collected by filtration and purified with n-hexane/diethyl ether to yield 1.64 g (70.2%, white powder) of the desired product.

$^1$H-NMR (CDCl$_3$, 200 MHz) δ 1.35 (6H, d, J=6.6 Hz), 1.78–1.84 (4H, m), 2.50 (2H, quint., J=6.2 Hz) 3.42–3.61 (4H, m), 3.83 (1H, quint., J=6.6 Hz), 3.96 (2H, t, J=6.6 Hz), 4.06 (2H, t, J=6.2 Hz); IR (KBr) 1703, 1649, 1439, 1327, 1136 cm$^{-1}$ viii) Synthesis of 7-[4-(imidazo[1,2-a]pyridin-5-ylthio)-butyl]-9-isopropyl-1,1-dioxo-3,4-dihydro-2H,6H-pyrimido[6,1-b][1,3]thiazine-6,8(7H)-dione To a suspension of 0.152 g (3.8 mmol) of 60% oily sodium hydride in 20 ml of N,N-dimethylformamide, 0.57 g (3.8 mmol) of 5-mercaptoimidazo[1,2-a]pyridine was added at room temperature, followed by stirring for 30 minutes. To this mixture, 1.22 g (3.5 mmol) of 7-(4-chlorobutyl)-9-isopropyl-1,1-dioxo-3,4-dihydro-2H,6H-pyrimido[6,1-b][1,3]thiazine-6,8(7H)-dione and 0.57 g (3.8 mmol) of sodium iodide were added, followed by stirring at 100° C. for 3 hours. After cooling, the reaction mixture was poured into water and extracted with ethyl acetate 3 times. The organic layer was washed with water and dried, after which the solvent was distilled off. The residue was purified by column chromatography (eluent, chloroform/methanol=25/1) to yield 1.11 g (68.6%, white powder) of the desired product.

$^1$H-NMR (CDCl$_3$, 200 MHz) δ 1.35 (6H, d, J=7.0 Hz), 1.62–1.84 (4H, m), 2.44–2.56 (2H, m), 3.03 (2H, t, J=6.8 Hz), 3.45–3.51 (2H, m), 3.83 (1H, quint., J=7.0 Hz), 3.93 (2H, t, J=7.0 Hz), 4.02 (1H, d, J=6.1 Hz), 6.92 (1H, dd, J=0.8, 7.0 Hz), 7.15 (1H, dd, J=7.4, 9.2 Hz), 7.58 (1H, d, J=9.2 Hz), 7.70 (1H, d, J=1.0 Hz), 7.86 (1H, s); IR (KBr) 2962, 1703, 1649, 1487, 1441, 1323, 1292, 783 cm$^{-1}$ ix) Synthesis of 7-[4-(imidazo[1,2-a]pyridin-5-ylthio)-butyl]-9-isopropyl-1,1-dioxo-3,4-dihydro-2H,6H-pyrimido[6,1-b][1,3]thiazine-6,8(7H)-dione hydrochloride To a solution of 1.11 g (2.4 mmol) 7-[4-(imidazo[1,2-a]pyridin-5-ylthio)butyl]-9-isopropyl-1,1-dioxo-3,4-dihydro-2H,6H-pyrimido[6,1-b][1,3]thiazine-6,8(7H)-dione in 15 ml of methanol, 0.3 ml (3.5 mmol) of concentrated hydrochloric acid was added. After the reaction mixture was concentrated to dryness, diethyl ether was added to the residue. The resulting crystal was collected by filtration and dried to yield 1.14 g (95.7%, light white crystal) of the desired product.

m.p. 177.0°–180.0° C.; $^1$H-NMR (D$_2$O, 200 MHz) δ 1.23 (6H, d, J=6.6 Hz), 1.74–1.84 (4H, m), 2.50–2.60 (2H, m), 3.30–3.39 (2H, m), 3.60–3.79 (3H, m), 3.71–4.03 (4H, m), 7.49 (1H, d, J=7.0 Hz), 7.79–7.96 (1H, m), 8.06 (1H, s), 8.18 (1H, m); Anal. Calcd for C$_{21}$H$_{27}$ClN$_4$O$_4$S$_2$.1.0H$_2$O; C, 48.78; H, 5.65; N, 10.84. Found: C, 48.86; H, 5.61; N, 10.82

Preparation Example 43

Synthesis of 7-[4-(imidazo[1,2-a]pyridin-5-ylthio)butyl]-1,1-dioxo-3,4-dihydro-2H,6H-pyrimido[6,1-b][1,3]thiazine-6,8(7H)-dione hydrochloride i) Synthesis of 3-benzylpyrimidine-2,4,6(1H,3H)-trione To a suspension of 24.78 g (165 mmol) of benzylurea and 25 ml (165 mmol) of diethyl malonate in 84 ml of methanol, 40.2 ml (165 mmol) of a 4.1M sodium methylate solution was added at room temperature, followed by refluxing for 16 hours. After the reaction mixture was cooled, the solvent was distilled off. After the residue was dissolved in water and insoluble substances were filtered out, the filtrate was adjusted to pH 3–4 by adding concentrated hydrochloric acid. The resulting precipitate was collected by filtration, washed with water and n-hexane-diethyl ether and dried to yield 32.12 g (89.2%, white crystal) of the desired product.

$^1$H-NMR (CDCl$_3$, 200 MHz) δ 3.65 (1H, s), 5.02 (2H, s), 7.26–7.35 (3H, m), 7.40–7.46 (2H, m), 8.48 (1H, s); IR (KBr) 3253, 1691, 1678, 1435, 1346, 1196, 700, 503 cm$^{-1}$ ii) Synthesis of 3-benzyl-6-chloropyrimidine-2,4(1H,3H)-dione To 16.8 ml of 50% ethanol, 78.7 ml (844 mmol) of phosphorus oxychloride was added dropwise, with stirring under ice cooling conditions. To this solution, 20.62 g (94.5 mmol) of 3-benzylpyrimidine-2,4,6(1H,3H)-trione was added portionwise. This mixture was stirred at 50° C. for 30 minutes and then at 100° C. for 90 minutes. After cooling, the reaction mixture was poured into ice water and stirred for 1 hour. The resulting precipitate was collected by filtration, washed with water and n-hexane and dried to yield 20.12 g (90.0%, white crystal) of the desired product.

$^1$H-NMR (CDCl$_3$, 200 MHz) δ 5.06 (2H, s), 5.89 (1H, s), 7.26–7.34 (3H, m), 7.43–7.48 (2H, m), 10.48 (1H, s); IR (KBr) 3089, 1728, 1618, 1498, 1437, 504 cm$^{-1}$ iii) Synthesis of 3-benzyl-6-chloro-1-(3-chloropropyl)pyrimidine-2,4(1H,3H)-dione To a suspension of 18.93 g (80 mmol) of 3-benzyl-6-chloropyrimidine-2,4(1H,3H)-dione and 17.69 g (128 mmol) of potassium carbonate in 120 ml of N,N-dimethylformamide, 15.8 ml (160 mmol) of 1-bromo-3-chloropropane was added at room temperature. This mixture was stirred at 90° C. for 3 hours. After cooling, the reaction mixture was concentrated to dryness; the resulting residue was dissolved in chloroform-water. After the organic layer was washed with water and dried, the solvent was distilled off to yield an oily substance, which was then purified by column chromatography (eluent, n-hexane/ethyl acetate=5/1→3/1) to yield 13.46 g (53.7%, light yellow powder) of the desired product.

$^1$H-NMR (CDCl$_3$, 200 MHz) δ 2.12–2.32 (2H, m), 3.40–3.63 (2H, m), 4.18–4.25 (2H, m), 5.09 (2H, s), 5.95 (1H, s), 7.26–7.34 (3H, m), 7.44–7.48 (2H, m); IR (KBr) 1703, 1662, 1435, 754 cm$^{-1}$ iv) Synthesis of 7-benzyl-3,4-dihydro-2H,6H-pyrimido[6,1-b][1,3]thiazine-6,8(7H)-dione To a solution of 13.46 g (43.0 mmol) of 3-benzyl-6-chloro-1-(3-chloropropyl)pyrimidine-2,4(1H,3H)-dione in 75 ml of N,N-dimethylformamide, 6.92 g of sodium hydrosulfide n-hydrate was added under ice cooling conditions, followed by stirring for 1 hour. The reaction mixture was concentrated to dryness; the resulting residue was dissolved in dichloromethane-water. The organic layer was washed with water and dried. The residue obtained by distilling off the solvent was purified by recrystallization (solvent, dichloromethane-diethyl ether) to yield 6.70 g (56.8%, white powder) of the desired product.

$^1$H-NMR (CDCl$_3$, 200 MHz) δ 2.22 (2H, quint., J=6.6 Hz), 3.04 (2H, t, J=6.6 Hz), 3.94–4.00 (2H, m), 5.09 (2H, s), 5.73 (1H, s), 7.26–7.32 (3H, m), 7.44–7.49 (2H, m); IR (KBr) 3086, 1687, 1645, 1570, 1431, 1014, 833, 756, 714 cm$^{-1}$ v) Synthesis of 3,4-dihydro-2H,6H-pyrimido[6,1-b][1,3]thiazine-6,8(7H)-dione To a solution of 6.31 g (23 mmol) of 7-benzyl-3,4-dihydro-2H,6H-pyrimido[6,1-b][1,3]thiazine-6,8(7H)-dione in 200 ml of toluene, 12.5 g (50 mmol) of boron tribromide was added under ice cooling conditions, followed by refluxing for 16 hours. After the reaction mixture was cooled, 50 ml of methanol was added, followed by stirring for 30 minutes. After this mixture was concentrated to dryness, methanoldiethyl ether was added to the residue. The resulting precipitate was collected by filtration, washed with diethyl ether and dried to yield 3.25 g (76.7%, light white powder) of the desired product.

$^1$H-NMR (DMSO-d$_6$, 200 MHz) δ 2.04–2.20 (2H, m), 3.07–3.20 (2H, m), 3.82 (2H, q, J=5.2 Hz), 5.51 (1H, s), 11.66 (1H, s); IR (KBr) 3080, 1738, 1603, 1566, 1327, 1260, 1142, 962, 824, 608 cm$^{-1}$ vi) Synthesis of 7-(4-chlorobutyl)-3,4-dihydro-2H,6H-pyrimido[6,1-b][1,3]thiazine-6,8(7H)-dione To a suspension of 2.76 g (15 mmol) of 3,4-dihydro-2H,6H-pyrimido[6,1-b][1,3]thiazine-6,8(7H)-dione and 3.32 g (24 mmol) of potassium carbonate in 50 ml of N,N-dimethyl-formamide, 3.46 ml (30 mmol) of 1-bromo-4-chlorobutane was added at room temperature, followed by stirring at 60° C. for 2 hours and then at 100° C. for 3 hours. After cooling, the reaction mixture was concentrated to dryness. The residue was dissolved in dichloromethane-water; the organic layer was washed with water and dried. The oily substance obtained by distilling off the solvent was purified by column chromatography (eluent, n-hexane/ethyl acetate=2/1→1/4) to yield 1.92 g (46.6%, white powder) of the desired product.

$^1$H-NMR (CDCl$_3$, 200 MHz) δ 1.78–1.83 (4H, m), 2.21–2.32 (2H, m), 3.08 (2H, t, J=6.2 Hz), 3.41–3.60 (2H, m), 3.92–4.03 (4H, m), 5.70 (1H, s); IR (neat) 1689, 1645, 1568, 1437, 758 cm$^{-1}$ vii) Synthesis of 7-(4-chlorobutyl)-1,1-dioxo-3,4-dihydro-2H,6H-pyrimido[6,1-b][1,3]thiazine-6,8(7H)-dione To a solution of 1.65 g (6 mmol) of 7-(4-chlorobutyl)-3,4-dihydro-2H,6H-pyrimido[6,1-b][1,3]thiazine-6,8(7H)-dione in 30 ml of dichloromethane, 2.07 g (6 mmol) of 50% m-chloroperbenzoic acid was added under ice cooling conditions, followed by stirring for 1 hour. After the resulting crystal was filtered off, the filtrate was washed with aqueous sodium hydroxide and dried. The oily substance (1-oxo compound) obtained by distilling off the solvent was used for the next reaction without purification. To a solution of the crude product in 10 ml of acetic acid, 1.2 ml (40 mmol) of 30% aqueous hydrogen peroxide was added at room temperature, followed by stirring at 100° C. for 1 hour. After cooling, the reaction mixture was poured into ice water; the aqueous layer was neutralized with aqueous sodium hydroxide (pH ~8). The reaction mixture was extracted with ethyl acetate. After the organic layer was dried, the solvent was distilled off. The residue was purified by column chromatography (eluent, n-hexane/ethyl acetate=1/2) to yield 0.70 g (38.0%, white powder) of the desired product.

$^1$H-NMR (CDCl$_3$, 200 MHz) δ 1.79–1.85 (4H, m), 2.46–2.60 (2H, m) 3.41–3.61 (4H, m), 3.98 (2H, t, J=7.0 Hz), 4.15–4.22 (2H, m), 6.48 (1H, s); IR (KBr) 1709, 1666, 1323, 1146, 760, 592, 469 cm$^{-1}$ viii) Synthesis of 7-[4-(imidazo[1,2-a]pyridin-5-ylthio)-butyl]-1,1-dioxo-3,4-dihydro-2H,6H-pyrimido[6,1-b][1,3]thiazine-6,8(7H)-dione To a suspension of 0.053 g (2.2 mmol) of 60% oily sodium hydride in 15 ml of N,N-dimethylformamide, 0.33 g (2.2 mmol) of 5-mercaptoimidazo[1,2-a]pyridine was added at room temperature, followed by stirring for 30 minutes. To this mixture, 0.61 g (2.0 mmol) of 7-(4-chlorobutyl)-1,1-dioxo-3,4-dihydro-2H,6H-pyrimido[6,1-b][1,3]thiazine-6,8 (7H)-dione and 0.33 g (2.2 mmol) of sodium iodide were added, followed by stirring at 100° C. for 3 hours. After cooling, the reaction mixture was poured into water and extracted with ethyl acetate 3 times. The organic layer was washed with water and dried, after which the solvent was distilled off. The residue was purified by recrystallization (solvent, chloroform/diethyl ether) to yield 0.442 g (52.6%, light green powder) of the desired product.

$^1$H-NMR (CDCl$_3$, 200 MHz) δ 1.64–1.84 (4H, m), 2.51 (2H, quint., J=6.2 Hz), 3.03 (2H, t, J=7.0 Hz), 3.48 (2H, t, J=7.0 Hz), 3.94 (2H, t, J=6.8 Hz), 4.14 (2H, t, J=6.2 Hz), 6.46 (1H, m), 6.95 (1H, d, J=6.6 Hz), 7.16 (1H, dd, J=7.4, 9.2 Hz), 7.57 (1H, d, J=8.8 Hz), 7.69 (1H, s), 7.85 (1H, s); IR (KBr) 1707, 1659, 1485, 1443, 1327, 1146, 756, 592 cm$^{-1}$ ix) Synthesis of 7-[4-(imidazo[1,2-a]pyridin-5-ylthio)-butyl]-1,1-dioxo-3,4-dihydro-2H,6H-pyrimido[6,1-b][1,3]thiazine-6,8(7H)-dione hydrochloride To a solution of 0.442 g (1.05 mmol) 7-[4-(imidazo[1,2-a]pyridin-5-ylthio)butyl]-1,1-dioxo-3,4-dihydro-2H,6H-pyrimido[6,1-b][1,3]thiazine-6,8(7H)-dione in 15 ml of methanol, 0.3 ml (3.5 mmol) of concentrated hydrochloric acid was added. After the reaction mixture was concentrated to dryness, diethyl ether was added to the residue. The resulting crystal was collected by filtration and dried to yield 0.405 g (84.3%, light white crystal) of the desired product.

m.p. 178.0°–179.0C; $^1$H-NMR (D$_2$O, 200 MHz) δ 1.68–1.82 (4H, m), 2.50–2.62 (2H, m), 3.27 (2H, t, J=7.0 Hz), 3.73 (2H, t, J=6.6 Hz), 3.90 (2H, t, J=7.0 Hz), 4.03 (2H, t, J=6.8 Hz), 6.49 (1H, s), 7.52 (1H, dd, J=1.6, 7.2 Hz), 7.75–7.91 (2H, m), 7.96–7.98 (1H, m), 8.21–8.23 (1H, m); Anal. Calcd for C$_{18}$H$_{21}$ClN$_4$O$_4$S$_2$.0.4H$_2$O: C, 46.58; H, 4.73; N, 12.07. Found:C, 46.76; H, 4.66; N, 12.01

Preparation Example 44

Synthesis of 5-carboethoxymethylene-3-[4-(imidazo[1,2-a]pyridin-5-ylthio)butyl]thiazolidine-2,4-dione hydrochloride i) Synthesis of 5-carboethoxymethylene-3-[4-(imidazo[1,2-a]pyridin-5-ylthio)butyl]thiazolidine-2,4-dione To a solution of 3.21 g (10 mmol) of 3-[4-(imidazo[1,2-a]pyridin-5-ylthio)butyl]thiazolidine-2,4-dione and 1.12 g (11 mmol) of ethylglycolic acid in 50 ml of ethanol, 0.01 ml (1.0 mmol) of piperidine was added, followed by refluxing for 16 hours. After the reaction mixture was cooled, the solvent was distilled off. The residue was dissolved in chloroform, washed with saturated aqueous sodium hydrogen carbonate and dried, after which the solvent was distilled off. The residue was purified by column chromatography (eluent, n-hexane/ethyl acetate=1/1→1/4→ethyl acetate) to yield 0.70 g (17.3%, yellow crystal) of the desired product.

$^1$H-NMR (CDCl$_3$, 200 MHz) δ 1.35 (3H, t, J=7.0 Hz), 1.62–1.88 (4H, m), 3.01 (2H, t, J=7.0 Hz), 3.74 (2H, t, J=7.2 Hz), 4.32 (2H, q, J=7.2 Hz), 6.91 (1H, dd, J=1.0, 7.0 Hz), 7.15 (1H, dd, J=7.0, 9.2 Hz), 7.58 (1H, d, J=9.0 Hz), 7.69 (1H, d, J=1.2 Hz), 7.84 (1H, s)

ii) Synthesis of 5-carboethoxymethylene-3-[4-(imidazo[1,2-a]pyridin-5-ylthio)butyl]thiazolidine-2,4-dione hydrochloride To a solution of 0.70 g (1.73 mmol) of 5-carboethoxymethylene-3-[4-(imidazo[1,2-a]pyridin-5-ylthio)butyl]thiazolidine-2,4-dione in 20 ml of methanol, 0.20 ml of concentrated hydrochloric acid was added, followed by stirring, after which the solvent was distilled off. The residue was washed with diethyl ether to yield 0.74 g (96.8%, white solid) of the desired product.

m.p. 119.0°–120.0° C.; $^1$H-NMR (CD$_3$OD, 200 MHz) δ 1.34 (3H, t, J=7.2 Hz), 1.76–1.90 (4H, m), 3.35 (2H, t, J=6.8

Hz), 3.75 (2H, t, J=6.2 Hz), 4.31 (2H, q, J=7.2 Hz), 6.94 (1H, s), 7.60 (1H, d, J=7.2 Hz), 7.82–8.00 (2H, m), 8.16 (1H, d, J=2.0 Hz), 8.33 (1H, d, J=1.8 Hz); Anal. Calcd for $C_{18}H_{20}ClN_3O_4S_2.0.5H_2O$: C, 47.94; H, 4.69; N, 9.32. Found: C, 48.13; H, 4.71; N, 9.60

Preparation Example 45

Synthesis of 5-butylidene-3-[4-(imidazo[1,2-a]pyridin-5-ylsulfinyl)butyl]thiazolidine-2,4-dione hydrochloride i) Synthesis of 5-(4-chlorobutylsulfinyl)imidazo[1,2-a]pyridine To a solution of 2.41 g (10 mmol) of 5-(4-chlorobutylthio)imidazo[1,2-a]]pyridine in 5 ml of concentrated sulfuric acid, 4 ml of concentrated nitric acid was added at 0° C., followed by stirring for 15 minutes. The reaction mixture was poured into ice water, neutralized with 50% aqueous sodium hydroxide, extracted with chloroform and dried, after which the solvent was distilled off. The residue was purified by column chromatography (eluent, ethyl acetate→ethyl acetate/ethanol=10/1) to yield 1.78 g (69.3%, brown-yellow oily substance) of the desired product.

$^1$H-NMR (CDCl$_3$, 200 MHz) δ 1.88–1.99 (4H, m), 3.10 (2H, t, J=7.6 Hz), 3.55 (2H, t, J=6.6 Hz), 7.34–7.37 (2H, m), 7.79–7.84 (2H, m), 7.94 (1H, s); IR (neat) 2956, 1624, 1493, 1450, 1284, 1142, 1066, 787, 737, 636 cm$^{-1}$ ii) Synthesis of 3-[4-(imidazo[1,2-a]pyridin-5-ylsulfinyl) butyl]thiazolidine-2,4-dione To a solution of 0.51 g (2.0 mmol) of 5-(4-chlorobutylsulfinyl)imidazo[1,2-a]pyridine and 0.355 g (2.0 mmol) of thiazolidine-2,4-dione in 10 ml of N,N-dimethylformamide, 0.30 ml (2.0 mmol) of 1,8-diazabicyclo [5.4.0]-7-undecene was added, followed by heating at 80° C. for 16 hours. After cooling, the reaction mixture was poured into water, extracted with ethyl acetate, washed with water and dried, after which the solvent was distilled off. The residue was purified by column chromatography (eluent, chloroform→chloroform/methanol=50/1) to yield 0.33 g (49.0%, light yellow oily substance) of the desired product.

$^1$H-NMR (CDCl$_3$, 200 MHz) δ 1.73–1.84 (4H, m), 3.10–3.16 (2H, m), 3.64 (2H, t, J=6.6 Hz), 3.94 (2H, s), 7.36–7.41 (2H, m), 7.79–7.84 (2H, m), 7.93 (1H, s); IR (neat) 2943, 1749, 1684, 1352, 1286, 1142, 1066, 1038, 789, 748 cm$^{-1}$ iii) Synthesis of 5-butylidene-3-[4-(imidazo[1,2-a]pyridin-5-ylsulfinyl)butyl]thiazolidine-2,4-dione To a solution of 0.33 g (0.98 mmol) of 3-[4-(imidazo[1, 2-a]pyridin-5-ylsulfinyl)butyl]thiazolidine-2,4-dione and 0.10 ml (1.1 mmol) of n-butyraldehyde in 5 ml of ethanol, 0.01 ml (0.1 mmol) of piperidine was added, followed by refluxing for 2 hours. After the reaction was cooled, the solvent was distilled off. The residue was dissolved in chloroform, washed with saturated aqueous sodium hydrogen carbonate and dried, after which the solvent was distilled off. The residue was purified by column chromatography (eluent, n-hexane/ethyl acetate=1/4→ethyl acetate) to yield 0.287 g (74.8%, yellow oily substance) of the desired product.

$^1$H-NMR (CDCl$_3$, 200 MHz) δ 0.99 (3H, t, J=7.4 Hz), 1.53–1.86 (6H, m), 2.22 (2H, q, J=7.6 Hz), 3.12–3.18 (2H, m), 3,70 (2H, t, J=6.6 Hz), 7.07 (1H, t, J=7.6 Hz), 7.33–7.36 (2H, m), 7.78–7.82 (2H, m), 7.94 (1H, d, J=0.8 Hz); IR (neat) 2958, 2872, 1741, 1682, 1635, 1352, 1284, 1140, 1068, 787, 735 cm$^{-1}$ iv) Synthesis of 5-butylidene-3-[4-(imidazo[1,2-a]pyridin-5-ylsulfinyl)butyl]thiazolidine-2,4-dione hydrochloride To a solution of 287 mg (0.73 mmol) of 5-butylidene-3-[4-(imidazo[1,2-a]pyridin-5-ylsulfinyl)butyl]thiazolidine-2,4-dione in 10 ml of methanol, 0.10 ml of concentrated hydrochloric acid was added, followed by stirring, after which the solvent was distilled off. The residue was washed with diethyl ether to yield 280 mg (89.6%, light yellow foamy substance) of the desired product.

$^1$H-NMR (CD$_3$OD, 200 MHz) δ 0.98 (3H, t, J=7.4 Hz), 1.59 (2H, quint., J=7.4 Hz), 1.70–1.84 (4H, m), 2.23 (2H, t, J=7.8 Hz), 3.27–3.44 (2H, m), 3.66 (2H, t, J=6.2 Hz), 6.98 (1H, t, J=7.8 Hz), 7.90 (1H, dd, J=3.0, 5.4 Hz), 8.13–8.16 (2H, m), 8.27 (1H, d, J=2.2 Hz), 8.59 (1H, d, J=2.0 Hz); Anal. Calcd for $C_{18}H_{22}ClN_3O_3S_2.0.6H_2O$: C, 49.27; H, 5.33; N, 9.58. Found: C, 49.55; H, 5.61; N, 9.07

Preparation Example 46

Synthesis of 5-butylidene-3-[4-(imidazo[1,2-a]pyridin-5-ylsulfonyl)butyl]thiazolidine-2,4-dione hydrochloride i) Synthesis of 5-(4-chlorobutylsulfonyl)imidazo[1,2-a]pyridine To a solution of 0.88 g (3.47 mmol) of 5-(4-chlorobutylsulfinyl)imidazo[1,2-a]pyridine in 15 ml of dichloromethane, 0.90 g (5.20 mmol) of m-chloroperbenzoic acid was added at 0° C., followed by stirring at room temperature for 64 hours. 0.6 g (3.47 mmol) of m-chloroperbenzoic acid was further added to the reaction mixture, followed by stirring for 5 hours. The reaction mixture was poured into saturated aqueous sodium hydrogen carbonate, extracted with dichloromethane and dried, after which the solvent was distilled off. The residue was purified by column chromatography (eluent, n-hexane/ethyl acetate= 1/4) to yield 0.28 g (29.7%, yellow oily substance) of the desired product.

$^1$H-NMR (CDCl$_3$, 200 MHz) δ 1.90–1.97 (4H, m), 3.30 (2H, t, J=7.4 Hz), 3.53 (2H, t, J=5.8 Hz), 7.36 (1H, dd, J=7.2, 9.0 Hz), 7.68 (1H, dd, J=1.0, 7.0 Hz), 7.86 (1H, d, J=1.4 Hz), 7.96 (1H, d, J=9.0 Hz), 8.29 (1H, s); IR (neat) 2960, 1522, 1452, 1331, 1288, 1142, 1093, 953, 825, 739, 650, 530 cm$^{-1}$ ii) Synthesis of 3-[4-(imidazo[1,2-a]pyridin-5-ylsulfonyl) butyl]thiazolidine-2,4-dione To a solution of 0.27 g (1.0 mmol) of 5-(4-chlorobutylsulfonyl)imidazo[1,2-a]pyridine and 0.177 g (1.0 mmol) of thiazolidine-2,4-dione in 7 ml of N,N-dimethylformamide, 0.15 ml (1.0 mmol) of 1,8-diazabicyclo [5.4.0]-undecene was added, followed by heating at 80° C. for 16 hours. After cooling, the reaction mixture was poured into water, extracted with ethyl acetate, washed with water and dried, after which the solvent was distilled off. The residue was purified by column chromatography (eluent, chloroform→chloroform/methanol=50/1) to yield 0.22 g (62.2%, light yellow oily substance) of the desired product.

$^1$H-NMR (CDCl$_3$, 200 MHz) δ 1.72–1.77 (4H, m), 3.31 (2H, t, J=7.4 Hz), 3.60 (2H, t, J=6.6 Hz), 3.93 (2H, s), 7.36 (1H, dd, J=7.2, 9.0 Hz), 7.66 (1H, dd, J=1.2, 7.2 Hz), 7.85 (1H, d, J=1.4 Hz), 7.96 (1H, d, J=9.0 Hz), 8.30 (1H, s); IR (neat) 2953, 1753, 1693, 1390, 1331, 1288, 1142, 1045, 955, 825, 793, 739 cm$^{-1}$ iii) Synthesis of 5-butylidene-3-[4-(imidazo[1,2-a]pyridin-5-ylsulfonyl)butyl]thiazolidine-2,4-dione To a solution of 0.22 g (0.62 mmol) of 3-[4-(imidazo[1, 2-a]pyridin-5-ylsulfonyl)butyl]thiazolidine-2,4-dione and 0.10 ml (1.1 mmol) of n-butyraldehyde in 5 ml of ethanol, 0.01 ml (0.1 mmol) of piperidine was added, followed by refluxing for 2 hours. After the reaction mixture was cooled, the solvent was distilled off. The residue was dissolved in chloroform, washed with saturated aqueous sodium hydrogen carbonate and dried, after which the solvent was distilled off. The residue was purified by column chromatography (eluent, n-hexane/ethyl acetate=1/4) to yield 0.269 g (quant., yellow oily substance) of the desired product.

$^1$H-NMR (CDCl$_3$, 200 MHz) δ 0.98 (3H, t, J=7.4 Hz), 1.55 (2H, quint., J=7.6 Hz), 1.73–1.81 (4H, m), 2.21 (2H, quint., J=7.4 Hz), 3.29–3.36 (2H, m), 3.63–3.69 (2H, m), 7.04 (1H, t, J=7.6 Hz), 7.34 (1H, dd, J=7.2, 9.0 Hz), 7.66 (1H, d, J=7.2 Hz), 7.86 (1H, s), 7.95 (1H, d, J=9.0 Hz), 8.31 (1H, s); IR (neat) 2960, 2878, 1741, 1682, 1635, 1331, 1288, 1138, 824, 737, 652, 528 cm$^{-1}$ iv) Synthesis of 5-butylidene-3-[4-(imidazo[1,2-a]pyridin-5-ylsulfonyl)butyl]thiazolidine-2,4-dione hydrochloride To a solution of 269 mg (0.66 mmol) of 5-butylidene-3-[4-(imidazo[1,2-a]pyridin-5-ylsulfonyl)butyl]thiazolidine-2,4-dione in 10 ml of methanol, 0.10 ml of concentrated hydrochloric acid was added, followed by stirring, after which the solvent was distilled off. The residue was washed with diethyl ether to yield 304 mg (quant., yellow oily substance) of the desired product.

$^1$H-NMR (CD$_3$OD, 200 MHz) δ 0.98 (3H, t, J=7.4 Hz), 1.63 (2H, quint., J=7.4 Hz), 1.68–1.80 (4H, m), 2.22 (2H, q, J=7.2 Hz), 3.16–3.68 (4H, m), 6.95 (1H, t, J=7.6 Hz), 8.16–8.18 (2H, m), 8.33–8.38 (2H, s), 8.71 (1H, s); Anal. Calcd for C$_{18}$H$_{22}$ClN$_3$O$_4$S$_2$: C, 48.70; H, 4.99; N, 9.46. Found: C, 48.45; H, 5.61; N, 8.53

Preparation Example 47

Synthesis of 5-butylidene-3-[3-(imidazo[1,2-a]pyridin-8-yloxy)propyl]thiazolidine-2,4-dione hydrochloride i) Synthesis of $^2$-amino-3-(3-chloropropyloxy)pyridine To a suspension of 48.7 ml (200 mmol) of a 4.1M sodium methoxide solution in 100 ml of dimethyl sulfoxide, 22.03 g (200 mmol) of 2-amino-3-hydroxypyridine was added at room temperature, followed by stirring at 80° C. for 10 minutes to dissolve the latter. After the reaction mixture was cooled, the methanol was distilled off. To this mixture, 19.8 ml (200 mmol) of 1-bromo-3-chloropropane was added at 0° C., followed by stirring for 30 minutes. The reaction mixture was poured into water (400 ml), extracted with chloroform, washed with2N aqueous sodium hydroxide and dried, after which the solvent was distilled off. The residue was purified by column chromatography (eluent, n-hexane/ethyl acetate=1/4→ethyl acetate). The obtained crude crystal was washed with diethyl ether-n-hexane to yield 20.48 g (54.8%, white powder) of the desired product.

$^1$H-NMR (CDCl$_3$, 200 MHz) δ 2.28 (2H, quint., J=5.8 Hz), 3.75 (2H, t, J=6.4 Hz), 4.15 (2H, t, J=5.8 Hz), 4.68 (2H, s), 6.62 (1H, dd, J=5.2, 7.6 Hz), 6.94 (1H, dd, J=1.2, 7.8 Hz), 7.68 (1H, dd, J=1.2, 5.0 Hz)

ii) Synthesis of $^3$-[$^3$-(2-aminopyridin-3-yloxy)propyl]thiazolidine-2,4-dione To a suspension of 9.33 g (50 mmol) of 2-amino-3-(3-chloropropyloxy)pyridine and 6.97 g (50 mmol) of thiazolidine-2,4-dione sodium salt in 200 ml of N,N-dimethylformamide, 7.49 g (50 mmol) of sodium iodide was added, followed by refluxing at 80° C. for 16 hours. After cooling, the reaction mixture was poured into water, extracted with ethyl acetate, washed with water and dried, after which the solvent was distilled off. The residue was purified by column chromatography (eluent, n-hexane/ethyl acetate=1/4→ethyl acetate) to yield 8.14 g (60.9%, yellow solid) of the desired product.

$^1$H-NMR (CDCl$_3$, 200 MHz) δ 2.16 (2H, quint., J=5.8 Hz), 3.87 (2H, t, J=6.8 Hz), 3.97 (2H, s), 4.02 (2H, t, J=5.8 Hz), 4.71 (2H, s), 6.60 (1H, dd, J=5.2, 7.8 Hz), 6.88 (1H, dd, J=1.4, 7.8 Hz), 7.67 (1H, dd, J=1.4, 5.0 Hz)

iii) Synthesis of 3-[3-(imidazo[1,2-a]pyridin-8-yloxy)propyl]thiazolidine-2,4-dione To a solution of 4.01 g (15 mmol) of 3-[3-(2-aminopyridin-3-yloxy)propyl]thiazolidine-2,4-dione in 40 ml of ethanol, 15 ml of a 40% chloroacetaldehyde solution was added at 60° C., followed by refluxing for 2 hours. After the reaction mixture was cooled, the solvent was distilled off. The residue was dissolved in chloroform, washed with saturated aqueous sodium hydrogen carbonate and dried, after which the solvent was distilled off. The residue was purified by column chromatography (eluent, n-hexane/ethyl acetate=1/4) to yield 2.92 g (66.8%, white powder) of the desired product.

$^1$H-NMR (CDCl$_3$, 200 MHz) δ 2.27 (2H, quint., J=6.0 Hz), 3.92 (2H, t, J=6.4 Hz), 4.09 (2H, s), 4.22 (2H, t, J=6.0 Hz), 6.41 (1H, d, J=7.4 Hz), 6.66 (1H, t, J=7.0 Hz), 7.55 (2H, s), 7.77 (1H, d, J=6.2 Hz)

iv) Synthesis of 5-butylidene-3-[3-(imidazo[1,2-a]pyridin-8-yloxy)propyl]thiazolidine-2,4-dione To a solution of 1.17 g (4.0 mmol) of 3-[3-(imidazo[1,2-a]pyridin-8-yloxy)propyl]thiazolidine-2,4-dione and 0.36 ml (4.0 mmol) of n-butyraldehyde in 15 ml of ethanol, 0.04 ml (0.4 mmol) of piperidine was added, followed by refluxing for 2 hours. After the reaction mixture was cooled, the solvent was distilled off. The residue was dissolved in chloroform, washed with saturated aqueous sodium hydrogen carbonate and dried, after which the solvent was distilled off. The residue was purified by column chromatography (eluent, n-hexane/ethyl acetate=1/4→ethyl acetate) to yield 1.07 g (77.5%, light orange oily substance) of the desired product.

$^1$H-NMR (CDCl$_3$, 200 MHz) δ 0.97 (3H, t, J=7.4 Hz), 1.57 (2H, quint., J=7.2 Hz), 2.15–2.33 (4H, m), 3.98 (2H, t, J=6.6 Hz), 4.21 (2H, t, J=6.6 Hz), 6.44 (1H, dd, J=1.0, 6.6 Hz), 6.66 (1H, dd, J=6.8, 8.2 Hz), 7.07 (1H, t, J=7.8 Hz), 7.54 (1H, d, J=1.2 Hz), 7.56 (1H, d, J=1.2 Hz), 7.77 (1H, dd, J=1.2, 7.8 Hz); IR (neat) 2960, 2873, 1743, 1686, 1547, 1362, 1281, 1169, 1113, 1078, 924, 771, 733 cm$^{-1}$ v) Synthesis of 5-butylidene-3-[3-(imidazo[1,2-a]pyridin-8-yloxy)propyl]thiazolidine-2,4-dione hydrochloride To a solution of 1.07 g (3.10 mmol) of 5-butylidene-3-[3-(imidazo[1,2-a]pyridin-8-yloxy)propyl]thiazolidine-2,4-dione in 50 ml of methanol, 0.30 ml of concentrated hydrochloric acid was added. After the solvent was distilled off, the residue was washed with diethyl ether to yield 1.16 g (97.9%, light orange foamy substance) of the desired product.

$^1$H-NMR (CD$_3$OD, 200 MHz) δ 0.96 (3H, t, J=7.4 Hz), 1.57 (2H, quint., J=7.0 Hz), 2.16–2.31 (4H, m), 4.01 (2H, t, J=6.6 Hz), 4.37 (2H, t, J=5.8 Hz), 7.02 (1H, t, J=7.6 Hz), 7.38–7.40 (2H, m), 8.06 (1H, d, J=2.2 Hz), 8.28 (1H, d, J=2.0 Hz), 8.42–8.46 (1H, m); Anal. Calcd for C$_{17}$H$_{20}$ClN$_3$O$_3$S.0.9H$_2$O: C, 51.29; H, 5.52; N, 10.56. Found: C, 51.49; H, 5.83; N, 10.52

Preparation Example 48

Synthesis of 5-butylidene-3-[4-(2-methylimidazo[1,2-a]pyridin-8-yloxy)butyl]thiazolidine-2,4-dione hydrochloride i) Synthesis of 5-butylidene-3-[4-(2-methylimidazo[1,2-a]pyridin-8-yloxy)butyl]thiazolidine-2,4-dione To a solution of 1.36 g (4.26 mmol) 3-[4-(2-methylimidazo[1,2-a]pyridin-8-yloxy)butyl]thiazolidine-2,4-dione and 0.38 ml (4.26 mmol) of n-butyraldehyde in 20 ml of ethanol, 0.04 ml (0.4 mmol) of piperidine was added, followed by refluxing for 2 hours. After the reaction mixture was cooled, the solvent was distilled off. The residue was dissolved in chloroform, washed with saturated aqueous sodium hydrogen carbonate and dried, after which the solvent was distilled off. The residue was purified by column chromatography (eluent, n-hexane/ethyl acetate=0/1) to yield 1.23 g (77.2%, yellow oily substance) of the desired product.

$^1$H-NMR (CDCl$_3$, 200 MHz) δ 0.98 (3H, t, J=7.8 Hz), 1.59 (2H, quint., J=7.4 Hz), 1.89–1.95 (4H, m), 2.21 (2H, q, J=7.4 Hz), 2.45 (3H, d, J=0.8 Hz), 3.78 (2H, t, J=6.6 Hz), 4.16 (2H, t, J=6.2 Hz), 6.39 (1H, dd, J=0.6, 7.6 Hz), 6.59 (1H, t, J=6.6 Hz), 7.08 (1H, t, J=7.8 Hz), 7.28 (1H, d, J=0.8 Hz), 7.66 (1H, dd, J=1.2, 6.6 Hz); IR (neat) 2958, 2873, 1749, 1686, 1635, 1545, 1354, 1282, 1107, 768, 735 cm$^{-1}$ ii) Synthesis of 5-butylidene-3-[4-(2-methylimidazo[1,2-a]pyridin-8-yloxy)butyl]thiazolidine-2,4-dione hydrochloride To a solution of 1.23 g (3.29 mmol) of 5-butylidene-3-[4-(2-methylimidazo[1,2-a]pyridin-8-yloxy)butyl]thiazolidine-2,4-dione in 30 ml of methanol, 0.33 ml of concentrated hydrochloric acid was added. After the solvent was distilled off, the residue was washed with diethyl ether to yield 1.41 g (quant., yellow oily substance) of the desired product.

$^1$H-NMR (CD$_3$OD, 200 MHz) δ 0.98 (3H, t, J=7.2 Hz), 1.59 (2H, quint., J=7.4 Hz), 1.78–1.83 (4H, m), 2.24 (2H, q, J=7.4 Hz), 2.56 (3H, s), 3.80 (2H, t, J=6.4 Hz), 4.38 (2H, t, J=5.6 Hz), 7.07 (1H, t, J=7.8 Hz), 7.33–7.35 (2H, m), 7.98 (1H, d, J=1.2 Hz), 8.31 (1H, dd, J=2.2, 5.2 Hz); Anal. Calcd for C$_{19}$H$_{24}$ClN$_3$O$_3$S.0.8H$_2$O: C, 53.78; H, 6.08; N, 9.90. Found: C, 54.02; H, 6.43; N, 9.79

Preparation Example 49

Synthesis of 5-butylidene-3-[4-(3-dimethylaminomethylimidazo[1,2-a]pyridin-5-ylthio)butyl]thiazolidine-2,4-dione dihydrochloride i) Synthesis of 5-butylidene-3-[4-(3-dimethylaminomethylimidazo[1,2-a]pyridin-5-ylthio)butyl]thiazolidine-2,4-dione To a solution of 0.27 ml (3.6 mmol) of formalin and 0.33 g (3.6 mmol) of a 50% aqueous dimethylamine solution in 20 ml of acetic acid, a solution of 1.13 g (3.0 mmol) of 5-butylidene-3-[4-(imidazo[1,2-a]pyridin-5-ylthio)butyl]thiazolidine-2,4-dione in 5 ml of acetic acid was added at 0° C., followed by stirring at 80° C. for 90 minutes. After cooling, the reaction mixture was poured into 50 ml of 50% aqueous sodium hydroxide under ice cooling conditions. The mixture was extracted with chloroform and dried, after which the solvent was distilled off. The residue was purified by column chromatography (eluent, chloroform/methanol=25/1) to yield 0.43 g (33.3%, yellow oily substance) of the desired product.

$^1$H-NMR (CDCl$_3$, 200 MHz) δ 0.98 (3H, t, J=7.4 Hz), 1.13–1.8 (6H, m), 2.18–2.27 (8H, m), 3.00 (2H, t, J=6.8 Hz), 3.70 (2H, t, J=7.0 Hz), 3.99 (2H, s), 6.82 (1H, dd, J=1.0, 7.0 Hz), 7.03–7.13 (2H, m), 7.48 (1H, s), 7.48–7.52 (1H, m)

ii) Synthesis of 5-butylidene-3-[4-(3-dimethylaminomethylimidazo[1,2-a]pyridin-5-ylthio)butyl]thiazolidine-2,4-dione dihydrochloride To a solution of 0.43 g (1.0 mmol) of 5-butylidene-3-[4-(3-dimethylaminomethylimidazo[1,2-a]pyridin-5-ylthio)butyl]thiazolidine-2,4-dione in 20 ml of methanol, 0.13 ml of concentrated hydrochloric acid was added. After the solvent was distilled off, the residue was washed with diethyl ether to yield 0.45 g (89.4%, yellow oily substance) of the desired product.

$^1$H-NMR (CD$_3$OD, 200 MHz) δ 0.97 (3H, t, J=7.2 Hz), 1.60 (2H, quint., J=7.6 Hz), 1.78–1.87 (4H, m), 2.24 (2H, q, J=7.2 Hz), 3.07 (6H, s), 3.26–3.35 (2H, m), 3.72 (2H, t, J=6.4 Hz), 5.18 (2H, s), 7.04 (1H, t, J=8.0 Hz), 7.73–7.77 (1H, m), 7.99–8.02 (2H, m), 8.55 (1H, s); Anal. Calcd for C$_{21}$H$_{30}$Cl$_2$N$_4$O$_2$S$_2$.1.0H$_2$O: C, 48.18; H, 6.16; N, 10.70. Found: C, 48.45; H, 6.33; N, 10.43

Preparation Example 50

Synthesis of 5-butylidene-3-[4-(3-bromoimidazo[1,2-a]pyridin-5-ylthio)butyl]thiazolidine-2,4-dione hydrochloride i) Synthesis of 5-butylidene-3-[4-(3-bromoimidazo[1,2-a]pyridin-5-ylthio)butyl]thiazolidine-2,4-dione To a solution of 1.13 g (3.0 mmol) of 5-butylidene-3-[4-(imidazo[1,2-a]pyridin-5-ylthio)butyl]thiazolidine-2,4-dione in 15 ml of carbon tetrachloride, 0.59 g (3.3 mmol) of N-bromosuccinimide was added at room temperature, followed by stirring at 80° C. for 90 minutes. After the reaction mixture was cooled, saturated aqueous sodium hydrogen carbonate was added. The organic layer was separated and dried, after which the solvent was distilled off. The residue was purified by column chromatography (eluent, n-hexane/ethyl acetate=2/1→1/4) to yield 1.11 g (81.4%, yellow oily substance) of the desired product.

$^1$H-NMR (CDCl$_3$, 200 MHz) δ 0.98 (3H, t, J=7.4 Hz), 1.53–1.85 (6H, m), 2.21 (2H, q, J=7.8 Hz), 2.98 (2H, t, J=7.0 Hz), 3.71 (2H, t, J=7.0 Hz), 6.89 (1H, dd, J=1.2, 7.0 Hz), 7.03–7.14 (2H, m), 7.55 (1H, dd, J=1.0, 8.8 Hz), 7.58 (1H, s); IR (neat) 2958, 1743, 1682, 1635, 1348, 781, 729, 623 cm$^{-1}$ ii) Synthesis of 5-butylidene-3-[4-(3-bromoimidazo[1,2-a]pyridin-5-ylthio)butyl]thiazolidine-2,4-dione hydrochloride To a solution of 1.11 g (2.44 mmol) of 5-butylidene-3-[4-(3-bromoimidazo[1,2-a]pyridin-5-ylthio)butyl]thiazolidine-2,4-dione in 30 ml of methanol, 0.25 ml of concentrated hydrochloric acid was added. After the solvent was distilled off, the residue was washed with diethyl ether to yield 1.18 g (98.5%, yellow oily substance) of the desired product.

$^1$H-NMR (CD$_3$OD, 200 MHz) δ 0.98 (3H, t, J=7.2 Hz), 1.59 (2H, quint., J=7.4 Hz), 1.72–1.87 (4H, m), 2.23 (2H, q, J=7.4 Hz), 3.35 (2H, t, J=6.8 Hz), 3.71 (2H, t, J=6.8 Hz), 7.59 (1H, d, J=7.4 Hz), 7.82–7.98 (2H, m), 8.15 (1H, d, J=2.0 Hz), 8.33 (1H, s); Anal. Calcd for C$_{18}$H$_{21}$ClN$_3$O$_2$BrS$_2$.0.2H$_2$O: C, 43.72; H, 4.36; N, 8.50. Found: C, 44.00, H, 4.69; N, 8.28

Preparation Example 51

Synthesis of 7-[4-(imidazo[1,2-a]pyridin-5-ylthio)butyl]-1-oxo-9-phenyl-3,4-dihydro-2H,6H-pyrimido[6,1-b][1,3]thiazine-6,8(7H)-dione hydrochloride To a solution of 166 mg (0.36 mmol) of 7-[4-(imidazo[1,2-a]pyridin-5-ylthio)butyl]-1-oxo-9-phenyl-3,4-dihydro-2H,6H-pyrimido[6,1-b][1,3]thiazine-6,8(7H)-dione in 5 ml of methanol, 8 μl of concentrated hydrochloric acid was added. After the solvent was distilled off, the residue was washed with diethyl ether to yield 132 mg (72.9%, light yellow foamy substance) of the desired product.

$^1$H-NMR (CD$_3$OD, 200 MHz) δ 1.72–1.90 (4H, m), 2.17–2.29 (1H, m), 2.58–2.67 (1H, m), 3.02 (1H, t, J=6.6 Hz), 3.33–3.53 (3H, m), 3.90–4.08 (4H, m), 7.21 (1H, d, J=7.6 Hz), 7.34–7.60 (5H, m), 7.81–7.91 (2H, m), 8.08–8.15 (1H, m), 8.27–8.30 (1H, m); Anal. Calcd for C$_{24}$H$_{25}$ClN$_4$O$_3$S$_2$.1.5H$_2$O: C, 52.98; H, 5.19; N, 10.30. Found: C, 53.01; H, 5.08; N, 10.39

Preparation Example 52

Synthesis of 5-(ethylthiomethylene)-3-[4-(imidazo[1,2-a]pyridin-5-ylthio)butyl]thiazolidine-2,4-dione hydrochloride i) Synthesis of 5-(ethylthiomethylene)thiazolidine-2,4-dione To a suspension of 5.20 g of 5-(ethoxymethylene)thiazolidine-2,4-dione (1:1.71 mixture with thiazolidine-2,4-dione, about 13.9 mmol) in 50 ml of ethanol, 5.0 g (59 mmol) of ethanethiol sodium salt was added at room temperature, followed by stirring under heating conditions for 3 hours. After cooling, the reaction mixture was poured into water and adjusted to a pH level of about 2. The resulting precipitate was collected by filtration, washed with water and then with n-hexane/diethyl ether and dried to yield 1.38 g (52.0%, light yellow powder) of the desired product.

$^1$H-NMR (CDCl$_3$, 200 MHz) δ 1.43 (3H, t, J=7.2 Hz), 3.01 (2H, q, J=7.4 Hz), 7.84 (1H, s), 8.96 (1H, s)

ii) Synthesis of 5-(ethylthiomethylene)-3-[4-(imidazo[1,2-a]pyridin-5-ylthio)butyl]thiazolidine-2,4-dione To a solution of 601 mg (2.5 mmol) of 5-(4-chlorobutylthio)imidazo[1,2-a]pyridine and 473 mg (2.5 mmol) of 5-(ethylthiomethylene)thiazolidine-2,4-dione in 5 ml of N,N-dimethylformamide, 0.37 ml (2.5 mmol) of 1,8-diazabicyclo[5.4.0]-7-undecene was added, followed by stirring at 80° C. for 16 hours. After the reaction mixture was cooled, water was added; the mixture was extracted with ethyl acetate and dried, after which the solvent was distilled off. The residue was purified by column chromatography (eluent, hexane/ethyl acetate=1/4→ethyl acetate) to yield 0.76 g (77.2%, light orange oily substance) of the desired product.

m.p. 159.0°–160.0° C.; $^1$H-NMR (CDCl$_3$, 200 MHz) δ 1.43 (3H, t, J=7.4 Hz), 1.58–1.86 (4H, m), 2.95–3.06 (4H, m), 3.69 (2H, t, J=7.0 Hz), 6.90 (1H, dd, J=0.6, 6.8 Hz), 7.15 (1H, dd, J=7.2, 9.2 Hz), 7.58 (1H, d, J=9.0 Hz), 7.69 (1H, d, J=1.2 Hz), 7.81 (1H, s), 8.83 (1H, s)

iii) Synthesis of 5-(ethylthiomethylene)-3-[4-(imidazo[1,2-a]pyridin-5-ylthio)butyl]thiazolidine-2,4-dione hydrochloride To a solution of 0.76 g (1.93 mmol) of 5-(ethylthiomethylene)-3-[4-(imidazo[1,2-a]pyridin-5-ylthio)butyl]thiazolidine-2,4-dione in 20 ml of methanol, 0.21 ml of concentrated hydrochloric acid was added. After the solvent was distilled off, the residue was washed with diethyl ether to yield 0.78 g (94.0%, yellow solid) of the desired product.

m.p. 159.0°–160.0° C.; $^1$H-NMR (CDCl$_3$, 200 MHz) δ 1.41 (3H, t, J=7.6 Hz), 1.73–1.84 (4H, m), 3.08 (2H, q, J=7.4 Hz), 3.35 (2H, t, J=4.8 Hz), 3.70 (2H, t, J=6.2 Hz), 7.58 (1H, d, J=7.4 Hz), 7.82–7.99 (2H, m), 7.97 (1H, s), 8.15 (1H, d, J=2.2 Hz), 8.32 (1H, d, J=2.2 Hz); Anal. Calcd for C$_{17}$H$_{20}$ClN$_3$O$_2$S$_3$.0.5H$_2$O: C, 46.51; H, 4.82; N, 9.57. Found: C, 46.49; H, 4.81; N, 9.57

Preparation Example 53

Synthesis of 7-[3-[2-(imidazo[1,2-a]pyridin-5-yl)ethyloxycarbonyl]aminopropyl]-1,1-dioxo-9-phenyl-3,4-dihydro-2H,6H-pyrimido[6,1-b][1,3]thiazine-6,8(7H)-dione hydrochloride To a solution of 258 mg (0.91 mmol) of 5-(2-phenoxycarbonyloxy)ethylimidazo[1,2-a]pyridine and 386 mg (1.0 mmol) of 3-(1,1,6,8-tetraoxo-9-phenyl-2,3,4,8-tetrahydropyrimido[6,1-b][1,3]thiazin-7-yl)propyl]amine hydrochloride in 5 ml of acetonitrile, 0.14 ml (1.0 mmol) of triethylamine was added, followed by stirring at 80° C. for 64 hours. After the reaction mixture was cooled, water was added; the mixture was extracted with methylene chloride and dried, after which the solvent was distilled off. The residue was purified by column chromatography (eluent, ethyl acetate) to yield 45 mg (9.2%, light orange foamy substance) of the desired product. To a solution of 45 mg (0.084 mmol) of the above compound in 5 ml of methanol, 3 drops of concentrated hydrochloric acid was added. After the solvent was distilled off, the residue was washed with diethyl ether to yield 45 mg (93.3%, yellow foamy substance) of the desired product.

m.p. 130.0°–132.0° C.; $^1$H-NMR (CD$_3$OD, 200 MHz) δ 1.77 (2H, quint., J=6.6 Hz), 2.48 (2H, quint., J=6.4 Hz), 3.06 (2H, t, J=6.4 Hz), 3.45–3.53 (4H, m), 3.96 (2H, t, J=7.0 Hz), 4.17 (2H, tr J=6.2 Hz), 4.49 (2H, t, J=6.0 Hz), 7.25–7.41 (6H, m), 7.82–7.87 (2H, m), 8.05 (1H, s), 8.36 (1H, s); Anal. Calcd for C$_{26}$H$_{28}$ClN$_5$O$_6$S.1.0H$_2$O: C, 52.74; H, 5.11; N, 11.83. Found: C, 53.00; H, 5.22; N, 11.68

Preparation Example 54

Synthesis of 5-butylidene-3-[5-(imidazo[1,2-a]pyridin-5-ylthio)-3,3-dimethylpentyl]thiazolidine-2,4-dione hydrochloride i) Synthesis of 3,3-dimethyl-1,5-pentanediol To a solution of 13.38 g (83.5 mmol) of 3,3-dimethylglutaric acid and 90 ml (60 mmol) of methanol in 200 ml of 1,2-dichloroethane, 4.18 ml of concentrated sulfuric acid was added at room temperature, followed by refluxing for 16 hours. After the reaction mixture was cooled, water was added. The organic layer was separated, washed with saturated aqueous sodium hydrogen carbonate and dried, after which the solvent was distilled off. The residue was purified by column chromatography (eluent, n-hexane/ethyl acetate=2/1) to yield ethyl 3,3-dimethylglutarate.

To a suspension of 3.80 g (100 mmol) of lithium aluminum hydride in 250 ml of tetrahydrofuran, the above product was added at room temperature, followed by stirring for 16 hours. Water was added to this reaction mixture until the excess lithium aluminum hydride was decomposed. The organic layer was dried; the resulting precipitate was filtered off, after which the solvent was distilled off to yield 10.62 g (96.2%, white crystal) of the desired product.

$^1$H-NMR (CDCl$_3$, 200 MHz) δ 0.95 (6H, s), 1.58 (4H, t, J=7.0 Hz), 3.74 (4H, t, J=7.0 Hz)

ii) Synthesis of 1-benzyloxymethoxy-3,3-dimethyl-5-pentanol

To a solution of 7.93 g (60 mmol) of 3,3-dimethyl-1,5-pentanediol and 10.45 ml (60 mmol) of diisopropylethylamine in 120 ml of dichloromethane, 8.35 ml (60 mmol) of benzylchloromethyl ether was added at room temperature, followed by stirring for 3 hours, after which saturated aqueous sodium hydrogen carbonate was added. The mixture was extracted with dichloromethane and dried, after which the solvent was distilled off. The residue was purified by column chromatography (eluent, n-hexane/ethyl acetate=2/1) to yield 5.50 g (36.3%, colorless oily substance) of the desired product.

$^1$H-NMR (CDCl$_3$, 200 MHz) δ 0.95 (6H, s), 1.53–1.63 (4H, m), 3.61–3.76 (4H, m), 4.61 (2H, s), 4.75 (2H, s), 7.35–7.37 (5H, m); IR (neat) 3425, 2933, 1454, 1380, 1110, 1043, 787, 698 cm$^{-1}$ iii) Synthesis of 5-(5-benzyloxymethoxy-3,3-dimethylpentylthio)imidazo[1,2-a]pyridine To a solution of 0.99 g (3.92 mmol) of 1-benzyloxymethoxy-3,3-dimethyl-5-pentanol and 0.60 ml (4.3 mmol) of triethylamine in 15 ml of dichloromethane, 0.33 ml (4.3 mmol) of methanesulfonyl chloride was added at 0° C., followed by stirring at room temperature for 30 minutes, after which saturated aqueous sodium hydrogen carbonate was added. The mixture was extracted with dichloromethane and dried, after which the solvent was distilled off to yield 1-benzyloxymethoxy-3,3-dimethyl-5-methanesulfonyloxypentane.

$^1$H-NMR (CDCl$_3$, 200 MHz) δ 0.97 (6H, s), 1.61–1.78 (4H, m), 2.98 (3H, s), 3.58–3.66 (2H, m), 4.29 (2H, t, J=8.0 Hz), 4.59 (2H, s), 4.74 (2H, s), 7.32–7.42 (5H, m); IR (neat) 2933, 1479, 1356, 1174, 951, 737, 699 cm$^{-1}$ To a solution of 0.586 g (3.9 mmol) of 5-mercaptoimidazo[1,2-a]pyridine and 0.56 ml (4.0 mmol) of triethylamine in 20 ml of ethanol, the above product was added at room temperature, followed by refluxing for 5 hours. After the reaction mixture was cooled, the solvent was distilled off. The residue was dissolved in dichloromethane. The organic layer was washed with water and dried, after which the solvent was distilled off. The residue was purified by column chromatography (eluent, n-hexane/ethyl acetate=1/2→1/4) to yield 0.71 g (47.4%, light yellow oily substance) of the desired product.

$^1$H-NMR (CDCl$_3$, 200 MHz) δ 0.93 (6H, s), 1.51–1.67 (4H, m), 2.94–3.03 (2H, m), 3.54–3.62 (2H, m), 4.57 (2H, s), 4.70 (2H, s), 6.87 (1H, d, J=7.0 Hz), 7.14 (1H, dd, J=7.4, 9.2 Hz), 7.31–7.35 (5H, m), 7.56 (1H, d, J=9.2 Hz), 7.69 (1H, d, J=1.6 Hz), 7.81 (1H, s); IR (neat) 2956, 1616, 1487, 1288, 1043, 957, 735, 698 cm$^{-1}$ iv) Synthesis of 5-(5-hydroxy-3,3-dimethylpentylthio) imidazo[1,2-a]pyridine To a solution of 0.71 g (1.85 mmol) of 5-(5-benzyloxymethyloxy-3,3-dimethylpentylthio)imidazo[1,2-a]pyridine in 10 ml of methanol, 0.33 ml (4.0 mmol) of concentrated hydrochloric acid was added, followed by stirring at 60° C. for 3 hours. After the reaction mixture was cooled, the solvent was distilled off. The residue was dissolved in 10 ml of water; 3 ml of 1N aqueous sodium hydroxide was added. To this mixture, 1N hydrochloric acid was added to pH 5–6. The mixture was extracted with dichloromethane and dried, after which the solvent was distilled off. The residue was purified by column chromatography (eluent, n-hexane/ethyl acetate=1/4→ethyl acetate) to yield 350 mg (71.6%, white crystal) of the desired product.

$^1$H-NMR (CDCl$_3$, 200 MHz) δ 0.93 (6H, s), 1.51–1.67 (4H, m), 2.94–3.03 (2H, m), 3.54–3.62 (2H, m), 4.57 (2H, s), 4.70 (2H, s), 6.87 (1H, d, J=7.0 Hz), 7.14 (1H, dd, J=7.4, 9.2 Hz), 7.31–7.35 (5H, m), 7.56 (1H, d, J=9.2 Hz), 7.69 (1H, d, J=1.6 Hz), 7.81 (1H, s); IR (KBr) 2956, 1616, 1487, 1288, 1043, 957, 735, 698 cm$^{-1}$ v) Synthesis of 3-[5-(imidazo[1,2-a]pyridin-5-ylthio)-3,3-dimethylpentyl]thiazolidine-2,4-dione To a solution of 304 mg (1.15 mmol) of 5-(5-hydroxy-3,3-dimethylpentylthio)imidazo[1,2-a]pyridine and 0.16 ml (1.15 mmol) of triethylamine in 5 ml of dichloromethane, 89 μl (1.15 mmol) of methanesulfonyl chloride was added at 0° C., followed by stirring at room temperature for 1 hour, after which saturated aqueous sodium hydrogen carbonate was added. The mixture was extracted with dichloromethane and dried, after which the solvent was distilled off to yield 5-(5-methanesulfonyloxy-3,3-dimethylpentylthio)imidazo [1,2-a]pyridine.

$^1$H-NMR (CDCl$_3$, 200 MHz) δ 0.96 (6H, s), 1.59–1.75 (4H, m), 2.93–3.02 (5H, m), 4.24 (2H, t, J=7.4 Hz), 6.91 (1H, d, J=7.0 Hz), 7.17 (1H, dd, J=7.0, 8.8 Hz), 7.59 (1H, dd, J=0.8, 8.8 Hz), 7.70 (1H, d, J=1.2 Hz), 7.83 (1H, d, J=1.2 Hz); IR (neat) 2960, 1616, 1487, 1350, 1290, 1173, 951, 930, 775, 735, 528 cm$^{-1}$ A solution of the above product and 278 mg (2.0 mmol) of thiazolidine-2,4-dione sodium salt in 5 ml of N,N-dimethylformamide was stirred at 100° C. for 3 hours. After cooling, the reaction mixture was poured into water and extracted with ethyl acetate. The organic layer was washed with water and dried, after which the solvent was distilled off. The residue was purified by column chromatography (eluent, n-hexane/ethyl acetate=1/4→ethyl acetate) to yield 339 mg (81.1%, light yellow oily substance) of the desired product.

$^1$H-NMR (CDCl$_3$, 200 MHz) δ 0.97 (6H, s), 1.42–1.51 (2H, m), 1.59–1.79 (2H, m), 2.96–3.05 (2H, m), 3.52–3.61 (2H, m), 3.94 (2H, s), 6.94 (1H, dd, J=0.8, 7.0 Hz), 7.18 (1H, dd, J=7.0, 9.0 Hz), 7.58 (1H, d, J=9.0 Hz), 7.70 (1H, d, J=1.4 Hz), 7.85 (1H, s); IR (neat) 2960, 1749, 1682, 1486, 1362, 1290, 1142, 773, 735 cm$^{-1}$ vi) Synthesis of 5-butylidene-3-[5-(imidazo[1,2-a]pyridin-5-ylthio)-3,3-dimethylpentyl]thiazolidine-2,4-dione To a solution of 339 mg (0.93 mmol) of 3-[5-(imidazo [1,2-a]pyridin-5-ylthio)-3,3-dimethylpentyl]thiazolidine-2,4-dione and 90 μl (1.0 mmol) of n-butyraldehyde in 5 ml of ethanol, 10 μl (0.1 mmol) of piperidine was added, followed by refluxing for 1.5 hours. After the reaction mixture was cooled, the solvent was distilled off. The residue was dissolved in chloroform, washed with saturated aqueous sodium hydrogen carbonate and dried, after which the solvent was distilled off. The residue was purified by column chromatography (eluent, hexane/ethyl acetate=2/1→1/2) to yield 310 mg (74.2%, light yellow oily substance) of the desired product.

$^1$H-NMR (CDCl$_3$, 200 MHz) δ 0.94–1.01 (9H, m), 1.47–1.65 (6H, m), 2.21 (2H, q, J=7.2 Hz), 2.98–3.06 (2H, m), 3.59–3.68 (2H, m), 6.93 (1H, dd, J=1.0, 7.4 Hz), 7.07 (1H, t, J=7.8 Hz), 7.17 (1H, dd, J=7.4, 9.2 Hz), 7.57 (1H, dd, J=1.2, 9.2 Hz), 7.82–7.99 (2H, m), 7.70 (1H, s), 7.84 (1H, s); IR (neat) 2960, 1743, 1682, 1487, 1358, 1146, 957, 773, 733 cm$^{-1}$ vii) Synthesis of 5-butylidene-3-[5-(imidazo[1,2-a]pyridin-5-ylthio)-3,3-dimethylpentyl]thiazolidine-2,4-dione hydrochloride To a solution of 310 mg (0.74 mmol) of 5-butylidene-3-[5-(imidazo[1,2-a]pyridin-5-ylthio)-3,3-dimethylpentyl] thiazolidine-2,4-dione in 5 ml methanol, 0.01 ml of concentrated hydrochloric acid was added. After the solvent was distilled off, the residue was washed with diethyl ether to yield 320 mg (95.0%, light yellow solid) of the desired product.

$^1$H-NMR (CD$_3$OD, 200 MHz) δ 0.98 (3H, t, J=7.4 Hz), 1.50–1.88 (6H, m), 2.23 (2H, q, J=7.4 Hz), 3.34 (2H, t, J=6.8 Hz), 3.72 (2H, t, J=6.6 Hz), 7.04 (1H, t, J=7.6 Hz), 7.58 (1H, dd, J=1.2, 7.4 Hz), 7.82–7.99 (2H, m), 8.14 (1H, d, J=2.2 Hz), 8.32 (1H, d, J=2.2Hz). ; Anal. Calcd for C 21 H$_{28}$ClN$_3$O$_2$S$_2$.0.5H$_2$O: C, 54.47; H, 6.31; N, 9.07. Found: C, 54.21; H, 6.45, N, 8.95.

Preparation Example 55

Synthesis of 5-butylidene-3-[5-(imidazo[1,2-a]pyridin-5-ylthio)-3,3-cyclopentylpentyl]thiazolidine-2,4-dione hydrochloride i) Synthesis of 3,3-cyclopentyl-1,5-pentanediol To a solution of 18.62 g (100 mmol) of 1,1-cyclopentanediacetic acid and 90 ml (60 mmol) of methanol in 200 ml of 1,2-dichloroethane, 4.18 ml of concentrated sulfuric acid was added at room temperature, followed by refluxing for 16 hours. After the reaction mixture was cooled, water was added. The organic layer was separated, washed with saturated aqueous sodium hydrogen carbonate and dried, after which the solvent was distilled off. The residue was purified by column chromatography (eluent, n-hexane/ethyl acetate=2/1) to yield ethyl 1,1-cyclopentanediacetate.

To a suspension of 3.80 g (100 mmol) of lithium aluminum hydride in 250 ml of tetrahydrofuran, the above product was added at room temperature, followed by stirring for 16 hours. Water was added to this reaction mixture until the excess lithium aluminum hydride was decomposed. The organic layer was dried; the resulting precipitate was filtered off, after which the solvent was distilled off. The residue was purified by column chromatography (eluent, n-hexane/ethyl acetate=2/1) to yield 9.34 g (59.0%, white crystal) of the desired product.

m.p. 38.0°–39.0° C.; $^1$H-NMR (CDCl$_3$, 200 MHz) δ 1.40–1.47 (4H, m), 1.58–1.66 (8H, m), 2.00 (2H, s), 3.74 (4H, t, J=7.0 Hz); IR (KBr) 3300, 2947, 2870, 1043, 1009 cm$^{-1}$ ii) Synthesis of 1-benzyloxymethoxy-3,3-cyclopentyl-5-pentanol To a solution of 7.91 g (50 mmol) of 3,3-cyclopentyl-1, 5-pentanediol and 8.71 ml (50 mmol) of diisopropylethylamine in 100 ml of dichloromethane, 6.95 ml (50 mmol) of benzylchloromethyl ether was added at room temperature, followed by stirring for 3 hours, after which saturated aqueous sodium hydrogen carbonate was added. The mixture was extracted with dichloromethane and dried, after which the solvent was distilled off. The residue was purified by column chromatography (eluent, n-hexane/ethyl acetate= 2/1) to yield 6.80 g (48.8%, colorless oily substance) of the desired product.

$^1$H-NMR (CDCl$_3$, 200 MHz) δ 1.43–1.48 (4H, m), 1.59–1.70 (8H, m), 3.60–3.75 (4H, m), 4.61 (2H, s), 4.76 (2H, s), 7.33–7.37 (5H, m); IR (neat) 3412, 2941, 1454, 1109, 1043, 737, 698 cm$^{-1}$ iii) Synthesis of 5-(5-benzyloxymethyloxy-3,3-cyclopentylpentylthio)imidazo[1,2-a]pyridine To a solution of 2.78 g (10 mmol) of 1-benzyloxymethoxy-3,3-cyclopentyl-5-pentanol and 1.53 ml (11 mmol) of triethylamine in 50 ml of dichloromethane, 0.85 ml (11 mmol) of methanesulfonyl chloride was added at 0° C., followed by stirring at room temperature for 30 minutes, after which saturated aqueous sodium hydrogen carbonate was added. The mixture was extracted with dichloromethane and dried, after which the solvent was distilled off to yield 1-benzyloxymethoxy-3,3-cyclopentyl-5-methanesulfonyloxypentane.

$^1$H-NMR (CDCl$_3$, 200 MHz) δ 1.40–1.50 (4H, m), 1.59–1.67 (8H, m), 2.97 (3H, s), 3.62 (2H, t, J=7.4 Hz), 4.30 (2H, t, J=7.2 Hz), 4.61 (2H, s), 4.74 (2H, s), 7.33–7.37 (5H, m); IR (neat) 2943, 1454, 1356, 1174, 1043, 953, 739, 700, 528 cm$^{-1}$ To a solution of 1.50 g (10 mmol) of 5-mercaptoimidazo[1,2-a]pyridine and 1.53 ml (11 mmol) of triethylamine in 50 ml of ethanol, the above product was added at room temperature, followed by refluxing for 5 hours. After the reaction mixture was cooled, the solvent was distilled off. The residue was dissolved in dichloromethane. The organic layer was washed with water and dried, after which the solvent was distilled off. The residue was purified by column chromatography (eluent, n-hexane/ethyl acetate=2/1→1/4) to yield 1.76 g (42.9%, light yellow oily substance) of the desired product.

$^1$H-NMR (CDCl$_3$, 200 MHz) δ 1.38–1.73 (12H, m), 2.95–3.03 (2H, m), 3.55 (2H, t, J=7.2 Hz), 4.56 (2H, s), 4.68 (2H, s), 6.88 (1H, dd, J=1.0, 7.2 Hz), 7.13 (1H, dd, J=7.2, 9.0 Hz), 7.32–7.35 (5H, m), 7.56 (1H, d, J=9.0 Hz), 7.69 (1H, d, J=1.2 Hz), 7.82 (1H, d, J=1.0 Hz); IR (neat) 3030, 2945, 1616, 1487, 1288, 1045, 956, 737, 698 cm$^{-1}$ iv) Synthesis of 5-(5-hydroxy-3,3-cyclopentylpentylthio)imidazo[1,2-a]pyridine To a solution of 1.64 g (4.0 mmol) of 5-(5-benzyloxymethyloxy-3,3-cyclopentylpentylthio)imidazo[1,2-a]pyridine in 20 ml of methanol, 0.83 ml (10 mmol) of concentrated hydrochloric acid was added, followed by stirring at 60° C. for 3 hours. After the reaction mixture was cooled, the solvent was distilled off. The residue was dissolved in 25 ml of water; 8 ml of 1N aqueous sodium hydroxide was added. To this mixture, 1N hydrochloric acid was added to pH 5–6. The mixture was extracted with dichloromethane and dried, after which the solvent was distilled off. The residue was purified by column chromatography (eluent, n-hexane/ethyl acetate=1/4→ethyl acetate) to yield 0.63 g (54.2%, white crystal) of the desired product.

m.p. 101.0°–102.0° C.; $^1$H-NMR (CDCl$_3$, 200 MHz) δ 1.39–1.71 (14H, m), 2.95–3.04 (2H, m), 3.63 (2H, t, J=7.4 Hz), 6.88 (1H, d, J=6.8 Hz), 7.15 (1H, dd, J=7.0, 9.2 Hz), 7.55 (1H, d, J=8.8 Hz), 7.68 (1H, d, J=1.2 Hz), 7.81 (1H, s); IR (KBr) 3224, 2951, 1489, 1298, 1209, 1043, 762, 727, 689 cm$^{-1}$ v) Synthesis of 3-[5-(imidazo[1,2-a]pyridin-5-ylthio)-3,3-cyclopentylpentyl]thiazolidine-2,4-dione To a solution of 0.58 g (2.0 mmol) of 5-(5-hydroxy-3,3-cyclopentylpentylthio)imidazo[1,2-a]pyridine and 0.31 ml (2.2 mmol) of triethylamine in 20 ml of dichloromethane, 0.17 ml (2.2 mmol) of methanesulfonyl chloride was added at 0° C., followed by stirring at room temperature for 1 hour, after which saturated aqueous sodium hydrogen carbonate was added. The mixture was extracted with dichloromethane and dried, after which the solvent was distilled off to yield 5-(5-methanesulfonyloxy-3,3-cyclopentylpentylthio)imidazo[1,2-a]pyridine.

$^1$H-NMR (CDCl$_3$, 200 MHz) δ 1.40–1.72 (12H, m), 1.80 (2H, t, J=7.0 Hz), 2.93–3.02 (5H, m), 4.20 (2H, t, J=7.4 Hz), 6.93 (1H, dd, J=1.2, 7.0 Hz), 7.17 (1H, dd, J=7.0, 8.8 Hz), 7.59 (1H, d, J=8.8 Hz), 7.71 (1H, d, J=1.2 Hz), 7.84 (1H, d, J=1.2 Hz); IR (neat) 2949, 1616, 1487, 1352, 1290, 1173, 955, 775, 735, 528 cm$^{-1}$ A solution of the above product and 0.56 g (4.0 mmol) of thiazolidine-2,4-dione sodium salt in 10 ml of N,N-dimethylformamide was stirred at 100° C. for 3 hours. After cooling, the reaction mixture was poured into water and extracted with ethyl acetate. The organic layer was washed with water and dried, after which the solvent was distilled off. The residue was purified by column chromatography (eluent, n-hexane/ethyl acetate=1/4→ethyl acetate) to yield 0.62 g (79.5%, light yellow oily substance) of the desired product.

$^1$H-NMR (CDCl$_3$, 200 MHz) δ 1.39–1.74 (14H, m), 2.21 (2H, q, J=7.4 Hz), 3.01–3.09 (2H, m), 3.49–3.57 (2H, m), 3.93 (2H, s), 6.97 (1H, d, J=7.0 Hz), 7.17 (1H, dd, J=7.0, 9.2 Hz), 7.57 (1H, d, J=8.8 Hz), 7.70 (1H, d, J=1.0 Hz), 7.86 (1H, s); IR (neat) 2949, 1747, 1680, 1487, 1362, 1288, 1147, 957, 775, 737, 663, 509, 471 cm$^{-1}$ vi) Synthesis of 5-butylidene-3-[5-(imidazo[1,2-a]pyridin-5-ylthio)-3,3-cyclopentylpentyl]thiazolidine-2,4-dione To a solution of 0.62 g (1.59 mmol) of 3-[5-(imidazo[1,2-a]pyridin-5-ylthio)-3,3-cyclopentylpentyl]thiazolidine-2,4-dione and 144 μl (1.6 mmol) of n-butyraldehyde in 10 ml of ethanol, 16 μl (0.16 mmol) of piperidine was added, followed by refluxing for 1.5 hours. After the reaction mixture was cooled, the solvent was distilled off. The residue was dissolved in chloroform, washed with saturated aqueous sodium hydrogen carbonate and dried, after which the solvent was distilled off. The residue was purified by column chromatography (eluent, hexane/ethyl acetate=2/1→1/2) to yield 0.63 g (89.3%, light yellow oily substance) of the desired product.

$^1$H-NMR (CDCl$_3$, 200 MHz) δ 0.98 (3H, t, J=7.4 Hz), 1.41–1.75 (14H, m), 2.21 (2H, q, J=7.4 Hz), 3.02–3.11 (2H, m), 3.56–3.64 (2H, m), 6.98 (1H, dd, J=1.0, 7.0 Hz), 7.06 (1H, t, J=7.6 Hz), 7.17 (1H, dd, J=7.0, 9.0 Hz), 7.56 (1H, d, J=9.0 Hz), 7.69 (1H, d, J=1.2 Hz), 7.85 (1H, d, J=0.8 Hz); IR (neat) 2954, 1741, 1684, 1489, 1358, 1147, 773, 735 cm$^{-1}$ vii) Synthesis of 5-butylidene-3-[5-(imidazo[1,2-a]pyridin-5-ylthio)-3,3-cyclopentylpentyl]thiazolidine-2,4-dione hydrochloride To a solution of 5-butylidene-3-[5-(imidazo[1,2-a]pyridin-5-ylthio)-3,3-cyclopentylpentyl]thiazolidine-2,4-dione in 5 ml methanol, 0.01 ml of concentrated hydrochloric acid was added. After the solvent was distilled off, the residue was washed with diethyl ether to yield 320 mg (95.0%, light yellow solid) of the desired product.

$^1$H-NMR (CD$_3$OD, 200 MHz) δ 0.98 (3H, t, J=7.8 Hz), 1.47–1.67 (10H, m), 1.81–1.90 (2H, m), 2.24 (2H, q, J=7.4 Hz), 3.30–3.38 (4H, m), 3.56–3.65 (2H, m), 7.05 (1H, t,

J=7.8 Hz), 7.68 (1H, dd, J=1.2, 7.4 Hz), 7.84 (1H, d, J=8.8 Hz), 7.98 (1H, dd, J=7.2, 9.0 Hz), 8.15 (1H, d, J=2.6 Hz), 8.34 (1H, d, J=2.2 Hz); Anal. Calcd for $C_{23}H_{30}ClN_3O_2S_2 \cdot 1.1H_2O$: C, 55.26; H, 6.49; N, 8.41. Found: C, 55.13; H, 6.58; N, 8.24

Preparation Example 56

Synthesis of 7-(4-(3-dimethylaminomethylimidazo[1,2-a]pyridin-5-ylthio)butyl-1,1-dioxo-9-phenyl-3,4-dihydro-2H,6H-pyrimido[6,1-b][1,3]thiazine-6,8(7H)-dione dihydrochloride i) Synthesis of 7-[4-(3-dimethylaminomethylimidazo[1,2-a]pyridin-5-ylthio)butyl]-1,1-dioxo-9-phenyl-3,4-dihydro-2H,6H-pyrimido[6,1-b][1,3]thiazine-6,8(7H)-dione To a solution of 0.45 g (0.93 mmol) of 7-[4-(imidazo[1,2-a]pyridin-5-ylthio)butyl]-1,1-dioxo-9-phenyl-3,4-dihydro-2H,6H-pyrimido[6,1-b][1,3]thiazine-6,8(7H)-dione in 10 ml of acetonitrile, 0.258 g (1.4 mmol) of N,N-dimethylmethylene ammonium iodide (Eschenmoser's salt) was added at room temperature, followed by refluxing for 2 hours. After the reaction mixture was cooled, the solvent was distilled off. The residue was dissolved in dichloromethane, washed with saturated aqueous sodium hydrogen carbonate and dried, after which the solvent was distilled off. The residue was purified by column chromatography (eluent, chloroform/methanol=25/1) to yield 0.40 g (77.6%, light yellow oily substance) of the desired product.

$^1$H-NMR (CDCl$_3$, 200 MHz) δ 1.62–1.88 (4H, m), 2.22 (6H, s), 2.51 (2H, quint., J=6.4 Hz), 3.00 (2H, t, J=6.8 Hz), 3.39 (2H, t, J=6.8 Hz), 3.95–4.02 (4H, m), 4.25 (2H, t, J=6.4 Hz), 6.82 (1H, dd, J=1.0, 7.0 Hz), 7.06 (1H, dd, J=7.2, 9.0 Hz), 7.28–7.33 (2H, m), 7.40–7.51 (5H, m); IR (neat) 2941, 1707, 1655, 1439, 1333, 1144, 750, 702 cm$^{-1}$ ii) Synthesis of 7-[4-(3-dimethylaminomethylimidazo[1,2-a]pyridin-5-ylthio)butyl]1,1-dioxo-9-phenyl-3,4-dihydro-2H,6H-pyrimido[6,1-b][1,3]thiazine-6,8(7H)-dione dihydrochloride To a solution of 0.40 g (0.722 mmol) of 7-[4-(3-dimethylaminomethylimidazo[1,2-a]pyridin-5-ylthio)butyl]-1,1-dioxo-9-phenyl-3,4-dihydro-2H,6H-pyrimido[6,1-b][1,3]thiazine-6,8(7H)-dione in 10 ml of methanol, 0.18 ml (2.2 mmol) of concentrated hydrochloric acid was added. After the reaction mixture was concentrated to dryness, the residue was washed with diethyl ether to yield 0.36 g (79.5%, light white foamy substance) of the desired product.

$^1$H-NMR (CD$_3$OD, 200 MHz) δ 1.80–1.90 (4H, m), 2.42–2.56 (2H, m), 2.98 (6H, s), 3.29–3.33 (2H, m), 3.51 (2H, t, J=6.6 Hz), 3.98–4.02 (2H, m), 4.17 (2H, t, J=6.2 Hz), 7.24–7.40 (5H, m), 7.72 (1H, dd, J=1.8, 6.6 Hz), 7.89–8.01 (2H, m), 8.49 (1H, s); Anal. Calcd for $C_{27}H_{33}Cl_2N_5O_4S_2 \cdot 2.8H_2O$: C, 47.90; H, 5.75; N, 10.34. Found: C, 48.10; H, 6.11; N, 10.47

Preparation Example 57

Synthesis of 5-heptylidene-3-[4-(imidazo[1,2-a]pyridin-5-ylthio)butyl]thiazolidine-2,4-dione hydrochloride i) Synthesis of 5-heptylidene-3-[4-(imidazo[1,2-a]pyridin-5-ylthio)butyl]thiazolidine-2,4-dione To a solution of 1.61 g (5.0 mmol) of 3-[4-(imidazo[1,2-a]pyridin-5-ylthio)butyl]thiazolidine-2,4-dione and 0.70 ml (5.0 mmol) of 1-heptanal in 20 ml of ethanol, 0.05 ml (0.5 mmol) of piperidine was added, followed by refluxing for 2 hours. After the reaction mixture was cooled, the solvent was distilled off. The residue was dissolved in dichloromethane, washed with water and dried, after which the solvent was distilled off. The residue was purified by column chromatography (eluent, n-hexane/ethyl acetate=4/1) to yield 1.82 g (87.3%, yellow oily substance) of the desired product.

$^1$H-NMR (CDCl$_3$, 200 MHz) δ 0.89 (3H, t, J=6.6 Hz), 1.26–1.36 (6H, m), 1.50–1.86 (6H, m), 2.22 (2H, q, J=7.4 Hz), 3.01 (2H, t, J=7.0 Hz), 3.70 (2H, t, J=7.0 Hz), 6.90 (1H, dd, J=1.0, 7.0 Hz), 7.07 (1H, t, J=7.8 Hz), 7.15 (1H, dd, J=7.2, 9.0 Hz), 7.58 (1H, d, J=9.0 Hz), 7.70 (1H, d, J=1.2 Hz), 7.84 (1H, s); IR (neat) 2927, 2856, 1743, 1687, 1633, 1487, 1352, 1288, 1144, 781, 735 cm$^{-1}$ ii) Synthesis of 5-heptylidene-3-[4-(imidazo[1,2-a]pyridin-5-ylthio)butyl]thiazolidine-2,4-dione hydrochloride To a solution of 1.99 g (4.76 mmol) of 5-heptylidene-3-[4-(imidazo[1,2-a]pyridin-5-ylthio)butyl]thiazolidine-2,4-dione in 30 ml of methanol, 0.42 ml of concentrated hydrochloric acid was added. After the solvent was distilled off, the residue was washed with diethyl ether to yield 2.31 g (quant., yellow-orange oily substance) of the desired product.

$^1$H-NMR (CD$_3$OD, 200 MHz) δ 0.91 (3H, t, J=6.4 Hz), 1.28–1.39 (6H, m), 1.52–1.59 (2H, m), 1.75–1.84 (4H, m), 2.25 (2H, q, J=7.2 Hz), 3.34 (2H, t, J=7.0 Hz), 3.71 (2H, t, J=6.6 Hz), 7.04 (1H, t, J=7.8 Hz), 7.58 (1H, dd, J=1.0, 7.4 Hz), 7.83 (1H, d, J=8.8 Hz), 7.95 (1H, dd, J=7.4, 9.2 Hz), 8.13 (1H, d, J=2.6 Hz), 8.13–8.33 (1H, m); Anal. Calcd for $C_{21}H_{28}ClN_3O_2S_2 \cdot 1.0H_2O$: C, 53.43; H, 6.41; N, 8.90. Found: C, 53.38; H, 6.52; N, 8.75

Preparation Example 58

Synthesis of 5-pentylidene-3-[4-(imidazo[1,2-a]pyridin-5-ylthio)butyl]thiazolidine-2,4-dione hydrochloride i) Synthesis of 5-pentylidene-3-[4-(imidazo[1,2-a]pyridin-5-ylthio)butyl]thiazolidine-2,4-dione To a solution of 1.61 g (5.0 mmol) of 3-[4-(imidazo[1,2-a]pyridin-5-ylthio)butyl]thiazolidine-2,4-dione and 0.431 g (5.0 mmol) of 1-pentanal in 20 ml of ethanol, 0.05 ml (0.5 mmol) of piperidine was added, followed by refluxing for 2 hours. After the reaction mixture was cooled, the solvent was distilled off. The residue was dissolved in dichloromethane, washed with water and dried, after which the solvent was distilled off. The residue was purified by column chromatography (eluent, n-hexane/ethyl acetate=4/1) to yield 1.70 g (87.4%, yellow oily substance) of the desired product.

$^1$H-NMR (CDCl$_3$, 200 MHz) δ 0.93 (3H, t, J=7.2 Hz), 1.22–1.81 (8H, m), 2.23 (2H, q, J=7.4 Hz), 3.01 (2H, t, J=7.0 Hz), 3.70 (2H, t, J=7.0 Hz), 6.90 (1H, dd, J=1.0, 7.0 Hz), 7.06 (1H, t, J=7.7 Hz), 7.15 (1H, dd, J=7.0, 9.0 Hz), 7.58 (1H, dd, J=1.0, 8.8 Hz), 7.69 (1H, d, J=1.2 Hz), 7.84 (1H, d, J=0.8 Hz); IR (neat) 2954, 1743, 1684, 1487, 1350, 1288, 1144, 735 cm$^{-1}$ ii) Synthesis of 5-pentylidene-3-[4-(imidazo[1,2-a]pyridin-5-ylthio)butyl]thiazolidine-2,4-dione hydrochloride To a solution of 1.70 g (4.36 mmol) of 5-pentylidene-3-[4-(imidazo[1,2-a]pyridin-5-ylthio)butyl]thiazolidine- 2,4-dione in 30 ml of methanol, 0.42 ml of concentrated hydrochloric acid was added. After the solvent was distilled off, the residue was washed with diethyl ether to yield 1.77 g (95.3%, yellow-orange oily substance) of the desired product.

$^1$H-NMR (CD$_3$OD, 200 MHz) δ 0.95 (3H, t, J=7.0 Hz), 1.32–1.53 (4H, m), 1.74–1.84 (4H, m), 2.26 (2H, q, J=7.4 Hz), 3.34 (2H, t, J=7.0 Hz), 3.71 (2H, t, J=7.2 Hz), 7.03 (1H, t, J=7.6 Hz), 7.59 (1H, dd, J=1.4, 7.4 Hz), 7.89 (1H, dd, J=1.2, 8.8 Hz), 7.96 (1H, dd, J=7.0, 8.8 Hz), 8.15 (1H, d, J=2.2 Hz), 8.33 (1H, dd, J=0.6, 2.2 Hz); Anal. Calcd for $C_{19}H_{24}ClN_3O_2S_2$: C, 53.57; H, 5.68; N, 9.86. Found: C, 53.62; H, 5.71; N, 9.62

Preparation Example 59

Synthesis of 5-hexylidene-3-[4-(imidazo[1,2-a]pyridin-5-ylthio)butyl]thiazolidine-2,4-dione hydrochloride i) Synthesis of 5-hexylidene-3-[4-(imidazo[1,2-a]pyridin-5-ylthio)butyl]thiazolidine-2,4-dione To a solution of 1.61 g (5.0 mmol) of 3-[4-(imidazo[1,2-a]pyridin-5-ylthio)butyl]thiazolidine-2,4-dione and 0.501 g (5.0 mmol) of 1-hexanal in 20 ml of ethanol, 0.05 ml (0.5 mmol) of piperidine was added, followed by refluxing for 2 hours. After the reaction mixture was cooled, the solvent was distilled off. The residue was dissolved in dichloromethane, washed with water and dried, after which the solvent was distilled off. The residue was purified by column chromatography (eluent, n-hexane/ethyl acetate=4/1) to yield 1.77 g (87.7%, yellow oily substance) of the desired product.

$^1$H-NMR (CDCl$_3$, 200 MHz) δ 0.91 (3H, t, J=6.6 Hz), 1.26–1.36 (4H, m), 1.51–1.86 (6H, m), 2.22 (2H, q, J=7.6 Hz), 3.01 (2H, t, J=7.0 Hz), 3.70 (2H, t, J=7.0 Hz), 6.90 (1H, d, J=7.0 Hz), 7.07 (1H, t, J=7.6 Hz), 7.15 (1H, dd, J=7.0, 9.0 Hz), 7.58 (1H, dd, J=1.0, 8.8 Hz), 7.69 (1H, d, J=1.4 Hz), 7.84 (1H, s); IR (neat) 2929, 1741, 1684, 1633, 1487, 1352, 1288, 1142, 735 cm$^{-1}$ ii) Synthesis of 5-hexylidene-3-[4-(imidazo[1,2-a]pyridin-5-ylthio)butyl]thiazolidine-2,4-dione hydrochloride To a solution of 1.77 g (4.39 mmol) of 5-hexylidene-3-[4-(imidazo[1,2-a]pyridin-5-ylthio)butyl]thiazolidine-2,4-dione in 30 ml of methanol, 0.42 ml of concentrated hydrochloric acid was added. After the solvent was distilled off, the residue was washed with diethyl ether to yield 1.89 g (97.9%, yellow-orange oily substance) of the desired product.

$^1$H-NMR (CD$_3$OD, 200 MHz) δ 0.92 (3H, t, J=6.4 Hz), 1.30–1.38 (4H, m), 1.53–1.60 (2H, m), 1.75–1.84 (4H, m), 2.25 (2H, q, J=7.6 Hz), 3.35 (2H, t, J=7.2 Hz), 3.71 (2H, t, J=6.2 Hz), 7.03 (1H, t, J=7.6 Hz), 7.59 (1H, dd, J=1.0, 7.2 Hz), 7.84 (1H, d, J=8.8 Hz), 7.95 (1H, dd, J=7.4, 9.2 Hz), 8.15 (1H, d, J=2.4 Hz), 8.33 (1H, dd, J=0.6, 2.2 Hz); Anal. Calcd for C$_{20}$H$_{26}$ClN$_3$O$_2$S$_2$.0.5H$_2$O: C, 53.50; H, 6.06; N, 9.36. Found; C, 53.36; H, 6.02; N, 9.18

Preparation Example 60

Synthesis of 5-octylidene-3-[4-(imidazo[1,2-a]pyridin-5-ylthio)butyl]thiazolidine-2,4-dione hydrochloride i) Synthesis of 5-octylidene-3-[4-(imidazo[1,2-a]pyridin-5-ylthio)butyl]thiazolidine-2,4-dione To a solution of 1.61 g (5.0 mmol) of 3-[4-(imidazo[1,2-a]pyridin-5-ylthio)butyl]thiazolidine-2,4-dione and 0.641 g (5.0 mmol) of 1-octanal in 20 ml of ethanol, 0.05 ml (0.5 mmol) of piperidine was added, followed by refluxing for 1.5 hours. After the reaction mixture was cooled, the solvent was distilled off. The residue was dissolved in dichloromethane, washed with water and dried, after which the solvent was distilled off. The residue was purified by column chromatography (eluent, n-hexane/ethyl acetate=4/1) to yield 1.54 g (71.4%, yellow oily substance) of the desired product.

$^1$H-NMR (CDCl$_3$, 200 MHz) δ 0.88 (3H, t, J=7.0 Hz), 1.26–1.36 (8H, m), 1.52–1.86 (6H, m), 2.22 (2H, q, J=7.4 Hz), 3.01 (2H, t, J=7.0 Hz), 3.69 (2H, t, J=7.0 Hz), 6.90 (1H, d, J=7.0 Hz), 7.06 (1H, t, J=7.4 Hz), 7.14 (1H, dd, J=7.4, 9.2 Hz), 7.58 (1H, d, J=8.8 Hz), 7.69 (1H, s), 7.84 (1H, s); IR (neat) 2927, 2856, 1741, 1684, 1489, 1352, 1288, 1144, 781, 735 cm$^{-1}$ ii) Synthesis of 5-octylidene-3-[4-(imidazo[1,2-a]pyridin-5-ylthio)butyl]thiazolidine-2,4-dione hydrochloride To a solution of 1.54 g (3.57 mmol) of 5-octylidene-3-[4-(imidazo[1,2-a]pyridin-5-ylthio)butyl]thiazolidine-2,4-dione in 30 ml of methanol, 0.34 ml of concentrated hydrochloric acid was added. After the solvent was distilled off, the residue was washed with diethyl ether to yield 1.65 g (98.7%, yellow-orange oily substance) of the desires product.

$^1$H-NMR (CD$_3$OD, 200 MHz) δ 0.90 (3H, t, J=6.6 Hz), 1.28–1.34 (8H, m), 1.52–1.59 (2H, m), 1.77–1.83 (4H, m), 2.25 (2H, q, J=7.4 Hz), 3.35 (2H, t, J=7.0 Hz), 3.71 (2H, t, J=6.2 Hz), 7.03 (1H, t, J=7.6 Hz), 7.59 (1H, d, J=7.0 Hz), 7.84 (1H, d, J=8.8 Hz), 7.91–7.98 (1H, m), 8.15 (1H, d, J=2.2 Hz), 8.32 (1H, d, J=1.8 Hz); Anal. Calcd for C$_{22}$H$_{30}$ClN$_3$O$_2$S$_2$.0.2H$_2$O: C, 56.02; H, 6.50; N, 8.91. Found: C, 55.95; H, 6.69; N, 8.69

Preparation Example 61

Synthesis of 5-nonylidene-3-[4-(imidazo[1,2-a]pyridin-5-ylthio)butyl]thiazolidine-2,4-dione hydrochloride i) Synthesis of 5-nonylidene-3-[4-(imidazo[1,2-a]pyridin-5-ylthio)butyl]thiazolidine-2,4-dione To a solution of 1.61 g (5.0 mmol) of 3-[4-(imidazo[1,2-a]pyridin-5-ylthio)butyl]thiazolidine-2,4-dione and 0.711 g (5.0 mmol) of 1-nonanal in 20 ml of ethanol, 0.05 ml (0.5 mmol) of piperidine was added, followed by refluxing for 1.5 hours. After the reaction mixture was cooled, the solvent was distilled off. The residue was dissolved in dichloromethane, washed with water and dried, after which the solvent was distilled off. The residue was purified by column chromatography (eluent, n-hexane/ethyl acetate=3/1) to yield 1.96 g (88.0%, yellow oily substance) of the desired product.

$^1$H-NMR (CDCl$_3$, 200 MHz) δ 0.85–0.88 (3H, m), 1.26–1.36 (10H, m), 1.50–1.78 (6H, m), 2.17–2.24 (2H, m), 3.02 (2H, t, J=7.2 Hz), 3.70 (2H, t, J=6.8 Hz), 6.91 (1H, dd, J=1.0, 7.0 Hz), 7.07 (1H, t, J=7.6 Hz), 7.15 (1H, dd, J=7.0, 8.8 Hz), 7.58 (1H, dd. J=0.8, 9.2 Hz), 7.70 (1H, d, J=1.4 Hz), 7.84 (1H, s); IR (neat) 2926, 2854, 1743, 1686, 1635, 1489, 1350, 1288, 1142, 735 cm$^{-1}$ ii) Synthesis of 5-nonylidene-3-[4-(imidazo[1,2-a]pyridin-5-ylthio)butyl]thiazolidine-2,4-dione hydrochloride To a solution of 1.96 g (4.40 mmol) of 5-nonylidene-3-[4-(imidazo[1,2-a]pyridin-5-ylthio)butyl]thiazolidine-2,4-dione in 30 ml of methanol, 0.42 ml of concentrated hydrochloric acid was added. After the solvent was distilled off, the residue was washed with diethyl ether to yield 2.01 g (94.8%, yellow-orange oily substance) of the desired product.

$^1$H-NMR (CD$_3$OD, 200 MHz) δ 0.90 (3H, t, J=7.0 Hz), 1.29–1.38 (10H, m), 1.52–1.60 (2H, m), 1.75–1.84 (4H, m), 2.25 (2H, q, J=7.2 Hz), 3.34 (2H, t, J=6.6 Hz), 3.71 (2H, t, J=6.6 Hz), 7.04 (1H, t, J=8.0 Hz), 7.58 (1H, dd, J=1.2, 7.4 Hz), 7.83 (1H, d, J=8.8 Hz), 7.95 (1H, dd, J=7.2, 8.8 Hz), 8.14 (1H, d, J=2.6 Hz), 8.32 (1H, d, J=2.2 Hz); Anal. Calcd for C$_{23}$H$_{32}$ClN$_3$O$_2$S$_2$.1.0H$_2$O: C, 55.24; H, 6.85; N, 8.40. Found: C, 55.46; H, 7.11; N, 8.28

Preparation Example 62

Synthesis of 5-(4-chlorophenyl)methylene-3-[4-(imidazo[1,2-a]pyridin-5-ylthio)butyl]oxazolidine-2,4-dione hydrochloride i) Synthesis of 5-(4-chlorophenyl)methylene-3-[4-(imidazo[1,2-a]pyridin-5-ylthio)butyl]oxazolidine-2,4-dione To a solution of 1.527 g (5.0 mmol) of 3-[4-(imidazo[1,2-a]pyridin-5-ylthio)butyl]oxazolidine-2,4-dione and 0.703 g (5.0 mmol) of 4-chlorobenzaldehyde in 20 ml of ethanol, 0.04 ml (0.5 mmol) of pyrrolidine was added, followed by refluxing for 23 hours. After the reaction mixture was cooled, the solvent was distilled off. The residue was dissolved in dichloromethane, washed with water and dried, after which the solvent was distilled off. The residue was purified by column chromatography (eluent, n-hexane/ethyl acetate=3/1) to yield 0.301 g (14.1%, white crystal) of the desired product.

$^1$H-NMR (CDCl$_3$, 200 MHz) δ 1.64–1.92 (4H, m), 3.03 (2H, t, J=7.0 Hz), 3.67 (2H, t, J=7.0 Hz), 6.71 (1H, s), 6.92

(1H, d, J=7.0 Hz), 7.15 (1H, dd. J=7.0, 9.0 Hz), 7.42 (2H, d, J=8.6 Hz), 7.57 (1H, dd, J=1.0, 9.0 Hz), 7.67–7.72 (3H, m), 7.85 (1H, d, J=0.8 Hz)

ii) Synthesis of 5-(4-chlorophenyl)methylene-3-[4-(imidazo[1,2-a]pyridin-5-ylthio)butyl]oxazolidine-2,4-dione hydrochloride To a solution of 0.301 g (0.70 mmol) of 5-(4-chlorophenyl)methylene-3-[4-(imidazo[1,2-a]pyridin-5-ylthio)butyl]oxazolidine-2,4-dione in 10 ml of methanol, 0.10 ml of concentrated hydrochloric acid was added. After the solvent was distilled off, the residue was crystallized by the addition of diethyl ether to yield 0.223 g (68.6%, light pink crystal) of the desired product.

m.p. 184.0°–185.0° C.; $^1$H-NMR (CD$_3$OD, 200 MHz), δ 1.81–1.92 (4H, m), 3.37 (2H, t, J=7.0 Hz), 3.68 (2H, t, J=6.6 Hz), 6.73 (1H, s), 7.47 (2H, d, J=8.4 Hz), 7.59 (1H, dd, J=1.2, 6.2 Hz), 7.41–7.83 (3H, m), 7.94 (1H, dd, J=7.4, 9.2 Hz), 8.13 (1H, d, J=2.2 Hz), 8.32 (1H, d, J=2.2 Hz); Anal. Calcd for C$_{21}$H$_{19}$Cl$_2$N$_3$O$_3$S.1.0H$_2$O: C, 52.29; H, 4.39; N, 8.71. Found: C, 52.29; H, 4.41; N, 8.55

Preparation Example 63

Synthesis of 5-decylidene-3-[4-(imidazo[1,2-a]pyridin-5-ylthio)butyl]oxazolidine-2,4-dione To a solution of 1.527 g (5.0 mmol) of 3-[4-(imidazo[1,2-a]pyridin-5-ylthio)butyl]oxazolidine-2,4-dione and 1.11 ml (5.0 mmol) of decanal in 20 ml of ethanol, 0.04 ml (0.5 mmol) of pyrrolidine was added, followed by refluxing for 20 hours. After the reaction mixture was cooled, the solvent was distilled off. The residue was dissolved in dichloromethane, washed with water and dried, after which the solvent was distilled off. The residue was purified by column chromatography (eluent, n-hexane/ethyl acetate 3/1→ethyl acetate). The resulting residue was crystallized from n-hexane to yield 0.13 g (5.8%, white crystal) of the desired product.

m.p. 46.0°–48.0° C.; $^1$H-NMR (CDCl$_3$, 200 MHz) δ 0.85–0.91 (3H, m), 1.22–1.36 (12H, m), 1.44–1.88 (6H, m), 2.28–2.39 (2H, m), 3.03 (2H, t, J=7.2 Hz), 3.61 (2H, t, J=6.8 Hz), 6.06 (1H, t, J=8.0 Hz), 6.92 (1H, d, J=7.0 Hz), 7.16 (1H, dd, J=7.2, 9.0 Hz), 7.60 (1H, d, J=9.0 Hz), 7.72 (1H, d, J=1.8 Hz), 7.84 (1H, d, J=2.2 Hz); IR (KBr) 2924, 2852, 1813, 1745, 1489, 1444, 1410, 764, 735 cm$^{-1}$

Preparation Example 64

Synthesis of 5-ethylidene-3-[4-(imidazo[1,2-a]pyridin-5-ylthio)butyl]oxazolidine-2,4-dione hydrochloride i) Synthesis of 5-ethylidene-3-[4-(imidazo[1,2-a]pyridin-5-ylthio)butyl]oxazolidine-2,4-dione To a solution of 1.527 g (5.0 mmol) of 3-[4-(imidazo[1,2-a]pyridin-5-ylthio)butyl]oxazolidine-2,4-dione and 0.311 ml (5.0 mmol) of acetaldehyde in 20 ml of ethanol, 0.05 ml (0.5 mmol) of piperidine was added, followed by refluxing for 17 hours. After the reaction mixture was cooled, the solvent was distilled off. The residue was dissolved in dichloromethane, washed with water and dried, after which the solvent was distilled off. The residue was purified by column chromatography (eluent, n-hexane/ethyl acetate=3/1) to yield 77 mg (4.65%, yellow oily substance) of the desired product.

$^1$H-NMR (CDCl$_3$, 200 MHz) δ 1.64–1.88 (4H, m), 1.93 (3H, d, J=5.8 Hz), 3.02 (2H, t, J=7.0 Hz), 3.62 (2H, t, J=7.0 Hz), 6.44 (1H, q, J=5.4 Hz), 6.91 (1H, d, J=7.0 Hz), 7.15 (1H, dd, J=7.0, 9.0 Hz), 7.59 (1H, d, J=8.8 Hz), 7.70 (1H, s), 7.85 (1H, s)

ii) Synthesis of 5-ethylidene-3-[4-(imidazo[1,2-a]pyridin-5-ylthio)butyl]oxazolidine-2,4-dione hydrochloride To a solution of 77 mg (0.23 mmol) of 5-ethylidene-3-[4-(imidazo[1,2-a]pyridin-5-ylthio)butyl]oxazolidine-2,4-dione in 5 ml of methanol, 0.10 ml of concentrated hydrochloric acid was added. After the solvent was distilled off, the residue was washed with diethyl ether to yield 90 mg (quant., brown oily substance) of the desired product.

$^1$H-NMR (CD$_3$OD, 200 MHz) δ 1.80–1.88 (4H, m), 1.92 (3H, d, J=5.0 Hz), 3.36 (2H, t, J=6.2 Hz), 3.56–3.64 (2H, m), 6.40 (1H, q, J=5.2 Hz), 7.60 (1H, d, J=7.0 Hz), 7.84–7.99 (2H, m), 8.16 (1H, d, J=1.8 Hz), 8.32 (1H, d, J=1.4 Hz); Anal. Calcd for C$_{16}$H$_{18}$ClN$_3$O$_3$S.1.5H$_2$O: C, 48.67; H, 5.36; N, 10.64. Found: C, 49.22; H, 5.69; N, 9.11

Preparation Example 65

Synthesis of 5-(5-phenylpentylidene)-3-[4-(imidazo[1,2-a]pyridin-5-ylthio)butyl]thiazolidine-2,4-dione hydrochloride i) Synthesis of 5-(5-phenylpentylidene)-3-[4-(imidazo[1,2-a]pyridin-5-ylthio)butyl]thiazolidine-2,4-dione To a solution of 1.61 g (5.0 mmol) of 3-[4-(imidazo[1,2-a]pyridin-5-ylthio)butyl]thiazolidine-2,4-dione and 4.2 g (10 mmol) of 5-phenylpentanal in 20 ml of ethanol, 0.05 ml (0.5 mmol) of piperidine was added, followed by refluxing for 2.5 hours. After the reaction mixture was cooled, the solvent was distilled off. The residue was dissolved in chloroform, washed with water and dried, after which the solvent was distilled off. The residue was purified by column chromatography (eluent, n-hexane/ethyl acetate=1/4) to yield 2.627 g (quant., brown oily substance) of the desired product.

$^1$H-NMR (CDCl$_3$, 200 MHz) δ 1.26–1.86 (8H, m), 2.25 (2H, q, J=7.6 Hz), 2.64 (2H, t, J=7.4 Hz), 3.01 (2H, t, J=7.0 Hz), 3.69 (2H, t, J=7.0 Hz), 6.90 (1H, dd, J=1.0, 7.2 Hz), 7.04 (1H, t, J=7.6 Hz), 7.10–7.29 (6H, m), 7.57 (1H, dd, J=1.0, 9.2 Hz), 7.70 (1H, d, J=1.2 Hz), 7.84 (1H, d, J=0.8 Hz)

ii) Synthesis of 5-(5-phenylpentylidene)-3-[4-(imidazo[1,2-a]pyridin-5-ylthio)butyl]thiazolidine-2,4-dione hydrochloride To a solution of 2.627 g (5.6 mmol) of 5-(5-phenylpentylidene)-3-[4-(imidazo[1,2-a]pyridin-5-ylthio)butyl]thiazolidine-2,4-dione in 50 ml of methanol, 0.5 ml of concentrated hydrochloric acid was added. After the solvent was distilled off, the residue was crystallized from dichloromethane-diethyl ether to yield 2.37 g (84.3%, white crystal) of the desired product.

m.p. 110.0°–112.0° C.; $^1$H-NMR (CD$_3$OD, 200 MHz), δ 1.57–1.83 (8H, m), 2.27 (2H, q, J=7.8 Hz), 2.63 (2H, t, J=7.4 Hz), 3.33 (2H, t, J=7.0 Hz), 3.70 (2H, t, J=6.6 Hz), 7.02 (1H, t, J=7.8 Hz), 7.14–7.29 (5H, m), 7.57 (1H, dd, J=1.4, 7.4 Hz), 7.82 (1H, dd, J=0.8, 9.2 Hz), 7.93 (1H, dd, J=7.2, 9.0 Hz), 8.14 (1H, d, J=2.4 Hz), 8.31 (1H, d, J=2.2 Hz); Anal. Calcd for C$_{25}$H$_{28}$ClN$_3$O$_2$S$_2$.0.5H$_2$O: C, 58.75; H, 5.72; N, 8.22. Found: C, 58.48; H, 5.80; N, 8.29

Preparation Example 66

Synthesis of 5-(2-pyridyl)methylene-3-[4-(imidazo[1,2-a]pyridin-5-ylthio)butyl]thiazolidine-2,4-dione hydrochloride i) Synthesis of 5-(2-pyridyl)methylene-3-[4-(imidazo[1,2-a]pyridin-5-ylthio)butyl]thiazolidine-2,4-dione To a solution of 1.61 g (5.0 mmol) of 3-[4-(imidazo[1,2-a]pyridin-5-ylthio)butyl]thiazolidine-2,4-dione and 0.54 g (5.0 mmol) of pyridine-2-a]aldehyde in 20 ml of ethanol, 0.05 ml (0.5 mmol) of piperidine was added, followed by refluxing for 6 hours. To the reaction mixture, 0.02 ml (0.2 mmol) of piperidine was added, followed by refluxing for 12 hours. After the reaction mixture was cooled, the solvent was distilled off. The residue was dissolved in chloroform, washed with water and dried, after which the solvent was distilled off. The residue was purified by column chromatography (eluent, ethyl acetate) to yield 1.483 g (72.2%, light yellow crystal) of the desired product.

¹H-NMR (CDCl₃, 200 MHz) δ 1.54–1.88 (4H, m), 3.03 (2H, t, J=7.0 Hz), 3.77 (2H, t, J=7.0 Hz), 6.92 (1H, d, J=7.2 Hz), 7.15 (1H, dd, J=7.0, 9.0 Hz), 7.28–7.33 (1H, m), 7.50–7.59 (2H, m), 7.70 (1H, d, J=1.4 Hz), 7.75–7.83 (1H, m), 7.78 (1H, s), 7.85 (1H, s), 8.77 (1H, dd, J=1.4, 5.6 Hz)

ii) Synthesis of 5-(2-pyridyl)methylene-3-[4-(imidazo[1,2-a]pyridin-5-ylthio)butyl]thiazolidine-2,4-dione hydrochloride To a solution of 1.483 g (3.61 mmol) of 5-(2-pyridyl)methylene-3-[4-(imidazo[1,2-a]pyridin-5-ylthio)butyl] thiazolidine-2,4-dione in 30 ml of methanol, 0.42 ml of concentrated hydrochloric acid was added. After the solvent was distilled off, the residue was crystallized from dichloromethane-diethyl ether to yield 1.61 g (99.8%, white crystal) of the desired product.

¹H-NMR (CD₃OD, 200 MHz) δ 1.75–1.91 (4H, m), 3.35 (2H, t, J=7.4 Hz), 3.76 (2H, t, J=6.6 Hz), 7.33–7.40 (1H, m), 7.57 (1H, dd, J=1.0, 7.2 Hz), 7.65 (1H, d, J=7.6 Hz), 7.76 (1H, s), 7.81–7.96 (3H, m), 8.11 (1H, d, J=2.2 Hz), 8.29–8.31 (1H, m), 8.70–8.73 (1H, m)

Preparation Example 67

Synthesis of 5-(3-phenylpropylidene)-3-[4-(imidazo[1,2-a]pyridin-8-yloxy)butyl]thiazolidine-2,4-dione hydrochloride i) Synthesis of 5-(3-phenylpropylidene)-3-[4-(imidazo[1,2-a]pyridin-5-yloxy)butyl]thiazolidine-2,4-dione To a solution of 1.527 g (5.0 mmol) of 3-[4-(imidazo[1,2-a]pyridin-8-yloxy)butyl]thiazolidine-2,4-dione and 0.659 ml (5.0 mmol) of 3-phenylpropionaldehyde in 20 ml of ethanol, 0.05 ml (0.5 mmol) of piperidine was added, followed by refluxing for 2.5 hours. After the reaction mixture was cooled, the solvent was distilled off. The residue was dissolved in chloroform, washed with water and dried, after which the solvent was distilled off. The residue was purified by column chromatography (eluent, ethyl acetate). The resulting residue was crystallized from dichloromethane-diethyl ether to yield 1.633 g (77.5%, light yellow crystal) of the desired product.

¹H-NMR (CDCl₃, 200 MHz) δ 1.91–1.95 (4H, m), 2.54 (2H, q, J=7.6 Hz), 2.85 (2H, t, J=7.6 Hz), 3.78 (2H, t, J=6.6 Hz), 4.17 (2H, t, J=5.8 Hz), 6.42 (1H, d, J=7.6 Hz), 6.66 (1H, dd, J=6.8, 7.4 Hz), 7.07 (1H, t, J=7.6 Hz), 7.17–7.31 (5H, m), 7.54 (1H, s), 7.56 (1H, s), 7.75 (1H, d, J=6.6 Hz)

ii) Synthesis of 5-(3-phenylpropylidene)-3-[4-(imidazo[1,2-a]pyridin-8-yloxy)butyl]thiazolidine-2,4-dione hydrochloride To a solution of 1.633 g (3.87 mmol) of 5-(3-phenylpropylidene)-3-[4-(imidazo[1,2-a]pyridin-8-yloxy)butyl]thiazolidine-2,4-dione in 30 ml of methanol, 0.70 ml of concentrated hydrochloric acid was added. After the solvent was distilled off, the residue was washed with diethyl ether to yield 1.597 g (90.0%, brown foamy substance) of the desired product.

m.p. 64.0°–65.0° C.; ¹H-NMR (CD₃OD, 200 MHz) δ 1.88–1.93 (4H, m), 2.56 (2H, q, J=7.6 Hz), 2.86 (2H, t, J=7.0 Hz), 3.77 (2H, t, J=6.6 Hz), 4.37 (2H, t, J=5.8 Hz), 7.05 (1H, t, J=7.6 Hz), 7.18–7.29 (5H, m), 7.37–7.39 (2H, m), 8.00 (1H, d, J=2.0 Hz), 8.24 (1H, d, J=1.0 Hz), 8.39 (1H, dd, J=3.0, 4.6 Hz); Anal. Calcd for C₂₃H₂₄ClN₃O₃S.1.5H₂O: C, 56.96; H, 5.61; N, 8.66. Found: C, 56.83; H, 5.65; N, 8.83

Preparation Example 68

Synthesis of 5-propylidene-3-[4-(imidazo[1,2-a]pyridin-8-yloxy)butyl]thiazolidine-2,4-dione hydrochloride i) Synthesis of 5-propylidene-3-[4-(imidazo[1,2-a]pyridin-8-yloxy)butyl]thiazolidine-2,4-dione To a solution of 1.53 g (5.0 mmol) of 3-[4-(imidazo[1,2-a]pyridin-8-yloxy)butyl]thiazolidine-2,4-dione and 0.36 ml (5.0 mmol) of 1-propanal in 20 ml of ethanol, 0.05 ml (0.5 mmol) of piperidine was added, followed by refluxing for 2.5 hours. After the reaction mixture was cooled, the solvent was distilled off. The residue was dissolved in dichloromethane, washed with purified water and dried, after which the solvent was distilled off. The, residue was purified by column chromatography (eluent, n-hexane/ethyl acetate=4/1). After the solvent was distilled off, the residue was recrystallized from ether to yield 1.14 g (41.7%, white crystal) of the desired product.

m.p. 70.0°–71.0° C.; ¹H-NMR (CDCl₃, 200 MHz) δ 1.16 (3H, t, J=7.5 Hz), 1.85–2.05 (4H, m), 2.25 (2H, q, J=7.5 Hz), 3.80 (2H, t, J=6.5 Hz), 4.18 (2H, t, J=5.7 Hz), 6.43 (1H, d, J=7.7 Hz), 6.66 (1H, t, J=7.1 Hz), 7.05 (1H, t, J=7.6 Hz), 7.55 (2H, dd, J=1.1, 4.8 Hz), 7.76 (1H, d, J=6.6 Hz); IR (KBr) 1743, 1686, 1637, 1549 cm⁻¹; Anal. Calcd for C₁₇H₁₉N₃O₃S: C, 59.11; H, 5.54; N, 12.16. Found: C, 58.85; H, 5.58; N, 12.00 ii) Synthesis of 5-propylidene-3-[4-(imidazo[1,2-a]pyridin-8-yloxy)butyl]-thiazolidine-2,4-dione hydrochloride To a methanol solution of 0.691 g (2.0 mmol) of 5-propylidene-3-[4-(imidazo[1,2-a]pyridin-8-yloxy)butyl] thiazolidine-2,4-dione, 0.5 ml of 4N hydrochloric acid-ethyl acetate was added, followed by stirring. After the solvent was distilled off, the residue was washed with ether to yield 0.79 g (quant., yellow oily substance) of the desired product.

¹H-NMR (D₂O, 200 MHz) δ 1.07 (3H, t, J=7.6 Hz), 1.80–2.00 (4H, m), 2.20 (2H, t, J=7.6 Hz), 3.65–3.80 (2H, m), 4.25–4.40 (2H, m), 7.04 (1H, d, J=2.2 Hz), 7.20–7.35 (2H, m), 7.86 (1H, d, J=2.2 Hz), 8.00–8.10 (1H, d, J=5.6 Hz); Anal. Calcd for C₁₇H₂₀ClN₃O₃S.0.6H₂O: C, 52.00; H, 5.44; N, 10.70. Found: C, 52.17; H, 5.77; N, 10.61

Preparation Example 69

Synthesis of 5-pentylidene-3-[4-(imidazo[1,2-a]pyridin-8-yloxy)butyl]thiazolidine-2,4-dione hydrochloride i) Synthesis of 5-pentylidene-3-[4-(imidazo[1,2-a]pyridin-8-yloxy)butyl]thiazolidine-2,4-dione To a solution of 1.53 g (5.0 mmol) of 3-[4-(imidazo[1,2-a]pyridin-8-yloxy)butyl]thiazolidine-2,4-dione and 0.53 ml (5.0 mmol) of 1-pentanal in 20 ml of ethanol, 0.05 ml (0.5 mmol) of piperidine was added, followed by refluxing for 3 hours. After the reaction mixture was cooled, the solvent was distilled off. The residue was dissolved in dichloromethane, washed with purified water and dried, after which the solvent was distilled off. The residue was purified by column chromatography (eluent, n-hexane/ethyl acetate=1/4). After the solvent was distilled off, the residue was recrystallized from ether to yield 1.11 g (59%, white crystal) of the desired product.

m.p. 64.0°–65.0° C.; ¹H-NMR (CDCl₃, 200 MHz) δ 0.93 (3H, t, J=7.1 Hz), 1.30–1.60 (4H, m), 1.80–2.05 (4H, m), 2.27 (2H, q, J=7.3 Hz), 3.80 (2H, t, J=6.7 Hz), 4.19 (2H, t, J=6.0 Hz), 6.47 (1H, d, J=6.8 Hz), 6.66 (1H, t, J=7.2 Hz), 7.07 (1H, t, J=7.6 Hz), 7.58 (2H, dd, J=1.2, 5.4 Hz), 7.76 (1H, d, J=5.8 Hz); IR (KBr) 2947, 2868, 1736, 1682, 1643, 741 cm⁻¹; Anal. Calcd for C₁₉H₂₃N₃O₃S: C, 61.10; H, 6.21; N, 11.25. Found: C, 60.92; H, 6.27; N, 11.21 ii) Synthesis of 5-pentylidene-3-[4-(imidazo[1,2-a]pyridin-8-yloxy)butyl]thiazolidine-2,4-dione hydrochloride To a methanol solution of 0.934 g (2.5 mmol) of 5-pentylidene-3-[4-(imidazo[1,2-a]pyridin-8-yloxy)butyl] thiazolidine-2,4-dione, 0.625 ml of 4N hydrochloric acid-ethyl acetate was added, followed by stirring. After the solvent was distilled off, the residue was washed with ether to yield 1.03 g (quant., white solid) of the desired product.

m.p. 69.0°–70.0° C.; ¹H-NMR (D₂O, 200 MHz) δ 0.86 (3H, t, J=7.2 Hz), 1.20–1.55 (4H, m), 1.78–2.00 (4H, m), 2.20 (2H, q, J=7.4 Hz), 3.70–3.80 (2H, m), 4.30–4.40 (2H, m), 7.05 (1H, t, J=7.7 Hz), 7.20–7.35 (2H, m), 7.86 (1H, d, J=2 Hz), 8.05 (1H, d, J=2.2 Hz), 8.23 (1H, dd, J=1.8, 5.6 Hz); Anal. Calcd for $C_{19}H_{24}ClN_3O_3S \cdot 1.0H_2O$: C, 53.33; H, 6.12; N, 9.82. Found: C, 53.28; H, 6.14; N, 10.50

Preparation Example 70

Synthesis of 5-hexylidene-3-[4-(imidazo[1,2-a]pyridin-8-yloxy)butyl]thiazolidine-2,4-dione hydrochloride i) Synthesis of 5-hexylidene-3-[4-(imidazo[1,2-a]pyridin-8-yloxy)butyl]thiazolidine-2,4-dione To a solution of 1.53 g (5 mmol) of 8-[4-(2,4-thiazolidinedione)butoxy]imidazo[1,2-a]pyridine and 0.61 ml (5 mmol) of 1-hexanal in 20 ml of ethanol, 0.05 ml (0.5 mmol) of piperidine was added at 50° C., followed by refluxing for 2 hours. After the reaction mixture was cooled, the solvent was distilled off. The residue was dissolved in dichloromethane, washed with purified water and dried, after which the solvent was distilled off. The residue was purified by column chromatography (eluent, n-hexane/ethyl acetate=1/4), after which the solvent was distilled off, to yield 1.73 g (89%, yellow oily substance) of the desired product.

$^1$H-NMR (CDCl$_3$, 200 MHz) δ 0.80–1.00 (3H, m), 1.20–1.45 (6H, m), 1.80–2.00 (4H, m), 2.22 (2H, q, J=7.5 Hz), 3.79 (2H, t, J=6.6 Hz), 4.15–4.25 (2H, m), 6.43 (1H, d, J=7.4 Hz), 6.66 (1H, t, J=7.1 Hz), 7.07 (1H, t, J=7.8 Hz), 7.55 (2H, d, J=3.4 Hz), 7.77 (1H, d, J=6.6 Hz); IR (neat) 2923, 1737, 1680, 1635, 1543, 735 cm$^{-1}$ ii) Synthesis of 5-hexylidene-3-[4-(imidazo[1,2-a]pyridin-8-yloxy)butyl]thiazolidine-2,4-dione hydrochloride To a methanol solution of 1.73 g (4.5 mmol) of 5-hexylidene-3-[4-(imidazo[1,2-a]pyridin-8-yloxy)butyl]thiazolidine-2,4-dione, 1 ml of 4N hydrochloric acid-ethyl acetate was added, followed by stirring. After the solvent was distilled off, the residue was washed with ether to yield 1.73 g of an oily substance, which was then purified by recrystallization to yield 1.58 g (74%, white crystal) of the desired product.

m.p. 77.0°–78.0° C.; $^1$H-NMR (D$_2$O, 200 MHz) δ 0.81 (3H, t, J=6.4 Hz), 1.10–1.55 (6H, m), 1.75–2.00 (4H, m), 2.10–2.25 (2H, m), 3.65–3.80 (2H, m), 4.20–4.40 (2H, m), 7.03 (1H, t, J=7.6 Hz), 7.15–7.35 (2H, m), 7.85 (1H, d, J=2.0 Hz), 8.04 (1H, d, J=2.0 Hz), 8.25 (1H, d, J=6.0 Hz); Anal. Calcd for $C_{20}H_{26}ClN_3O_3S \cdot 0.9H_2O$: C, 54.57; H, 6.37; N, 9.55. Found: C, 54.36; H, 6.49; N, 9.96

Preparation Example 71

Synthesis of 5-octylidene-3-[4-(imidazo[1,2-a]pyridin-8-yloxy)butyl]thiazolidine-2,4-dione hydrochloride i) Synthesis of 5-octylidene-3-[4-(imidazo[1,2-a]pyridin-8-yloxy)butyl]thiazolidine-2,4-dione To a solution of 1.53 g (5 mmol) of 8-[4-(2,4thiazolidinedione)butoxy]imidazo[1,2-a]pyridine and 0.78 ml (5 mmol) of 1-octanal in 20 ml of ethanol, 0.05 ml (0.5 mmol) of piperidine was added at 50° C., followed by refluxing for 3.5 hours. After the reaction mixture was cooled, the solvent was distilled off. The residue was dissolved in dichloromethane, washed with purified water and dried, after which the solvent was distilled off. The residue was purified by column chromatography (eluent, n-hexane/ethyl acetate=1/4), after which the solvent was distilled off, to yield 2.03 g (98%, yellow oily substance) of the desired product.

$^1$H-NMR (CDCl$_3$, 200 MHz) δ 0.80–0.95 (3H, m), 1.15–1.40 (2H, m), 1.40–1.60 (2H, m), 1.80–2.05 (4H, m), 2.22 (2H, q, J=7.3 Hz), 3.79 (2H, t, J=6.4 Hz), 4.17 (2H, t, J=5.6 Hz), 6.42 (1H, d, J=7.6 Hz), 6.65 (1H, t, J=7.2 Hz), 7.06 (1H, t, J=7.7 Hz), 7.54 (2H, d, J=4.3 Hz), 7.75 (1H, d, J=7.0 Hz); IR (neat) 2927, 2856, 1743, 1687, 1635, 1549, 735 cm$^{-1}$ ii) Synthesis of 5-octylidene-3-[4-(imidazo[1,2-a]pyridin-8-yloxy)butyl]thiazolidine-2,4-dione hydrochloride To a methanol solution of 2.03 g (4.9 mmol) of 5-octylidene-3-[4-(imidazo[1,2-a]pyridin-8-yloxy)butyl]thiazolidine-2,4-dione, 1.25 ml of 4N hydrochloric acid-ethyl acetate was added, followed by stirring. After the solvent was distilled off, the residue was washed with ether to yield 1.71 g (77.2%, white solid) of the desired product.

m.p. 70.0°–72.0° C.; $^1$H-NMR (D$_2$O, 200 MHz) δ 0.77 (3H, t, J=6.6 Hz), 1.00–1.30 (8H, m), 1.30–1.50 (2H, m), 1.70–2.00 (4H, m), 2.12 (2H, q, J=7.5 Hz), 3.60–3.70 (2H, m), 4.10–4.25 (2H, m), 6.90–7.20 (3H, m), 7.79 (1H, d, J=2.0 Hz), 7.96 (1H, d, J=2.0 Hz), 8.11 (1H, d, J=6.4 Hz); Anal. Calcd for $C_{22}H_{30}ClN_3O_3S \cdot 0.6H_2O$: C, 57.09; H, 6.79; N, 9.08. Found: C, 56.84; H, 7.02; N, 9.48

Preparation Example 72

Synthesis of 5-decylidene-3-[4-(imidazo[1,2-a]pyridin-8-yloxy)butyl]thiazolidine-2,4-dione hydrochloride i) Synthesis of 5-decylidene-3-[4-(imidazo[1,2-a]pyridin-8-yloxy)butyl]thiazolidine-2,4-dione To a solution of 1.53 g (5 mmol) of 8-[4-(2,4-thiazolidinedione)butoxy]imidazo[1,2-a]pyridine and 0.53 ml (5 mmol) of 1-decanal in 20 ml of ethanol, 0.05 ml (0.5 mmol) of piperidine was added at 50° C., followed by refluxing for 3 hours. After the reaction mixture was cooled, the solvent was distilled off. The residue was dissolved in dichloromethane, washed with purified water and dried, after which the solvent was distilled off. The residue was purified by column chromatography (eluent, n-hexane/ethyl acetate=1/4), after which the solvent was distilled off, to yield 2.12 g (95.6%, yellow oily substance) of the desired product.

$^1$H-NMR (CDCl$_3$, 200 MHz) δ 0.88 (3H, t, J=6.5 Hz), 1.15–1.45 (12H, m), 1.45–1.60 (2H, m), 1.95 (4H, t, J=3.1 Hz), 2.22 (2H, q, J=7.3 Hz), 3.80 (2H, t, J=6.4 Hz), 4.19 (2H, t, J=5.5 Hz), 6.44 (1H, d, J=7.4 Hz), 6.67 (1H, t, J=7.2 Hz), 7.08 (1H, t, J=7.6 Hz), 7.56 (2H, d, J=5.6 Hz), 7.77 (1H, d, J=6.8 Hz); IR (neat) 2923, 2846, 1730, 1635, 1549, 735 cm$^{-1}$ ii) Synthesis of 5-decylidene-3-[4-(imidazo[1,2-a]pyridin-8-yloxy)butyl]thiazolidine-2,4-dione hydrochloride To a methanol solution of 2.12 g (4.8 mmol) of 5-decylidene-3-[4-(imidazo[1,2-a]pyridin-8-yloxy)butyl]thiazolidine-2,4-dione, 1.25 ml of 4N hydrochloric acid-ethyl acetate was added, followed by stirring. After the solvent was distilled off, the residue was washed with ether to yield 1.88 g (81.6%, white solid) of the desired product.

m.p. 88.0°–90.0° C.; $^1$H-NMR (D$_2$O, 200 MHz) δ 0.70–0.90 (3H, m), 1.05–1.35 (12H, m), 1.35–1.55 (2H, m), 1.70–1.95 (4H, m), 2.00–2.20 (2H, m), 3.60–3.80 (2H, m), 4.05–4.20 (2H, m), 6.85–7.10 (3H, m), 7.73 (1H, d, J=2.0 Hz), 7.90 (1H, d, J=2.0 Hz), 8.04 (1H, d, J=4.2 Hz); Anal. Calcd for $C_{24}H_{34}ClN_3O_3S \cdot 0.8H_2O$: C, 58.30; H, 7.26; N, 8.50. Found: C, 58.16; H, 7.53; N, 8.36

Preparation Example 73

Synthesis of 5-butylidene-3-[4-(imidazo[1,2-a]pyridin-8-yloxy)butyl]thiazolidine-2,4-dione hydrochloride i) Synthesis of 5-butylidene-3-[4-(imidazo[1,2-a]pyridin-8-yloxy)butyl]thiazolidine-2,4-dione To a solution of 1.25 g (4.32 mmol) of 3-[4-(imidazo[1,2-a]pyridin-8-yloxy)butyl]thiazolidine-2,4-dione and 0.39 ml (4.32 mmol) of 1-butanal in 20 ml of ethanol, 0.036 ml (0.43 mmol) of pyrrolidine was added at 60° C., followed by refluxing for 19 hours (1 and 2 hours later, 0.39 ml (4.32 mmol) was further added; 3 hours later, 0.39 ml (4.32 mmol) of 1-butanal and 0.036 ml (0.43 mmol) of pyrrolidine were further added). After the reaction mixture was cooled, the solvent was distilled off. The residue was dissolved in dichloromethane, washed with purified water and dried, after which the solvent was distilled off. The residue was purified by column chromatography (eluent, n-hexane/ethyl acetate=1/4), after which the solvent was distilled off, to yield 0.17 g (11.5%, yellow oily substance) of the desired product.

$^1$H-NMR (CDCl$_3$, 200 MHz) δ 0.97 (3H, t, J=7.4 Hz), 1.54 (2H, q, J=7.4 Hz), 1.90–2.10 (4H, m), 2.33 (2H, q, J=7.6 Hz), 3.60–3.80 (2H, m), 4.15–4.25 (2H, m), 6.06 (1H, t, J=8.1 Hz), 6.44 (1H, d, J=7.4 Hz), 6.68 (1H, t, J=7.2 Hz), 7.55–7.65 (2H, m), 7.78 (1H, d, J=6.6 Hz); IR (neat) 2958, 1822, 1741, 1280, 1112 cm$^{-1}$ ii) Synthesis of 5-butylidene-3-[4-(imidazo[1,2-a]pyridin-8-yloxy)butyl]thiazolidine-2,4-dione hydrochloride To a methanol solution of 0.17 g (0.59 mmol) of 5-butylidene-3-[4-(imidazo[1,2-a]pyridin-8-yloxy)butyl] thiazolidine-2,4-dione, 0.13 ml of 4N hydrochloric acid-ethyl acetate was added, followed by stirring, after which the solvent was distilled off, to yield 0.19 g (84.8%, yellow oily substance) of the desired product.

$^1$H-NMR (D$_2$O, 200 MHz) δ 0.92 (3H, t, J=7.4 Hz), 1.51 (2H, q, J=7.4 Hz), 1.85–2.00 (2H, m), 2.30 (2H, q, J=7.5 Hz), 3.65–3.75 (2H, m), 4.30–4.45 (2H, m), 6.18 (1H, t, J=8.1 Hz), 7.20–7.35 (2H, m), 7.87 (1H, d, J=2.2 Hz), 8.06 (1H, d, J=2.2 Hz), 8.25 (1H, dd, J=2.4, 5.2 Hz); Anal. Calcd for C$_{18}$H$_{22}$ClN$_3$O$_4$.0.8H$_2$O: C, 54.84; H, 6.03; N, 10.66. Found: C, 54.81; H, 6.22; N, 10.45

Preparation Example 74

Synthesis of 5-pentylidene-3-[4-(imidazo[1,2-a]pyridin-8-yloxy)butyl]thiazolidine-2,4-dione hydrochloride i) Synthesis of 5-pentylidene-3-[4-(imidazo[1,2-a]pyridin-8-yloxy)butyl]thiazolidine-2,4-dione To a solution of 1.45 g (5 mmol) of 3-[4-(imidazo[1,2-a]pyridin-8-yloxy)butyl]thiazolidine-2,4-dione and 0.53 ml (5 mmol) of 1-pentanal in 20 ml of ethanol, 0.05 ml (0.5 mmol) of pyrrolidine was added at 60° C., followed by refluxing for 19 hours (2.5 hours later, 0.53 ml (5 mmol) of 1-pentanal and 0.05 ml (0.5 mmol) of pyrrolidine were further added). After the reaction mixture was cooled, the solvent was distilled off. The residue was dissolved in dichloromethane, washed with purified water and dried, after which the solvent was distilled off. The residue was purified by column chromatography (eluent, n-hexane/ethyl acetate=1/1→1/4), after which the solvent was distilled off, to yield 0.29 g (16.3%, yellow oily substance) of the desired product.

$^1$H-NMR (CDCl$_3$, 200 MHz) δ 0.93 (3H, t, J=7.1 Hz), 1.30–1.55 (4H, m), 1.90–2.10 (4H, m), 2.35 (2H, q, J=7.4 Hz), 3.60–3.80 (2H, m), 4.15–4.30 (2H, m), 6.05 (1H, t, J=8.1 Hz), 6.50 (1H, d, J=7.0 Hz), 6.73 (1H, t, J=7.1 Hz), 7.59 (2H, dd, J=1.2, 9.0 Hz), 7.79 (1H, d, J=7.6 Hz); IR (neat) 2956, 1817, 1734, 1550, 798 cm$^{-1}$ ii) Synthesis of 5-pentylidene-3-[4-(imidazo[1,2-a]pyridin-8-yloxy)butyl]thiazolidine-2,4-dione hydrochloride To a methanol solution of 0.29 g (0.82 mmol) of 5-pentylidene-3-[4-(imidazo[1,2-a]pyridin-8-yloxy)butyl] thiazolidine-2,4-dione, 0.25 ml of 4N hydrochloric acid-ethyl acetate was added, followed by stirring, after which the solvent was distilled off, to yield 0.33 g (quant., yellow oily substance) of the desired product.

$^1$H-NMR (D$_2$O, 200 MHz) δ 0.89 (3H, t, J=7.1 Hz), 1.30–1.55 (4H, m), 1.80–2.10 (4H, m), 2.20–2.40 (2H, m), 3.65–3.80 (2H, m), 4.30–4.45 (2H, m), 6.18 (1H, t, J=8.1 Hz), 7.30–7.40 (2H, m), 7.87 (1H, d, J=2.0 Hz), 8.07 (1H, d, J=2.2 Hz), 8.20–8.28 (1H, m); Anal. Calcd for C$_{19}$H$_{24}$ClN$_3$O$_4$.0.5H$_2$O: C, 56.64; H, 6.25; N, 10.43. Found: C, 56.98; H, 6.68; N, 10.27

Preparation Example 75

Synthesis of 5-hexylidene-3-[4-(imidazo[1,2-a]pyridin-8-yloxy)butyl]oxazolidine-2,4-dione hydrochloride i) Synthesis of 5-hexylidene-3-[4-(imidazo[1,2-a]pyridin-8-yloxy)butyl]oxazolidine-2,4-dione To a solution of 386 mg (0.99 mmol) of 5-(1-hydroxyhexyl)-3-[4-(imidazo[1,2-a]pyridin-8-yloxy)butyl] oxazolidine-2,4-dione in 8 ml of pyridine, 4 ml of acetic anhydride was added, followed by stirring at room temperature for 2 hours and then at 90° C. for 21 hours. The mixture was dissolved in dichloromethane, washed with saturated aqueous sodium hydrogen carbonate and dried, after which the solvent was distilled off. The residue was purified by column chromatography (eluent, ethyl acetate/hexane=4/1→ethyl acetate) to yield 79.2 mg (22%, yellow oily substance) of the desired product.

$^1$H-NMR (CDCl$_3$, 200 MHz) δ 0.85–1.00 (3H, m), 1.25–1.60 (6H, m), 1.95–2.10 (4H, m), 2.25–2.40 (2H, m), 3.65–3.80 (2H, m), 4.15–4.25 (2H, m), 6.05 (1H, t, J=8.1 Hz), 6.48 (1H, d, J=7.4 Hz), 6.69 (1H, t, J=4.8 Hz), 7.59 (2H, dd, J=1.2, 9.6 Hz), 7.79 (1H, d, J=6.0 Hz)

ii) Synthesis of 5-hexylidene-3-[4-(imidazo[1,2-a]pyridin-8-yloxy)butyl]oxazolidine-2,4-dione hydrochloride To a methanol solution of 96 mg (0.25 mmol) of 5-hexylidene-3-[4-(imidazo[1,2-a)pyridin-8-yloxy)butyl] oxazolidine-2,4-dione, 0.063 ml of 4N hydrochloric acid-ethyl acetate was added, followed by stirring, after which the solvent was distilled off, to yield 100 mg (98.1%, yellow oily substance) of the desired product.

$^1$H-NMR (D$_2$O, 200 MHz) δ 0.80–0.95 (3H, m), 1.25–1.60 (6H, m), 1.85–2.10 (4H, m), 2.33 (2H, q, J=7.6 Hz), 3.65–3.75 (2H, m), 4.30–4.45 (2H, m), 6.19 (1H, t, J=7.6 Hz), 7.30–7.40 (2H, m), 7.89 (1H, d, J=2.2 Hz), 8.08 (1H, d, J=2.2 Hz), 8.27 (1H, dd, J=2.6, 4.8 Hz); Anal. Calcd for C$_{20}$H$_{26}$ClN$_3$O$_4$.1.0H$_2$O: C, 56.40; H, 6.63; N, 9.87. Found: C, 56.24; H, 6.53; N, 9.49

Preparation Examples 76 and 77

Synthesis of 5-(Z)-butylidene-3-[4-(3-trifluoroacetylimidazo[1,2-a]pyridin-8-yloxy)butyl] oxazolidine-2,4-dione and 5-(E)-butylidene-3-[4-(3-trifluoroacetylimidazo[1,2-a]pyridin-8-yloxy)butyl] oxazolidine-2,4-dione i) Synthesis of 3-[4-(3-trifluoroacetylimidazo(1,2-a)pyridin-8-yloxy)butyl]oxazolidine-2,4-dione To a solution of 868 mg (3 mmol) of 3-[4-(imidazo[1,2-a]pyridin-8-yloxy)butyl]oxazolidine-2,4-dione in 40 ml of dichloromethane, 5 ml (30 mmol) of trifluoroacetic anhydride and 5 ml of triethylamine were added, followed by stirring at room temperature for 1.5 hours. The mixture was dissolved in dichloromethane, washed with saturated aqueous sodium hydrogen carbonate and dried, after which the solvent was distilled off. The residue was purified by column chromatography (eluent, n-hexane/ethyl acetate=1/1→1/4). After the solvent was distilled off, the residue was recrystallized from ether to yield 472 mg (40.8%, white crystal) of the desired product.

$^1$H-NMR (CDCl$_3$, 200 MHz) δ 1.90–2.10 (4H, m), 3.69 (2H, t, J=6.7 Hz), 4.30 (2H, t, J=5.8 Hz), 4.72 (2H, s), 7.00 (1H, d, J=8.0 Hz), 7.15 (1H, t, J=7.4 Hz), 8.49 (1H, q, J=1.8 Hz), 9.23 (1H, dd, J=0.9, 6.7 Hz); IR (KBr) 1805, 1730, 1664, 1556, 1510, 906 cm$^{-1}$ ii) Synthesis of 5-(Z)-butylidene-3-[4-(3-trifluoroacetylimidazo[1,2-a]pyridin-8-yloxy)butyl]

oxazolidine-2,4-dione and 5-(E)-butylidene-3-[4-(3-trifluoroacetylimidazo(1,2-a]pyridin-8-yloxy)butyl]oxazolidine-2,4-dione To a solution of 870 mg (2.27 mmol) of 3-[4-(3-trifluoroacetylimidazo[1,2-a]pyridin-8-yloxy)butyl]oxazolidine-2,4-dione and 0.20 ml (2.27 mmol) of 1-butanal in 20 ml of ethanol, 0.019 ml (0.23 mmol) of pyrrolidine was added at 60° C., followed by refluxing for 16 hours (3 hours later, 0.20 ml (2.27 mmol) of 1-butanal and 0.019 ml (0.23 mmol) of pyrrolidine were further added). After the reaction mixture was cooled, the solvent was distilled off. The residue was dissolved in ethyl acetate, washed with purified water and dried, after which the solvent was distilled off. The residue was purified by column chromatography (eluent, n-hexane/ethyl acetate=2/1→1/4) to yield 0.12 g (11.9%, white crystal) of the desired product (Z-configuration) and 0.03 g (3.0%, white crystal) of the desired product (E-configuration). Z-configuration (Preparation Example 76)

m.p. 90.0°–91.0° C.; $^1$H-NMR (CDCl$_3$, 200 MHz) δ 0.97 (3H, t, J=7.3 Hz), 1.45–1.70 (2H, m), 1.85–2.05 (4H, m), 2.33 (2H, q, J=7.5 Hz), 3.65–3.80 (2H, m), 4.25–4.35 (2H, m), 6.06 (1H, t, J=8.0 Hz), 6.99 (1H, dd, J=1.0, 7.8 Hz), 7.15 (1H, dd, J=6.8, 8.0 Hz), 8.45–8.55 (1H, m), 9.22 (1H, dd, J=1.0, 6.8 Hz); IR (KBr) 1819, 1735, 1657, 1556, 1257, 903 cm$^{-1}$; Anal. Calcd for C$_{20}$H$_{20}$F$_3$N$_3$O$_5$: C, 54.67; H, 4.59; N, 9.56. Found: C, 54.48; H, 4.52; N, 9.52

E-configuration (Preparation Example 77)

$^1$H-NMR (CDCl$_3$, 200 MHz) δ 0.97 (3H, t, J=7.3 Hz), 1.53 (2H, q, J=7.3 Hz), 1.90–2.10 (4H, m), 2.66 (2H, q, J=7.8 Hz), 3.65–3.80 (2H, m), 4.25–4.35 (2H, m), 6.02 (1H, t, J=8.5 Hz), 6.99 (1H, d, J=7.8 Hz), 7.15 (1H, dd, J=7.0, 7.8 Hz), 8.45–8.55 (1H, m), 9.22 (1H, dd, J=0.6, 6.6 Hz); IR (KBr) 1822, 1740, 1655, 1556, 1252, 903 cm$^{-1}$

Preparation Example 78

Synthesis of imidazo[1,2-a]pyridin-5-acetic [3-(1,1,6,8-tetraoxo-9-phenyl-2,3,4,8-tetrahydropyrimido[6,1-b][1,3]thiazin-7-yl)propyl]amide hydrochloride i) Synthesis of imidazo[1,2-a]pyridin-5-acetic [3-(1,1,6,8-tetraoxo-9-phenyl-2,3,4,8-tetrahydropyrimido[6,1-b][1,3]thiazin-7-yl)propyl]amide To a dichloromethane solution of 601 mg (2.5 mmol) of imidazo[1,2-a]pyridin-5-acetic acid and 383 mg (2.5 mmol) of HOBt, 479 mg (2.5 mmol) of WSC and 0.5 ml (3.6 mmol) of triethylamine were added. After the reaction mixture was stirred at 0° C. for 30 minutes, 1.158 g (3 mmol) of 3-(1,1,6,8-tetraoxo-9-phenyl-2,3,4,8-tetrahydropyrimido[6,1-b][1,3]thiazin-7-yl)propylamine hydrochloride and 0.84 ml (6 mmol) of triethylamine were added, followed by stirring at room temperature for 3 hours and then at 40° C. for 14 hours. After water was added, the mixture was extracted with dichloromethane and dried, after which the solvent was distilled off. The residue was purified by column chromatography (eluent, chloroform→chloroform/methanol=25/1) to yield 74.7 mg (5.9%, yellow oily substance) of the desired product.

$^1$H-NMR (CDCl$_3$, 200 MHz) δ 1.70–1.90 (2H, m), 2.40–2.55 (2H, m), 3.10–3.25 (2H, m), 3.35 (2H, t, J=6.9 Hz), 3.79 (2H, t, J=6.3 Hz), 3.85 (2H, s), 4.17 (2H, t, J=6.3 Hz), 6.55–6.70 (1H, m), 6.76 (1H, d, J=6.6 Hz), 7.13 (1H, dd, J=6.8, 9.0 Hz), 7.20–7.35 (2H, m), 7.35–7.50 (3H, m), 7.50–7.60 (1H, m), 7.60 (1H, d, J=1.4 Hz), 7.65 (1H, d, J=1.2 Hz); IR (neat) 3060, 2930, 1640, 1450, 1300, 1140, 920, 730 cm$^{-1}$ ii) Synthesis of imidazo[1,2-a]pyridin-5-acetic [3-(1,1,6,8-tetraoxo-9-phenyl-2,3,4,8-tetrahydropyrimido[6,1-b][1,3]thiazin-7-yl)propyl]amide hydrochloride To a methanol solution of 75 mg (0.15 mmol) of imidazo[1,2-a]pyridin-5-acetic [3-(1,1,6,8-tetraoxo-9-phenyl-2,3,4,8-tetrahydropyrimido[6,1-b][1,3]thiazine-7-yl)propyl]amide, 0.1 ml of 4N hydrochloric acid-ethyl acetate was added, followed by stirring, after which the solvent was distilled off, to yield 75 mg (92.0%, light yellow oily substance) of the desired product.

m.p. 140.0°–141.0° C.; $^1$H-NMR (D$_2$O, 200 MHz) δ 1.80–2.00 (2H, m), 2.50–2.65 (2H, m), 3.29 (2H, t, J=6.2 Hz), 3.65 (2H, t, J=6.4 Hz), 4.00 (2H, t, J=6.9 Hz), 4.14 (2H, t, J=6.1 Hz), 4.25 (2H, s), 7.25–7.55 (6H, m), 7.80–8.00 (3H, m), 7.99 1H, d, J=2.6 Hz); Anal. Calcd for C$_{25}$H$_{26}$ClN$_5$O$_5$S.1.0H$_2$O: C, 53.43; H, 5.02; N, 12.46. Found: C, 53.70; H, 5.47; N, 11.71

Preparation Example 79

Synthesis of 4-(imidazo[1,2-a]pyridin-5-ylthio)butanoic [3-(1,1,6,8-tetraoxo-9-phenyl-2,3,4,8-tetrahydropyrimido[6,1-b][1,3]thiazin-7-yl)propyl]amide hydrochloride i) Synthesis of 4-(imidazo[1,2-a]pyridin-5-ylthio)butanoic [3-(1,1,6,8-tetraoxo-9-phenyl-2,3,4,8-tetrahydropyrimido[6,1-b][1,3]thiazin-7-yl)propyl]amide To a dichloromethane solution of 590 mg (2.5 mmol) of 4-(imidazo[1,2-a]pyridine-5-ylthio)butanoic acid and 383 mg (2.5 mmol) of HOBt, 479 mg (2.5 mmol) of WSC and 0.42 ml (3 mmol) of triethylamine were added. After the reaction mixture was stirred at 0° C. for 1.5 hours, 1.158 g (3 mmol) of 3-(1,1,6,8-tetraoxo-9-phenyl-2,3,4,8-tetrahydropyrimido[6,1-b][1,3]thiazin-7-yl)propylamine hydrochloride and 0.84 ml (6 mmol) of triethylamine were added, followed by stirring at room temperature for 16 hours. After water was added, the mixture was extracted with dichloromethane and dried, after which the solvent was distilled off. The residue was purified by column chromatography (eluent, chloroform→chloroform/methanol=25/1) to yield 683.9 mg (48.2%, white oily substance) of the desired product.

$^1$H-NMR (CDCl$_3$, 200 MHz) δ 1.70–1.95 (2H, m), 1.95–2.10 (2H, m), 2.33 (2H, t, J=7.0 Hz), 2.45–2.60 (2H, m), 3.05 (2H, t, J=7.2 Hz), 3.15–3.30 (2H, m), 3.39 (2H, t, J=6.8 Hz), 4.02 (2H, t, J=6.4 Hz), 4.27 (2H, t, J=6.8 Hz), 6.24 (1H, br), 6.92 (1H, dd, J=1.0, 7.0 Hz), 7.13 (1H, dd, J=7.0, 9.0 Hz), 7.20–7.40 (2H, m), 7.40–7.50 (3H, m), 7.56 (1H, dd, J=1.0, 10.0 Hz), 7.67 (1H, d, J=1.2 Hz), 7.81 (1H, d, J=0.8 Hz); IR (neat) 3300, 2930, 2360, 1650, 1440, 1330, 1140, 870, 750, 700 cm$^{-1}$ ii) Synthesis of 4-(imidazo[1,2-a]pyridin-5-ylthio)butanoic [3-(1,1,6,8-tetraoxo-9-phenyl- 2,3,4,8-tetrahydropyrimido[6,1-b][1,3]thiazine-7-yl)propyl]amide hydrochloride To a methanol solution of 683 mg (1.2 mmol) of 4-(imidazo[1,2-a]pyridin-5-ylthio)butanoic [3-(1,1,6,8-tetraoxo-9-phenyl-2,3,4,8-tetrahydropyrimido[6,1-b][1,3]thiazine-7-yl)propyl]amide, 0.5 ml of 4N hydrochloric acid-ethyl acetate was added, followed by stirring. After the solvent was distilled off, the residue was washed with ether to yield 658 mg (90.7%, white crystal) of the desired product.

m.p. 113.0°–114.0° C.; $^1$H-NMR (D$_2$O, 200 MHz) δ 1.75–1.90 (2H, m), 1.90–2.10 (2H, m), 2.41 (2H, t, J=7.2 Hz), 2.45–2.60 (2H, m), 3.15–3.30 (4H, m), 3.55–3.70 (2H, m), 3.96 (2H, t, J=7.1 Hz), 4.12 (2H, t, J=6.1 Hz), 7.15–7.30 (2H, m), 7.30–7.50 (4H, m), 7.20–7.85 (3H, m), 7.94 (1H, d, J=2.2 Hz), 8.14 (1H, d, J=1.8 Hz); Anal. Calcd for C$_{27}$H$_{30}$ClN$_5$O$_5$S$_2$.2.0H$_2$O: C, 50.66; H, 5.35; N, 10.94. Found: C, 50.33; H, 5.40; N, 10.57

Preparation Example 80

Synthesis of 5-[3-(4-methoxyphenyl)propylidene]-3-[4-(imidazo[1,2-a]pyridin-5-ylthio)butyl]thiazolidine-2,4-dione hydrochloride i) Synthesis of 5-[3-(4-methoxyphenyl)propylidene]-3-[4-(imidazo[1,2-a]pyridin-5-yl-thio)butyl]thiazolidine-2,4-dione To a solution of 964 mg (3.0 mmol) of 3-[4-(imidazo[1,2-a]pyridin-5-ylthio)butyl]thiazolidine-2,4-dione and 657 mg (4.0 mmol) of 3-(4-methoxyphenyl)-1-propanal in 20 ml of ethanol, 26 mg (0.3 mmol) of piperidine was added, followed by refluxing for 3.5 hours. After the reaction mixture was cooled, the solvent was distilled off. The residue was dissolved in dichloromethane, washed with purified water and dried, after which the solvent was distilled off. The residue was purified by column chromatography (eluent, chloroform/methanol=50/1) to yield 1.08 g (76.8%, yellow oily substance) of the desired product.

$^1$H-NMR (CDCl$_3$, 200 MHz) δ 1.60–1.90 (4H, m), 2.51 (2H, q, J=7.4 Hz), 2.80 (2H, t, J=7.3 Hz), 3.01 (2H, t, J=6.8 Hz), 3.68 (2H, t, J=6.8 Hz), 3.79 (3H, s), 6.84 (2H, d, J=8.4 Hz), 6.90 (1H, d, J=6.8 Hz), 7.06 (1H, t, J=7.7 Hz), 7.10 (2H, d, J=8.4 Hz), 7.15 (1H, dd, J=7.2, 7.7 Hz), 7.58 (1H, d, J=8.8 Hz), 7.69 (1H, s), 7.84 (1H, s); IR (neat) 2930, 1680, 1510, 1250, 1140, 1040, 730 cm$^{-1}$ ii) Synthesis of 5-[3-(4-methoxyphenyl)propylidene]-3-[4-(imidazo[1,2-a]pyridin-5-ylthio)butyl]thiazolidine-2,4-dione hydrochloride To a methanol solution of 1.08 g (2.3 mmol) of 5-[3-(4-methoxyphenyl)propylidene]-3-[4-(imidazo[1,2-a]pyridin-5-ylthio)butyl]thiazolidine-2,4-dione, 0.8 ml of 4N hydrochloric acid-ethyl acetate was added, followed by stirring. After the solvent was distilled off, the residue was dissolved in methanol and recrystallized from ether to yield 995 mg (85.6%, white crystal) of the desired product.

m.p. 88.0°–89.0° C.; $^1$H-NMR (CDCl$_3$, 200 MHz) δ 1.70–1.95 (4H, m), 2.53 (2H, q, J=7.3 Hz), 2.81 (2H, t, J=7.3 Hz), 3.20 (2H, t, J=6.7 Hz), 3.71 (2H, t, J=6.5 Hz), 3.79 (3H, s), 6.84 (2H, d, J=8.6 Hz), 7.07 (1H, t, J=7.5 Hz), 7.10 (2H, d, J=8.4 Hz), 7.30 (1H, d, J=7.4 Hz), 7.72 (1H, dd, J=7.7, 9.0 Hz), 7.90 (1H, s), 7.92 (1H, s), 8.24 (1H, d, J=9.0 Hz); Anal. Calcd for C$_{24}$H$_{26}$ClN$_3$O$_3$S$_2$.1.0H$_2$O: C, 55.21; H, 5.41; N, 8.05. Found; C, 55.29; H, 5.45; N, 8.39

Preparation Example 81

Synthesis of 5-[3-(2-methoxyphenyl)propylidene]-3-[4-(imidazo[1,2-a]pyridin-5-ylthio)butyl]thiazolidine-2,4-dione hydrochloride i) Synthesis of 5-[3-(2-methoxyphenyl)propylidene]-3-[4-(imidazo[1,2-a]pyridin-5-ylthio)butyl]thiazolidine-2,4-dione To a solution of 964 mg (3.0 mmol) of 3-[4-(imidazo[1,2-a]pyridin-5-ylthio)butyl]thiazolidine-2,4-dione and 657 mg (4.0 mmol) of 3-(2-methoxyphenyl)-1-propanal in 20 ml of ethanol, 26 mg (0.3 mmol) of piperidine was added, followed by refluxing for 3.5 hours. After the reaction mixture was cooled, the solvent was distilled off. The residue was dissolved in dichloromethane, washed with purified water and dried, after which the solvent was distilled off. The residue was purified by column chromatography (eluent, chloroform/methanol=50/1) to yield 1.40 g (quant., yellow oily substance) of the desired product.

$^1$H-NMR (CDCl$_3$, 200 MHz) δ 1.60–1.85 (4H, m), 2.45–2.60 (2H, m), 2.84 (2H, t, J=7.4 Hz), 3.01 (2H, t, J=7.0 Hz), 3.68 (2H, t, J=6.9 Hz), 3.84 (3H, s), 6.80–6.95 (3H, m), 7.05–7.25 (4H, m), 7.58 (1H, d, J=9.2 Hz), 7.69 (1H, s), 7.84 (1H, s); IR (neat) 2930, 1670, 1490, 1240, 1140, 1030, 750 cm$^{-1}$ ii) Synthesis of 5-[3-(2-methoxyphenyl)propylidene]-3-[4-(imidazo[1,2-a]pyridin-5-ylthio)butyl]thiazolidine-2,4-dione hydrochloride To a methanol solution of 1.40 g (3.0 mmol) of 5-[3-(2-methoxyphenyl)propylidene]-3-[4-(imidazo[1,2-a]pyridin-5-ylthio)butyl]thiazolidine-2,4-dione, 1.0 ml of 4N hydrochloric acid-ethyl acetate was added, followed by stirring, after which the solvent was distilled off, to yield 1.22 g (80.4%, white oily substance) of the desired product.

$^1$H-NMR (CDCl$_3$, 200 MHz) δ 1.70–1.90 (4H, m), 2.50–2.60 (2H, m), 2.85 (2H, t, J=7.5 Hz), 3.15–3.30 (2H, m), 3.65–3.75 (2H, m), 3.85 (3H, s), 6.89 (2H, t, J=8.1 Hz), 7.10–7.35 (4H, m), 7.65–7.80 (1H, m), 7.85–7.95 (2H, m), 8.20–8.30 (1H, m); Anal. Calcd for C$_{24}$H$_{26}$ClN$_3$O$_3$S$_2$.0.5H$_2$O: C, 56.18; H, 5.30; N, 8.19. Found: C, 56.10; H, 5.40; N, 7.89

Preparation Example 82

Synthesis of 5-[3-(4-fluorophenyl)propylidene]-3-[4-(imidazo[1,2-a]pyridin-5-ylthio)butyl]thiazolidine-2,4-dione hydrochloride i) Synthesis of 5-[3-(4-fluorophenyl)propylidene]-3-[4-(imidazo[1,2-a]pyridin-5-ylthio)butyl]thiazolidine-2,4-dione To a solution of 964 mg (3.0 mmol) of 3-[4-(imidazo[1,2-a]pyridin-5-ylthio)butyl]thiazolidine-2,4-dione and 609 mg (4.0 mmol) of 3-(4-fluorophenyl)-1-propanal in 20 ml of ethanol, 26 mg (0.3 mmol) of piperidine was added, followed by refluxing for 4.5 hours. After the reaction mixture was cooled, the solvent was distilled off. The residue was dissolved in dichloromethane, washed with purified water and dried, after which the solvent was distilled off. The residue was purified by column chromatography (eluent, chloroform/methanol=50/1) to yield 0.88 g (64.2%, yellow oily substance) of the desired product.

$^1$H-NMR (CDCl$_3$, 200 MHz) δ 1.55–1.90 (4H, m), 2.52 (2H, q, J=7.7 Hz), 2.83 (2H, t, J=7.5 Hz), 3.01 (2H, t, J=7.0 Hz), 3.68 (2H, t, J=6.9 Hz), 6.90 (1H, dd, J=1.0, 7.2 Hz), 6.96 (2H, d, J=8.8 Hz), 7.03 (1H, t, J=7.5 Hz), 7.14 (1H, dd, J=7.0, 9.0 Hz), 7.15 (2H, d, J=8.8 Hz), 7.58 (1H, d, J=9.0 Hz), 7.69 (1H, s), 7.83 (1H, s); IR (neat) 2940, 1680, 1490, 1140, 960, 820, 730 cm$^{-1}$ ii) Synthesis of 5-[3-(4-fluorophenyl)propylidene]-3-[4-(imidazo[1,2-a]pyridin-5-ylthio)butyl]thiazolidine-2,4-dione hydrochloride To a methanol solution of 0.88 g (1.9 mmol) of 5-[3-(4-fluorophenyl)propylidene]-3-[4-(imidazo[1,2-a]pyridin-5-ylthio)butyl]thiazolidine-2,4-dione, 1.0 ml of 4N hydrochloric acid-ethyl acetate was added, followed by stirring. After the solvent was distilled off, the residue was dissolved in methanol and recrystallized from hexane to yield 0.78 g (83.1%, white crystal) of the desired product.

m.p. 155.0°–156.0° C.; $^1$H-NMR (CDCl$_3$, 200 MHz) δ 1.70–1.90 (4H, m), 2.53 (2H, q, J=7.5 Hz), 2.85 (2H, t, J=7.5 Hz), 3.20 (2H, t, J=6.8 Hz), 3.71 (2H, t, J=6.6 Hz), 6.99 (2H, t, J=8.7 Hz), 7.04 (1H, t, J=7.6 Hz), 7.14 (2H, dd, J=5.4, 8.6 Hz), 7.31 (1H, d, J=7.6 Hz), 7.73 (1H, dd, J=7.5, 9.0 Hz), 7.90 (1H, s), 7.92 (1H, s), 8.24 (1H, d, J=9.0 Hz); Anal. Calcd for C$_{23}$H$_{23}$ClFN$_3$O$_2$S$_2$: C, 56.14; H, 4.71; N, 8.54. Found: C, 55.96; H, 4.70; N, 8.58

Preparation Example 83

Synthesis of 5-[3-(2-fluorophenyl)propylidene]-3-[4-(imidazo[1,2-a]pyridin-5-ylthio)butyl]thiazolidine-2,4-dione hydrochloride i) Synthesis of 5-[3-(2-fluorophenyl)propylidene)-3-[4-(imidazo[1,2-a]pyridin-5-ylthio)butyl]thiazolidine-2,4-dione To a solution of 964 mg (3.0 mmol) of 3-[4-(imidazo[1,2-a]pyridin-5-ylthio)butyl]thiazolidine-2,4-dione and 609 mg (4.0 mmol) of 3-(2-fluorophenyl)-1-propanal in 20 ml of ethanol, 26 mg (0.3 mmol) of piperidine was added, followed by refluxing for 4.5 hours. After the reaction mixture was cooled, the solvent was distilled off. The residue was dissolved in dichloromethane, washed with purified water and dried, after which the solvent was distilled off. The residue was purified by column chromatography (eluent, chloroform/methanol=50/1) to yield 1.11 g (81.5%, yellow oily substance) of the desired product.

$^1$H-NMR (CDCl$_3$, 200 MHz) δ 1.55–1.90 (4H, m), 2.54 (2H, q, J=7.7 Hz), 2.89 (2H, t, J=7.6 Hz), 3.01 (2H, t, J=6.9 Hz), 3.68 (2H, t, J=7.0 Hz), 6.90 (1H, d, J=7.0 Hz), 6.95–7.25 (6H, m), 7.58 (1H, d, J=9.0 Hz), 7.69 (1H, s), 7.84 (1H, s); IR (KBr) 2930, 1680, 1490, 1140, 760 cm$^{-1}$ ii) Synthesis of 5-[3-(2-fluorophenyl)propylidene]-3-[4-(imidazo[1,2-a]pyridin-5-ylthio)butyl]thiazolidine-2,4-dione hydrochloride To a methanol solution of 1.11 g (2.5 mmol) of 5-(3-(2-fluorophenyl)propylidene]-3-[4-(imidazo[1,2-a]pyridin-5-ylthio)butyl]thiazolidine-2,4-dione, 1.0 ml of 4N hydrochloric acid-ethyl acetate was added, followed by stirring. After the solvent was distilled off, the residue was dissolved in methanol and recrystallized from ether to yield 0.94 g (76.8%, white crystal) of the desired product.

m.p. 137.0°–139.0° C.; $^1$H-NMR (CDCl$_3$, 200 MHz) δ 1.60–1.90 (4H, m), 2.56 (2H, q, J=7.4 Hz), 2.90 (2H, t, J=7.3 Hz), 3.20 (2H, t, J=6.7 Hz), 3.71 (2H, t, J=6.4 Hz), 7.08 (1H, t, J=7.3 Hz), 7.00–7.25 (4H, m), 7.30 (1H, d, J=7.8 Hz), 7.73 (1H, dd, J=7.6, 9.0 Hz), 7.90 (1H, s), 7.92 (1H, s), 8.25 (1H, d, J=9.2 Hz); Anal. Calcd for C$_{23}$H$_{23}$ClFN$_3$O$_2$S$_2$.0.2H$_2$O: C, 55.74; H, 4.76; N, 8.48. Found: C, 55.67; H, 4.78; N, 8.40

Preparation Example 84
Synthesis of 5-[3-(2-chlorophenyl)propylidene]-3-[4-(imidazo[1,2-a]pyridin-5-ylthio)butyl]thiazolidine-2,4-dione hydrochloride i) Synthesis of 5-[3-(2-chlorophenyl)propylidene]-3-[4-(imidazo[1,2-a]pyridin-5-ylthio)butyl)thiazolidine-2,4-dione To a solution of 964 mg (3.0 mmol) of 3-[4-(imidazo[1,2-a]pyridin-5-ylthio)butyl]thiazolidine-2,4-dione and 738 mg (4.4 mmol) of 3-(2-chlorophenyl)-1-propanal in 20 ml of ethanol, 26 mg (0.3 mmol) of piperidine was added, followed by refluxing for 4.5 hours. After the reaction mixture was cooled, the solvent was distilled off. The residue was dissolved in dichloromethane, washed with purified water and dried, after which the solvent was distilled off. The residue was purified by column chromatography (eluent, chloroform/methanol=50/1) to yield 1.37 g (96.5%, yellow oily substance) of the desired product.

$^1$H-NMR (CDCl$_3$, 200 MHz) δ 1.55–1.90 (4H, m), 2.56 (2H, q, J=7.6 Hz), 2.90–3.10 (4H, m), 3.69 (2H, t, J=7.0 Hz), 6.90 (1H, d, J=7.0 Hz), 7.08 (1H, t, J=7.7 Hz), 7.10–7.25 (4H, m), 7.30–7.40 (1H, m), 7.58 (1H, d, J=9.0 Hz), 7.69 (1H, s), 7.84 (1H, s); IR (neat) 2940, 1680, 1490, 1350, 1140, 750 cm$^{-1}$ ii) Synthesis of 5-[3-(2-chlorophenyl)propylidene]-3-[4-(imidazo[1,2-a]pyridin-5-ylthio)butyl]thiazolidine-2,4-dione hydrochloride To a methanol solution of 1.37 g (2.9 mmol) of 5-[3-(2-chlorophenyl)propylidene]-3-[4-(imidazo[1,2-a]pyridin-5-ylthio)butyl]thiazolidine-2,4-dione, 1.0 ml of 4N hydrochloric acid-ethyl acetate was added, followed by stirring, after which the solvent was distilled off, to yield 1.23 g (83.1%, brown oily substance) of the desired product.

$^1$H-NMR (CDCl$_3$, 200 MHz) δ 1.60–1.95 (4H, m), 2.50–2.65 (2H, m), 2.98 (2H, t, J=7.6 Hz), 3.21 (2H, t, J=6.6 Hz), 3.72 (2H, t, J=6.7 Hz), 7.10 (1H, t, J=7.7 Hz), 7.15–7.40 (5H, m), 7.65–7.80 (1H, m), 7.90 (1H, s), 7.92 (1H, s), 8.25 (1H, d, J=8.8 Hz); Anal. Calcd for C$_{23}$H$_{23}$Cl$_2$N$_3$O$_2$S$_2$.0.5H$_2$O: C, 53.38; H, 4.67; N, 8.12. Found: C, 53.46; H, 4.85; N, 8.00

Preparation Example 85
Synthesis of 5-[3-(4-chlorophenyl)propylidene]-3-[4-(imidazo[1,2-a]pyridin-5-ylthio)butyl]thiazolidine-2,4-dione hydrochloride i) Synthesis of 5-[3-(4-chlorophenyl)propylidene]-3-[4-(imidazo[1,2-a]pyridin-5-ylthio)butyl]thiazolidine-2,4-dione To a solution of 964 mg (3.0 mmol) of 3-[4-(imidazo[1,2-a]pyridin-5-ylthio)butyl]thiazolidine-2,4-dione and 738 mg (4.4 mmol) of 3-(2-chlorophenyl)-1-propanal in 20 ml of ethanol, 26 mg (0.3 mmol) of piperidine was added, followed by refluxing for 4 hours. After the reaction mixture was cooled, the solvent was distilled off. The residue was dissolved in dichloromethane, washed with purified water and dried, after which the solvent was distilled off. The residue was purified by column chromatography (eluent, chloroform/methanol=50/1) to yield 1.25 g (88.3%, yellow oily substance) of the desired product.

$^1$H-NMR (CDCl$_3$, 200 MHz) δ 1.55–1.90 (4H, m), 2.52 (2H, q, J=7.6 Hz), 2.83 (2H, t, J=7.5 Hz), 3.01 (2H, t, J=7.0 Hz), 3.68 (2H, t, J=6.9 Hz), 6.90 (1H, d, J=7.0 Hz), 7.02 (1H, t, J=7.5 Hz), 7.11 (2H, d, J=8.4 Hz), 7.14 (1H, dd, J=7.2, 9.0 Hz), 7.27 (2H, d, J=8.4 Hz), 7.58 (1H, d, J=8.8 Hz), 7.70 (1H, s), 7.84 (1H, s); IR (neat) 2940, 1680, 1490, 1350, 1140, 810, 750 cm$^{-1}$ ii) Synthesis of 5-[3-(4-chlorophenyl)propylidene]-3-[4-(imidazo[1,2-a]pyridin-5-ylthio)butyl]thiazolidine-2,4-dione hydrochloride To a methanol solution of 1.25 g (2.7 mmol) of 5-[3-(4-chlorophenyl)propylidene]-3-[4-(imidazo[1,2-a]pyridin-5-ylthio)butyl]thiazolidine-2,4-dione, 1.0 ml of 4N hydrochloric acid-ethyl acetate was added, followed by stirring. After the solvent was distilled off, the residue was dissolved in methanol and recrystallized from ether to yield 1.02 g (74.1%, white crystal) of the desired product.

m.p. 153.0°–155.0° C.; $^1$H-NMR (CDCl$_3$, 200 MHz) δ 1.60–1.90 (4H, m), 2.54 (2H, q, J=7.4 Hz), 2.85 (2H, t, J=7.4 Hz), 3.19 (2H, t, J=6.9 Hz), 3.70 (2H, t, J=6.7 Hz), 7.03 (1H, t, J=7.5 Hz), 7.12 (2H, d, J=8.6 Hz), 7.27 (2H, d, J=8.4 Hz), 7.30 (1H, d, J=7.0 Hz), 7.72 (1H, dd, J=7.5, 9.0 Hz), 7.89 (1H, s), 7.92 (1H, s), 8.24 (1H, d, J=9.0 Hz); Anal. Calcd for C$_{23}$H$_{23}$Cl$_2$N$_3$O$_2$S$_2$: C, 54.33; H, 4.56; N, 8.26. Found: C, 54.28; H, 4.65; N, 8.08

Test Example 1
Inhibitory activity of adhesion molecule expression

Test method: To human umbilical cord vascular endothelial cells (purchased from Kurabo), cultured on gelatin-coated plates, compounds at various concentrations (test compounds) were added, followed by incubation at 37° C. for 15 minutes. Human tumor necrosis factor (TNFα, purchased from Genzyme) was then added to a final concentration of 1 ng/ml, followed by incubation at 37° C. for 3 hours for ELAM-1 expression or for 5 hours for ICAM-1 expression. After the reaction, cells were fixed with glutaraldehyde; the amounts of ELAM-1 and ICAM-1 expressed were determined by cell-ELISA. Anti-ELAM-1 antibody BBA-2 and an anti-ICAM-1 antibody BBA-4 were used as the first antibodies for the defection of ELAM-1 and ICAM-1, respectively, and horse radish peroxidase-labeled rabbit anti-mouse IgG antibody was used as the second antibody to determine the amount of adhesion molecules expressed on cells observed. The compound concentration at which 50% expression was expressed as the 50% inhibitory concentration (IC$_{50}$), with the amount of expression in the absence of compounds as 100 and the amount of expression in the absence of TNFα as 0.

Results: Table 1 shows the IC$_{50}$ values of the test compounds. It is evident that the compounds of the present invention exhibit inhibitory activity of adhesion molecule expression

TABLE 1

Inhibitory Activity of Adhesion Molecule Expression

| Compound (Preparation Example Number) | IC$_{50}$ ($\mu$M) ICAM-1 | ELAM-1 |
|---|---|---|
| 2 | 3.0 | 2.9 |
| 3 | 4.2 | 5.0 |
| 5 | 3.5 | 5.3 |
| 6 | 6.3 | 7.3 |
| 7 | 3.1 | 2.3 |
| 8 | 4.4 | 3.8 |
| 9 | 2.4 | 2.6 |
| 10 | 2.4 | 2.3 |
| 11 | 2.9 | 1.9 |
| 12 | 4.9 | 4.4 |
| 13 | 6.3 | 5.1 |
| 14 | 6.1 | 5.1 |
| 15 | 7.0 | 6.2 |
| 19 | 3.9 | 3.0 |
| 21 | 4.0 | 3.3 |
| 22 | 4.6 | 2.9 |
| 23 | 7.0 | 3.6 |
| 24 | 1.1 | 0.8 |
| 25 | 8.0 | 4.0 |
| 26 | 3.7 | 4.1 |
| 27 | 6.5 | 5.0 |
| 32 | 5.7 | 3.2 |
| 33 | 6.3 | 2.8 |
| 34 | 6.1 | 5.2 |
| 35 | 4.6 | 3.4 |
| 36 | 3.7 | 2.1 |
| 38 | 3.7 | 3.4 |
| 39 | 2.4 | 3.3 |
| 40 | 1.8 | 1.1 |
| 41 | 0.9 | 0.5 |
| 42 | 1.5 | 1.0 |
| 43 | 3.5 | 2.2 |
| 47 | 4.2 | 3.0 |
| 48 | 6.4 | 4.6 |
| 50 | 6.9 | 4.7 |
| 51 | 6.8 | 2.8 |
| 53 | 6.3 | 6.2 |
| 54 | 5.0 | 6.1 |
| 55 | 5.5 | 7.3 |
| 56 | 5.7 | 3.9 |
| 57 | 7.1 | 7.9 |
| 60 | 9.0 | 9.2 |
| 65 | 5.3 | 5.0 |
| 67 | 3.9 | 3.4 |
| 68 | 5.0 | 3.2 |
| 69 | 6.1 | 4.0 |
| 70 | 6.9 | 5.3 |
| 71 | 5.2 | 4.6 |
| 72 | 5.6 | 6.4 |
| 75 | 6.1 | 3.5 |
| 76 | 7.1 | 6.7 |
| 77 | 6.0 | 6.3 |
| 79 | 5.9 | 6.1 |
| 80 | 4.1 | 4.6 |
| 81 | 4.3 | 6.1 |
| 82 | 3.6 | 4.3 |
| 83 | 3.8 | 3.7 |
| 84 | 3.6 | 4.1 |
| 85 | 3.9 | 4.3 |

Test Example 2
Diabetic nephritis improving action in Wistar fatty rats (rat model of hereditary obese diabetes mellitus)

Test method: Male Wistar fatty rats at 9 weeks of age were divided into two groups according to plasma glucose level, urinary total protein excretion and body weight: a control group and a test compound group (n=6). The test compound, in suspension in 0.5% methyl cellulose (Wako Pure Chemical) at 2 ml/kg, was orally administered by gavage once a day for 12 consecutive weeks. For the control group, only the 0.5% methyl cellulose suspension was orally administered in the same manner as the test compounds. At every 3 weeks, plasma glucose, urinary total protein and albumin excretion were quantitated by the enzyme method, the Lowry method (Journal of Biological Chemistry, Vol. 193, pp. 265–275 (1951)] and the method of Mohamed et al. [Journal of Immunology Methods, Vol. 74, pp. 17–22 (1984)], respectively.

Results: Table 2 shows the effects of the test compounds on plasma glucose level, urinary total protein and urinary albumin excretion. It is evident that the compounds of the present invention possess as diabetic nephritis-improving activity.

TABLE 2

Diabetic Nephritis-Improving Action Test
Test Example 3

| Compound (Preparation Example Number) | Dose (mg/kg/day) | Plasma Glucose (mg/dl) | Urinary Total Protein (mg/day) | Urinary Albumin (mg/day) |
|---|---|---|---|---|
| Control | | 352.00 ± 36.09 | 145.19 ± 34.99 | 35.69 ± 15.44 |
| 2 | 50 | 333.67 ± 46.41 | 96.64 ± 18.31* | 20.49 ± 6.95 |
| Control | | 368.83 ± 24.35 | 131.53 ± 22.81 | 24.53 ± 7.19 |
| 3 | 50 | 253.17 ± 34.14* | 97.61 ± 16.26* | 22.34 ± 7.24 |

Each figure represents the mean ± standard deviation.
*p < 0.05 (vs control by Student's t-test)

Immunosuppressive action on mouse skin allograft

Test method: Male BIOBR mice and C57BL/10 mice, both at 6 weeks of age, were used as donors and recipients, respectively, and Grafts were prepared by killing donors by cervical vertebral dislocation, collecting full-thickness skin grafts from tail using a razor and tweezers, and cutting them into about 5 mm square pieces. Each graft was kept standing on gauze soaked with physiological saline, and used as soon as the recipient was prepared. Transplantation beds were prepared as follows. The recipient's back was clipped using clippers and sterilized with Isodine. Under ether anesthesia, back skin was picked up with tweezers, and a full-thickness skin graft was cut out into an about 5 mm square piece using scissors. The graft was transferred to the transplantation bed thus prepared, and fixed firmly using bandage. At 7 days after surgery, the bandage was removed, and the mice were observed every day to determine the day of complete necrosis of the graft as the rejection day. The compound was intraperitoneally administered in suspension in 5% gum arabic for 16 days after surgery.

Results: Table 3 shows the rejection days of the graft from the mice treated with test compounds. It is evident that the compound of the present invention possesses immunosupressive action on mouse skin allograft.

TABLE 3

Mouse Homologous Skin Transplantation Test

| Compound (Preparation Example Number) | Dose (mg/kg/day) | Mean Rejection Day |
|---|---|---|
| Control | | 13.0 |
| 22 | 50 | 18.8 |

TABLE 3-continued

Mouse Homologous Skin Transplantation Test

| Compound (Preparation Example Number) | Dose (mg/kg/day) | Mean Rejection Day |
|---|---|---|
| Control | | 13.5 |
| 24 | 10 | 27.0 |

Industrial Applicability

The present invention provides new imidazo[1,2-a]pyridine derivatives that possess excellent inhibitory activity of adhesion molecule expression, diabetic nephritis improving activity and immunosuppressive activity for organ transplantation and these derivatives are useful as an adhesion protein expression suppressor, diabetic nephritis improving drug or immunosuppressor for organ transplantation.

We claim:
1. A compound represented by the formula:

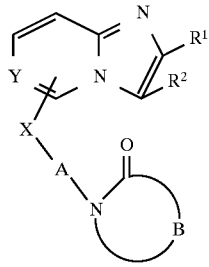

wherein X represents a bond, —S(O)m—, —O—, —NR$^{3a}$—, —Alk—, —Alk—W— or —S—Alk—W—; wherein Alk represents a divalent hydrocarbon group unsubstituted or substituted with 1 or 2 substituents selected from the group consisting of halogens, lower alkoxy groups, acyl groups, carboxyl groups, hydroxyl group, pyridylthio group, nitro group, cyano group and oxo group, (i) wherein said acyl groups are selected from the group consisting of lower alkanoyl groups unsubstituted or substituted with 1–3 halogens, lower alkylsulfonyl groups, lower alkylsulfinyl groups, $C_{6-10}$ arylcarbonyl groups, carbamoyl groups, lower alkylcarbamoyl groups, lower alkenylcarbamoyl groups, and cyclic aminocarbonyl groups wherein the dialkyl moiety has formed a 5- or 6-membered ring structure in combination with the nitrogen of a carbamoyl group, and (ii) wherein said carboxyl group unesterified or esterified resulting in a lower alkoxycarbonyl group;

W represents —O—, —NR$^{3a}$—,—CO—O— or —O—CO—NR$^{3a}$—, wherein R$^{3a}$ represents a hydrogen or a hydrocarbon group wherein said hydrocarbon group is unsubstituted or substituted at any position with 1 to 5 substituents selected from the group consisting of nitro group, hydroxyl group, oxo group, thioxo group, cyano group, sulfone group, halogens, lower alkoxy groups, phenoxy group, halogenophenoxy groups, lower alkylthio groups, phenylthio group, amino groups, carboxyl groups, acyl groups, and heterocyclic groups, wherein (i) said amino groups are unsubstituted or substituted with substituents selected from the group consisting of lower alkyl groups and acyl groups, (ii) said acyl group as a substituent of said hydrocarbon group or as a substituent of said amino group are selected from the group consisting of the same acyl groups which are recited as substituents for Alk above, and (iii) said carboxyl group is unesterified or esterified resulting in a lower alkoxycarbonyl group;

m represents an integer from 0 to 2); Y represents CH or N;

R$^1$ and R$^2$, independently represent (i) a hydrogen, (ii) a hydrocarbon group, wherein said hydrocarbon group is unsubstituted or substituted at any position with 1 to 5 substituents selected from the group consisting of the same group of substituents recited as substituents for said hydrocarbon of R$^{3a}$ above, (iii) a halogen, (iv) a nitro group, (v) a nitroso group, (vi) an amino group unprotected or protected with a protecting group selected from the group consisting of amide-forming protective groups, carbamate-forming protecting groups, and trityl and phthaloyl, (vi) a carboxyl group, wherein said carboxyl group is unesterified or esterified resulting in a lower alkoxycarbonyl group, and (vii) an acyl group, wherein said acyl group is selected from the group consisting of the same acyl groups recited as substituents for Alk above;

A represents a divalent hydrocarbon group that is unsubstituted or substituted with 1 or 2 substituents selected from the group consisting of said group of substituents recited for Alk above;

B represents the following formula:

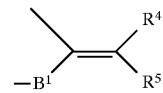

wherein B$^1$ represents —(CH$_2$)$_f$— or —CZ$^1$—Z$^2$— (f represents an integer from 1 to 6; Z$^1$ represents O or S; Z$^2$ represents O, S, —Alk$^1$—, —Alk$^1$—S— or NR$^{3b}$; Alk$^1$ represents a divalent hydrocarbon group that is unsubstituted or substituted with 1 or 2 substituents selected from the group consisting of said group of substituents recited for Alk above; R$^{3b}$ represents a hydrogen or a hydrocarbon group unsubstituted or substituted by the same groups recited as substituents for the hydrocarbon groups of R$^1$ or R$^2$ above); R$^4$ and R$^5$ independently represent (i) a hydrogen or a carboxyl group unesterified or esterified, resulting in a lower alkoxycarbonyl group, (ii) an amino group unsubstituted or substituted, wherein said substituents are selected from the group consisting of lower alkyl groups and acyl groups, wherein said acyl groups are selected from the group consisting of the same group of acyl groups recited as substituents of A above; (iii) a heterocyclic group that is unsubstituted or substituted with 1 to 4 substituents selected from the group consisting of halogens, lower alkyl groups, lower alkenyl groups, lower alkoxy groups, nitro group, cyano group, hydroxy group, lower alkoxycarbonyl groups, carboxy groups, carbamoyl groups, lower alkylcarbamoyl groups, and lower alkenylcarbamoyl groups, (iv) —W$^1$, (v) —S—W$^1$, (vi) —O—W$^1$, wherein W$^1$ represents a hydrogen or a hydrocarbon group that is unsubstituted or substituted at any position 1 to 5 with substituents selected from the group consisting of nitro group, hydroxyl group, oxo group, thioxo group, cyano group, sulfone group, halogens, lower alkoxy groups, phenoxy group, halogenophenoxy groups, lower alkylthio groups, phenylthio group, amino groups, carboxyl groups, acyl groups, and heterocyclic groups, wherein (i) said amino groups are unsubstituted or are substituted with substituents selected from the group consisting of lower alkyl groups and acyl groups, (ii) said acyl group as a substituent of said hydrocarbon group or as a substituent of said amino group are selected from the group consisting of the same acyl groups which are recited as substituents for Alk above, and (iii) said carboxyl group is unesterified or esterified resulting in a lower alkoxycarbonyl group; or $R^4$ and $R^5$ are uncombined or combined to form a ring selected from the group consisting of cyclopropyl, cyclobutyl, cyclopentyl and cyclohexyl; or B represents the following formula:

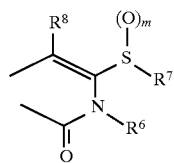

wherein $R^6$ and $R^7$ independently represent (i) a hydrocarbon group that is unsubstituted or substituted by the same groups of substituents for the hydrocarbon group of $R^1$ or $R^2$ above, (ii) a heterocyclic group that is unsubstituted or substituted with 1 to 4 substituents selected from the group consisting of halogens, lower alkyl groups, lower alkenyl groups, lower alkoxy groups, nitro group, cyano group, hydroxy group, lower alkoxycarbonyl groups, carboxy groups, carbamoyl groups, lower alkylcarbamoyl groups, and lower alkenylcarbamoyl groups; or (iii) $R^6$ and $R^7$ are uncombined or combined to form a ring wherein the ring formed by combining $R^6$ and $R^7$ is represented by the formula:

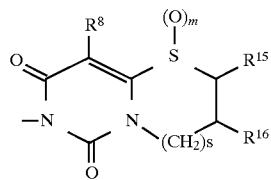

wherein $R^{15}$ represents a (i) hydrogen, (ii) a lower alkyl group that is unsubstituted or substituted with 1 or 2 substituents selected from the group consisting of halogens, lower alkoxy groups, hydroxy group, lower alkoxycarbonyl groups, carboxyl group, carbamoyl groups, lower alkylcarbamoyl groups, and pyridylthio groups, (iii) an aralkyl group being a phenyl-lower alkyl group or a naphthyl-lower alkyl group, wherein the phenyl moiety of the phenyl-lower alkyl group and the naphthyl moiety of the naphthyl-lower alkyl group that is unsubstituted or substituted with 1 to 4 substituents selected from the group consisting of halogens, lower alkyl groups, lower alkenyl groups, lower alkoxy groups, nitro group, cyano group, hydroxy group, lower alkoxycarbonyl groups, carbamoyl groups, lower alkylcarbamoyl groups and lower alkenylcarbamoyl groups, and (iv) an aryl group that is unsubstituted or substituted with 1 to 4 substituents selected from the group consisting of halogens, lower alkyl groups, lower alkenyl groups, lower alkoxy groups, nitro group, cyano group, oxo group, hydroxy group, amino groups, lower acylamino groups, lower alkoxycarbonyl groups, carbamoyl groups, lower alkylcarbamoyl groups, and lower alkenylcarbamoyl groups, (v) a lower alkoxy group, (vi) a lower alkylthio group, (vii) an aryloxy group, (viii) an arylthio group, (ix) —COOR$^{15a}$ or (x) —CH$_2$COOR$^{15a}$ ($R^{15a}$ represents a lower alkyl group); $R^{16}$ represents a hydrogen or a lower alkyl group; s represents an integer from 0 to 4, or the formula:

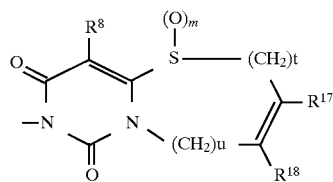

wherein $R^{17}$ and $R^{18}$ independently represent a hydrogen or a lower alkyl group; t and u independently represent an integer from 0 to 2; $R^8$ represents a hydrogen, a hydrocarbon group unsubstituted or substituted, a heterocyclic group unsubstituted or substituted, a nitro group, a cyano group, an amino group unprotected or protected, a halogen, or an acyl group, wherein said unsubstituted or substituted hydrocarbon group, unprotected or protected amino group, or acyl group for $R^8$ are selected from the group consisting of the same groups recited as said unsubstituted or substituted hydrocarbon groups, unprotected or protected amino groups or acyl groups for $R^1$ and $R^2$, and wherein said unsubstituted or substituted heterocyclic group for $R^8$ is selected from the group consisting of the same group recited as heterocyclic group substituents for $R^4$ and $R^5$ above; m represents an integer from 0 to 2 or a salt thereof.

2. The compound of claim 1, wherein said divalent hydrocarbon group represented by Alk, A and Alk$^1$ is a divalent $C_{1-15}$ chain hydrocarbon group, a $C_{5-8}$ cyclic hydrocarbon group or a combination thereof.

3. The compound of claim 1 wherein the substituents for said divalent hydrocarbon group represented by Alk, A and Alk$^1$ are (i) a halogen, (ii) a lower alkoxy group, (iii) a hydroxyl group, (iv) a carboxyl group is unesterified or esterified with a lower alkoxycarbonyl group (v) an acyl group selected from the group consisting of lower alkanoyl groups, lower alkylsulfonyl groups, lower alkylsulfinyl groups, $C_{6-10}$ arylcarbonyl groups, carbamoyl groups, lower alkylcarbamoyl groups, lower alkenylcarbamoyl groups, cyclic aminocarbonyl groups wherein the dialkyl moiety has formed a 5- or 6-membered ring structure in combination with the nitrogen of a carbamoyl group, and lower alkanoyl group that is unsubstituted or substituted by 1–3 halogens (vi) a pyridylthio group, (vii) a nitro group, (vii) a cyano group, and (viii) an oxo group.

4. The compound of claim 1 wherein said hydrocarbon group represented by $R^{3a}$, $R^1$, $R_2$, $R^{3b}$, $W^1$, $R^6$, $R^7$ and $R^8$ is a $C_{1-30}$ chain hydrocarbon group, a $C_{3-14}$ cyclic hydrocarbon group or a combination thereof.

5. The compound of claim 1 wherein said hydrocarbon group represented by $R^{3a}$, $R^1$, $R^2$, $R^{3b}$, $W^1$, $R^6$, $R^7$ and $R^8$ is a $C_{1-30}$ alkyl group, a $C_{2-30}$ alkenyl group, a $C_{3-8}$ cycloalkyl group, a $C_{5-8}$ cycloalkenyl group, an aryl group or an aralkyl group.

6. The compound of claim 1, wherein the substituents for said hydrocarbon group represented by $R^{3a}$, $R^1$, $R^2$, $R^{3b}$, $W^1$, $R^6$, $R^7$ and $R^8$ are selected from the group consisting of (i)

a nitro group, (ii) a hydroxyl group, (iii) an oxo group, (iv) a thioxo group, (v) a cyano group, (vi) a sulfone group, (vii) a halogen, (viii) a lower alkoxy group, (ix) a phenoxy group, (x) a halogenophenoxy group, (xi) a lower alkylthio group, (xii) a phenylthio group, (xiii) an amino group that is unsubstituted or substituted with a lower alkyl group and acyl groups, wherein said acyl groups are selected from the group consisting of lower alkanoyl groups unsubstituted or substituted with 1–3 halogens, lower alkylsulfonyl groups, lower alkylsulfinyl groups, $C_{6-10}$ arylcarbonyl groups, carbamoyl groups, lower alkylcarbamoyl groups, lower alkenylcarbamoyl groups, and cyclic aminocarbonyl groups wherein the dialkyl moiety has formed a 5- or 6-membered ring structure in combination with the nitrogen of a carbamoyl group, (xiv) a carboxyl group unesterified or esterified resulting in a lower alkoxycarbonyl group (xv) an acyl group selected from the group consisting of lower alkanoyl groups, lower alkylsulfonyl groups, lower alkylsulfinyl groups, $C_{6-10}$ arylcarbonyl groups, carbamoyl groups, lower alkylcarbamoyl groups, lower alkenylcarbamoyl groups, and cyclic aminocarbonyl groups wherein the dialkyl moiety has formed a 5- or 6-membered ring structure in combination with the nitrogen of a carbamoyl group, and a lower alkanoyl group that is unsubstituted or substituted by 1–3 halogens, and (xvi) a heterocyclic group.

7. The compound of claim 1, wherein the substituent for said amino group represented by $R^4$ and $R^5$ is a lower alkyl group or an acyl group, wherein said acyl groups are selected from the group consisting of lower alkanoyl groups that is unsubstituted or substituted with 1–3 halogens, lower alkylsulfonyl groups, lower alkylsulfinyl groups, $C_{6-10}$ arylcarbonyl groups, carbamoyl groups, lower alkylcarbamoyl groups, lower alkenylcarbamoyl groups, and cyclic aminocarbonyl groups wherein the dialkyl moiety has formed a 5- or 6-membered ring structure in combination with the nitrogen of a carbamoyl group.

8. The compound of claim 1, wherein said heterocyclic group represented by $R^4$, $R^5$, $R^6$, $R^7$ and $R^8$ is a 5- or 6-membered monocyclic heterocyclic group containing 1 to 4 heteroatoms selected from the group consisting of atoms of oxygen, sulfur and nitrogen, or a bicyclic heterocyclic group containing 1 to 6 heteroatoms selected from the group consisting of atoms of oxygen, sulfur and nitrogen.

9. The compound of claim 1, wherein said heterocyclic group represented by $R^4$, $R^5$, $R^6$, $R^7$ and $R^8$ is thienyl, furyl, pyranyl, pyrrolyl, imidazolyl, pyrazolyl, isothiazolyl, isoxazolyl, pyridyl, pyrazinyl, pyrimidinyl, pyridazinyl, pyrrolidinyl, pyrrolinyl, imidazonyl, piperidyl, piperazinyl, morpholinyl, isobenzofuranyl, chromenyl, benzothienyl, indolizinyl, isoindolyl, indolyl, 3H-indolyl, 1H-indazolyl, purinyl, isoquinolyl, quinolyl, phthalazyl, naphthyridinyl, quinoxalinyl, quinazolinyl, cinnolinyl, isochromanyl, indolinyl, isoindolinyl, 1,2,3,4-tetrahydro-2-quinolyl or 1,2,3,4-tetrahydro-2-isoquinolyl.

10. The compound of claim 1, wherein X is S, S(O), $S(O)_2$, O, —N($R^3$)—, —$(CH_2)_i$—O—, —$(CH_2)_i$—N($R^3$)—, —$CH_2$—, —CH=CH—, —$(CH_2)_j$—CO—N($R^3$)—, —S—$(CH_2)_k$—CO—N($R^3$)—, —$(CH_2)_j$—COO—, —S—$(CH_2)_k$—COO— or —$(CH_2)_i$—O—CO—N($R^3$)—, wherein $R^3$ is selected from the group consisting of (i) hydrogen, (ii) a lower alkyl group, (iii) a lower alkenyl group, wherein said lower alkyl and alkenyl groups each independently are unsubstituted or substituted with 1 or 2 substituents selected from the group consisting of halogens, lower alkoxy groups, hydroxy group, lower alkoxycarbonyl groups, carboxyl group, carbamoyl groups, lower alkylcarbamoyl groups, and pyridylthio groups, (iv) an aralkyl group being a phenyl-lower alkyl group or a naphthyl-lower alkyl group, wherein the phenyl moiety of the phenyl-lower alkyl group and the naphthyl moiety of the naphthyl-lower alkyl group is unsubstituted or substituted with 1 to 4 substituents selected from the group consisting of halogens, lower alkyl groups, lower alkenyl groups, lower alkoxy groups, nitro group, cyano group, hydroxy group, lower alkoxycarbonyl groups, carbamoyl groups, lower alkylcarbamoyl groups and lower alkenylcarbamoyl groups, and (v) an aryl group that is unsubstituted or substituted with 1 to 4 substituents selected from the group consisting of halogens, lower alkyl groups, lower alkenyl groups, lower alkoxy groups, nitro group, cyano group, oxo group, hydroxy group, amino groups, lower acylamino groups, lower alkoxycarbonyl groups, carbamoyl groups, lower alkylcarbamoyl groups, and lower alkenylcarbamoyl groups; i represents an integer of 1 or 2, j represents an integer of 0 or 1, and k represents an integer from 1 to 5.

11. The compound of claim 1, wherein X is S, O or —$CH_2$—.

12. The compound of claim 1, wherein Y is CH.

13. The compound of claim 1, wherein each of $R^1$ and $R^2$ is (i) a hydrogen, (ii) a lower alkyl group that is unsubstituted or substituted with the same substituents recited as substituents for said lower alkyl groups of $R^3$ in claim 10, (iii) an aryl group that is unsubstituted or substituted with the same substituents recited as substituents for said aryl groups of $R^3$ in claim 10, (iv) a lower alkoxycarbonyl group, or (v) a halogeno-lower alkanoyl group.

14. The compound of claim 1, wherein each of $R^1$ and $R^2$ is a hydrogen, a lower alkyl group, a phenyl group, a lower alkoxycarbonyl group or a halogeno-lower alkylcarbonyl group.

15. The compound of claim 1, wherein A is a divalent $C_{1-15}$ chain hydrocarbon group that is unsubstituted or substituted with the same substituents recited for A in claim 1.

16. The compound of claim 1 wherein A is a $C_{1-6}$ alkylene group.

17. The compound of claim 1, wherein X is bound to the 5-position of an imidazo[1,2-a]pyridine ring or an imidazo[1,2-c]pyrimidine ring.

18. The compound of claim 1, wherein X is bound to the 8-position of an imidazo[1,2-a]pyridine ring or an imidazo[1,2-c]pyrimidine ring.

19. The compound of claim 1 represented by the formula:

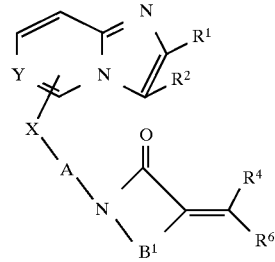

wherein X represents a bond, —S(O)m—, —O—, —$NR^{3a}$—, —Alk—, —Alk—W— or —S—Alk—W— (Alk represents a divalent hydrocarbon group that is unsubstituted or substituted as in claim 1; W represents —O—, —NR3a—, —CO—O— or —O—CO—$NR^{3a}$—; $R^{3a}$ represents a hydrogen or a hydrocarbon group that is unsubstituted or substituted as in claim 1; m represents an integer from 0 to 2); Y represents CH or N; $R^1$ and $R^2$ independently represent a hydrogen, a hydrocarbon group that is unsubstituted or substituted as in claim 1, a halogen, a nitro group, a nitroso group, an amino group unprotected or protected as in claim 1, a carboxyl group unesterified or esterified as in claim 1, or an acyl group as recited in claim 1; A represents a divalent hydrocarbon group that is unsubstituted or substituted as in claim 1; $B^1$ represents —$(CH_2)_f$— or —$CZ^1$—$Z^2$— (f represents an integer from 1 to 6; $Z^1$ represents O or S; $Z^2$ represents O, S, —$Alk^1$—, —$Alk^1$—S— or $NR^{3b}$; $Alk^1$ represents a divalent chain hydrocarbon group that is unsubstituted or substituted as in claim 1; $R^{3b}$ represents a hydrogen or a hydrocarbon group that is unsubstituted or substituted as in claim 1); $R^4$ and $R^5$ independently represent a hydrogen, a carboxyl group unesterified or esterified as in claim 1, an amino group that is unsubstituted or substituted as in claim 1, a heterocyclic group that is unsubstituted or substituted as in claim 1, —$w^1$—,—S—$W^1$ or —O—$W^1$, wherein $W^1$ is a hydrocarbon group that is unsubstituted or substituted with the same substituents recited as substituents for said hydrocarbon group of $R^1$ and $R^2$ in claim 1; $R^4$ and $R^5$ are uncombined or combined to form a ring or a salt thereof.

20. The compound of claim 19, wherein $B^1$ is —$(CH_2)_f$—, —CO—O—, —CO—S—, —CS—S—, —CO—$CH_2$—, —CO—$CH_2$—S— or —CO—$N(R^3)$—, wherein $R^3$ is same as $R^3$ in claim 10; f represents an integer from 1 to 6.

21. The compound of claim 19, wherein $B^1$ is —CO—S—, —CO—O—, —CO—$CH_2$— or —CO—$N(R^3)$— wherein $R^3$ is the same as $R^3$ in claim 10.

22. The compound of claim 19, wherein $B^1$ is —CO—S— or —CO—O—.

23. The compound of claim 19, wherein $R^4$ and $R^5$ independently are selected from the group consisting of (i) a hydrogen, (ii) a lower alkyl group that is unsubstituted or substituted with the same substituents recited for the alkyl group of $R^3$ in claim 10, (iii) an aryl group that is unsubstituted or substituted with the same substituents recited for the aryl group of $R^3$ in claim 10, (iv) an amino group that is unsubstituted or substituted with a lower alkyl groups or acyl group, wherein said acyl group is selected from the group consisting of the same groups as acyl groups recited as substituents of the hydrocarbon group for A in claim 1, and (iv) a heterocyclic group that is unsubstituted or substituted with 1 to 4 substituents selected from the group consisting of halogens, lower alkyl groups, lower alkenyl groups, lower alkoxy groups, nitro group, cyano group, hydroxy group, lower alkoxycarbonyl groups, carboxy groups, carbamoyl groups, lower alkylcarbamoyl groups and lower alkenylcarbamoyl groups.

24. The compound of claim 19, whrerein $R^4$ and $R^5$ independently represent a hydrogen or a lower alkyl group that is unsubstituted or substituted with the same substituents recited for the lower alkyl group of $R^3$ in claim 10.

25. The compound of claim 19, wherein X is S, O or —$CH_2$—.

26. The compound of claim 19, wherein Y is CH.

27. The compound of claim 19, wherein A is a $C_{1-6}$ alkylene group.

28. The compound of claim 19, wherein $R^1$ and $R^2$ independently represent a hydrogen, a lower alkyl group, a phenyl group, a lower alkoxycarbonyl group or a halogeno-lower alkylcarbonyl group.

29. The compound of claim 19, wherein X is bound to the 5-position of an imidazo[1,2-a]pyridine ring or an imidazo [2-c]pyrimidine ring.

30. The compound of claim 1, represented by the formula:

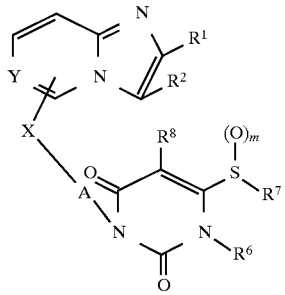

wherein X represents a bond, —S(O)m—, —O—, —$NR^{3a}$—, —Alk—, —Alk—W— or —S—Alk—W— (Alk represents a divalent hydrocarbon group that is unsubstituted or substituted as in claim 1; W represents —O—, —$NR^{3a}$—, —CO—O— or —O—CO—$NR^{3a}$—; $R^{3a}$ represents a hydrogen or a hydrocarbon group that is unsubstituted or substituted as in claim 1; m represents an integer from 0 to 2); Y represents CH or N; $R^1$ and $R^2$ whether identical or not, represent a hydrogen, a hydrocarbon group that is unsubstituted or substituted as in claim 1, a halogen, a nitro group, a nitroso group, an amino group unprotected or protected as in claim 1, a carboxyl group unesterified or esterified as in claim 1 or an acyl group, wherein said acyl group is the same as that recited for $R^1$ and $R^2$ in claim 1; A represents a divalent hydrocarbon group that is unsubstituted or substituted as in claim 1; $R^6$ and $R^7$ independently represent a hydrocarbon group that is unsubstituted or substituted as in claim 1 or a heterocyclic group that is unsubstituted or substituted as in claim 1; or $R^6$ and $R^7$ are uncombined or combined to form a ring as in claim 63; $R^8$ represents a hydrogen, a hydrocarbon group that is unsubstituted or substituted as in claim 1, a heterocyclic group that is unsubstituted or substituted as in claim 1, a nitro group, a cyano group, an amino group unprotected or protected as in claim 1, a halogen or an acyl group, wherein said acyl group is the same as that recited for $R^8$ in claim 1; and m represents an integer from 0 to 2, or a salt thereof.

31. The compound of claim 30, wherein $R^6$ and $R^7$ independently represent a lower alkyl group that is unsubstituted or substituted with a hydrogen or a hydrocarbon group that is unsubstituted or substituted at any position with 1 to 5 substituents selected from the group consisting of nitro group, hydroxyl group, oxo group, thioxo group, cyano group, sulfone group, halogens, lower alkoxy groups, phenoxy group, halogenophenoxy groups, lower alkylthio groups, phenylthio group, amino groups, carboxyl groups, acyl groups, and heterocyclic groups, wherein (i) said amino groups are unsubstituted or substituted with substituents selected from the group consisting of lower alkyl groups and acyl groups, (ii) said acyl group as a substituent of said hydrocarbon group or as a substituent of said amino group are selected from the group consisting of the same acyl groups which are recited as substituents for Alk above, and (iii) said carboxyl group is unesterified or esterified resulting in a lower alkoxycarbonyl group;, or $R^6$ and $R^7$ are uncombined or combined to form —$CH(R^{15})$—$CH(R^{16})$—$(CH_2)_s$—($R^{15}$ and $R^{16}$ independently represent a hydrogen or a lower alkyl group; s represents an integer of 0 or 1).

32. The compound of claim 30, wherein $R^8$ is a hydrogen, a lower alkyl group unsubstituted or substituted with the same substituents recited for the alkyl group of $R^3$ in claim 10, or an aryl group unsubstituted or substituted with the same substituents recited for the aryl group of $R^3$ in claim 10.

33. The compound of claim 30, wherein $R^8$ is a hydrogen, a lower alkyl group, an aralkyl group or a phenyl group.

34. The compound of claim 30, wherein m is 1 or 2.

35. The compound of claim 30, wherein X is S, O or —CH$_2$—.

36. The compound of claim 30, wherein Y is CH.

37. The compound of claim 30, wherein A is a $C_{1-6}$ alkylene group.

38. The compound of claim 30, wherein $R^1$ and $R^2$ independently represent a hydrogen, a lower alkyl group, a phenyl group, a lower alkoxycarbonyl group or a halogeno-lower alkylcarbonyl group.

39. The compound of claim 30, wherein x is bound to the 5-position of an imidazo[1,2-a]pyridine ring or an imidazo[1,2-c]pyrimidine ring.

40. A process for producing the compound of claim 1, having S, O, —(CH$_2$)$_i$—O— or —(CH$_2$)$_i$—N(R$^3$)— for X which comprises reacting a compound represented by the formula:

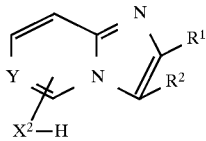

wherein $X^2$ represents S, O, —(CH$_2$)$_i$—O— or —(CH$_2$)$_i$—N(R$^3$)—(wherein $R^3$ is the same as $R^3$ in claim 20; the other symbols have the same definitions as those given in claim 1, or a salt thereof with a compound represented by the formula:

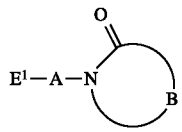

wherein $E^1$ represents a leaving group; the other symbols have the same definitions as those given in claim 1, or a salt thereof.

41. A pharmaceutical composition, which contains a compound of claim 1.

42. An inhibitor of the expression of adhesion molecules associated with inflammatory cell infiltration or immune cell antigen recognition, which contains the compound of claim 1.

43. An agent for treating and preventing diabetic nephritis, which contains a compound of claim 1.

44. An immunosuppressor for organ transplantation, which contains a compound of claim 1.

45. A method for prophylaxis or therapy of autoimmune diseases which comprises administering an effective amount of a compound of claim 1 and a pharmaceutically acceptable excipient to a mammal.

46. A process for producing a compound of claim 1 which comprises reacting a compound represented by the formula:

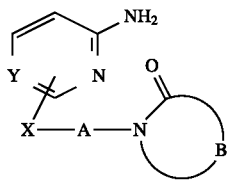

wherein the symbols have the same definitions as those given in claim 1, or a salt thereof with a compound represented by the formula:

$$R^1\text{—CO—CH(E)—}R^2$$

wherein E represents a halogen; the other symbols have the same definitions as those given in claim 1, or a salt thereof.

47. A process for producing a compound of claim 1 having S, O or N(R$^3$) for X which comprises reacting a compound represented by the formula:

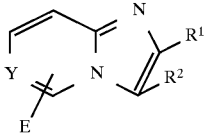

wherein E represents a halogen; the other symbols have the same definitions as those given in claim 1, or a salt thereof with a compound represented by the formula:

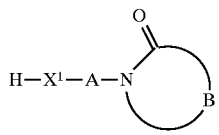

wherein $X^1$ represents S, O or —N(R$^3$)—; wherein $R^3$ is selected from the group consisting of (i) hydrogen, (ii) a lower alkyl group, (iii) a lower alkenyl group, wherein said lower alkyl and alkenyl groups each independently is unsubstituted or substituted with 1 or 2 substituents selected from the group consisting of halogens, lower alkoxy groups, hydroxy group, lower alkoxycarbonyl groups, carboxyl group, carbamoyl groups, lower alkylcarbamoyl groups, and pyridylthio groups, (iv) an aralkyl group being a phenyl-lower alkyl group or a naphthyl-lower alkyl group, wherein the phenyl moiety of the phenyl-lower alkyl group and the naphthyl moiety of the naphthyl-lower alkyl group is unsubstituted or substituted with 1 to 4 substituents selected from the group consisting of halogens, lower alkyl groups, lower alkenyl groups, lower alkoxy groups, nitro group, cyano group, hydroxy group, lower alkoxycarbonyl groups, carbamoyl groups, lower alkylcarbamoyl groups and lower alkenylcarbamoyl groups, and (v) an aryl group that is unsubstituted or substituted with 1 to 4 substituents selected from the group consisting of halogens, lower alkyl groups, lower alkenyl groups, lower alkoxy groups, nitro group, cyano group, oxo group, hydroxy group, amino groups, lower acylamino groups, lower alkoxycarbonyl groups, carbamoyl groups, lower alkylcarbamoyl groups, and lower alkenylcarbamoyl groups; the other symbols have the same definitions as those given in claim 1, or a salt thereof.

48. A process for producing a compound of claim 1 having —(CH$_2$)$_j$—CON(R$^3$)—, —(CH$_2$)$_j$—COO—, —S—(CH$_2$)$_k$—CON(R$^3$)— or —S—(CH$^2$)$_k$—COO— for X which comprises reacting a compound represented by the formula:

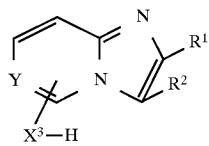

wherein $X^3$ represents —$(CH_2)_j$—COO—; wherein j represents 0 or 1 or —S—$(CH_2)_k$—COO—; wherein k represents an integer from 1 to 5; the other symbols have the same definitions as those given in claim 1, or a salt thereof with a compound represented by the formula:

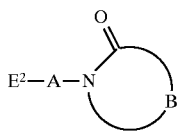

wherein $E^2$ represents HN($R^3$)—; wherein $R^3$ is selected from the group consisting of (i) hydrogen, (ii) a lower alkyl group, (iii) a lower alkenyl group, wherein said lower alkyl and alkenyl groups each independently are unsubstituted or substituted with 1 or 2 substituents selected from the group consisting of halogens, lower alkoxy groups, hydroxy group, lower alkoxycarbonyl groups, carboxyl group, carbamoyl groups, lower alkylcarbamoyl groups, and pyridylthio groups, (iv) an aralkyl group being a phenyl-lower alkyl group or a naphthyl-lower alkyl group, wherein the phenyl moiety of the phenyl-lower alkyl group and the naphthyl moiety of the naphthyl-lower alkyl group is unsubstituted or substituted with 1 to 4 substituents selected from the group consisting of halogens, lower alkyl groups, lower alkenyl groups, lower alkoxy groups, nitro group, cyano group, hydroxy group, lower alkoxycarbonyl groups, carbamoyl groups, lower alkylcarbamoyl groups and lower alkenylcarbamoyl groups, and (v) an aryl group that is unsubstituted or substituted with 1 to 4 substituents selected from the group consisting of halogens, lower alkyl groups, lower alkenyl groups, lower alkoxy groups, nitro group, cyano group, oxo group, hydroxy group, amino groups, lower acylamino groups, lower alkoxycarbonyl groups, carbamoyl groups, lower alkylcarbamoyl groups, and lower alkenylcarbamoyl groups, or HO—; the other symbols have the same definitions as those given in claim 1, or a salt thereof.

49. A process for producing a compound of claim 1 having —$(CH_2)_i$—OCON($R^3$)— for X which comprises reacting a compound represented by the formula:

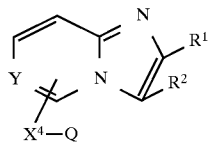

wherein $X^4$ represents —$(CH_2)_i$—OCO—; wherein i represents 1 or 2; Q represents a leaving group; the other symbols have the same definitions as those given in claim 1, or a salt thereof with a compound represented by the formula:

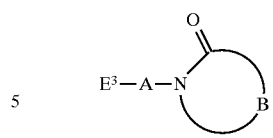

wherein $E^3$ represents HN($R^3$)—; wherein $R^3$ is selected from the group consisting of (i) hydrogen, (ii) a lower alkyl group, (iii) a lower alkenyl group, wherein said lower alkyl and alkenyl groups each independently are unsubstituted or substituted with 1 or 2 substituents selected from the group consisting of halogens, lower alkoxy groups, hydroxy group, lower alkoxycarbonyl groups, carboxyl group, carbamoyl groups, lower alkylcarbamoyl groups, and pyridylthio groups, (iv) an aralkyl group being a phenyl-lower alkyl group or a naphthyl-lower alkyl group, wherein the phenyl moiety of the phenyl-lower alkyl group and the naphthyl moiety of the naphthyl-lower alkyl group are unsubstituted or substituted with 1 to 4 substituents selected from the group consisting of halogens, lower alkyl groups, lower alkenyl groups, lower alkoxy groups, nitro group, cyano group, hydroxy group, lower alkoxycarbonyl groups, carbamoyl groups, lower alkylcarbamoyl groups and lower alkenylcarbamoyl groups, and (v) an aryl group that is unsubstituted or substituted with 1 to 4 substituents selected from the group consisting of halogens, lower alkyl groups, lower alkenyl groups, lower alkoxy groups, nitro group, cyano group, oxo group, hydroxy group, amino groups, lower acylamino groups, lower alkoxycarbonyl groups, carbamoyl groups, lower alkylcarbamoyl groups, and lower alkenylcarbamoyl groups; the other symbols have the same definitions as those given in claim 1, or a salt thereof.

50. A process for producing the compound of claim 1 which comprises reacting a compound represented by the formula:

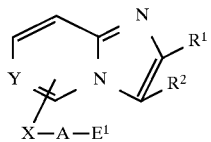

wherein $E^1$ represents a leaving group; the other symbols have the same definitions as those given in claim 1, or a salt thereof with a compound represented by the formula:

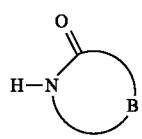

wherein the symbols have the same definitions as those given in claim 1, or a salt thereof.

51. A process for producing the compound of claim 19 which comprises reacting a compound represented by the formula:

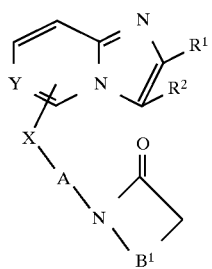
wherein the symbols have the same definitions as those given in claim 1, or a salt thereof with a compound represented by the formula:
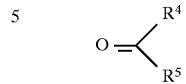
wherein the symbols have the same definitions as those given in claim 1.
* * * * *

UNITED STATES PATENT AND TRADEMARK OFFICE
CERTIFICATE OF CORRECTION

PATENT NO. : 5,840,732
DATED : November 24, 1998
INVENTOR(S) : Muneo TAKATANI et al.

It is certified that error appears in the above-identified patent and that said Letters Patent is hereby corrected as shown below:

Column 33, line 36, delete "H-$X^1$-N" and insert -- H-$X^1$-A-N --. Also Column 128, Claim 19, line 56, delete "$R^6$" and insert --$R^5$--.

Signed and Sealed this

Eighteenth Day of May, 1999

Attest:

Attesting Officer

Q. TODD DICKINSON

Acting Commissioner of Patents and Trademarks